United States Patent
Leftheris et al.

(10) Patent No.: US 6,653,304 B2
(45) Date of Patent: Nov. 25, 2003

(54) CANNABINOID RECEPTOR MODULATORS, THEIR PROCESSES OF PREPARATION, AND USE OF CANNABINOID RECEPTOR MODULATORS FOR TREATING RESPIRATORY AND NON-RESPIRATORY DISEASES

(75) Inventors: Katerina Leftheris, Skillman, NJ (US); Hong Wu, Lawrenceville, NJ (US); Stephen Wrobleski, Whitehouse Station, NJ (US); Ping Chen, Belle Mead, NJ (US); John Hynes, Washington Crossing, PA (US); John Tokarski, Princeton, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/779,109

(22) Filed: Feb. 8, 2001

(65) Prior Publication Data

US 2002/0119972 A1 Aug. 29, 2002

Related U.S. Application Data

(60) Provisional application No. 60/181,818, filed on Feb. 11, 2000.

(51) Int. Cl.$^7$ .................... C07D 403/12; C07D 471/04; A61K 31/40; A61K 31/415
(52) U.S. Cl. .................... 514/232.8; 514/292; 544/126; 546/81
(58) Field of Search .................... 544/126; 546/81; 514/232.8, 292

(56) References Cited

U.S. PATENT DOCUMENTS

| | | | |
|---|---|---|---|
| 4,317,682 A | 3/1982 | Katsura et al. | 106/288 B |
| 4,581,354 A | 4/1986 | Bell | 514/210 |
| 4,748,247 A * | 5/1988 | Abou-Gharbia | 544/357 |
| 5,013,732 A | 5/1991 | Bell | 514/210 |
| 5,102,889 A * | 4/1992 | Martin et al. | 514/292 |
| 5,189,049 A | 2/1993 | Frehel et al. | 514/371 |
| 5,294,612 A | 3/1994 | Bacon et al. | 514/234.2 |
| 5,567,711 A | 10/1996 | Sheppard et al. | 514/303 |
| 5,641,778 A | 6/1997 | Maibaum et al. | 514/237.8 |
| 5,643,922 A | 7/1997 | Sheppard et al. | 514/303 |
| 5,654,305 A | 8/1997 | Sheppard et al. | 514/253 |
| 5,681,954 A | 10/1997 | Yamamoto et al. | 544/114 |
| 6,100,259 A | 8/2000 | Xiang et al. | 514/236.5 |

FOREIGN PATENT DOCUMENTS

| | | |
|---|---|---|
| EP | 353983 * | 2/1990 |
| EP | 0 429 257 A2 | 11/1990 |
| EP | 0445781 A1 | 9/1991 |
| EP | 485962 * | 5/1992 |
| EP | 0656354 A1 | 6/1995 |
| FR | 2735774 | 12/1996 |
| WO | WO93/20078 | 10/1993 |
| WO | WO 96/11929 | 4/1996 |
| WO | WO 96/25397 | 8/1996 |
| WO | WO 97/00860 | 1/1997 |
| WO | WO97/29079 | 2/1997 |
| WO | WO97/09308 | 3/1997 |
| WO | WO 98/41519 | 9/1998 |
| WO | WO 00/12074 | 3/2001 |

OTHER PUBLICATIONS

Chi Hung et al., CAPLUS Abstract No. 107:236553, 1987.*
Kawashima et al., CAPLUS Abstract No. 118:201913, 1993.*
Wring et al., CAPLUS Abstract No. 122:40389, 1995.*
Knaggs et al., CAPLUS Abstract No. 122:101315, 1995.*
Engler et al., Lewis Acid–Directed Cyclocondensation of Piperidone Enol Ethers, J. Org. Chem., vol. 65, No. 8, pp. 2444–2457, Mar. 23, 2000.*
De Benedetti et al., CAPLUS Abstract No. 133:159627, 2000.*
Trofimov et al., Chemical Abstract 84:43754, 1976.*
Ali et al., Chemical Abstract 101:171139, 1984.*
Zefirov et al., Chemical Abstract 118:168952, 1993.*
Levacher et al. Tetrahedron vol. 47, No. 3, pp. 429–440, 1991.

* cited by examiner

*Primary Examiner*—Deepak Rao
(74) *Attorney, Agent, or Firm*—Anastasia P. Winslow; Laurelee A. Duncan

(57) ABSTRACT

Use of a compound for treating a respiratory disease in a mammal wherein the compound is a cannabinoid receptor modulator is disclosed. Compounds useful as cannabinoid receptor modulators for treating respiratory and non-respiratory leukocyte-activation associated diseases comprise compounds of formula (I),

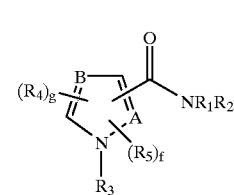

(I)

in which A and B are nitrogen or carbon, provided only one of A and B is nitrogen; and $R_1$–$R_6$ are as defined in the specification, wherein $R_2$ with $R_5$ may form a ring, and/or two $R_4$ groups may form a six-membered aryl or heteroaryl ring, optionally having a substituent $R_6$ forming a ring with $R_3$.

8 Claims, No Drawings

CANNABINOID RECEPTOR MODULATORS, THEIR PROCESSES OF PREPARATION, AND USE OF CANNABINOID RECEPTOR MODULATORS FOR TREATING RESPIRATORY AND NON-RESPIRATORY DISEASES

RELATED APPLICATIONS

This application is related to, and pursuant to 35 U.S.C. §119(e) claims the benefit of priority of, U.S. application Ser. No. 60/181,818, filed Feb. 11, 2000, the entire contents of which is incorporated herein by reference.

FIELD OF THE INVENTION

The present invention relates to compounds and compositions comprising cannabinoid receptor modulators, to processes for preparing such compounds and compositions, and to the use of cannabinoid receptor modulators in treating respiratory and non-respiratory diseases.

BACKGROUND OF THE INVENTION

Delta-9 THC, the principle active component of marijuana, is a member of a large family of lipophilic compounds (i.e., cannabinoids) that mediate physiological and psychotropic effects including immunosuppression, analgesia, inflammation, emesis, and intraocular pressure. Cannabinoids work through selective binding to G-protein coupled cannabinoid receptors. Two types of cannabinoid receptors have been cloned including CB1 (L. A. Matsuda et al. *Nature,* Vol. 346 [1990], pp. 561–564), and CB2 (S. Munro et al, *Nature,* Vol. 365 [1993], pp. 61–65). The CB1 receptor is found mainly on cells of the central nervous system, while the CB2 receptor is found mainly on cells of the peripheral nervous system including cells comprising the immune system such as lymphoid cells.

Compounds that reportedly bind to the cannabinoid G-protein receptors are disclosed in European Patent Documents Nos. EP 0570920 and EP 0444451; International Publications Nos. WO 97/29079, WO 99/02499, WO 98/41519, and WO 9412466; U.S. Pat. Nos. 4,371,720, 5,081,122, 5,292,736, and 5,013,387; and French Patent No. FR 2735774, each of which is incorporated herein by reference.

SUMMARY OF THE INVENTION

Applicants have discovered that cannabinoid receptor modulators including cannabinoid receptor agonists are useful in treating respiratory disease, such as chronic pulmonary obstructive disorder, emphysema, asthma, and bronchitis. In one aspect of the invention, there is provided the use of cannabinoid receptor modulators in treating respiratory disease in a mammal comprising administering to said mammal an effective amount of at least one cannabinoid receptor modulator. Advantageously, the cannabinoid receptor modulator for this aspect of the invention is a CB2-receptor modulator.

The present invention is also directed to compounds and pharmaceutical compositions comprising at least one cannabinoid receptor modulator, and to the use of at least one such compound in treating respiratory and non-respiratory leukocyte activation-associated disorders, wherein the compound has the formula (I):

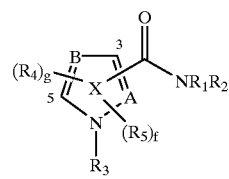

or a pharmaceutically-acceptable salt or hydrate thereof, in which:

A and B are selected from carbon and nitrogen so that ring X defines a pyrrole, pyrazole, or imidazole ring; wherein when A is nitrogen, the group —C(=O)NR$_1$R$_2$ is attached to atom C-3 and R$_5$ does not exist; and when A is carbon, one of the group —C(=O)NR$_1$R$_2$ and R$_5$ is attached to A and the other of —C(=O)NR$_1$R$_2$ and R$_5$ is attached to atom C-3; and when B is carbon, two R$_4$ groups attached to B and atom C-5, respectively, optionally form a fused 6-membered aryl or 6-membered heteroaryl having one heteroatom which is nitrogen, wherein said aryl or heteroaryl has three or four groups R$_6$;

f is 0 or 1;

g is 1 or 2;

R$_1$ and R$_2$ are independently selected from hydrogen, alkyl, substituted alkyl, heterocycloalkyl, cycloalkyl, aryl, and heterocyclo; or R$_2$ together with R$_1$ or R$_5$ forms a five or six membered heterocyclo;

R$_3$ is hydrogen, alkyl, substituted alkyl, heterocycloalkyl, alkenyl, substituted alkenyl, alkynyl, substituted alkynyl, cycloalkyl, aryl, heterocyclo, or alkoxy, or forms a heterocyclo with one of R$_6$;

R$_4$ is attached to atom C-5 and optionally B and at each occurrence independent of each other R$_4$ is selected from hydrogen, alkyl, substituted alkyl, heterocycloalkyl, alkenyl, substituted alkenyl, alkynyl, substituted alkynyl, cycloalkyl, aryl, heterocyclo, hydroxy, alkoxy, amino, aminoalkyl, cyano, halogen, alkylamide, NR$_8$C(=O)R$_9$, and S(O)$_n$R$_{10}$; or when B is carbon, optionally two R$_4$ groups taken together form a six-membered aryl or heteroaryl having three or four R$_6$;

R$_5$ is attached to A or atom C-3 and is hydrogen, alkyl, substituted alkyl, heterocycloalkyl, alkenyl, substituted alkenyl, alkoxy, aryl, or heterocyclo; or R$_5$ together with R$_2$ forms a heterocyclo;

R$_6$ at each occurrence independent of each other R$_6$ is selected from hydrogen, alkyl, substituted alkyl, heterocycloalkyl, alkenyl, substituted alkenyl, alkynyl, substituted alkynyl, aryl, cycloalkyl, substituted aryl, heterocyclo, hydroxy, alkoxy, amino, aminoalkyl, cyano, halogen, alkylamide, nitro, NR$_8$C(=O)R$_9$, S(O)$_n$R$_{10}$, —C(=O)R$_8$, —CO$_2$R$_8$, —S(O)$_2$NR$_8$R$_{10}$, —C(=O)N(R$_8$)O(R$_9$), —C(=O)NR$_8$R$_9$, and —OC(=O)R$_{10}$; and/or one R$_6$ group together with R$_3$ forms a heterocyclo;

R$_8$ and R$_9$ at each occurrence independent of each other R$_8$ and R$_9$ are selected from hydrogen, alkyl, substituted alkyl, heterocycloalkyl, alkenyl, substituted alkenyl, alkynyl, substituted alkynyl, cycloalkyl, aryl, and heterocyclo; or R$_8$ and R$_9$ together form a three-to-eight membered heterocyclo; or R$_8$ together with R$_{10}$ forms a three-to-eight membered heterocyclo; and $R_{10}$ at each occurrence independent of each other $R_{10}$ is selected from alkyl, substituted alkyl, heterocycloalkyl, alkenyl, substituted alkenyl, alkynyl, and substituted alkynyl, or forms a heterocyclo with $R_8$; and u is 0, 1, 2 or 3.

According to another aspect of the invention, there are provided pharmaceutical compositions useful for treating respiratory disease comprising an effective amount of at least one cannabinoid receptor modulator according to formula (I) in a pharmaceutically-acceptable carrier or modulator. In a further aspect of the invention, there are provided compounds useful as cannabinoid receptor modulators and pharmaceutical compositions comprising such cannabinoid receptor modulators, wherein the compounds comprise selected compounds according to formula (I), as defined hereinafter. In a still further aspect of the invention, there is provided a process of preparing one or more intermediates to compounds of formula (I), and processes for preparing compounds of formula (I).

DETAILED DESCRIPTION OF THE INVENTION

The following are definitions of terms used in this specification. The initial definition provided for a group or term herein applies to that group or term throughout the present specification, individually or as part of another group, unless otherwise indicated.

The term "alkyl" refers to straight or branched chain hydrocarbon groups having 1 to 12 carbon atoms, preferably 1 to 8 carbon atoms. The expression "lower alkyl" refers to alkyl groups of 1 to 4 carbon atoms.

The term "substituted alkyl" refers to an alkyl group as defined above having one, two or three substituents selected from the group consisting of halo, cyano, nitro, amino, aminoalkyl, hydroxy, $OR_a$, —SH, keto (=O), —C(=O)H, —CO$_2$H, —C(=O)($R_a$), —CO$_2$($R_a$), —SO$_3$H, —S(O)$_{0-2}$($R_a$), —S(O)$_2$NR$_a$R$_b$, —C(=O)N($R_a$)O($R_b$), —C(=O)N($R_a$)$_2$, —OC(=O)$R_a$, cycloalkyl, or aryl, wherein at each occurrence each of the groups $R_a$, $R_b$ are independently selected from alkyl, substituted alkyl, heterocycloalkyl, alkenyl, substituted alkenyl, alkynyl, substituted alkynyl, cycloalkyl, aryl, and heterocyclo; or $R_a$ and $R_b$ taken together form a three-to-eight membered heterocyclo.

When the term "alkyl" is used to suffix another group, such as in "arylalkyl", "heterocycloalkyl" or cycloalkyl alkyl," the term defines with more specifity at least one of the groups that a substituted alkyl will contain. In other words, in these instances the specifically-named groups are bonded directly through a substituted or unsubstituted alkyl chain as defined above. For example, an arylalkyl includes benzyl, and a heterocycloalkyl includes ethyl-morpholino or any other straight or branched hydrocarbon chain of 1 to 12 carbon atoms having a substituted or unsubstituted heterocyclo as one of its substituents.

The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond. When reference is made to a substituted alkenyl, the alkenyl group will have one to three substituents as recited above for alkyl groups.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond. A "substituted alkynyl" is substituted with one to three substituents as recited above for alkyl groups.

The term "alkylene" refers to a chain bridge of 1 to 5 carbon atoms connected by single bonds {e.g., —(CH$_2$)$_x$— wherein x is 1 to 5}, which may be branched with 1 to 3 lower alkyl groups.

The term "alkenylene" refers to a chain bridge of 2 to 5 carbon atoms having one or two double bonds connected by single bonds and which may be branched with 1 to 3 lower alkyl groups. Exemplary alkenylene groups include —CH=CH—CH=CH—, —CH$_2$—CH=CH—, —CH$_2$—CH=CH—CH$_2$—, —C(CH$_3$)$_2$CH=CH— and —CH(C$_2$H$_5$)—CH=CH—.

The term "alkynylene" refers to a chain bridge of 2 to 5 carbon atoms that has a triple bond therein, is connected by single bonds, and may be branched with 1 to 3 lower alkyl groups. Exemplary alkynylene groups include —C≡C—, —CH$_2$—C≡C—, —CH(CH$_3$)—C≡C— and —C≡C—CH(C$_2$H$_5$)CH$_2$—. When reference is made to a substituted alkylene, substituted alkenylene, or substituted alkynylene, these groups may have 1 to 3 substituents as defined above for alkyl groups.

The term "alkoxy" refers to the group $OR_o$, wherein the group $R_o$ is selected from alkyl, alkenyl, alkynyl, cycloalkyl, aryl, heterocyclo, substituted alkyl, heterocycloalkyl, substituted alkenyl, or substituted alkynyl.

The term "amino" refers to —NH$_2$, and the term "aminoalkyl" refers to —NR$_c$R$_d$, wherein $R_c$ and $R_d$ are independently selected from hydrogen, alkyl, substituted alkyl, heterocycloalkyl, alkenyl, substituted alkenyl, alkynyl, substituted alkynyl, cycloalkyl, aryl, heterocyclo, and —C(=O)$R_e$; or $R_c$ and $R_d$ are taken together to form a three-to-eight membered saturated or unsaturated heterocyclo ring which may have one to three substituents as defined below for heterocyclo groups. $R_e$ is selected from alkyl, substituted alkyl, heterocycloalkyl, alkenyl, substituted alkenyl, alkynyl, substituted alkynyl, cycloalkyl, aryl, and heterocyclo.

The term "alkylthio" refers to an alkyl or substituted alkyl group as defined above being further substituted with one of the groups —SH or —SR$_s$, wherein $R_s$ is selected from alkyl, substituted alkyl, heterocycloalkyl, alkenyl, substituted alkenyl, alkynyl, substituted alkynyl, cycloalkyl, aryl, and heterocyclo.

The term "alkylamide" refers to the group —C(=O)NR$_f$R$_g$, wherein $R_f$ and $R_g$ are independently selected from hydrogen, alkyl, substituted alkyl, heterocycloalkyl, alkenyl, substituted alkenyl, alkynyl, substituted alkynyl, cycloalkyl, aryl, and heterocyclo; or $R_f$ and $R_g$ taken together form a three-to-eight membered heterocyclo.

The terms "ar" or "aryl" refer to aromatic cyclic groups, for example, 6 membered monocyclic, 10 membered bicyclic or 12 membered tricyclic ring systems, which contain 6 to 14 carbon atoms. Exemplary aryl groups include phenyl, naphthyl, biphenyl and anthracenyl. Whenever reference is made to an aryl group (including without limitation in these definitions and in the claims), unless otherwise specifically indicated the aryl may have one to three substituents selected from the group consisting of $R_a$, halo, cyano, nitro, amino, aminoalkyl, hydroxy, $OR_a$, —SH, —C(=O)H, —CO$_2$H, C(=O)($R_a$), —CO$_2$($R_a$), —SO$_3$H, —S(O)$_{0-2}$($R_a$), —S(O)$_2$NR$_a$R$_b$, —C(=O)N($R_a$)O($R_b$), —C(=O)N($R_a$)$_2$, and —OC(=O)$R_a$ wherein at each occurrence each of the groups $R_a$, $R_b$ are independently selected from alkyl, substituted alkyl, heterocycloalkyl, alkenyl, substituted alkenyl, alkynyl, substituted alkynyl, cycloalkyl, aryl, and heterocyclo, or taken together form a substituted or unsubstituted heterocyclo.

The term "cycloalkyl" refers to fully saturated and partially unsaturated cyclic hydrocarbon groups of 3 to 12 carbon atoms. Cycloalkyl groups may be bicyclic, e.g., such as in bicycloheptane and bicyclooctane. Whenever reference is made to a cycloalkyl (including without limitation in these definitions and in the claims), unless otherwise specifically indicated the cycloalkyl may have one to three substituents selected from the group consisting of $R_a$, halo, cyano, nitro, amino, aminoalkyl, hydroxy, $OR_a$, —SH, keto (=O), —C(=O)H, —CO$_2$H, —C(=O)($R_a$), —CO$_2$($R_a$), —SO$_3$H, —S(O)$_{0-2}$($R_a$), —S(O)$_2$NR$_a$R$_b$, —C(=O)N($R_a$)O($R_b$), —C(=O)N($R_a$)$_2$, and —OC(=O)$R_a$, wherein at each occurrence each of the groups $R_a$, $R_b$ are independently selected from alkyl, substituted alkyl, heterocycloalkyl, alkenyl, substituted alkenyl, alkynyl, substituted alkynyl, cycloalkyl, aryl, and heterocyclo, or taken together form a heterocyclo.

The terms "halogen" and "halo" refer to fluorine, chlorine, bromine and iodine.

The terms "heterocycle", "heterocyclic" or "heterocyclo" refer to fully saturated or unsaturated, including aromatic (i.e. "heteroaryl") cyclic groups, for example, 4 to 7 membered monocyclic, 7 to 11 membered bicyclic, or 10 to 15 membered tricyclic ring systems, which have at least one heteroatom in at least one carbon atom-containing ring, and each ring of the heterocyclo is optionally substituted as defined below. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. Each ring of the heterocyclic group may have one or more (preferably one or two) substitutents selected from $R_a$, halo, cyano, nitro, amino, aminoalkyl, hydroxy, $OR_a$, —SH, keto (=O), —C(=O)H, —CO$_2$H, —C(=O)($R_a$), —CO$_2$($R_a$), —SO$_3$H, —S(O)$_{0-2}$($R_a$), —S(O)$_2$NR$_a$R$_b$, —C(=O)N($R_a$)O($R_b$), —C(=O)N($R_a$)$_2$, —OC(=O)$R_a$, wherein at each occurrence each of the groups $R_a$, $R_b$ are independently selected from alkyl, substituted alkyl, alkenyl, substituted alkenyl, alkynyl, substituted alkynyl, cycloalkyl, aryl, monocyclic heterocycloalkyl or monocyclic heterocyclo, or taken together form a heterocyclo.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like. The term "diazapine" refers to a heterocyclo having at least one seven atom ring with two nitrogen atoms in said seven atom ring.

Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

The term "heteroaryl" refers to aromatic heterocyclic groups.

Exemplary heteroaryl groups include pyrrolyl, pyrazolyl, imidazolyl, oxazolyl, isoxazolyl, thiazolyl, thiadiazolyl, isothiazolyl, furyl, thienyl, oxadiazolyl, pyridinyl, pyrazinyl, pyrimidinyl, pyridazinyl, triazolyl, triazinyl, and the like.

When reference is made to specifically-named heterocyclo, such as 1,2,3,4-tetrahydroquinoline, triazaspirodecane, morpholine, piperidine, pyrrolidine, thienyl, oxazole, and diazapine, and so forth, these rings may have one or more substituents as defined above for heterocyclo groups.

The term "unsaturated ring" includes partially or fully unsaturated and aromatic rings. When reference is made to an unsaturated heterocyclo, this means at least one ring of the heterocyclo is unsaturated (partially or fully), i.e., in a bicyclic or tricyclic heterocyclo, only one ring of the heterocyclo need be at least partially unsaturated to comprise an unsaturated heterocyclo as defined herein.

Included within compounds of formula (I) are those compounds where A and B comprise carbon to define pyrrole-based compounds; where A is nitrogen and B is carbon to define pyrazole-based compounds; and where A is carbon and B is nitrogen to define imidazole-based compounds, as further defined below. One skilled in the field may make appropriate selections to provide stable compounds.

Pyrrole-based Compounds

Compounds of formula (I) include pyrrole-based compounds useful as cannabinoid receptor modulators having formula (II), and pharmaceutically-acceptable salts thereof:

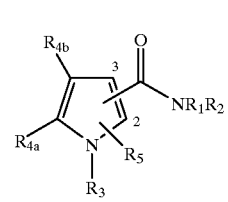

(II)

in which
one of $R_5$ and the group —C(=O)NR$_1$R$_2$ is attached to atom C-2 and the other of $R_5$ and the group —C(=O)NR$_1$R$_2$ is attached to atom C-3 of the pyrrole ring;

$R_1$ and $R_2$ are independently selected from hydrogen, alkyl, substituted alkyl, heterocycloalkyl, cycloalkyl, aryl, and heterocyclo; or $R_2$ together with $R_1$ forms a heterocyclo; or $R_2$ and $R_5$ form a heterocyclo and $R_1$ is hydrogen, alkyl, substituted alkyl, heterocycloalkyl, cycloalkyl, aryl, or heterocyclo;

$R_3$ is hydrogen, alkyl, substituted alkyl, heterocycloalkyl, alkenyl, substituted alkenyl, alkynyl, substituted alkynyl, aryl, heterocyclo, or alkoxy, or forms a heterocyclo with $R_{4a}$;

$R_{4a}$ and $R_{4b}$ are (i) selected from hydrogen, alkyl, substituted alkyl, heterocycloalkyl, alkenyl, substituted alkenyl, alkynyl, substituted alkynyl, aryl, heterocyclo, hydroxy, alkoxy, amino, aminoalkyl, cyano, halogen, alkylamide, $NR_8C(=O)R_9$, and $S(O)_uR_{10}$; or (ii) taken together form a fused six-membered aryl or heteroaryl having three or four $R_6$;

$R_5$ is hydrogen, alkyl, substituted alkyl, heterocycloalkyl, alkenyl, substituted alkenyl, alkynyl, substituted alkynyl, alkoxy, aryl, or heterocyclo; or $R_5$ is taken together with $R_2$ to form a heterocyclo;

$R_6$ at each occurrence is selected independently of each other $R_6$ from hydrogen, alkyl, substituted alkyl, alkenyl, substituted alkenyl, alkynyl, substituted alkynyl, aryl, cycloalkyl, substituted aryl, heterocyclo, hydroxy, alkoxy, amino, aminoalkyl, cyano, halogen, alkylamide, nitro, $NR_8C(=O)R_9$, $S(O)_uR_{10}$, $—C(=O)R_8$, $—CO_2R_8$, $—S(O)_2NR_8R_{10}$, $—C(=O)N(R_8)O(R_9)$, $—C(=O)NR_8R_9$, and $—OC(=O)R_{10}$; or one group $R_6$ forms a heterocyclo with $R_3$ and each other $R_6$ is selected from hydrogen, alkyl, substituted alkyl, alkenyl, substituted alkenyl, alkynyl, substituted alkynyl, aryl, cycloalkyl, substituted aryl, heterocyclo, hydroxy, alkoxy, amino, aminoalkyl, cyano, halogen, alkylamide, nitro, $NR_8C(=O)R_9$, $S(O)_uR_{10}$, $—C(=O)R_8$, $—CO_2R_8$, $—S(O)_2NR_8R_{10}$, $—C(=O)N(R_8)O(R_9)$, $—C(=O)NR_8R_9$, and $—OC(=O)R_{10}$;

$R_8$ and $R_9$ at each occurrence independent of each other $R_8$ and $R_9$ are selected from hydrogen, alkyl, substituted alkyl, heterocycloalkyl, alkenyl, substituted alkenyl, alkynyl, substituted alkynyl, cycloalkyl, aryl, and heterocyclo; or $R_8$ and $R_9$ taken together form a three-to-eight membered heterocyclo; or $R_8$ together with $R_{10}$ forms a three-to-eight membered heterocyclo; and $R_{10}$ at each occurrence independent of each other $R_{10}$ is selected from alkyl, substituted alkyl, heterocycloalkyl, alkenyl, substituted alkenyl, alkynyl, and substituted alkynyl, or forms a heterocyclo with $R_8$, and u is 0, 1, 2 or 3.

Accordingly, included within compounds of formula (II) are cannabinoid receptor modulators comprising 2-carboxamide and 3-carboxamide pyrroles, e.g., compounds having formula (IIa) or (IIb), and pharmaceutically-acceptable salts thereof:

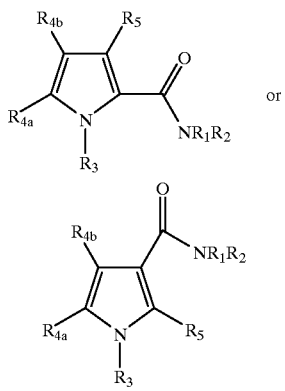

(IIa)

or (IIb)

wherein $R_1$ and $R_2$ are (i) independently selected from hydrogen, alkyl, substituted alkyl, heterocycloalkyl, aryl, cycloalkyl, and heterocyclo; or (ii) taken together form a heterocyclo that is unsaturated or selected from optionally-substituted 1,2,3,4-tetrahydroquinoline, triazaspirodecane, morpholine, piperidine, pyrrolidine, and diazapine;

$R_3$ is hydrogen, alkyl, substituted alkyl, heterocycloalkyl, alkenyl, substituted alkenyl, alkynyl, substituted alkynyl, aryl, or heterocyclo;

$R_{4a}$ and $R_{4b}$ are independently selected from hydrogen, alkyl, substituted alkyl, heterocycloalkyl, alkenyl, substituted alkenyl, alkynyl, substituted alkynyl, aryl, heterocyclo, hydroxy, alkoxy, amino, aminoalkyl, cyano, halogen, alkylamide, $NR_8C(=O)R_9$, and $S(O)_uR_{10}$;

$R_5$ is hydrogen, alkyl, substituted alkyl, heterocycloalkyl, alkenyl, substituted alkenyl, alkynyl, substituted alkyny, alkoxy, aryl, or heterocyclo; and $R_{10}$ is alkyl, substituted alkyl, heterocycloalkyl, alkenyl, substituted alkenyl, alkynyl, or substituted alkynyl, and u is 0, 1, 2 or 3.

With respect to compounds of formulae (IIa) and (IIb) useful as cannabinoid receptor modulators, 3-carboxamide pyrroles are preferred. Additionally, advantageously $R_1$ is alkyl, substituted alkyl, heterocycloalkyl, aryl, cycloalkyl, or heterocyclo, and $R_2$ is hydrogen or $C_{1-3}$alkyl. $R_3$ is preferably heterocycloalkyl (particularly morpholinylethyl), and $R_{4a}$ and $R_{4b}$ are hydrogen, halogen, lower alkyl, or alkoxy (more preferably $C_{1-5}$alkoxy, OPh, or OBn). Also preferred are those carboxamide pyrroles where $R_1$ is $—CHR_{17}R_{18}$, wherein $R_{17}$ and $R_{18}$ are selected from substituted alkyl, $—CO_2$(alkyl), and alkylamide, or where $R_{17}$ and $R_{18}$ together form a cycloalkyl, an aryl, or a heterocyclo wherein said heterocyclo has sulfur or at least one of nitrogen and oxygen as its heteroatom(s).

Further included within compounds of formula (II) are compounds comprising bicyclic or tricyclic ringed systems having formula (IIc) or (IId), and pharmaceutically-acceptable salts thereof:

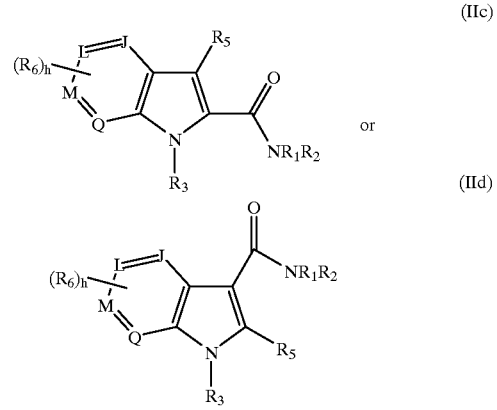

(IIc)

or (IId)

wherein J, L, M and Q are carbon or nitrogen, provided that only one of J, L, M and Q is nitrogen;

$R_1, R_2, R_3, R_5$ and $R_6$ are as defined above for compounds of formula (II), provided that when $R_3$ forms a ring with one of $R_6$, Q is carbon and $R_2$ is selected independently of $R_5$; and h is 3 or 4.

In compounds of formula (II), particularly (IIc) and (IId), when $R_1$ and $R_2$ together form a heterocyclo ring, advantageously said ring is unsaturated or is selected from optionally-substituted 1,2,3,4-tetrahydroquinoline, triazaspirodecane, morpholine, piperidine, pyrrolidine, and diazapine. When $R_1$ and $R_2$ independently comprise heterocyclo, advantageously said heterocyclo has as its heteroatom or heteroatoms either (i) sulfur or, (ii) at least one of nitrogen and oxygen. For example, $R_1$ and $R_2$ may independently comprise pyridine, pyrazole, imidazole, tetrazole, oxazole, oxadiazole, thiophene, morpholine, and so forth. Advantageously, $R_5$ is not phenyl when attached to atom C-3 and at least one $R_6$ is alkoxy (preferably O—$C_{1-5}$alkyl, OPh, or OBn), and two $R_6$ groups are not simultaneously selected from amino and aminoalkyl.

Further included within compounds of formula (IIc) and (IId) are compounds comprising tricyclic ringed systems having formula (IIe) or (IIf), respectively, and pharmaceutically-acceptable salts thereof:

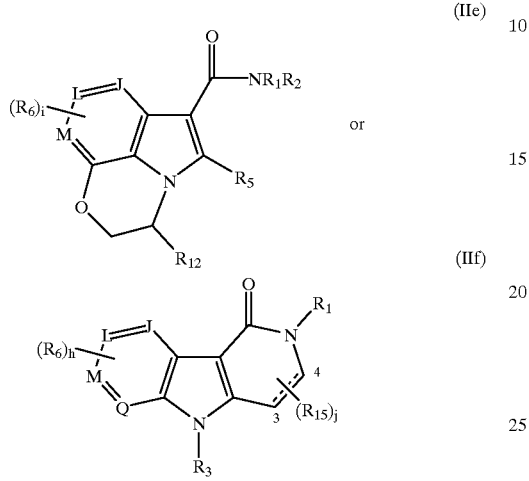

(IIe)

(IIf)

wherein J, L, M, and Q are carbon or nitrogen, provided that only one of J, L, M and Q is nitrogen; $R_1$, $R_2$, $R_3$, $R_5$, $R_6$, $R_8$, $R_9$ and $R_{10}$ are as defined above for compounds of formula (IIa) and (IIb); $R_{12}$ and $R_{15}$ selected independently of each other are hydrogen, alkyl, substituted alkyl, heterocycloalkyl, alkenyl, substituted alkenyl, alkynyl, substituted alkynyl, aryl, heterocyclo, hydroxy, alkoxy, amino, aminoalkyl, cyano, halogen, alkylamide, nitro, $NR_8C(=O)R_9$, $S(O)_uR_{10}$, keto (=O), —C(=O)$R_8$, —$CO_2R_8$, —S(O)$_2NR_8R_{10}$, —C(=O)N($R_8$)O($R_9$), —C(=O)$NR_8R_9$, or —OC(=O)$R_{10}$; i is 2 or 3; and j is 2 or 4. In compounds of formula (II), including (IIa) through (IIe), as they appear the groups J, L, M, and Q are preferably carbon; preferably $R_1$ is substituted alkyl and $R_2$ is hydrogen or $C_{1-3}$alkyl; $R_3$ and $R_{12}$ are —(CH$_2$)$_n$—Z or —O—(CH$_2$)$_n$—Z, wherein Z is CH$_3$, CO$_2$H, amino, aminoalkyl, alkylamide, alkoxy, heterocyclo, aryl, or cycloalkyl, and n is 1 or 2; $R_5$ and $R_{15}$ are hydrogen, halogen, methoxy, or lower alkyl; and each $R_6$ is hydrogen, alkoxy, lower alkyl, or halogen. More preferably, $R_3$ and $R_{12}$ are morpholinyl$C_{1-3}$alkyl.

Pyrazole-Based Compounds

Included within compounds of formula (I) are pyrazole-based compounds useful as cannabinoid receptor modulators having formula (III), and pharmaceutically-acceptable salts thereof:

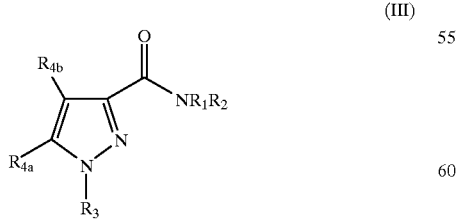

(III)

in which $R_1$ and $R_2$ are (i) independently selected from hydrogen, alkyl, substituted alkyl, heterocycloalkyl, cycloalkyl, aryl, and heterocyclo; or (ii) taken together form a heterocyclo;

$R_3$ is hydrogen, alkyl, substituted alkyl, heterocycloalkyl, alkenyl, substituted alkenyl, alkynyl, substituted alkynyl, cycloalkyl, aryl, heterocyclo, or alkoxy; or forms a heterocyclo with $R_{4a}$;

$R_{4a}$ and $R_{4b}$ are (i) selected from hydrogen, alkyl, substituted alkyl, heterocycloalkyl, alkenyl, substituted alkenyl, alkynyl, substituted alkynyl, aryl, heterocyclo, hydroxy, alkoxy, amino, aminoalkyl, cyano, halogen, alkylamide, $NR_8C(=O)R_9$, and $S(O)_uR_{10}$; or (ii) taken together form a fused six-membered aryl or heteroaryl having three or four $R_6$;

$R_6$ at each occurrence is selected independently of each other $R_6$ from hydrogen, alkyl, substituted alkyl, alkenyl, substituted alkenyl, alkynyl, substituted alkynyl, aryl, cycloalkyl, substituted aryl, heterocyclo, hydroxy, alkoxy, amino, aminoalkyl, cyano, halogen, alkylamide, nitro, $NR_8C(=O)R_9$, $S(O)_uR_{10}$, —C(=O)$R_8$, —$CO_2R_8$, —S(O)$_2NR_8R_{10}$, —C(=O)N($R_8$)O($R_9$), —C(=O)$NR_8R_9$, and —OC(=O)$R_{10}$; or one group $R_6$ forms a heterocyclo with $R_3$ and each other $R_6$ is selected from hydrogen, alkyl, substituted alkyl, alkenyl, substituted alkenyl, alkynyl, substituted alkynyl, aryl, cycloalkyl, substituted aryl, heterocyclo, hydroxy, alkoxy, amino, aminoalkyl, cyano, halogen, alkylamide, nitro, $NR_8C(=O)R_9$, $S(O)_uR_{10}$, —C(=O)$R_8$, —$CO_2R_8$, —S(O)$_2NR_8R_{10}$, —C(=O)N($R_8$)O($R_9$), —C(=O)$NR_8R_9$, and —OC(=O)$R_{10}$;

$R_8$ and $R_9$ at each occurrence independent of each other are selected from hydrogen, alkyl, substituted alkyl, heterocycloalkyl, alkenyl, substituted alkenyl, alkynyl, substituted alkynyl, cycloalkyl, aryl, and heterocyclo; or $R_8$ and $R_9$ taken together form a three-to-eight membered heterocyclo; or $R_8$ together with $R_{10}$ forms a three-to-eight membered heterocyclo; and $R_{10}$ is selected from alkyl, substituted alkyl, heterocycloalkyl, alkenyl, substituted alkenyl, alkynyl, and substituted alkynyl, and u is 0, 1, 2 or 3.

Included within compounds of formula (III) are compounds comprising bicyclic ringed systems having formula (IIIa):

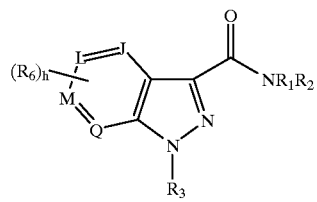

(IIIa)

wherein J, L, M and Q are carbon or nitrogen provided that only one of J, L, M and Q is nitrogen; $R_1$, $R_2$, $R_8$, $R_9$, and $R_{10}$ are as defined above for compounds of formula (III); $R_3$ is hydrogen, alkyl, substituted alkyl, heterocycloalkyl, alkenyl, substituted alkenyl, alkynyl, substituted alkynyl, aryl, heterocyclo, or alkoxy; $R_6$ at each occurrence is selected independently of each other $R_6$ from hydrogen, alkyl, substituted alkyl, alkenyl, substituted alkenyl, alkynyl, substituted alkynyl, aryl, cycloalkyl, substituted aryl, heterocyclo, hydroxy, alkoxy, amino, aminoalkyl, cyano, halogen, alkylamide, nitro, $NR_8C(=O)R_9$, $S(O)_uR_{10}$, —C(=O)$R_8$, —$CO_2R_8$, —S(O)$_2NR_8R_{10}$, —C(=O)N($R_8$)O($R_9$), —C(=O)$NR_8R_9$, and —OC(=O)$R_{10}$; and h is 3 or 4.

Advantageously, in compounds of formula (IIIa), J, L, M, and Q are carbon. In compounds of formula (III) and (IIIa), when $R_1$ and $R_2$ together form a heterocyclo ring, advantageously said ring is unsaturated or is selected from optionally-substituted 1,2,3,4-tetrahydroquinoline, triazaspirodecane, morpholine, piperidine, pyrrolidine, and diazapine; when $R_1$ and $R_2$ independently comprise heterocyclo, said heterocyclo has as its heteroatom or heteroatoms either (i) sulfur or, (ii) at least one of nitrogen and oxygen; and two $R_6$ groups are not simultaneously selected from amino and amino alkyl. Preferably, $R_1$ is substituted alkyl, and $R_2$ is hydrogen or $C_{1-3}$alkyl; $R_3$ is morpholinyl $C_{1-3}$alkyl; $R_5$ and $R_{15}$ are hydrogen, halogen, methoxy, or lower alkyl; and each $R_6$ is selected from hydrogen, alkoxy, lower alkyl, or halogen.

Also included within compounds of formula (III) are compounds comprising bicyclic ringed systems having formula (IIIb):

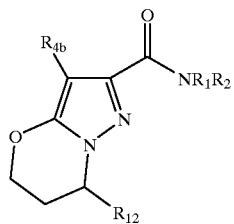

(IIIb)

wherein $R_1$, $R_2$, $R_{4b}$, $R_8$, $R_9$, and $R_{10}$ are as defined above for compounds of formula (III); and $R_{12}$ is selected from hydrogen, alkyl, substituted alkyl, heterocycloalkyl, alkenyl, substituted alkenyl, alkynyl, substituted alkynyl, aryl, cycloalkyl, substituted aryl, heterocyclo, hydroxy, alkoxy, amino, aminoalkyl, cyano, halogen, alkylamide, nitro, $NR_8C(=O)R_9$, $S(O)_uR_{10}$, $-C(=O)R_8$, $-CO_2R_8$, $-S(O)_2NR_8R_{10}$, $-C(=O)N(R_8)O(R_9)$, $-C(=O)NR_8R_9$, and $-OC(=O)R_{10}$. Preferably, $R_{12}$ is $(CH_2)_n-Z$, wherein Z is $CH_3$, $CO_2H$, amino, aminoalkyl, alkylamide, alkoxy, aryl, cycloalkyl, or heterocyclo (preferably morpholinyl), and n is 1 or 2.

Imidazole-Based Compounds

Also included within compounds of formula (I) are imidazole-based compounds having formula (IV), or pharmaceutically-acceptable salts thereof:

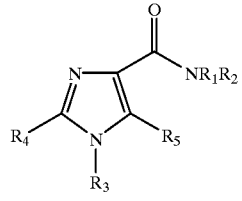

(IV)

in which
$R_1$ and $R_2$ are independently selected from hydrogen, alkyl, substituted alkyl, heterocycloalkyl, aryl, cycloalkyl, and heterocyclo; or taken together form a heterocyclo;
$R_3$ is hydrogen, alkyl, substituted alkyl, heterocycloalkyl, alkenyl, substituted alkenyl, alkynyl, substituted alkynyl, cycloalkyl, aryl, or heterocyclo;
$R_4$ is hydrogen, alkyl, substituted alkyl, heterocycloalkyl, alkenyl, substituted alkenyl, alkynyl, substituted alkynyl, aryl, heterocyclo, hydroxy, alkoxy, amino, aminoalkyl, cyano, halogen, alkylamide, $NR_8C(=O)R_9$, or $S(O)_uR_{10}$;
$R_5$ is hydrogen, alkyl, substituted alkyl, heterocycloalkyl, alkenyl, substituted alkenyl, alkynyl, substituted alkynyl, alkoxy, aryl, or heteroaryl; and
$R_{10}$ is alkyl, substituted alkyl, heterocycloalkyl, alkenyl, substituted alkenyl, alkynyl, or substituted alkynyl, and u is 0, 1, 2 or 3.

In compounds of formula (IV), advantageously $R_1$ is substituted alkyl (more preferably $CHR_{17}R_{18}$, as defined herein); $R_2$ is hydrogen or $C_{1-3}$alkyl; $R_3$ is $-(CH_2)_n-Z$, wherein Z is $CH_3$, $CO_2H$, amino, aminoalkyl, alkylamide, alkoxy, aryl, cycloalkyl, or heterocyclo (preferably morpholinyl), and n is 1 or 2; and $R_4$ and $R_5$ are hydrogen, halogen, methoxy, or lower alkyl.

When reference is made herein to compounds of formula (I), such reference includes compounds of formulae (II), (III) and (IV). Compounds of formula (I) include salts, prodrugs and solvates. The term "salt(s)" as employed herein denotes acidic and/or basic salts formed with inorganic and/or organic acids and bases. Zwitterions (internal or inner salts) are included within the term "salt(s)" as used herein and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are contemplated as within the scope of the invention as they may be useful, for example, in isolation or purification steps employed during preparation. Salts of the compounds of the formula (I) may be formed, for example, by reacting a compound of formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula (I), or a salt and/or solvate thereof. Solvates of the compounds of formula (I) are preferably hydrates.

All stereoisomers of the present compounds, such as those which may exist due to asymmetric carbons on the R substituents of the compound of formula (I), including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

According to the invention, cannabinoid receptor modulators, including compounds of formula (I), are typically employed as part of a pharmaceutical composition including a pharmaceutically-acceptable carrier for treating respiratory and/or non-respiratory diseases. The pharmaceutical compositions comprising at least one cannabinoid receptor modulator for treating respiratory disease and/or comprising compounds of formula (I), may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The cannabinoid receptor modulators for treating respiratory disease and/or compounds of formula (I) may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally, such as by inhalation spray; topically, such as in the form of a cream or ointment; or rectally, such as in the form of suppositories; and in dosage unit formulations containing non-toxic, pharmaceutically-acceptable vehicles or diluents. The cannabinoid receptor modulators may, for example, be administered in a form suitable for immediate release or extended release. Immediate release or extended release may be achieved by the use of suitable pharmaceutical compositions comprising the cannabinoid receptor modulators, or, particularly in the case of extended release, by the use of devices such as subcutaneous implants or osmotic pumps. The cannabinoid receptor modulators may also be administered in the form of liposomes.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The cannabinoid receptor modulators, including those for treating respiratory disease and/or compounds of formula (I), may also be delivered through the oral cavity by sublingual and/or buccal administration. Molded tablets, compressed tablets or freeze-dried tablets are exemplary forms which may be used. Exemplary compositions include those formulating the cannabinoid receptor modulators with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound employed in the present invention may be determined by one of ordinary skill in the art, and includes exemplary dosage amounts for an adult human of from about 0.1 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to inflammatory, immunological, or respiratory cell-associated diseases and disorders.

Preferred Compounds

Particularly preferred compounds of the invention are compounds of formula (I) represented by the following structures:

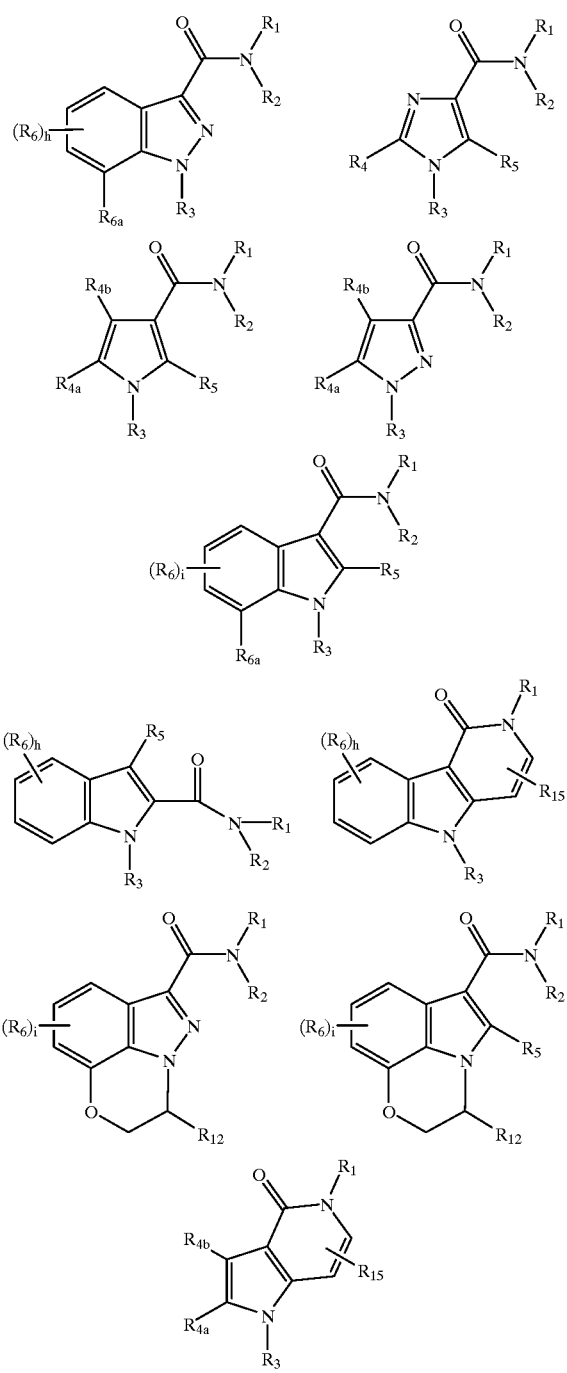

wherein:

R₁ and R₂ are independently selected from hydrogen, alkyl substituted alkyl heterocycloalkyl, cycloalkyl, aryl, or heterocyclo having at its heteroatom or heteratoms either sulfur or at least one of nitrogen and oxygen; or taken together form a heterocyclo that is unsaturated or selected from optionally-substituted 1,2,3,4-tetrahydroquinoline, triazaspirodecane, morpholine, piperidine, pyrrolidine, and diazapine;

$R_3$ and $R_{12}$ are —$(CH_2)_n$—Z or —O—$(CH_2)_n$—Z;

$R_4$, $R_{4a}$, $R_{4b}$ and $R_6$ at each occurrence are selected from hydrogen, halogen, $C_{1-6}$alkyl, cyano, nitro, hydroxy, alkoxy, and phenyl;

$R_5$ is hydrogen, methyl, or ethyl;

$R_{6a}$ is hydrogen or $OR_8$, wherein $R_8$ is hydrogen, $C_{1-6}$alkyl, aryl, or arylalkyl;

$R_{15}$ is hydrogen, halogen, or alkyl;

Z is $CH_3$, $CO_2H$, amino, aminoalkyl, alkylamide, alkoxy, heterocyclo, aryl, or cycloalkyl, h is 4;

i is 3; and n is 1 or 2.

More preferred compounds are those represented by the above-referenced structures, wherein R₁ is substituted alkyl or forms a heterocyclo with R₂ that is unsaturated or selected from optionally-substituted 1,2,3,4-tetrahydroquinoline, triazaspirodecane, morpholine, piperidine, pyrrolidine, and diazapine;

R₂ is hydrogen, methyl, ethyl, or propyl, or forms a heterocyclo with R₁ that is unsaturated or selected from optionally-substituted 1,2,3,4-tetrahydroquinoline, triazaspirodecane, morpholine, piperidine, pyrrolidine, and diazapine;

$R_3$ and $R_{12}$ are —$(CH_2)_n$—Z;

$R_4$, $R_{4a}$, $R_{4b}$ and $R_6$ at each occurrence are selected from hydrogen, halogen, $C_{1-4}$alkyl, hydroxy, and alkoxy;

$R_5$ is hydrogen or methyl;

$R_{6a}$ is hydrogen or $OR_8$, wherein $R_8$ is hydrogen, $C_{1-6}$alkyl, aryl, or arylalkyl;

$R_{15}$ is hydrogen, halogen, or $C_{1-2}$alkyl;

Z is heterocyclo;

n is 1 or 2;

h is 4; and i is 3.

Further preferred compounds are those represented by the above-preferred structures, wherein $R_1$ is —$CHR_{17}R_{18}$;

$R_2$ is hydrogen or methyl;

$R_3$ and $R_{12}$ are $(CH_2)_n$-morpholinyl;

$R_4$, $R_{4a}$, $R_{4b}$ and $R_6$ at each occurrence are selected from hydrogen, $C_{1-4}$alkyl, hydroxy, and alkoxy;

$R_5$ is hydrogen or methyl;

$R_{6a}$ is hydrogen or $OR_8$, wherein $R_8$ is hydrogen, $C_{1-5}$alkyl, phenyl, or benzyl;

$R_{15}$ is hydrogen, halogen, or $C_{1-4}$alkyl;

$R_{17}$ and $R_{18}$ are (i) selected independently from hydrogen and —$(CH_2)_s$—$(CR_{21}R_{22})_v$—$(CH_2)_t$—W; or (ii) $R_{17}$ and $R_{18}$ together form cycloalkyl, aryl, or heterocyclo having as its heteroatom or heteroatoms sulfur or at least one of oxygen and nitrogen;

W at each occurrence is selected independently from $CH_3$, alkylamide, aminoalkyl, alkylthio, alkoxy, hydroxy, cyano, —$CO_2R_{19}$, —$C(=O)R_{19}$, —$C(=O)N(R_{19})O(R_{20})$, —$NR_{19}(C=O)R_{20}$, aryl, cycloalkyl, and heterocyclo having as its heteroatom or heteroatoms sulfur or at least one of oxygen and nitrogen;

$R_{19}$ and $R_{20}$ are selected from hydrogen, alkyl, substituted alkyl, heterocycloalkyl, alkenyl, substituted alkenyl, alkynyl, substituted alkynyl, cycloalkyl, aryl, and heterocyclo;

$R_{21}$ and $R_{22}$ are hydrogen, alkyl, hydroxy, or hydroxyalkyl;

h is 4;

i is 3;

n is 1 or 2;

s and t are 0, 1 or 2; and v is 0 or 1.

Also preferred are compounds as immediately defined above where $R_{17}$ and $R_{18}$ are (i) —$(CH_2)_s$—W, wherein W at each occurrence is selected from —$CH_3$, $C_{1-4}$alkylthio, $C_{1-4}$alkoxy, hydroxy, —$CO_2H$, —$CO_2C_{1-4}$alkyl, —C(=O)N$(C_{1-4}$alkyl$)_2$, —C(=O)NH($C_{1-4}$alkyl), —C(=O)NH(cycloalkyl), —C(=O)H, —C(=O)$NH_2$, —C(=O)$C_{1-4}$alkyl, —C(=O)N($C_{1-4}$alkyl)O($C_{1-4}$alkyl), —NH(C=O)$C_{1-4}$alkyl, —N($C_{1-4}$alkyl)(aryl), —NH(C=O)aryl, phenyl, imidazole, biphenyl, pyridine, pyrrolidine, thiophene, pyrazole, imidazole, tetrazole, oxazole, oxadiazole, and napthyl, wherein said group W is optionally substituted with one to four groups selected from $C_{1-4}$alkyl, hydroxy, halogen, $C_{1-4}$alkoxy, trifluoromethyl, amino, acetylamino, heterocyclo, benzyl, or aryl; or (ii) taken together form a three-to-eight membered cycloalkyl or bicycloalkyl optionally substituted with one to four groups selected from $C_{1-4}$alkyl, $C_{1-4}$alkoxy, aryl, cycloalkyl, and heterocyclo.

Methods of Preparation

Compounds of formula (I), cannabinoid receptor modulators illustrated in the Examples hereinafter, and intermediates for use in preparing the compounds of formula (I), may be prepared using the methods illustrated in the following Schemes A through N. Schemes A and B and G through J show schemes for preparing compounds of formula (I); schemes C through F show methods for preparing compounds useful as cannabinoid receptor modulators and as intermediates in preparing compounds of formula (I); schemes K through M describe in more detail inventive processes claimed herein for preparing compounds of formula (I); and scheme N illustrates a general procedure for Pd catalyzed indole cyclizations useful in preparing compounds of formula (I). For all of the schemes and compounds, the groups A, B, J, L, M, Q, $R_1$–$R_6$, $R_{15}$, and $R_{16}$, are as described above for a compound of formula I, unless otherwise indicated. Suitable selections may be made by one skilled in the field of appropriate groups for each of the groups X, R*, R', R", $R_a$, $R_b$, or other groups generally referenced in these schemes. Solvents, temperatures, pressures, and other reaction conditions also may readily be selected by one of ordinary skill in the art. All documents cited are incorporated herein by reference in their entirety, and abbreviations that appear hereinafter are used in these schemes for ease of reference. Starting materials are commercially available or can be readily prepared by one of ordinary skill in the art.

The methods described herein may be carried out with starting materials and/or reagents in solution or alternatively, where appropriate, with one or more starting materials or reagents bound to a solid support {see (1) Thompson, L. A. and Ellman, J. A., *Chemical Reviews*, 96, pp. 555–600 (1996); (2) Terrett, N. K., et al, *Tetrahedron*, 51, pp. 8135–8173 (1995); (3) Gallop, M. A. et al, *Journal of Medicinal Chemistry*, 37, 1233–1251 (1994); (4) Gordon, E. M. et al, *Journal of Medicinal Chemistry*, 37, pp. 1385–1401 (1994); (5) Balkenhohl, F., et al, *Angewandte Chemie International Edition in English*, 35, pp. 2288–2337 (1996); (6) Balkenhohl, F. et al, *Angewandte Chemie*, 108, pp. 2436–2487 (1996); and (7) Sofia, M. J., *Drugs Discovery Today*, 1, pp. 27–34 (1996)}.

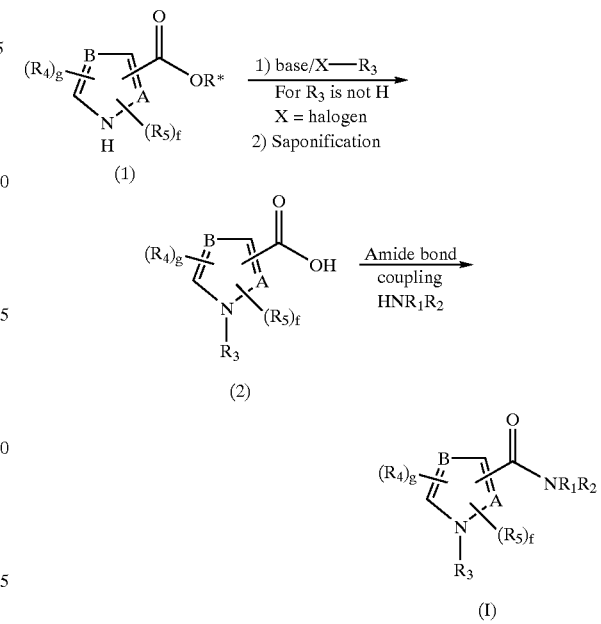

Scheme A

Starting compound (1), wherein A and B are nitrogen or carbon and R* is a carboxyl protecting group such as alkyl or arylalkyl, can be treated with a base and an alkylating agent. Exemplary bases include LDA, $K_2CO_3$, sodium hydride, and sodium/potassium hexamethyldisilazide, and exemplary alkylating agents include $R_3X$ where X is a leaving group, such as a halogen or a triflate, and $R_3$ is preferably alkyl, arylalkyl, cycloalkylalkyl, or heterocycloalkyl. Saponification with an aqueous base such as LiOH then gives compound (2).

Compound (2) may be reacted with an amine using reaction conditions well known in the art for peptide bond synthesis {see, for example, Bodanszky and Bodanszky, *The Practice of Peptide Chemistry*, Springer-Verlag (1984); Bodanszky, *Principles of Peptide Synthesis*, Springer-Verlag (1984)} to give a compound of formula (I). Exemplary reagents for activating the carboxyl group of compound (2) for reacting with the amine include BOP chloride, BOP reagent, HATU, carbodiimides such as DCC and EDC, either alone or in combination with a hydroxybenzotriazole.

Alternatively, compound (1) can be isolated and then treated with an appropriate amine in a nonprotic solvent such as THF or DMF in the presence of base, for example, an organic base such as TEA, DIPEA, DBU, or sodium/potassium hexamethyldisilazide, or an inorganic base such as sodium, potassium or cesium carbonate or sodium or potassium hydride.

Alternatively, compound (2) may be prepared, for example, by reaction with thionyl chloride or oxalyl chloride, followed by subsequent reaction with an amine to provide a compound of formula (I).

Compound (1) is commercially available or may be readily prepared by one skilled in the field, or where A and B are carbon may be prepared as described below in Scheme J.

Scheme B
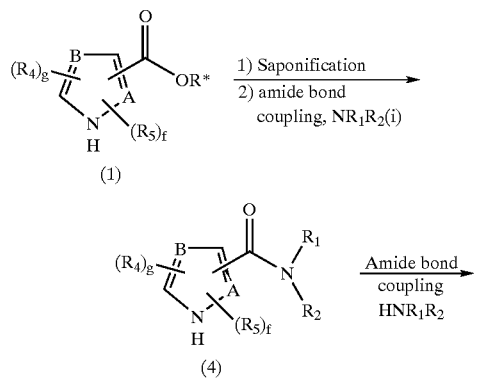
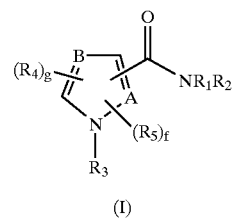
Starting compound (1) can be saponified followed by treatment with an amine under standard amide bond forming conditions (described above in Scheme A) to give compound (4). Treatment of compound (4) with a suitable base and an alkylating agent $R_3X$ (as described above for Scheme A) gives a compound of formula (I).
Scheme C
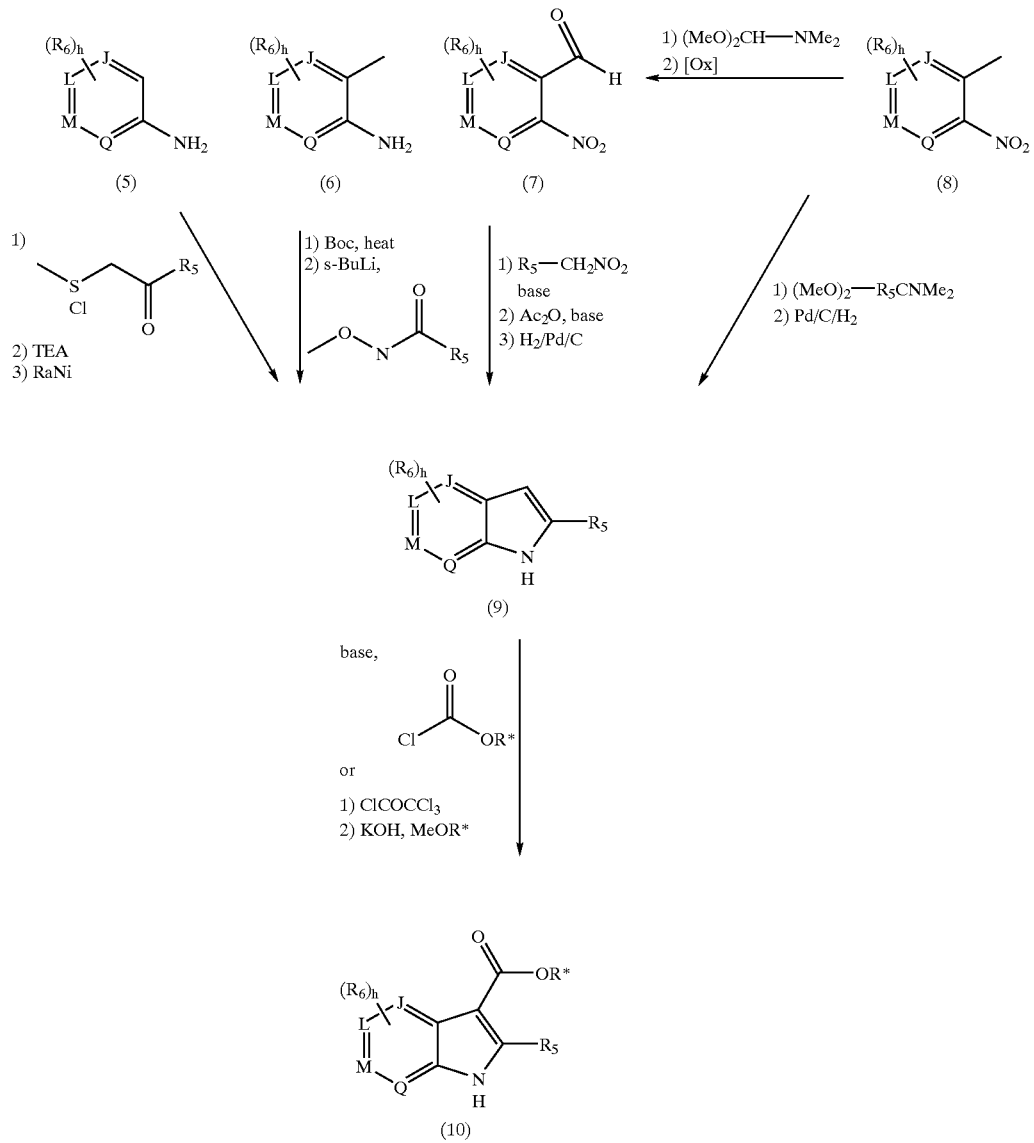

Schemes C and D set forth methods for preparing pyrrole-based fused heterocylic compounds (10) which may be used as starting materials (1) in Schemes A and B, i.e. where two $R_4$ groups form a fused ring. These compounds (10) may be used to form compounds of formula (I). Alternatively, compounds of formula (10) may be used in Scheme H, below, to form compounds of formula (Ib) or (Ic).

Compound (9) can be prepared alternatively from compounds (5), (6), (7) or (8) as follows:

(i) from compound (5) by treatment with beta ketochlorosulfides and a base such as TEA followed by desulfurization using raney nickel (Gassman et al. *Journal of the American Chemical Society*, Vol. 96, pp. 5512–5517 (1974);

(ii) from compound (6) by treatment with an aniline protecting group such as Boc followed by treatment with an organolithium such as sec-BuLi and an o-methyl hydroxamate;

(iii) from compound (7) by treatment with a nitroalkane followed by acetylation and hydrogenation; or (iv) from compound (8) by treatment with an alkylamide dimethyl acetal (such as N,N-dimethyl acetamide dimethyl acetal) followed by hydrogenation.

Compound (9) can be converted to compound (10) by treatment with a base such as methyl magnesium bromide and an alkyl chloroformate such as ethyl chloroformate.

Alternatively, compound (9) can be converted to compound (10) by treatment with trichloromethyl acid chloride and base such as collidine followed by conversion to an alkyl ester with an alkoxide (such as KOH) and an alcohol (such as MeOH).

Scheme D

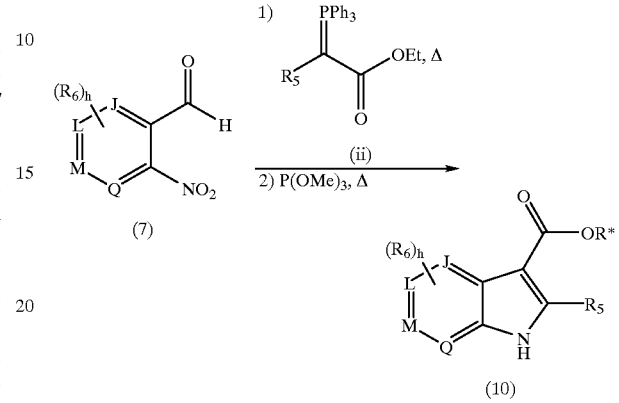

As an alternative to scheme C, compound (10) can be prepared directly from compound (7) by treatment with a Wittig reagent such as (ii) followed by reduction/cyclization.

Scheme E

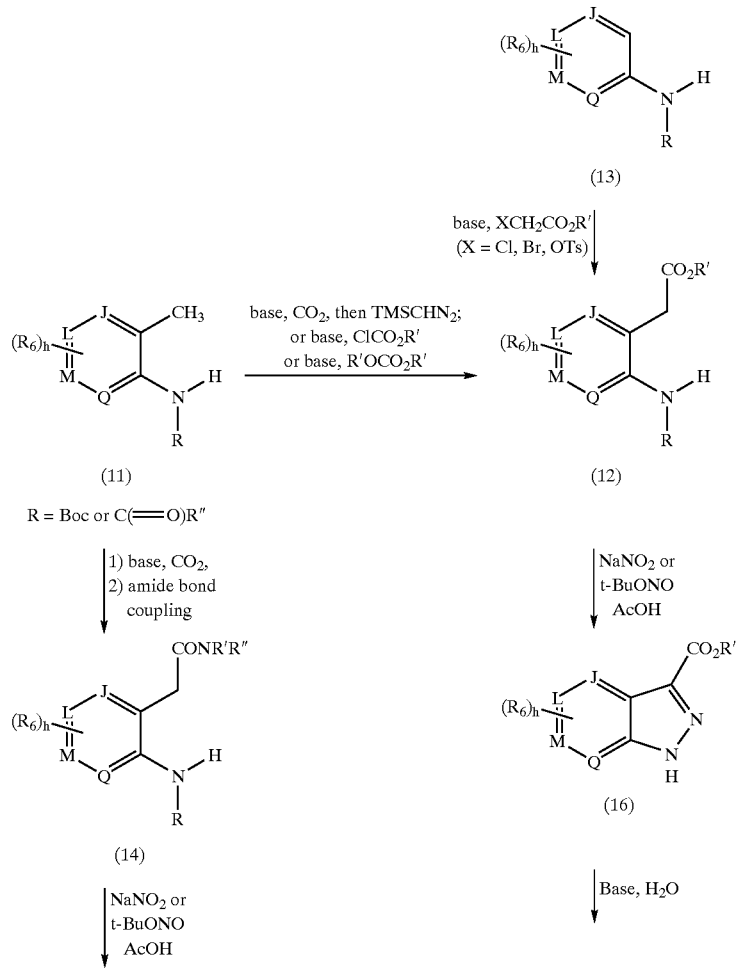

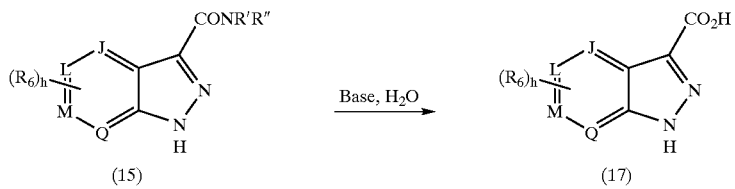

Schemes E and F describe methods for preparing pyrazole-based compounds (17), which may used to make compounds of formula (I) in accordance with the methods of Schemes A and B.

Compound (17) can be prepared from compound (11) or compound (12), e.g., via base-catalyzed hydrolysis of either compound (15) or compound (16).

Compound (11) can be converted to compound (14) via a one-carbon extension sequence (e.g., carboxylation with base and a suitable agent followed by an amide bond coupling). Compound (14) can be converted to compound (15) upon treatment with a nitroso agent, such as sodium nitrite or tert-butyl nitrite. Compound 12 can be converted to compound (16) under the same conditions.

Compound (12) can be prepared from compound (11) or compound (13), i.e., from compound (11) via a one-carbon extension sequence (carboxylation with base and a suitable agent) or from compound (13) via a two-carbon extension sequence (alkylation with base and a suitable agent).

Scheme F

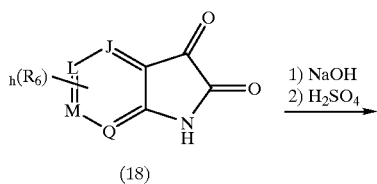

-continued

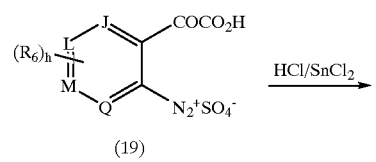

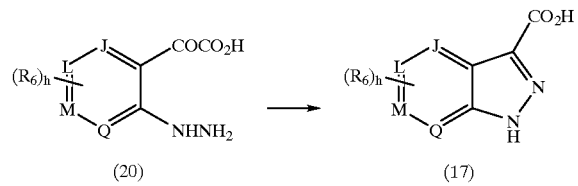

Alternatively to Scheme E, compound (17) can be prepared from compound (18) as shown in Scheme F, i.e., by conversion of compound (18) to compound (19) via base-catalyzed ring opening followed by diazotization, reduction of compound (19) to compound (20), and ring closure of compound (20) to give compound (17).

Scheme G

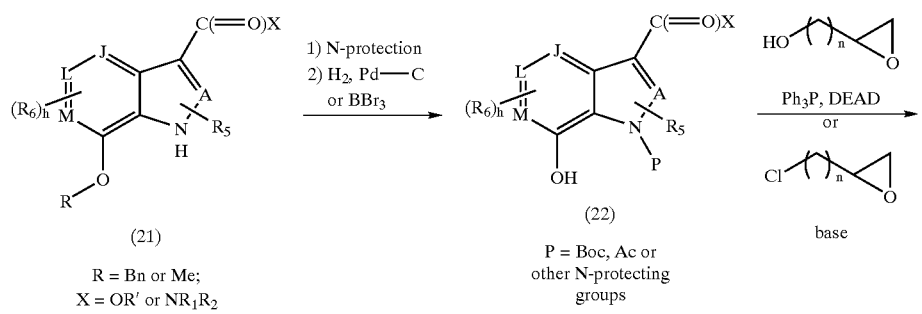

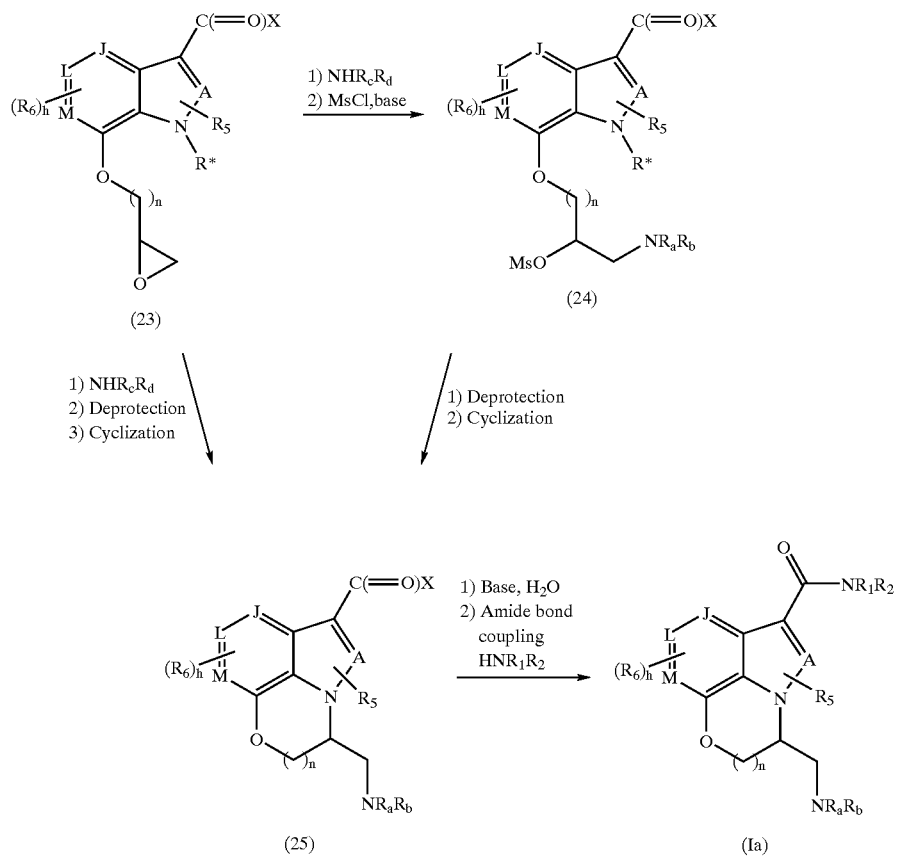

Compounds of formula (Ia) wherein A is nitrogen or carbon can be prepared from compound (21) as shown in Scheme G. Compound (21) can be N-protected and unmasked (removal of O-benzyl or O-methyl) to give compound (22). O-alkylation of compound (22) gives compound (23).

Compound (23) can be converted to compound (25) directly via a three-step sequence: a) reaction with a suitable amine; b) removal of N-protecting group; and c) cyclization under Mitsunobu conditions. "Mitsunobu conditions" are known in the field and defined in Oyo Mitsunobu, *"The Use of Diethyl Azodicarboxylate and Triphenylphosphine in Synthesis and Transformation of Natural Products"*, Synthesis (1981), pp 1–28, which is incorporated herein by reference. Alternatively, compound (23) can be converted to compound (25) via compound (24), i.e., treatment of compound (23) with a suitable amine followed by mesylation of alcohol moiety gives compound (24), and removal of the N-protecting group of compound (24) followed by ring closure gives compound (25).

Base-catalyzed hydrolysis of compound (25) followed by an amide bond coupling reaction with a suitable amine provides compound of formula (Ia).

Scheme H

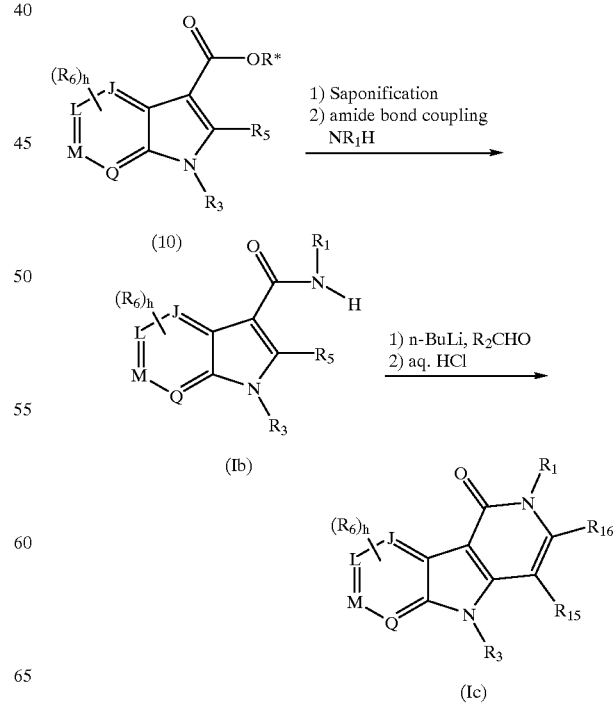

Scheme H describes the preparation of compounds of formula (Ic) starting with compounds of formula (10) (see Scheme C), and the methods of Schemes A and B. Compound (10) can be saponified followed by treatment with an amine under standard amide bond forming conditions (described in Scheme A) to give a compound (Ib), also a compound of formula (I). Compound (Ic) can be prepared from compound (Ib) by treatment with an organolithium (such as n-BuLi) followed by an aldehyde derivative $R_2CHO$, followed by treatment with an aqueous acid such as HCl (see, e.g., Clark, R. D. et al, *Journal of Medicinal Chemistry,* Vol. 36 (1993), pp. 2645–2657) ("Clark").

Scheme I

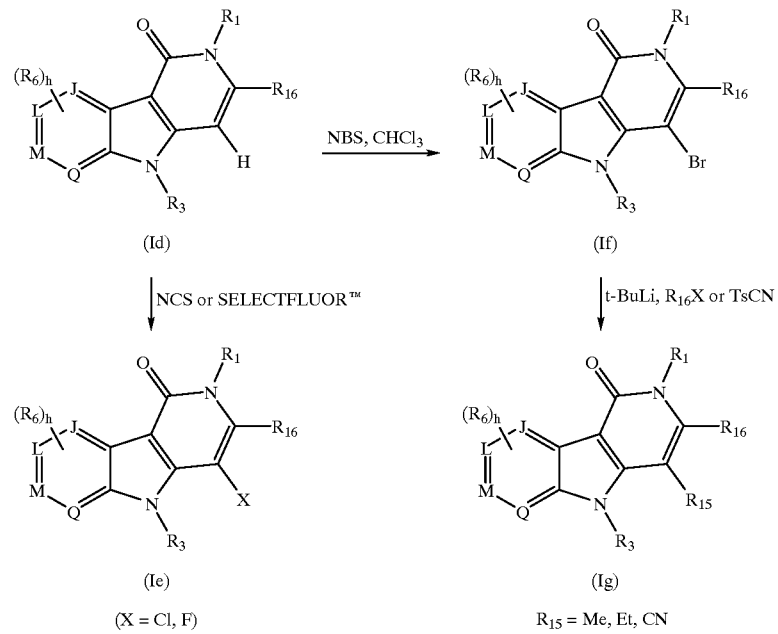

(X = Cl, F)   $R_{15}$ = Me, Et, CN

Scheme I illustrates methods for preparing compounds of formulae (Ie), (If), and (Ig) from compound (Id). Compound (Ie) can be prepared from compound (Id) by treatment with NCS or SELECTFLUOR™. Compound (If) can be prepared from compound (Id) by treatment with NBS. Compound (Ig) can be prepared from compound (If) by treatment with an organolithium (such as t-BuLi) followed by treatment with an alkyl halide $R_{16}X$ or tosyl cyanide (TsCN).

Compound (Id) can be prepared from Scheme H, wherein $R_{15}$ is hydrogen.

Scheme J

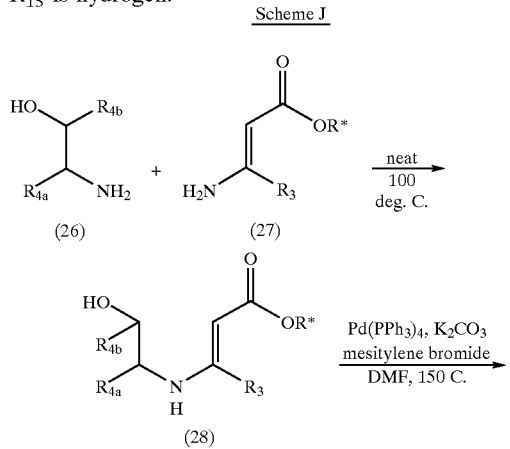

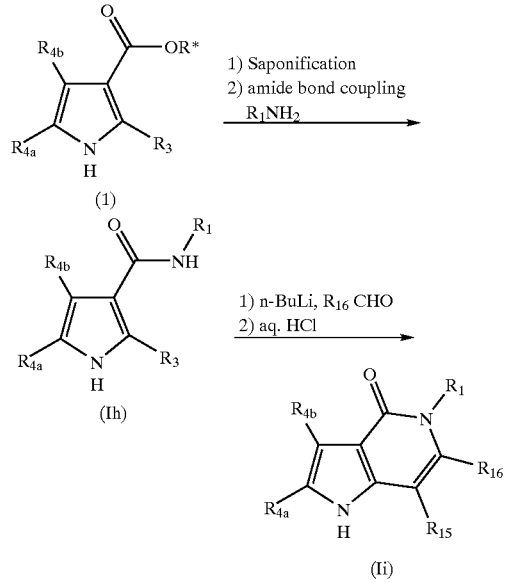

Scheme J describes the formulation of compounds of formula (Ih) and (Ii). Compound (28) can be prepared by heating a mixture compound (26) and (27). Compound (1) can be prepared from compound (28) by treatment with a palladium catalyst such as Pd(PPh$_3$)$_4$, an inorganic base such as K$_2$CO$_3$, and an aryl halide such as mesitylene bromide {see, e.g., Aoyagi, et al. *Tetrahedron Letters*, 37, 9203–9206 (1996)}. Compound (1) can be saponified followed by treatment with an amine under standard amide bond forming conditions (described above in Scheme A) to give a compound of formula (Ih). Compound of formula (Ii) can be prepared from compound (Ih) by treatment with an organolithium (such as n-butyllithium) followed by an aldehyde derivative R$_5$CHO followed by treatment with an aqueous acid such as HCl (see, e.g Clark, cited above in Scheme H).

Scheme K describes an inventive process for making compounds of formula (Ij). Compound (7a) may be produced by reacting compound (7) (see Scheme C) with a nitro alkyl under appropriate conditions such as in the presence of a halide salt (e.g. potassium fluoride) and a crown ether (e.g. 18-crown-6).

Compound (7a) can be converted to a leaving group such as with acetic anhydride in sodium acetate and a fluoride-containing agent such as KF in the presence of 18-crown-6 to give a compound (7b).

Compound (7b) can be reduced under standard hydrogenation conditions (e.g. H$_2$/Pd/C) in a suitable solvent such as EtOH/AcOH/EtOAc to provide compound (9).

Compound (9) can be treated with R$_3$-halide in the presence of a base such as NaOH and a suitable solvent such as DMSO to form a compound of formula (29).

Compound (29) can be treated with trihaloacetyl halide (e.g. where the halide is chloride) to give compound (30). In the case where R$_3$ does not comprise a basic substituent, a suitable base such as collidine and a suitable solvent such as DCE are necessary to give compound (30). In the case where R$_3$ contains a basic substituent, addition of an external base such as collidine is not needed.

Compound (30) can be treated with an appropriate amine in the presence of a suitable base to form amides of formula (Ij). Alternatively, compound (30) can be hydrolyzed to the carboxylate using a base such as NaOH followed by standard amide bond coupling methods known in the art to form compounds of formula (Ij).

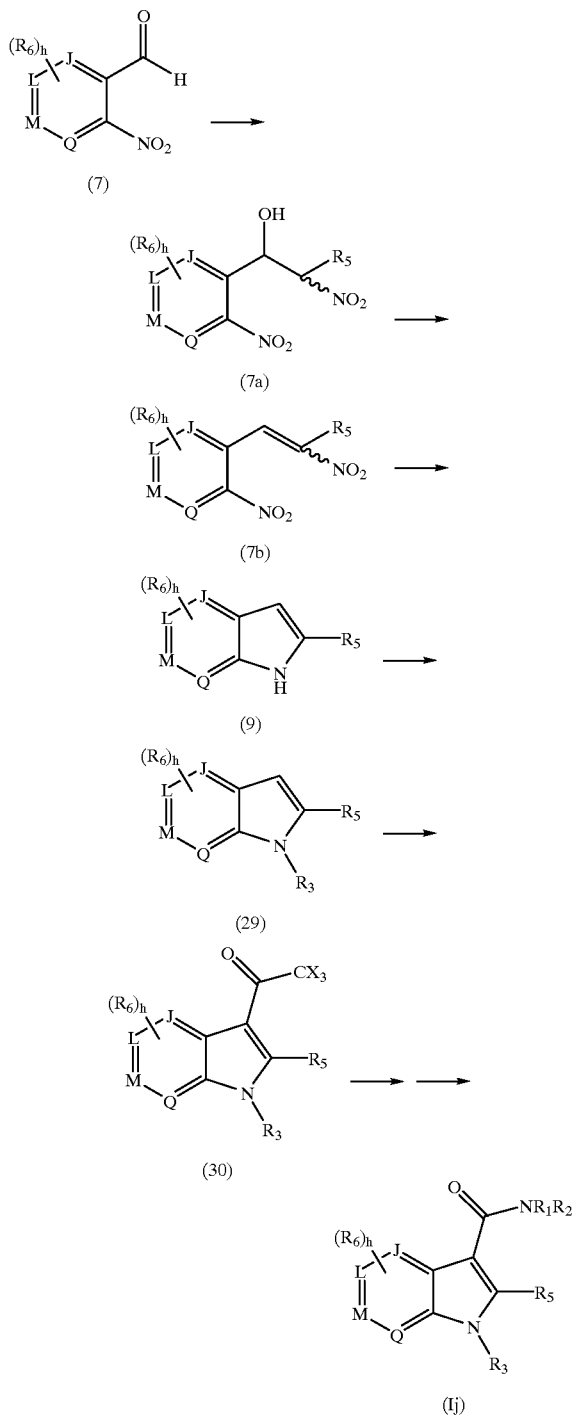

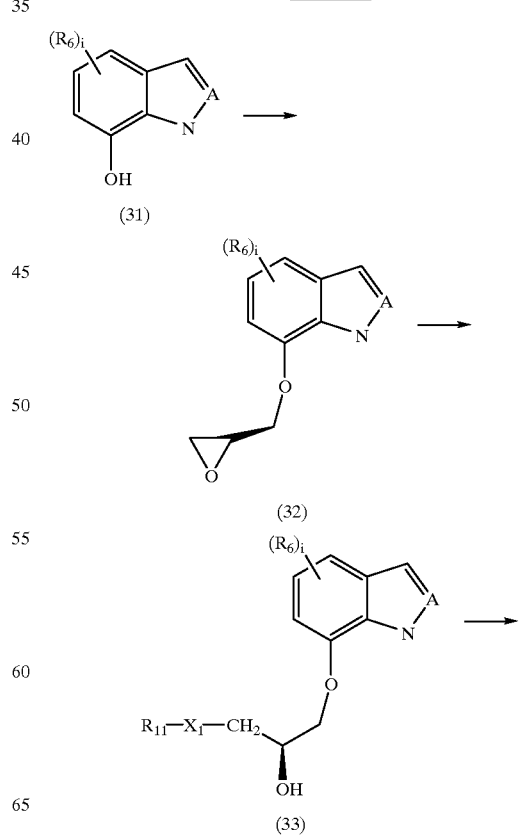

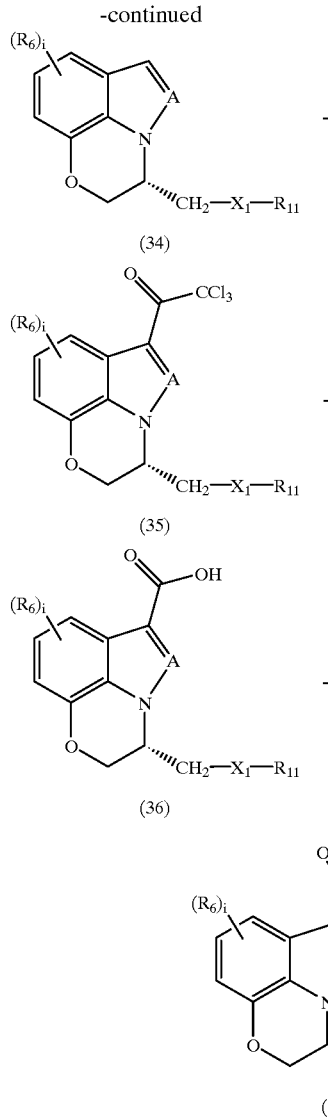

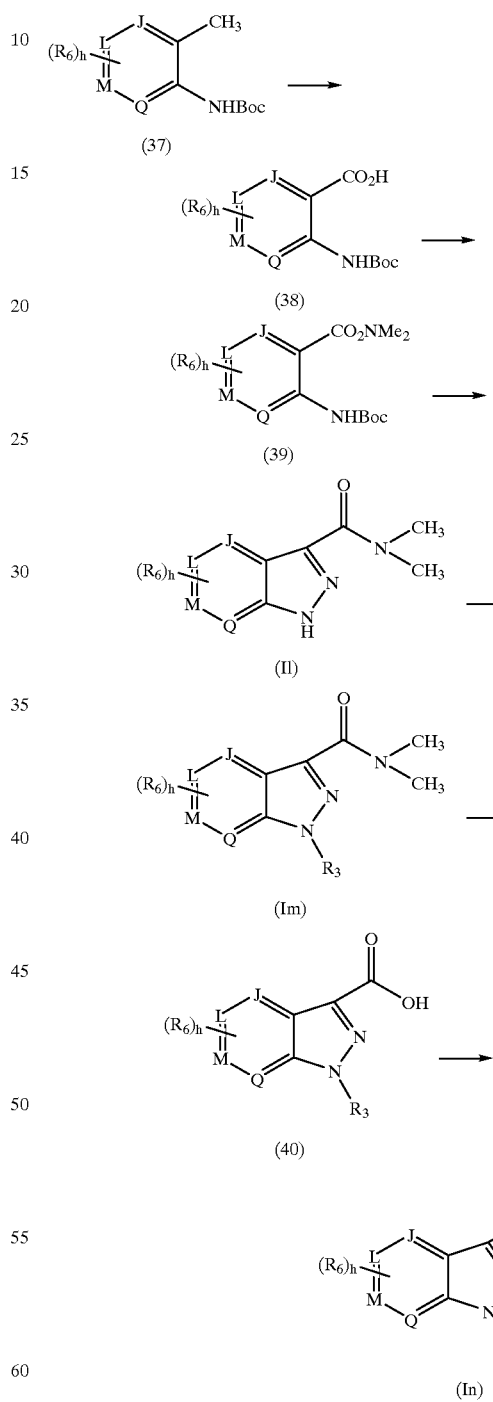

Compound (35) can be hydrolyzed under basic conditions to give compound (36). Compound (36) can be coupled to an amine using standard amide bond coupling techniques (EDC/HOBT or acid chloride) to give compounds of formula (Ik).

Scheme L shows an inventive process for preparing compounds of formula (Ik), wherein A is nitrogen or $CR_5$ as defined herein.

The process comprises subjecting a compound (31) to alkylation {e.g. with (R)-(+)-glycidol under standard Mitsunobu conditions (DEAD, $Ph_3P$)} to give compound (32). Alternatively, compound (31) can be reacted with (R)-(−)-epichalohydrin in base to give compound (32).

Compound (32) undergoes ring opening in the presence of a nucleophile $R_{11}$—$X_1$ (or $R_{11}$—$X_1$—H where H is hydrogen) wherein $R_{11}$ is selected from alkylene, substituted alkylene, alkenylene, substituted alkenylene, cycloalkyl, aryl, and heterocyclo, and $X_1$ (or $X_1$—H) is any nucleophile which can ring open an epoxide including, but not limited to alcohols, amines, thiols, azides and carbon nucleophiles to give compound (33).

Compound (33) can undergo cyclization under Mitsunobu conditions (DEAD, $PPh_3$) to give compound (34). Alternatively, compound (33) can be treated with a sulfonyl halide to provide a sulfonate which can cyclize to form compound (34).

Compound (34) can be treated with trihaloacetyl halide (e.g. trichloroacetyl chloride) under elevated temperatures (preferably from about 40 to 120° C.) to give compound (35).

Scheme M shows an inventive process for making compounds of formulae (Il) and (Im).

The process comprises reacting compound (37) with an alkyl lithium and carbon dioxide to form compound (38).

Compound (38) is reacted with a dialkyl amine under standard amide bond conditions (such as EDCI, HOBt) to form compound (39).

Compound (39) is treated with a nitrite such as $NaNO_2$ in aqueous acid (such as acetic acid) at elevated temperatures (preferably from about 50 to 140° C.) to give compound of formula (Il).

Compound of formula (Il) is treated with $R_3$-halide in the presence of a base such as sodium hydride to give a compound of formula (Im), wherein $R_3$ is other than hydrogen.

Compound of formula (Im) is hydrolyzed under aqueous basic conditions to form compound (41).

Compound (41) is coupled to an amine under standard amide bond coupling conditions (e.g. EDC/HOBT or acid chloride) to provide compounds of formula (In).

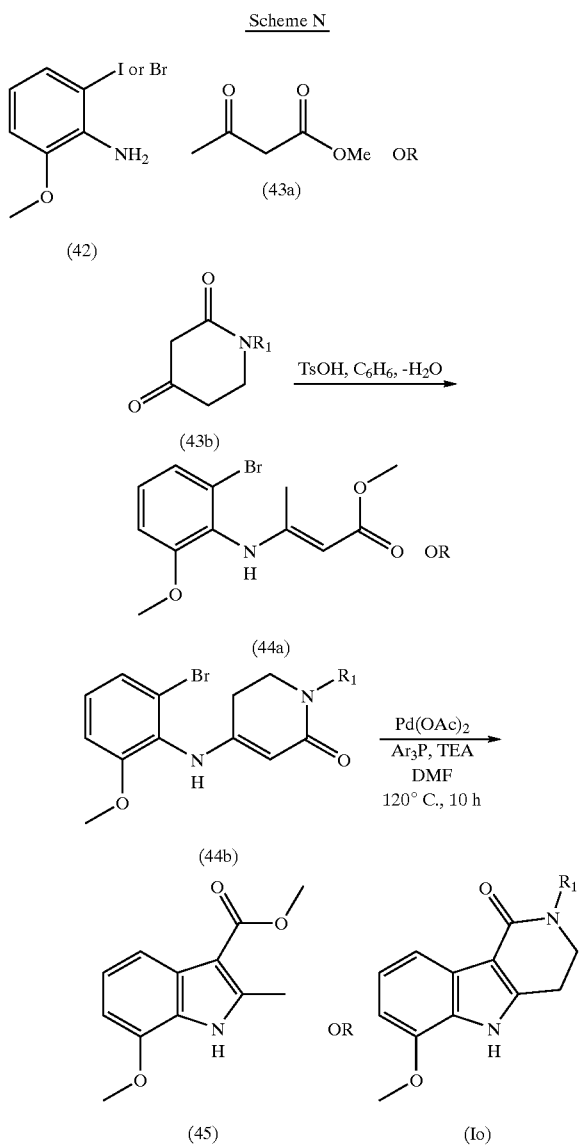

Scheme N shows a general procedure for Pd-catalyzed indole cyclizations that can be used to make compounds of formula (Io) or cannabinoid receptor modulators or intermediates (45) for making compounds of formula (I).

A mixture of ortho-halo aniline (42) and beta-keto ester (43a) or amide (43b) (1.2 equiv) are heated with azeotropic removal of water in the presence of an acid catalyst for 24 h to give enamides (44a) or (44b).

Pd-catalyzed cyclization of enamides (44a) or (44b) is carried out using 10–20 mole % Pd and 21–42 mole % phosphine ligand to give compounds (45) or compounds of formula (Io). Tri-ortho tolyl phosphine is the preferred ligand. Isolation of the indoles can be performed by column chromatography.

Utility

Applicants have discovered that modulators to the cannabinoid receptor are effective for treating respiratory diseases. Respiratory diseases for which cannabinoid receptor modulators are useful include but are not limited to chronic pulmonary obstructive disorder, emphysema, asthma, and bronchitis. Such cannabinoid receptor modulators include each of the compounds described in the examples herein, including compounds of formula (I), as well as those compounds described Examples 1–2, 14–16, and 67–71 herein. Applicants' discovery that cannabinoid receptor modulators are useful for treating respiratory diseases also pertains to cannabinoid receptor modulators previously identified as effective for other uses, such as cannabinoid receptor modulators described in European Patent Documents Nos. EP 0570920 and EP 0444451; International Publications Nos. WO 97/29079, WO 99/02499, WO 98/41519, and WO 9412466; U.S. Pat. Nos. 4,371,720, 5,081,122, 5,292,736, and 5,013,387; and French Patent No. FR 2735774.

Applicants also have discovered a group of novel cannabinoid receptor modulators of formula (I) useful for treating any cannabinoid-receptor mediated diseases, including the respiratory diseases referenced above and non-respiratory diseases. Exemplary non-respiratory cannabinoid receptor-mediated diseases include transplant rejection, rheumatoid arthritis, multiple sclerosis, inflammatory bowel disease, lupus, graft v. host disease, T-cell mediated hypersensitivity disease, psoriasis, Hashimoto's thyroiditis, Guillain-Barre syndrome, cancer, contact dermatitis, allergic rhinitis, and ischemic or reperfusion injury.

The compounds employed in the present invention for treatment of respiratory or non-respiratory diseases stimulate inhibitory pathways in cells, particularly in leukocytes, lung epithelial cells, or both, and are thus useful in treating such diseases. As used with reference to the utilities described herein, the term "treating" or "treatment" encompasses prevention, partial alleviation, or cure of the disease or disorder. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

For example, CB2 receptor modulators are useful in treating a number of diseases mentioned above (for example, the treatment of inflammatory diseases), since CB2 receptor modulators prevent monocyte/macrophage activation and the release of inflammatory cytokines. The treatment of leukocyte-mediated diseases is one particularly preferred embodiment of the present invention through use of the compounds of formula (I). Compounds which selectively inhibit leukocyte activation and proliferation are preferred.

In addition, CB receptor modulators are useful in treating respiratory disorders. Such compounds block the activation of lung epithelial cells by moeties such as allergic agents, inflammatory cytokines or smoke, thereby limiting release of mucin, cytokines, and chemokines. Another preferred embodiment of the present invention comprises use of novel cannabinoid receptor modulator compounds to treat respiratory disease wherein the compounds selectively inhibit lung epithelial cell activation.

The cannabinoid receptor modulators for treating respiratory disease or non-respiratory diseases in accordance with the present invention may be used with other therapeutic agents such as those described below. Such other therapeutic agent(s) may be administered prior to, simultaneously with, or following the administration of the cannabinoid receptor modulators in accordance with the invention.

Exemplary of such other therapeutic agents which may be used in combination with cannabinoid receptor modulators include the following: cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, steroids such as prednisone or dexamethasone, gold compounds, antiproliferative agents such as methotrexate, FK506 (tacrolimus, Prograf), mycophenolate mofetil, cytotoxic drugs such as azathiprine and cyclophosphamide, TNF-α inhibitors such as tenidap, anti-TNF antibodies or soluble TNF receptor such as etanercept (Enbrel), rapamycin (sirolimus or Rapamune), leflunomide (Arava), and cyclooxygenase-2 (COX-2) inhibitors such as celecoxib (Celebrex) and rofecoxib (Vioxx), or derivatives thereof, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., Et Al, "*Cleavable CD40Ig Fusion Proteins and the Binding to Sgp39*", *J. Immunol. Methods* (Netherlands), 188(1), pp. 1–7 (Dec. 15, 1995); Hollenbaugh, D., et al, "*The Human T Cell Antigen Gp39, A Member of the TNF Gene Family, Is a Ligand for the CD40 Receptor: Expression of a Soluble Form of Gp39 with B Cell Co-Stimulatory Activity*", *EMBO J* (England), 11(12), pp. 4313–4321 (December 1992); and Moreland, L. W. et al., "*Treatment of Rheumatoid Arthritis with a Recombinant Human Tumor Necrosis Factor Receptor (P75)-Fc Fusion Protein*," New England J. of Medicine, 337(3), pp. 141–147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

Use of the compounds of the present invention as encompassed by formula (I) in treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present invention inhibit the Fc gamma dependent production of TNF alpha in human monocytes/macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present invention inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

Membrane Binding Assay Using Human CB1 or CB2

The following assay has been carried out using the human cannabinoid receptor expressed in CHO cells.

Radioactive tracer label (WIN 55,212-2 Mesylate [5,7-3H] for CB2, CP55,940 for CB1) and test compound are incubated together in a 96-well tissue culture plate. All reagents are dissolved or resuspended in binding buffer (10 mM HEPES, pH 7.4, 1 mM EDTA, 5 mM $MgCl_2$, 0.3% BSA). The reaction is initiated by the addition of membranes (50 ug) from CHO-K1 cells expressing either CB1 or CB2). The plates are incubated 2 hours with shaking at room temperature and the reaction is harvested on a Wallac Filtermat B with 7 wash cycles using wash buffer (10 mM HEPES, pH 7.4, 0.1% BSA). The filter is counted in a Betaplate scintillation counter to ascertain the cannabinoid inhibitory activity of the test compound (activity inversely proportional to the amount of labeled WIN-55212-2 incorporated). Routinely the radiolabel was used at a concentration of 10 nM but the exact concentration of reagents and the amount of label can be varied as needed.

This assay is advantageous as it can be conducted in a 96-well format that is readily automated. Different labeled cannabinoid ligands can be substituted into the assay. The recombinant cannabinoid receptors may be obtained from commercial sources and can be expressed in CHO or insect cell culture (*Spodoptera frugiperda* cells).

Cell Assays (1) Monocyte/Macrophage cytokine production

Freshly isolated human monocytes, or the human monocytic cell line THP-1, are incubated at $1 \times 10^6$ cells/ml in RPMI 1640 media containing 10% FBS with the test compound for 30 minutes and then stimulated by the addition of either lipopolysaccharide (LPS) or immune complexes (IC). Cells are incubated for 6 h at 37° C. at which time the cell supernatants are removed and assayed for cytokines (TNF, IL-1β, IL-6, IL-8) using commercially available ELISA kits. The cannabinoid agonists inhibit the production of inflammatory cytokines.

(2) Activation of Lung Epithelial Cells

The ability of the cannabinoids to inhibit mucin, chemokine/cytokine production from lung epithelial cells is evaluated with human lung epithelial cell lines H292 and A549. Epithelial cells are cultured overnight in 48 well microtiter plates in complete RMPI 1650 (200 μl/well) at a density of $2 \times 10^5$ cells/ml. The media is removed and replaced with fresh media. Test compounds in 50 μl isotonic buffer are added and incubated for 1 hour at 37° C. Cell activation is triggered by the addition of a stimulatory agent comprising one of EGF, smoke conditioned media, TNF-α or IL-1β. In this assay, the IC50 for Win-55212-2<20 mcM. After a desired period of time (e.g., 24 h) the cell supernatants are removed and assayed for mucin cytokine and chemokines by ELISA. The cannabinoid agonists inhibit mucin and IL-8 production from lung epithelial cells.

In addition to Win-55212-2 (described in French Patent document FR 2,735774 A1, incorporated herein), compounds of formula (I) demonstrated activity in the above lung epithelial cell assay, particularly indole and indazole-based amino acid esters described herein.

(3) T cell Proliferation Assays

The ability of the cannabinoids to inhibit the proliferation of normal human peripheral blood T cells that have been stimulated to grow with anti-CD3 plus anti-CD28 antibodies is evaluated. A 96 well plate is coated with a monoclonal antibody to CD3 (such as G19-4), the antibody is allowed to bind, and then the plate is washed. The antibody bound to the plate serves to stimulate the cells. Normal human peripheral blood T cells are added to the wells along with test compound plus anti-CD28 antibody to provide co-stimulation. After a desired period of time (e.g., 3 days), the [3H]-thymidine is added to the cells, and after further incubation to allow incorporation of the label into newly synthesized DNA, the cells are harvested and counted in a scintillation counter to measure cell proliferation.

(4) Degranulation of RBL-cells

RBL 2H3 cells are cultured overnight in complete MEM at a density of $1 \times 10^6$ cells/ml at 37° C. in 100 ul medium. Test compounds in 50 μl isotonic buffer are added and incubated for 2 hours at 37° C. Cell degranulation is triggered by the addition of 25 μl DNP-BSA IgE complex (300 ng/ml DNP-BSA) and incubated an additional 30 min. at 37° C. Fifty μl of the cell supernatant from each well is removed and placed in a second 96-well plate which contains 50 μl of substrate solution [90 ml NAGA (hex) buffer (70 ml 0.2M $NaPO_4$, 20 ml 0.4M Citric Acid Monohydrate pH 4.5)+135 ml $dH_2O$, 615 mg p-Nitrophenyl N-acetyl D-glucosaminide]. The reaction is stopped by the addition of 100 μl NAGA stop solution (0.2M Glycine, 0.2M NaCl, 0.2M NaOH) and the plate read at 405 nm on a microtiter plate reader. The compounds of the Examples herein show a desired activity in the assays described.

EXAMPLES

The following Examples illustrate embodiments of the present invention and are not intended to limit the scope of the claims.

Abbreviations

The following abbreviations are employed hereinbefore and in the Examples:
Ph=phenyl
Bn=benzyl
t-Bu=tertiary butyl
Me=methyl
Et=ethyl
MeOH=methanol
EtOH=ethanol
$Et_2O$=diethyl ether
EtOAc=ethyl acetate
Pen=pentyl
Boc=tert-butyloxycarbonyl
BOP chloride=bis-(2-oxo-3-oxazolidinyl)phosphinic chloride
Cbz=carbobenzyloxy or carbobenzoxy or benzyloxycarbonyl
Cbz-Cl=benzyl chloroformate m-CPBA=meta chloroperbenzoic acid
hex=hexane(s)
Morph=morpholine or morpholinyl
BOP reagent=benzotriazol-1-yloxy-tris (dimethylamino) phosphonium hexafluorophosphate
EDC or EDCI=3-ethyl-3'-(dimethylamino)propyl-carbodiimide
EDC.HCl=EDC hydrochloride
DBU=1,8-diazabicyclo[5.4.0]undec-7-ene
DCC=dicyclohexylcarbodiimide
DCE=1,2 dichloroethane
DCM=dichloromethane
DEAD=diethyl azodicarboxylate
DIAD=diisopropyl azodicarboxylate
DIPEA=diisopropylethylamine
DMA.HCl=dimethylamine hydrochloride
DMAP=4-dimethylaminopyridine
DME=1,2 dimethoxyethane
DMF=dimethyl formamide
DMSO=dimethyl sulfoxide
DIBALH=diisobutyl aluminum hydride
HATU=[O-(7-azabenzotriazol-1-yl)-1,1,3,3-tetramethyl-uronium]hexafluorophosphate
HOAc or AcOH=acetic acid
HOBT or HOBT.H$_2$O=1-hydroxybenzotriazole hydrate
HOAT=1-Hydroxy-7-azabenzotriazole
LDA=lithium diisopropylamide
NBS=N-bromosuccinimide
NCS=N-chlorosuccinimide
NMM=N-methyl morpholine
TFA=trifluoroacetic acid
TEA=triethylamine
THF=tetrahydrofuran
Cs$_2$CO$_3$=cesium carbonate
HCl=hydrochloric acid or hydrochloride
KOH=potassium hydroxide
K$_2$CO$_3$=potassium carbonate
LiAlH$_4$=lithium aluminum hydride
LiOH=lithium hydroxide
n-BuLi=n-butyllithium
t-BuLi=t-butyllithium
NaCl=sodium chloride
NaOH=sodium hydroxide
NaHCO$_3$=sodium bicarbonate
Pd/C=palladium on carbon
Ph$_3$P=triphenylphosphine
Pd(OAc)$_2$=Palladium acetate
Pd(Ph$_3$P)$_4$=tetrakis triphenylphosphine palladium
Ar=argon
N$_2$=nitrogen
DI=deionized
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
ret. t.=HPLC retention time (minutes)
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point HPLC Conditions When a letter is given in a parenthetical following the HPLC retention times, this reference denotes the HPCL conditions. HPLC retention times were determined using a linear elution gradient of mixtures of solvent A and solvent B (solvent A=10% MeOH/90% water/0.1% TFA and solvent B=90% MeOH/10% water/0.1% TFA) where the gradient begins with 100% solvent A and increases in a linear rate to 100% solvent B over the specified total elution time. All products were detected using a UV detector at a wavelength of 220 nm.

Condition A: YMC S5 ODS 4.6 mm×50 mm Ballistic chromatography column with a 4 minute total gradient elution time and a flow rate of 4 mL/minute.

Condition B: YMC S5 Pro 4.6 mm×33 mm Ballistic chromatography column with a 2 minute total gradient elution time and a flow rate of 5 mL/minute.

Condition C: YMC S5 Turbopak Pro 4.6 mm×33 mm Ballistic chromatography column with a 2 minute total gradient elution time and a flow rate of 5 mL/minute.

Condition D: YMC ODSA 5u C18 4.6 mm×50 mm Ballistic chromatography column with a 4 minute total gradient elution time and a flow rate of 4 mL/minute.

Condition E: YMC S5 Turbopak Pro 4.6 mm×33 mm Ballistic chromatography column with a 2 minute total gradient elution time and a flow rate of 4 mL/minute.

Tables

In the tables, structures are provided for the compounds of the examples. In some instances a nitrogen atom may be shown bonded to two groups; since nitrogen has a valency of three, it should be understood in those instances that the nitrogen group is also bonded to a hydrogen atom. A bond extending from a ring or chain may denote a methyl group, as reflected by the compound names.

Example 1

5-pentyloxy-6-methoxyindole-2-carboxylic acid

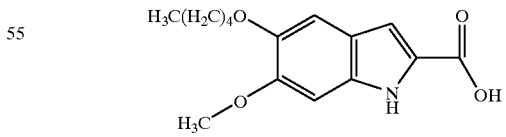

A. N-phenylsulfonyl 5-benzyloxy-6-methoxyindole

A solution of 5-benzyloxy-6-methoxyindole (990 mg, 3.9 mmol) in DMF (3 mL) was added to a solution of NaH (234 mg, 5.9 mmol, 60% in oil) in DMF (1 mL) at 0° C. The ice bath was removed, and the reaction mixture allowed to stir at RT for 30 min. The reaction flask was cooled to 0° C. and PhSO$_2$Cl (0.6 mL, 4.7 mmol) was added via syringe. The ice bath was removed and the reaction mixture stirred at RT for 24 h. Water (25 mL) was added and the aqueous layer extracted with Et$_2$O (4×50 mL). The combined organic extracts were washed with brine, dried over Na$_2$SO$_4$, filtered and concentrated in vacuo to give an oil. The residue was purified by column chromatography (25% then 40% EtOAc/hex) to furnish N-phenylsulfonyl 5-benzyloxy-6-methoxyindole as a crystalline solid (1.38 g, 90% yield).

B. Ethyl N-phenylsulfonyl 5-benzyloxy-6-methoxy-indole-2-carboxylate

To a solution of compound A (120 mg, 0.3 mmol) in THF at −78° C. was added nBuLi dropwise (140 μL, 0.35 mmol, 2.57M in hex), and the reaction mixture was stirred at 0° C. for 20 min. The reaction mixture was recooled to −78° C., ClCO$_2$Et (37 μl, 0.38 mmol) was added, and the mixture was stirred for 45 min and then allowed to warm to RT slowly. The reaction mixture was quenched with sat aq. NH$_4$Cl, diluted with water, and extracted into EtOAc (3×40 mL). The combined organic extracts were dried over Na$_2$SO$_4$, filtered, and concentrated in vacuo to give an oil. The residue was purified by column chromatography (25% EtOAc/hex) to furnish the above-titled compound B as a yellow glass which was used directly in the next step.

C. Ethyl N-phenylsulfonyl 5-hydroxy-6-methoxyindole-2-carboxylate

Hydrogenolysis of Compound B in 1/1 MeOH/EtOAc with 10% Pd—C/H$_2$ balloon followed by column chromatography (50% EtOAc/hex) furnished the above-titled compound C (77 mg, 58% yield).

D. Ethyl N-phenylsulfonyl 5-pentyloxy-6-methoxy-indole-2-carboxylate

To a solution of compound C (38 mg, 0.17 mmol), K$_2$CO$_3$ (36 mg, 0.27 mmol) in DMF (2 mL) was added 1-bromopentane (27 μl, 0.21 mmol), and the reaction was heated at 65° C. for 18 h. Another 30 μL of 1-bromopentane was added, and the reaction was heated to 85° C. for another 18 h. The reaction was cooled, poured into water (10 mL) and extracted with Et$_2$O (3×50 mL). The combined organic extracts were dried over MgSO$_4$, filtered, and concentrated in vacuo to give an oil. The residue was purified by column chromatography (10% EtOAc/hex) to furnish the above-titled compound D as a white crystalline solid (36 mg, 73% yield).

E. 5-Pentyloxy-6-methoxyindole-2-carboxylate

Treatment of ethyl N-phenylsulfonyl 5-pentyloxy-6-methoxyindole-2-carboxylate (Compound D) with 3 N NaOH (0.3 mL) in EtOH (2 mL) at reflux for 24 h followed by the usual workup (as outlined above) afforded 5-pentyloxy-6-methoxyindole-2-carboxylic acid.

Example 2

1-[2-(Morpholino)ethyl]-5-methoxy-2-indolecarboxylate

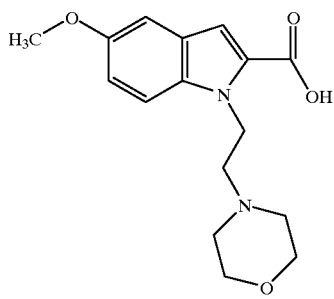

A. 1-[2-(Morpholino)ethyl]-5-methoxy-2-indolecarboxylate methyl ester

A solution of methyl 5-methoxy-2-indolecarboxylate (36 mg, 0.17 mmol) and N-(2-chloroethyl)morpholine.HCl (39 mg, 0.21 mmol) in DMF (2 mL) at 0° C. was added to NaH (18 mg, 0.44 mmol, 60% in oil) in one portion. The ice bath was removed and the reaction mixture allowed to stir for 1 h at RT and then at 65° C. for 16 h. Water (2 mL) was added and the mixture was partitioned between EtOAc and water. Upon extraction with EtOAc (3×25 ml), the combined organic extracts were dried over Na$_2$SO$_4$, filtered, and concentrated in vacuo. The residue was purified by column chromatography (25% then 50% EtOAc/hex) to furnish the above-titled compound A as a white solid (32 mg, 58% yield).

B. 1-[2-(Morpholino)ethyl]-5-methoxy-2-indolecarboxylate

The methyl ester from step A (31.2 mg, 0.4 mmol) was stirred in a mixture of 3N NaOH (0.5 mL) and EtOH (3 mL) for 20 h, acidified with conc. HCl/pH 7.0 buffer, and extracted into EtOAc. The combined extracts were dried over Na$_2$SO$_4$, filtered, and concentrated in vacuo to yield the compound of Example 2.

Examples 3–12

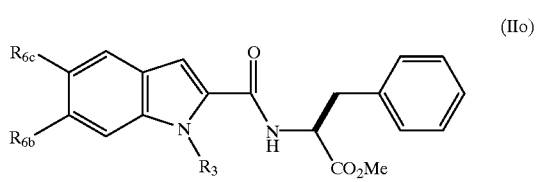

The following procedure was used to prepare the compounds of Examples 3–12 having formula (IIo), wherein the values for $R_{6b}$, $R_{6c}$ and $R_3$ are as shown in Table 1 below.

General Procedure

To a solution of carboxylic acid (0.54 mmol), L-phenylalanine methyl ester (118 mg, 0.54 mmol), EDC (120 mg, 0.6 mmol), HOBT (82 mg, 0.6 mmol) in DCM (5 mL) was added DIPEA (280 μL, 1.6 mmol), and the reaction mixture was stirred at RT for 7 h. The reaction mixture was poured into DCM (50 mL) and washed with water (15 mL). The organic layer was dried over Na$_2$SO$_4$, filtered, and concentrated in vacuo. The residue was purified by column chromatography (25% then 40% then 50% EtOAc/hex) to furnish the appropriate amide.

TABLE 1

| EX. NO | $R_{6b}$ | $R_{6c}$ | $R_3$ | COMPOUND NAME | DATA MS (M + H) and HPLC ret. t (min). and conditions |
|---|---|---|---|---|---|
| 3 | OMe | OPen | H | N-[[6-Methoxy-5-(pentyloxy)-1H-indol-2-yl]carbonyl]-L phenylalanine methyl ester | 438.2/ 4.36 (A) |
| 4 | H | OMe | H | N-[(5-Methoxy-1H-indol-2-yl)carbonyl]-L-phenylalanine methyl ester | 352.2/3.02 (A) |
| 5 | OBn | OMe | H | N-[[5-Methoxy-6-(phenylmethoxy)-1H-indol-2-yl]carbonyl]-L-phenylalanine methyl ester | 459.3/3.39 (A) |
| 6 | H | OPen | H | N-[[5-(Pentyloxy)-1H-indol-2-yl]carbonyl]-L-phenylalanine methyl ester | 409.3/4.47 (A) |
| 7 | OPen | OMe | H | N-[[5-Methoxy-6-(pentyloxy)-1H-indol-2-yl]carbonyl]-L-phenylalanine methyl ester | 439.3/4.24 (A) |
| 8 | H | OMe | (CH₂)₂-morpholinyl | N-[[5-Methoxy-1-[2-(4-morpholinyl)ethyl]-1H-indol-2-yl]carbonyl]-L-phenylalanine methyl ester | 465.3/2.98 (A) |
| 9 | OMe | H | H | N-[(6-Methoxy-1H-indol-2-yl)carbonyl]-L-phenylalanine methyl ester | 352.5/3.70 (A) |
| 10 | OMe | H | CH₃ | N-[(6-Methoxy-1-methyl-1H-indol-2-yl)carbonyl]-L-phenylalanine methyl ester | 366.2/3.87 (A) |
| 11 | OMe | H | (CH₂)₂-morpholinyl | N-[[6-Methoxy-1-[2-(4-morpholinyl)ethyl]-1H-indol-2-yl]carbonyl]-L-phenylalanine methyl ester | 465.2/3.06 (A) |
| 12 | H | (CH₂)₂-O-(CH₂)₂-morpholinyl | H | N-[[5-[2-(4-Morpholinyl)ethoxy]-1H-indol-2-yl]carbonyl]-L-phenylalanine methyl ester | 451.2/2.73 (A) |

Example 13a

1-(4-Ethylmorpholinyl)-2-methyl-7-methoxyindole-3-carboxylic acid

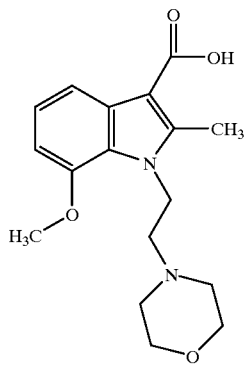

A. 1-(2-Nitro-3-methoxyphenyl)-2-nitropropanol

To a 2 L round-bottomed flask equipped with a magnetic stirrer and a $N_2$ bubbler were added 2-nitro-3-methoxybenzaldehyde (125.7 g, 0.6939 mol), nitroethane (73 g, 0.97 mol), 18-C-6 (18 g), isopropanol (420 mL) and KF (20 g). The mixture was stirred at RT for 16 h. The solvent was removed under vacuum to give an oil. Isopropanol (100 mL) and water (250 mL) were added. The mixture was placed under vacuum to give a slurry. The slurry was stirred for 1 h and filtered. The cake was washed with water (4×100 mL) and dried to give 1-(2-nitro-3-methoxyphenyl)-2-nitropropanol as a diastereomeric mixture in a ratio of 3:2 (170.3 g, 96% yield). $^1$H NMR for major isomer (CDCl$_3$) δ1.38 (d, J=6.9 Hz, 3H), 2.94 (s, 1H), 3.92 (s, 3H), 4.90 (m, 1H), 5.08 (d, J=8.6 Hz, 1H), 7.05–7.52 (m, 3H). $^1$H NMR for minor isomer (CDCl$_3$) δ1.55 (d, J=6.9 Hz, 3H), 2.94 (s, 1H), 4.80 (m, 1H), 5.46 (d, J=3.0 Hz), 7.05–7.52 (m, 3H).

B. 1-(2-Nitro-3-methoxyphenyl)-2-nitropropene

To a 5 L three-necked round-bottomed flask equipped with a mechanical stirrer and a $N_2$ bubbler were added 1-(2-nitro-3-methoxyphenyl)-2-nitropropanol (170 g, 0.66 mol), acetic anhydride (450 mL), 18-Crown-6 (17 g) and KF (38.25 g). The reaction mixture was stirred at RT for 64 h, then cooled in an ice-water bath. Water (2250 mL) was added slowly. The resulting slurry was stirred at 0° C. for 2 h and then filtered. The cake was washed with DI water (3×250 mL) and suction dried for 20 h to give 1-(2-nitro-3-methoxyphenyl)-2-nitropropene (150.7 g, 96% yield). $^1$H NMR (CDCl$_3$) δ2.30 (s, 3H), 3.95 (s, 3H), 6.94 (d, J=7.8 Hz, 1H), 7.13 (d, J=8.5 Hz, 1H), 7.53 (pseudo t, J=8.1 Hz, 1H), 7.89 (s, 1H).

C. 2-Methyl-7-methoxyindole

To a 2 L hydrogenation flask were added 1-(2-Nitro-3-methoxyphenyl)-2-nitropropene (44 g, 0.1850 mol), 10% Pd/C (4.4 g, 50% water wet), EtOAc (600 mL), acetic acid (90 mL) and absolute EtOH (75 mL). The reaction mixture was hydrogenated at <60 psi for 3 h and then filtered. The cake was washed with EtOAc (3×100 mL). The filterate was concentrated to remove EtOAc and EtOH. DI water (200 mL) was then added slowly. The resulting slurry was stirred for 0.5 h at RT and filtered. The cake was washed with 1:2 HOAc/H$_2$O (2×30 mL) 1:4 HOAc/H$_2$O (50 mL), water (2×80 mL) and suction dried for 18 h to give 2-methyl-7-methoxyindole (8.3 g, 62% yield). $^1$H NMR (CDCl$_3$) δ2.42 (s, 3H), 3.94 (s, 3H), 6.18 (pseudo t, J=1.1 Hz, 1H), 6.57 (d, J=7.7 Hz, 1H), 6.97 (pseudo t, J=7.7 Hz, 1H), 7.12 (d, J=7.7 Hz, 1H), 8.10 (s, 1H).

D. 1-[2-(4-Morpholino)ethyl]-2-methyl-3-methoxymethyl-7-methoxyindole

To a stirred suspension of N-(2-chloroethyl)morpholine hydrochloride (13 g, 0.07 mol) was added (13.2 g, 0.2 mol) in 100 mL of DMSO of 85% powdered KOH. After stirring for 10 minutes, the reaction mixture was heated to 100° C. and then stirred at this temperature for 3–5 h. The reaction mixture was cooled to RT and diluted with 100 mL of water and 200 mL of ether. The organic layer was separated, and the aqueous layer was extracted with ether (2×100 mL). The organic layers were combined, washed with water (2×100 mL) and dried over anhydrous Na$_2$SO$_4$ and filtered. The solvent was removed under reduced pressure to give the above compound D as a light yellow oil (13.59 g, 99% yield). $^1$H NMR (CDCl$_3$) δ2.42 (s, 3H), 2.52 (m, 4H), 2.62 (t, J=7.1 Hz, 2H), 3.75 (m, 4H), 3.90 (s, 3H), 4.42 (t, J=7.1 Hz, 2H), 6.17 (s, 1H), 6.55 (d, J=7.8 Hz, 1H), 6.90 (dd, J=7.8, 8.0 Hz, 1H), 7.10 (d, J=8.0 Hz, 1H).

E. 1-[2-(4-Morpholino)ethyl]-2-methyl-3-trichloroacetyl-7-methoxyindole hydrochloride To a solution of the methoxyindole from step D (13 g, 0.048 mol) in DCE (400 mL) was added trichloroacetyl chloride (26 g, 0.14 mol). The solution was refluxed for 6–8 h and then cooled to RT. The resulting slurry was filtered, washed with ether (2×100 mL) and dried to give the above-titled methoxyindole hydrochloride (21 g, 94% yield). $^1$H NMR (CDCl$_3$) δ2.85 (s, 3H), 2.95 (m, 2H), 3.30 (m, 2H), 3.55 (m, 2H), 4.05 (m, 5H), 4.32 (m, 2H), 5.15 (m, 2H), 6.75 (d, J=7.8 Hz, 1H), 7.15 (dd, J=7.8, 8.0 Hz, 1H), 7.85 (d, J=8.0 Hz, 1H).

F. 1-[(4-Morpholino)ethyl]-2-methyl-7-methoxyindole-3-carboxylic acid

To a solution of the compound from step E (19 g, 0.048 mol) in THF (100 mL) was added NaOH solution (100 mL, 1N, 0.1 mol). The reaction mixture was stirred about 1–2 h. The resulting slurry was filtered and washed with ether (2×50 mL). The filtrate was transferred into a separation funnel and the phases were separated. The aqueous layer was washed with ether (2×100 mL). The cake and aqueous layer were combined and the pH adjusted to 4 with HCl (6N). The slurry was filtered, washed with ether (2×100 mL), and the solid was dried to give the above-titled carboxylic acid (15 g, 95% yield). $^1$H NMR (DMSO-d$_6$) δ2.44 (s, 3H), 2.58 (s, 2H), 2.72 (s, 4H), 3.56 (s, 4H), 3.90(s, 3H), 4.42 (s, 2H), 6.67 (d, J=7.8 Hz, 1H), 7.00 (dd, J=7.8, 8.0 Hz, 1H), 7.65 (d, J=8.0 Hz, 1H).

Example 13b

2-Methyl-3-methoxycarbonyl-7-methoxyindole

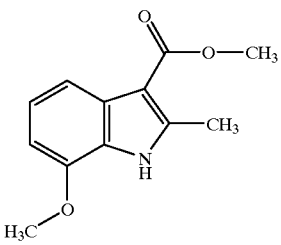

A. 2-Methyl-3-trichloroacetyl-7-methoxyindole

To a 2 L round-bottomed flask equipped with a magnetic stirrer and a $N_2$ bubbler were added 2-methyl-7- methoxyindole (12 g, 74 mmol), acetonitrile (125 mL) and collidine (15 mL, 113 mmol). The mixture was stirred to give a solution and was cooled with an ice water bath. Trichloroacetyl chloride (14 mL, 112 mmol) was added. The cooling bath was removed and the reaction mixture stirred at RT for 3 h. 1N HCl (500 mL) was then added over 10 minutes. The resulting slurry was stirred at RT for 30 minutes and filtered. The cake was washed with DI water (3×50 mL) and suction dried for 17 h to give 2-methyl-3-trichloroacetyl-7-methoxyindole (22.8 g, 96% yield). $^1$H NMR (CDCl$_3$) δ2.79 (s, 3H), 3.96 (s, 3H), 6.71 (d, J=7.9 Hz, 1H), 7.19 (dd, J=7.9, 8.4 Hz, 1H), 7.82 (d, J=8.4 Hz, 1H), 8.92 (s, 1H).

B. 2-Methyl-3-methoxycarbonyl-7-methoxyindole

To a 1 L round-bottomed flask equipped with a magnetic stirrer and a N$_2$ bubbler were added 2-methyl-3-trichloroacetyl-7-methoxyindole (22.8 g, 74.37 mmol) and MeOH (150 mL). The mixture was stirred at RT to give a slurry. KOH (42.5 wt %, 2 mL) was added and the reaction stirred for 5 min. HCl (0.1N, 500 mL) was added dropwise. The slurry was stirred at RT for 1 h and filtered. The cake was washed with DI water (3×30 mL) and suction dried for 18 h to give 2-methyl-3-methoxycarbonyl-7-methoxyindole (15.57 g, 96% yield). $^1$H NMR (CDCl$_3$) δ2.71 (s, 3H), 3.89 (s, 3H), 3.92 (s, 3H), 6.63 (d, J=7.9 Hz, 1H), 7.12 (dd, J=7.9, 8.0 Hz, 1H), 7.66 (d, J=8.0 Hz, 1H), 8.84 (s, 1H).

Example 14

2-Methyl-7-methoxy-6-azaindole

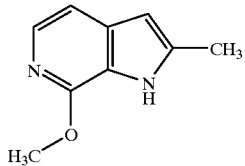

2-Methoxy-3-nitro-4-methyl pyridine (200 mg, 1.2 mmol) and dimethylacetamide dimethylacetal (0.5 mL) were heated at 130° C. for 18 h. The reaction mixture was cooled and concentrated in vacuo to a deep purple-red oil. Benzene (4 mL) and 10% Pd/C (25 mg) were added and the solution hydrogenated at 45 psi for 18 h (Parr apparatus). The red coloration disappeared. The crude reaction mixture was purified directly by silica gel chromatography (20% EtOAc/hex) to furnish 2-methyl-7-methoxy-6-azaindole (112 mg, 57% yield). LC-MS 163.1, M+H.

Example 15

2-Methyl-7-benzyloxy indole

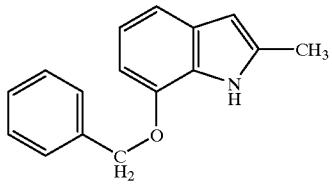

A. 2-Methyl-7-hydroxy indole

To a solution of 2-methyl-7-methoxy indole (814 mg, 5.0 mmol) in CH$_2$Cl$_2$ (20 mL) at 0° C. was added BBr$_3$ (15 mL, 15 mmol, 1M in CH$_2$Cl$_2$), and then the ice bath was removed and stirring was continued for 3 h. Ice was added and the reaction mixture diluted with water (30 mL). The aqueous layer was extracted with EtOAc (3×100 mL), dried over Na$_2$SO$_4$, filtered, and concentrated in vacuo. The residue was purified via passage through a short silica gel column (20% then 50% EtOAc/hex) to afford 2-methyl-7-hydroxy indole as an unstable solid (99% yield).

B. 2-Methyl-7-benzyloxy indole

To the compound from step A, acetone (15 mL) was added followed by benzyl bromide (670 μL, 5.6 mmol) and Cs$_2$CO$_3$ (1.8 g, 5.6 mmol) and the reaction mixture stirred at RT for 18 h. A second aliquot of BnBr (140 μL) and Cs$_2$CO$_3$ (380 mg) was added and stirring continued for 24 h. The reaction mixture was poured into EtOAc and water, the layers were separated, and the aqueous layer was further extracted with EtOAc (3×50 mL). The combined organic extracts were washed with 1N NaOH and water and dried over MgSO$_4$, filtered, and concentrated in vacuo. Purification by column chromatography (hexanes then 5% EtOAc/hex) afforded 2-methyl-7-benzyloxy indole as an unstable solid (898 mg, 81% yield). $^1$H NMR impure; 238.17, M+H.

Example 16

7-Methoxy-1-morpholinoethyl indazole-3-carboxylic acid, sodium salt

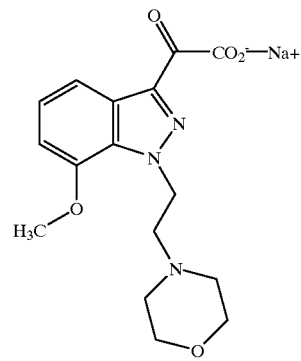

A. 3-Methoxy-2(tert-butyloxy)amino]phenylacetic acid dimethyl acetamide

To a solution of 3-methoxy-2[(tert-butyloxy)amino]-phenylacetic acid (8.3 g, 30 mmol) and EDC.HCl (8.51 g, 44.4 mmol) were added 1-hydroxybenzotriazole (4.80 g, (35.5 mmol) and DMA.HCl (9.7 g, 120 mmol) in 90 mL of DMF at RT. DIPEA (26 mL, 148 mmol) was added, and the resulting solution was stirred for 48 h. The reaction mixture was concentrated in vacuo and the resulting oil was dissolved in 350 mL of DCM and washed with aqueous 1 N NaOH (3×125 mL), 6% aqueous citric acid solution (3×100 mL), water (100 mL), and brine (100 mL). After drying over anhydrous sodium sulfate, the resulting solution was decanted and concentrated on a rotary evaporator to afford a reddish-orange oil as the crude product. This material was dissolved in Et$_2$O (ca 100 mL) and reconcentrated on the rotary evaporator yielding a yellow solid that was subsequently triturated with two 35-mL portions of hexanes to remove any residual DMF. The resulting solid was dried in vacuo to give the above-titled compound A (7.1 g, 78% yield) as a yellow solid. LC-MS (MH$^+$ 309.2).

B. 7-Methoxy-3-dimethylamido indazole

To a stirring solution of 1.3 g (4.12 mmol) of compound A in 4% aqueous acetic acid at 95° C. was slowly added an aqueous solution of 0.85 g (12.4 mmol) of sodium nitrite in 1.4 mL of water over 2 h. After the addition was complete, HPLC analysis showed nearly complete consumption of the substrate. The reaction mixture was cooled to RT and concentrated on a rotary evaporator, and the resulting solid was suspended in approximately 30 mL of water. The product was collected by vacuum filtration and washed with water (20 mL), then dried in vacuo to afford the above-titled compound B (0.74 g, 82%) as a yellow solid.

C. 7-Methoxy-1-morpholinoethyl-3-dimethylamido indazole

To a RT solution of 0.55 g (2.50 mmol) of compound B and 0.75 g (5.00 mmol) of 4-(2-chloroethyl)morpholine in 5 mL of anhydrous DMF was added 0.2 g (5.00 mmol) of 60% sodium hydride dispersion in two portions over 10 minutes. The reaction mixture was allowed to stir at RT for 14 h, then an additional 0.75 g (5.00 mmol) of 4-(2-chloroethyl) morpholine was added, and the mixture was heated to 40° C. for an additional 2 h. The mixture was allowed to cool to RT and slowly 10 mL of water was added. The mixture was extracted with EtOAc (4×30 mL), and the combined extracts were washed with water (3×7 mL), brine (7 mL), then dried over anhydrous sodium sulfate, decanted, and concentrated in vacuo to afford a yellow liquid which partially solidified upon standing. This material was triturated with three 20-mL portions of hexanes and the remaining white solid was dried in vacuo to afford 0.60 g (72%) of the above-titled compound C. LC-MS (MH$^+$ 333.3).

D. 7-Methoxy-1-morpholinoethyl indazole-3-carboxylic acid, sodium salt

To 0.10 g (0.301 mmol) of compound C was added 0.5 mL of 3 N aqueous KOH and 0.5 mL of EtOH, and the resulting solution was heated at 80° C. for 16 h then cooled to RT and concentrated. The residue was dissolved in water (5 mL) and brought to a pH of 7 by addition of 1 N aqueous HCl then reconcentrated. The resulting residue was redissolved in water (5 mL) and made basic (pH>10) by adding a few drops of 1 N aqueous NaOH. The aqueous solution was concentrated and the remaining solid treated with toluene, the toluene was evaporated and the residue dissolved in methylene chloride (~10 mL). The resulting solution was dried over sodium sulfate, filtered, and concentrated in vacuo to afford 0.079 g (80% yield) of the above-titled carboxylate salt D as a white solid. LC-MS (MH$^+$ 306.2).

Examples 17–66

General Procedure

The compounds of Examples 17–66 as shown in Table 2 were prepared with the following procedure. To a solution of carboxylic acid (0.05 mmol, 15.9 mg) in 3 ml DCE was added thionyl chloride (0.15 mmol, 18 mg). The mixture was stirred at RT under $N_2$ for 3 h. An amine (0.11 mmol) in 2 ml DCE was added, the mixture was stirred for 2 h, and acetic anhydride (0.1 mmol) was added. After 0.5 h, the reaction was quenched with 0.5 N NaOH aqueous solution. The organic layer was subjected to cation exchange resin, the resin was washed with 20 ml MeOH, then 8 ml 2 M $NH_3$ in MeOH, and the basic solution was evaporated to give the following amides:

TABLE 2

| EX. NO. | STRUCTURE | COMPOUND NAME | DATA MS (M + H)/HPLC ret. t (min) and conditions |
|---|---|---|---|
| 17 | Chiral structure shown | 7-Methoxy-2-methyl-N-[(1S)-1-(5-methyl-2-oxazolyl)-2-phenylethyl]-1-[2-(4-morpholinyl)ethyl]-1H-indole-3-carboxamide | 503.3/3.14 (A) |

TABLE 2-continued

| EX. NO. | STRUCTURE | COMPOUND NAME | DATA MS (M + H)/HPLC ret. t (min) and conditions |
|---|---|---|---|
| 18 | 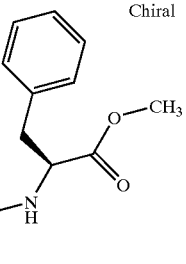 Chiral | N-[[6-Methoxy-2-methyl-7-(pentyloxy)-1H-indol-3-yl]carbonyl]-L-phenylalanine methyl ester | 453.29/4.44 (A) |
| 19 | 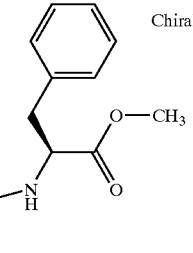 Chiral | N-[[5-Methoxy-2-methyl-1-[2-(4-morpholinyl)ethyl]-1H-indol-3-yl]carbonyl]-L-phenylalanine methyl ester | 480.36/2.94 (A) |
| 20 | 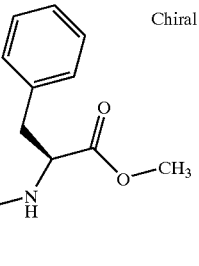 Chiral | N-[[6-Methoxy-2-methyl-1-[2-(4-morpholinyl)ethyl]-1H-indol-3-yl]carbonyl]-L-phenylalanine methyl ester | 480.33/3.09 (A) |

TABLE 2-continued
| EX. NO. | STRUCTURE | COMPOUND NAME | DATA MS (M + H)/HPLC ret. t (min) and conditions |
|---|---|---|---|
| 21 | 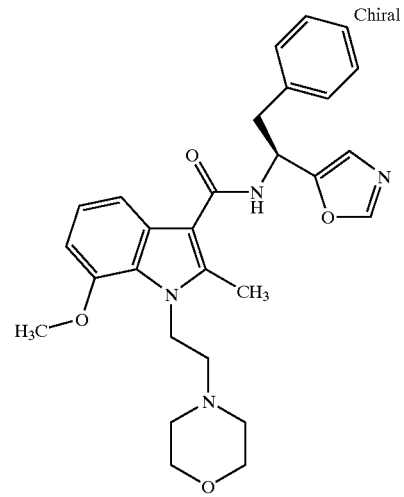 | 7-Methoxy-2-methyl-N-[(1S)-1-(5-oxazolyl)-2-phenylethyl]-1-[2-(4-morpholinyl)ethyl]-1H-indole-3-carboxamide | 489.2/2.94 (A) |
| 22 | 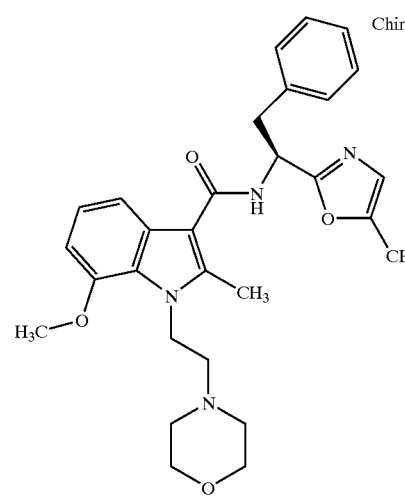 | 7-Methoxy-2-methyl-N-[(1S)-1-(5-methyl-2-oxazolyl)-2-phenylethyl]-1-[2-(4-morpholinyl)ethyl]-1H-indole-3-carboxamide | 503.3/3.19 (A) |
| 23 | 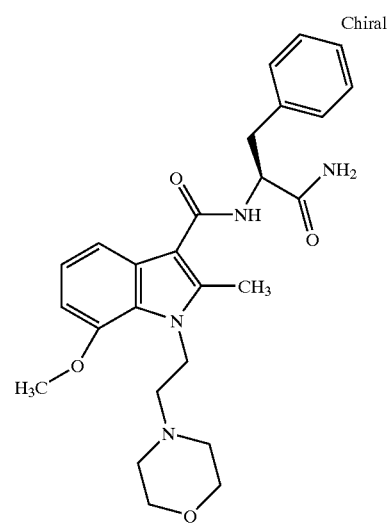 | N-[[7-Hydroxy-2-methyl-1-[2-(4-morpholinyl)ethyl]-1H-indol-3-yl]carbonyl]-L-phenylalaninamide | 465.49/2.73 (A) |

TABLE 2-continued

| EX. NO. | STRUCTURE | COMPOUND NAME | DATA MS (M + H)/HPLC ret. t (min) and conditions |
|---|---|---|---|
| 24 | 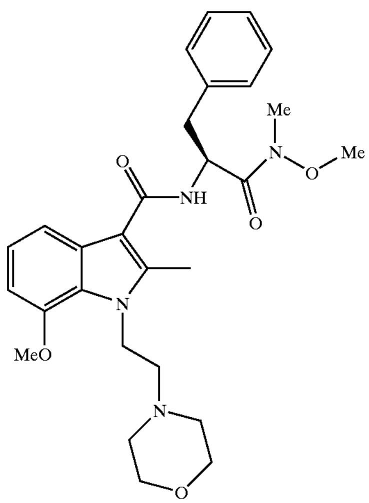 | N-Methoxy-N²-[[7-methoxy-2-methyl-1-[2-(4-morpholinyl)ethyl]-1H-indol-3-yl]carbonyl]-N-methyl-L-phenylalaninamide | 509.50/3.15 (A) |
| 25 | 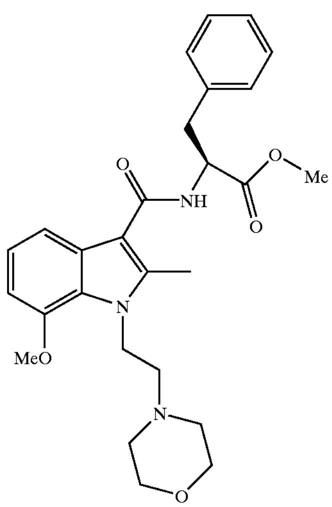 | N-[[2,7-Dimethyl-1-[2-(4-morpholinyl)ethyl]-1H-indol-3-yl]carbonyl]-L-phenylalanine methyl ester | 462.6/3.14 (A) |
| 26 | Chiral | 7-Methoxy-2-methyl-N-[(1S)-1-(3-methyl-1,2,4-oxadiazol-5-yl)-2-phenylethyl]-1-[2-(4-morpholinyl)ethyl]-1H-indole-3-carboxamide | 503.6/2.50 (A) |

TABLE 2-continued
| EX. NO. | STRUCTURE | COMPOUND NAME | DATA MS (M + H)/HPLC ret. t (min) and conditions |
|---|---|---|---|
| 27 | 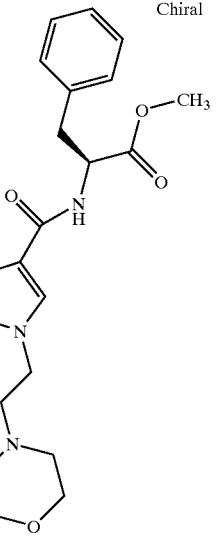 Chiral | N-[[1-Methyl-5-(pentyloxy)-1H-indol-2-yl]carbonyl]-L-phenylalanine methyl ester | 333.2/2.77 (A) |
| 28 | 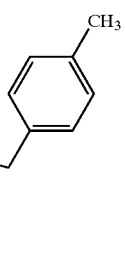 | 2-Methyl-N-[2-(4-methylphenyl)ethyl]-1-[2-(4-morpholinyl)ethyl]-1H-indole-3-carboxamide | 406.24/3.30 (B) |
| 29 | 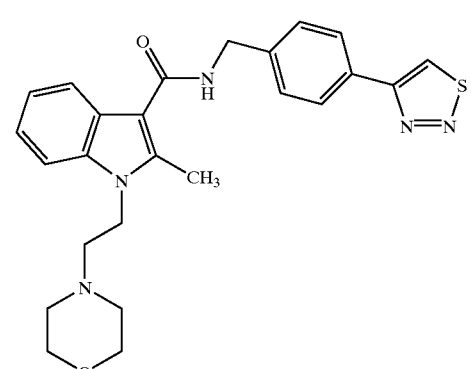 | 2-Methyl-1-[2-(4-morpholinyl)ethyl]-N-[[4-(1,2,3-thiadiazol-4-yl)phenyl]methyl]-1H-indole-3-carboxamide | 462.24/2.82 (B) |

TABLE 2-continued

| EX. NO. | STRUCTURE | COMPOUND NAME | DATA MS (M + H)/HPLC ret. t (min) and conditions |
|---|---|---|---|
| 30 | 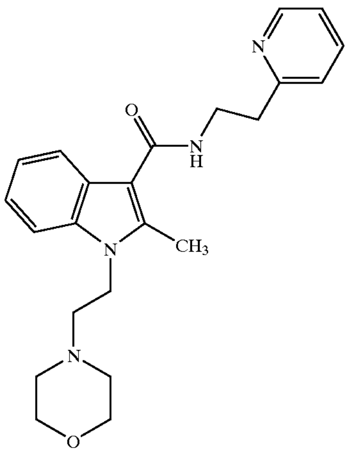 | 2-Methyl-1-[2-(4-morpholinyl)ethyl]-N-[2-(2-pyridinyl)ethyl]-1H-indole-3-carboxamide | 393.26/1.41 (B) |
| 31 | Chiral | N-[[7-Methoxy-2-methyl-1-[2-(4-morpholinyl)ethyl]-1H-indole-3-yl]carbonyl]-D-phenylalanine methyl ester | 480.5/3.10(A) |
| 32 | 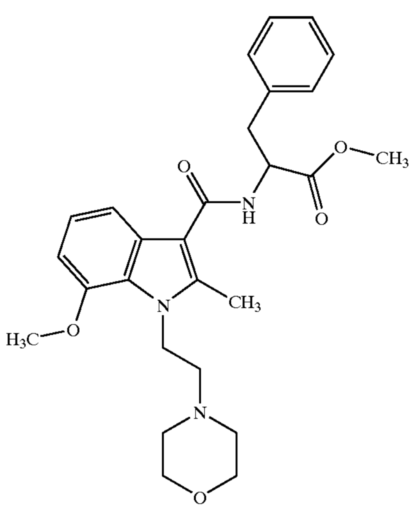 | N-[[7-Methoxy-2-methyl-1-[2-(4-morpholinyl)ethyl]-1H-indol-3-yl]carbonyl]-DL-phenylalanine methyl ester | 480.5/3.10(A) |

TABLE 2-continued
| EX. NO. | STRUCTURE | COMPOUND NAME | DATA MS (M + H)/HPLC ret. t (min) and conditions |
|---|---|---|---|
| 33 | 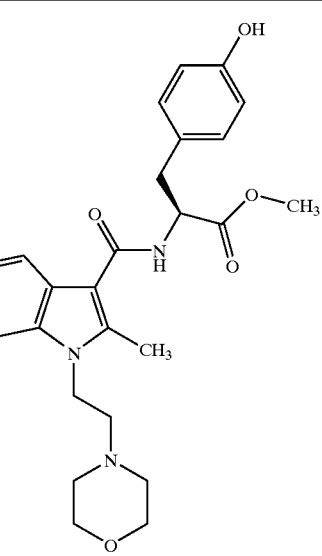 | N-[[7-Methoxy-2-methyl-1-[2-(4-morpholinyl)ethyl]-1H-indol-3-yl]carbonyl]-L-tyrosine methyl ester | 495.6/2.66 (A) |
| 34 | 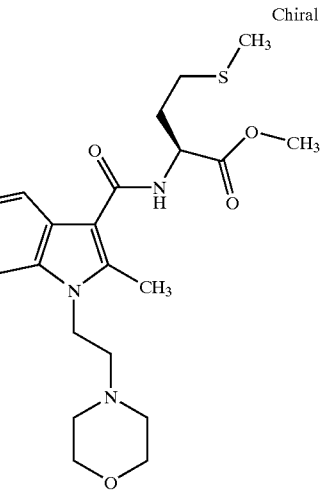 | N-[[7-Methoxy-2-methyl-1-[2-(4-morpholinyl)ethyl]-1H-indol-3-yl]carbonyl]-L-methionine methyl ester | 464.6/2.72 (A) |
| 35 | 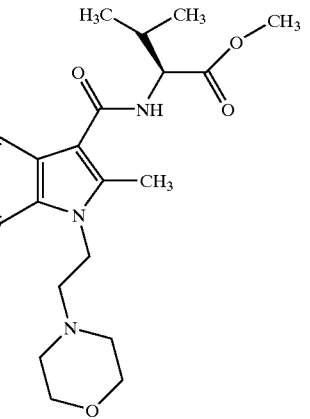 | N-[[7-Methoxy-2-methyl-1-[2-(4-morpholinyl)ethyl]-1H-indol-3-yl]carbonyl]-3-methyl-L-valine methyl ester | 446.7 3.12 (A) |

TABLE 2-continued

| EX. NO. | STRUCTURE | COMPOUND NAME | DATA MS (M + H)/HPLC ret. t (min) and conditions |
|---|---|---|---|
| 36 | 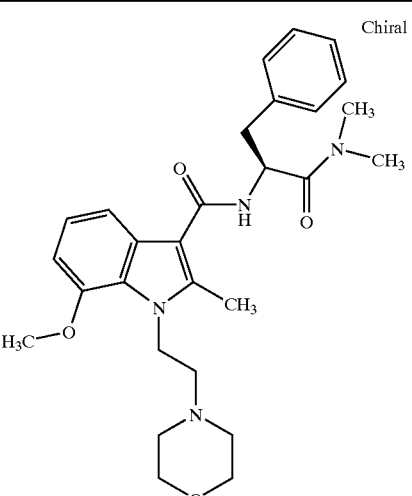 Chiral | N²-[[7-Methoxy-2-methyl-1-[2-(4-morpholinyl)ethyl]-1H-indol-3-yl]carbonyl]-N,N-dimethyl-L-phenylalaninamide | 493.4 2.97 (A) |
| 37 | 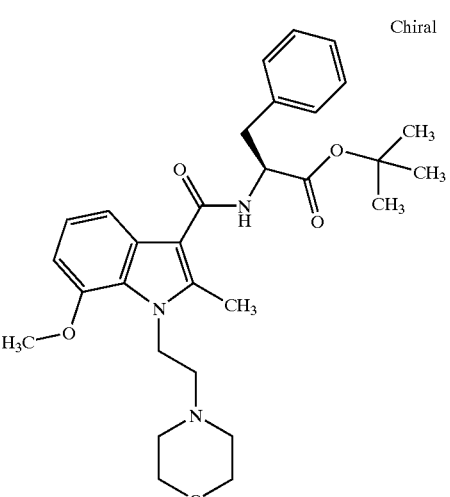 Chiral | N-[[7-Methoxy-2-methyl-1-[2-(4-morpholinyl)ethyl]-1H-indol-3-yl]carbonyl]-L-phenylalanine 1,1-dimethylethyl ester | 422.8 3.61 (A) |
| 38 | 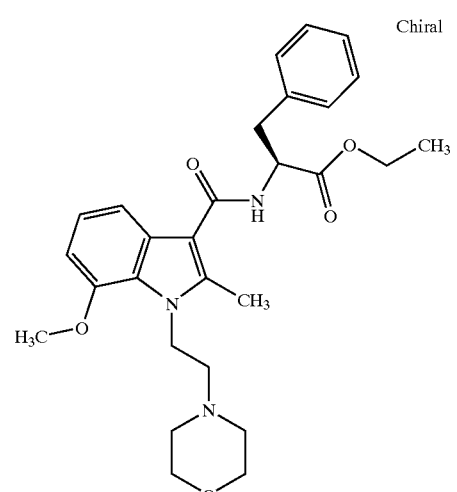 Chiral | N-[[7-Methoxy-2-methyl-1-[2-(4-morpholinyl)ethyl]-1H-indol-3-yl]carbonyl]-L-phenylalanine ethyl ester | 494.4 3.28 (A) |

TABLE 2-continued
| EX. NO. | STRUCTURE | COMPOUND NAME | DATA MS (M + H)/HPLC ret. t (min) and conditions |
|---|---|---|---|
| 39 | 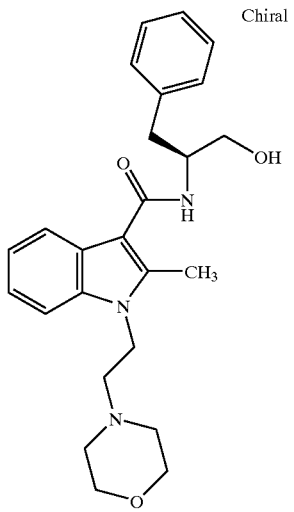 Chiral | (1S)-N-[1-(Hydroxymethyl)-2-phenylethyl]-2-methyl-1-[2-(4-morpholinyl)ethyl]-1H-indole-3-carboxamide | 422.31 2.60 (A) |
| 40 | 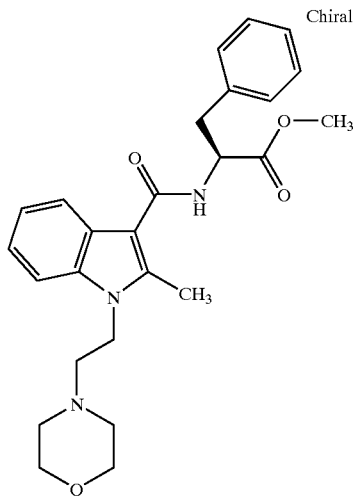 Chiral | N-[[2-Methyl-1-[2-(4-morpholinyl)ethyl]-1H-indol-3-yl]carbonyl]-L-phenylalanine methyl ester | 450.38 2.97 (A) |
| 41 | 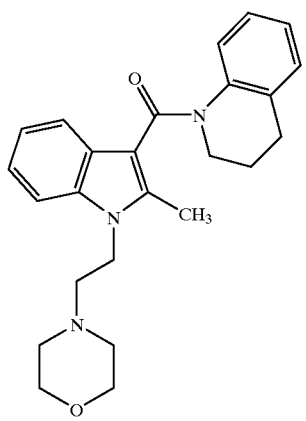 | 1,2,3,4-Tetrahydro-1-[[2-methyl-1-[2-(4-morpholinyl)ethyl]-1H-indol-3-yl]carbonyl]quinoline | 404.40 3.07 (A) |

TABLE 2-continued
| EX. NO. | STRUCTURE | COMPOUND NAME | DATA MS (M + H)/HPLC ret. t (min) and conditions |
|---|---|---|---|
| 42 | 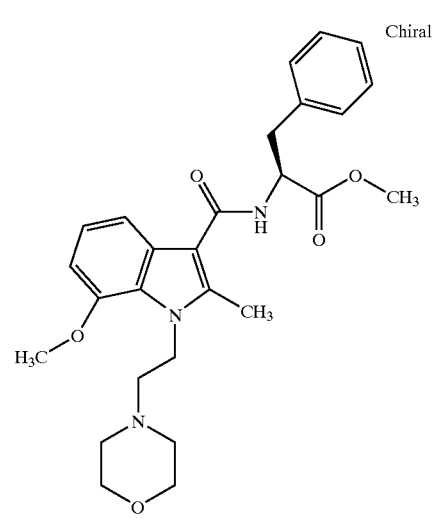 Chiral | N-[[7-Methoxy-2-methyl-1-[2-(4-morpholinyl)ethyl]-1H-indol-3-yl]carbonyl]-L-phenylalanine methyl ester | 480.39 3.05 (A) |
| 43 | 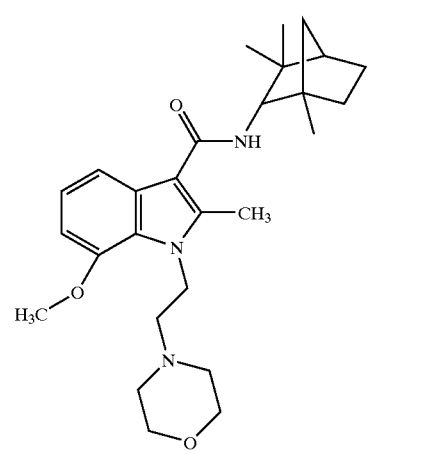 | 7-Methoxy-2-methyl-1-[2-(4-morpholinyl)ethyl]-N-(1,3,3-trimethyl-bicyclo[2.2.1]heptan-2-yl)-1H-indole-3-carboxamide | 455.51 3.80 (A) |
| 44 | 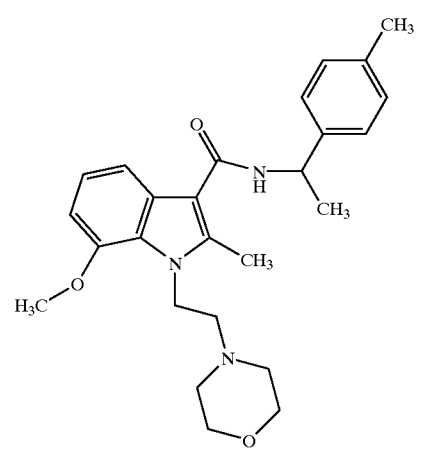 | 7-Methoxy-2-methyl-3-[1-(4-methylphenyl)ethyl]-1-[2-(4-morpholinyl)ethyl]-1H-indole-3-carboxamide | 437.4 3.26 (A) |

TABLE 2-continued

| EX. NO. | STRUCTURE | COMPOUND NAME | DATA MS (M + H)/HPLC ret. t (min) and conditions |
|---|---|---|---|
| 45 | 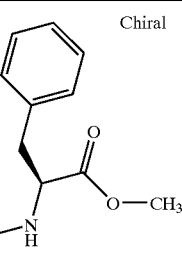 Chiral | N-[1-[2-(4-morpholinyl)ethyl]-1H-indazol-3-yl]carbonyl]-L-phenylalanine methyl ester | 436.5 (A) |
| 46 | 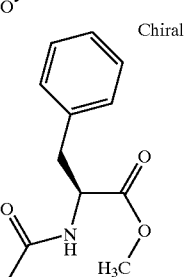 Chiral | N-[[7-benzyloxy-2-methyl-1-[2-(4-morpholinyl)ethyl]-1H-indol-3-yl]carbonyl]-L-phenylalanine methyl ester | 555.7 3.60 (A) |
| 47 | 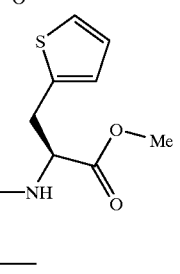 | (αS)-α-[[[7-Methoxy-2-methyl-1-[2-(4-morpholinyl)ethyl]-1H-indol-3-yl]carbonyl]amino]-2-thiophenepropanoic acid methyl ester | 486.5 3.00 (A) |

TABLE 2-continued

| EX. NO. | STRUCTURE | COMPOUND NAME | DATA MS (M + H)/HPLC ret. t (min) and conditions |
|---|---|---|---|
| 48 | 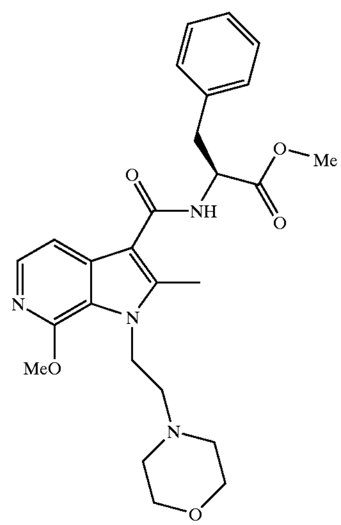 | N-[[7-Methoxy-2-methyl-1-[2-(4-morpholinyl)ethyl]-6-aza-1H-indol-3-yl]carbonyl]-L-phenylalanine methyl ester | 480.6 2.58 (A) |
| 49 | Chiral | N-[[7-Methoxy-1-[2-(4-morpholinyl)ethyl]-1H-indazol-3-yl]carbonyl]-L-phenylalanine methyl ester | 466.5 (A) |
| 50 | 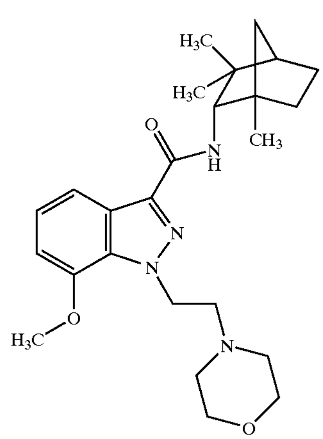 | 7-Methoxy-1-[2-(4-morpholinyl)ethyl]-N-(1,3,3-trimethylbicyclo[2.2.1]heptan-2-yl)-1H-indazol-3-carboxamide | 440.6 (A) |

TABLE 2-continued

| EX. NO. | STRUCTURE | COMPOUND NAME | DATA MS (M + H)/HPLC ret. t (min) and conditions |
|---|---|---|---|
| 51 | 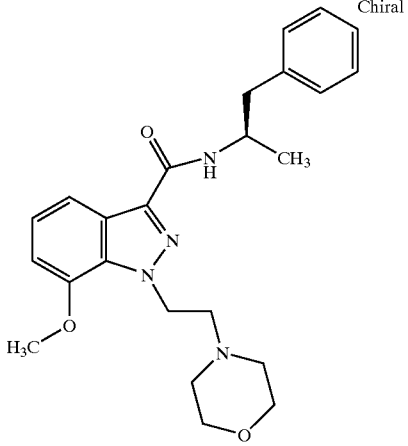 Chiral | N-[[7-Methoxy-1-[2-(4-morpholinyl)ethyl]-1H-indazol-3-yl]carbonyl]-R-amphetamide | 422.5 (A) |
| 52 | 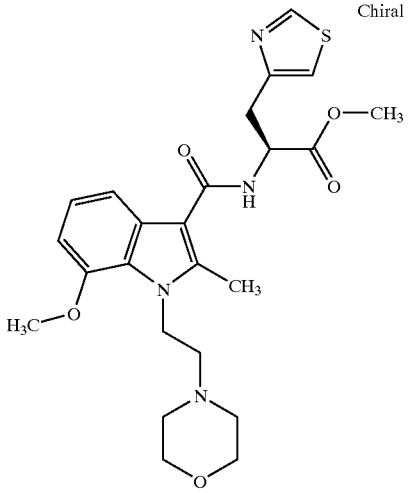 Chiral | (αS)-α-[[[7-Methoxy-2-methyl-1-[2-(4-morpholinyl)ethyl]-1H-indol-3-yl]carbonyl]amino]-2-thiazolepropanoic acid methyl ester | 487.2 2.44 (A) |
| 53 | 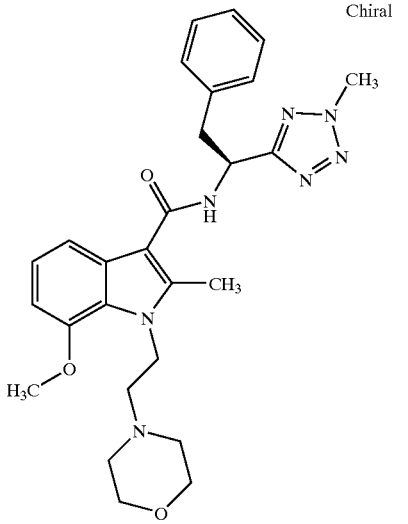 Chiral | 7-Methoxy-2-methyl-N-[(1S)-1-(3-methyl)-tetrazolyl)-2-phenylethyl]-1-[2-(4-morpholinyl)ethyl]-1H-indole-3-carboxamide and 7-Methoxy-2-methyl-N-[(1S)-1-(2-methyl)-tetrazolyl)-2-phenylethyl]-1-[2-(4-morpholinyl)ethyl]-1H-indole-3-carboxamide (1:1 mixture) | 503.6 (A) |

TABLE 2-continued

| EX. NO. | STRUCTURE | COMPOUND NAME | DATA MS (M + H)/HPLC ret. t (min) and conditions |
|---|---|---|---|
| 54 | 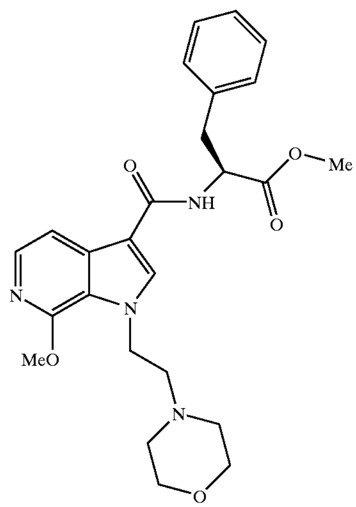 | N-[[7-Methoxy-1-[2-(4-morpholinyl)ethyl]-1H-indol-3-yl]carbonyl]-L-phenylalanine methyl ester | 465.6 (A) |
| 55 | 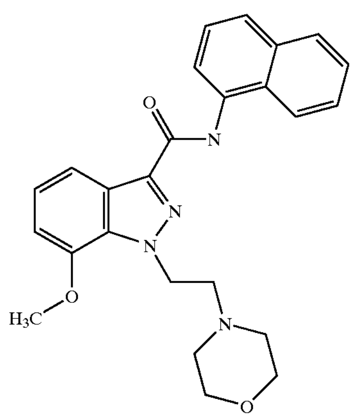 | N-[[7-Methoxy-1-[2-(4-morpholinyl)ethyl]-1H-indazol-3-yl]carbonyl]-1-naphthyl amide | 430.5 (A) |
| 56 | 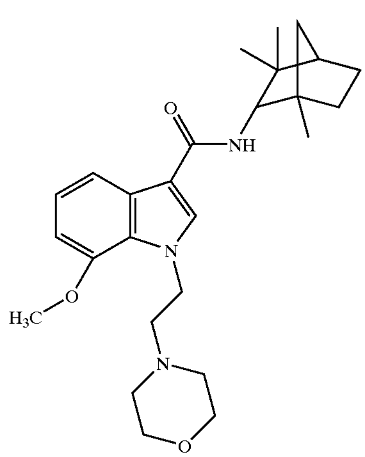 | 7-Methoxy-1-[2-(4-morpholinyl)ethyl]-N-(1,3,3-trimethylbicyclo[2.2.1]heptan-2-yl)-1H-indole-3-carboxamide | 439.6 (A) |

TABLE 2-continued

| EX. NO. | STRUCTURE | COMPOUND NAME | DATA MS (M + H)/HPLC ret. t (min) and conditions |
|---|---|---|---|
| 57 | 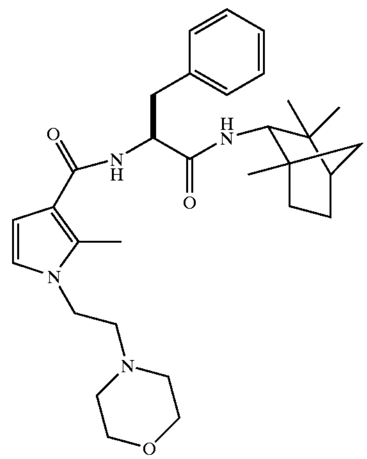 | 2-Methyl-1-[2-(4-morpholinyl)ethyl]-N-(1,3,3-trimethylbicyclo[2.2.1]heptan-2-yl)-1H-pyrrole-3-carboxamide | 374.41<br>3.28 (A) |
| 58 | 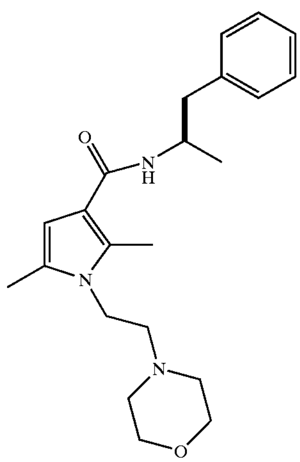 | 2,5-Dimethyl-N-[(1R)-1-methyl-2-phenylethyl]-1-[2-(4-morpholinyl)ethyl]-1H-pyrrole-3-carboxamide | 370.28<br>2.64 (A) |
| 59 | 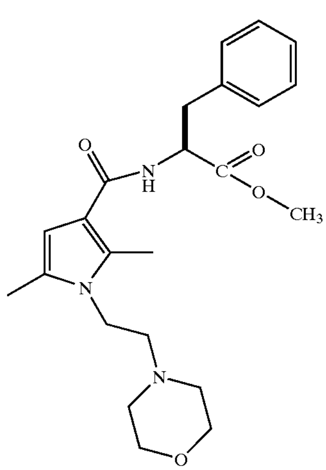 | N-[[2,5-Dimethyl-1-[2-(4-morpholinyl)ethyl]-1H-pyrrol-3-yl]carbonyl]-L-phenylalanine methyl ester | 414.26<br>2.49 (A) |

TABLE 2-continued

| EX. NO. | STRUCTURE | COMPOUND NAME | DATA MS (M + H)/HPLC ret. t (min) and conditions |
|---|---|---|---|
| 60 | 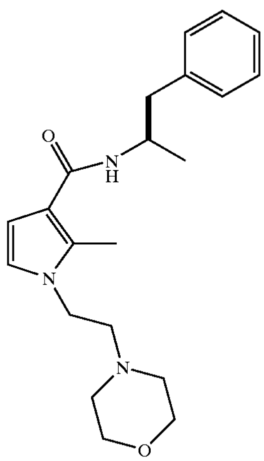 | 2-Methyl-N-[(1R)-1-methyl-2-phenylethyl]-1-[2-(4-morpholinyl)ethyl]-1H-pyrrole-3-carboxamide | 356.31 2.46 (A) |
| 61 | 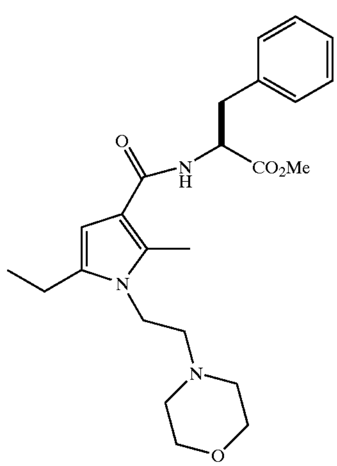 | N-[[5-Ethyl-2-methyl-1-[2-(4-morpholinyl)ethyl]-1H-pyrrol-3-yl]carbonyl]-L-phenylalanine methyl ester | 428.29 2.88 (A) |
| 62 | 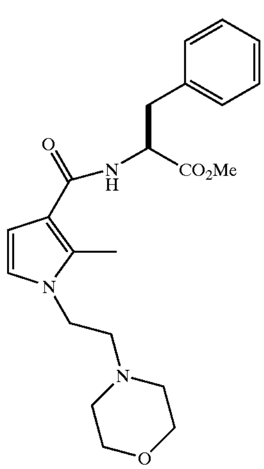 | N-[[2-Methyl-1-[2-(4-morpholinyl)ethyl]-1H-pyrrol-3-yl]carbonyl]-L-phenylalanine methyl ester | 400.28 2.48 (A) |

TABLE 2-continued
| EX. NO. | STRUCTURE | COMPOUND NAME | DATA MS (M + H)/HPLC ret. t (min) and conditions |
|---|---|---|---|
| 63 | 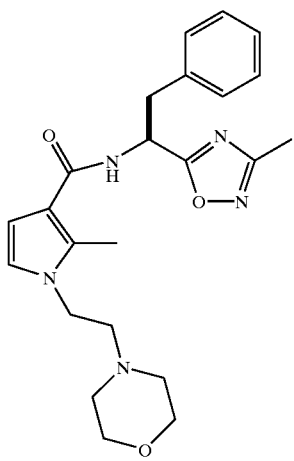 | 2-Methyl-N-[(1S)-1-(3-methyl-1,2,4-oxadiazol-5-yl)-2-phenylethyl]-1-[2-(4-morpholinyl)ethyl-1H-pyrrole-3-carboxamide | 504.35 3.10 (A) |
| 64 | 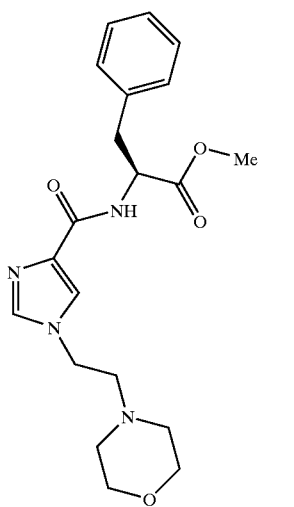 | N-[[1-[2-(4-Morpholinyl)ethyl]-1H-imidazol-4-yl]carbonyl]-L-phenylalanine methyl ester | 387.30 2.33 (A) |
| 65 | 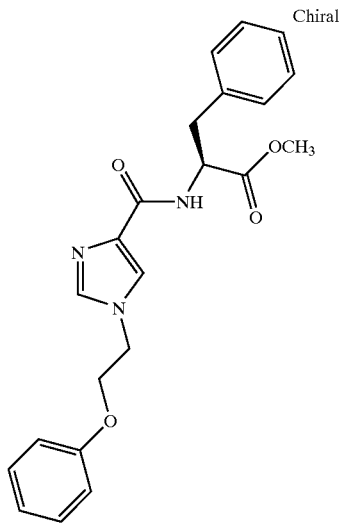 | N-[[1-(2-Phenoxyethyl)-1H-imidazol-4-yl]carbonyl]-L-phenylalanine methyl ester | 394.25 2.87 (B) |

TABLE 2-continued

| EX. NO. | STRUCTURE | COMPOUND NAME | DATA MS (M + H)/HPLC ret. t (min) and conditions |
|---|---|---|---|
| 66 | 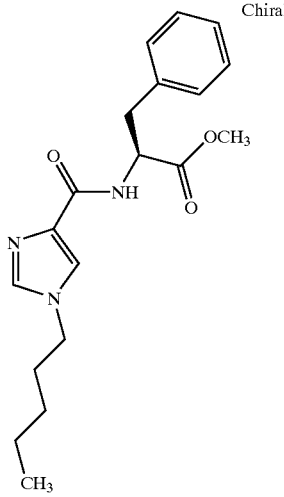 | N-[(1-Pentyl-1H-imidazol-4-yl)carbonyl]-L-phenylalanine methyl ester | 344.29<br>3.39 (A) |

Example 67

(R)-1-(3-Methyl-[1,2,4]oxadiazol-5-yl)-2-phenylethylamine

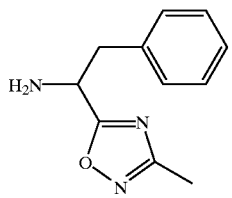

A. (R)-[1-(3-methyl-[1,2,4]oxadiazol-5-yl)-2-phenylethyl]carbamic acid tertbutyl ester To a solution of N-Boc-L-phenylalanine (2.0 g, 7.5 mmol) in CH₂Cl₂ (20 mL) at 0° C. was added DCC (780 mg, 3.8 mmol) in CH₂Cl₂ (20 mL) via cannula. The reaction mixture was stirred for 1 h, the precipitate filtered off, and the filtrate concentrated to dryness. Acetamidoxime (195 mg, 2.64 mmol) and pyridine (20 mL) were added and the reaction mixture heated at reflux for 1.5 h and then at RT for 16 h. The reaction mixture was poured into EtOAc (50 mL) and washed with 10% citric acid (3×25 mL). The organic layer was dried over Na₂SO₄, filtered, and concentrated in vacuo. Purification by column chromatography (25% EtOAc/hex) furnished (R)-[1-(3-methyl-[1,2,4]oxadiazol-5-yl)-2-phenylethyl]carbamic acid tertbutyl ester (790 mg, 99% yield). 304.22, M+H.

B. (R)-1-(3-methyl-[1,2,4]oxadiazol-5-yl)-2-phenylethylamine

To the carbamate from step A was added 4 N HCl in dry dioxane (10 mL) and the mixture was stirred for 4 h. The reaction mixture was concentrated to dryness, dissolved in 10% HCl (100 mL) and washed with CH₂Cl₂ (2×50 mL). The aqueous layer was made basic with 3N NaOH and extracted with CH₂Cl₂ (3×50 mL). The combined organic extracts were dried over Na₂SO₄, filtered, and concentrated in vacuo to give the above-titled Example 67 (506 mg, 94% yield). 204.18, M+H.

Example 68

4-Methyl-2-[[1-phenyl-2-L-amino]ethyl]oxazole

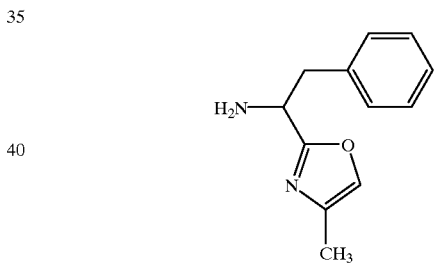

A. CBZ-L-Phenyl alanyl-1-amino-2-propanol

CBZ-L-Phenyl alanine (1 mmol, 300 mg), BOP reagent (1.5 mmol, 660 mg), NMM (5 mmol, 570 mg) and 1-amino-2-propanol (1.5 mmol, 113 mg) were mixed in 20 ml DMF. The mixture was stirred and heated to 50° C. overnight, quenched with EtOAc (30 ml), washed with NaHCO₃ (aq. Sat.), NaHSO₄ (aq, Sat.) and water, and dried over MgSO₄ to give 330 mg of the above-titled compound A.

B. CBZ-L-Phenyl alanyl-1-amino-2-oxo-propane 0.2 M COCl₂ in CH₂Cl₂ was added into 5 ml methylene chloride and cooled to −78° C., then 0.5 ml DMSO was added dropwise and the mixture was stirred for 0.5 h at −78° C. 330 mg crude product from step A dissolved in 2 ml DMSO and 4 ml methylene chloride were added, and the reaction mixture was stirred for one hour at −78° C., then stirred at RT for one hour. The mixture was added into 20 ml methylene chloride, washed with NaHCO₃ and NaHSO₄ and water, dried over MgSO₄, and the solvent was evaporated to give 340 mg of the above-titled compound B as a crude product.

C. 4-Methyl-2-[[1-phenyl-2-(CBZ)-L-amino]ethyl]oxazole

Compound B was dissolved in POCl₃ (10 ml), and the mixture was stirred at RT under N₂ overnight. The reaction mixture was carefully poured into iced 1N NaOH solution, extracted with EtOAC, washed with brine, dried over MgSO₄, and the solvent evaporated to give 312 mg of crude compound C.

D. 4-Methyl-2-[[1-phenyl-2-L-amino]ethyl]oxazole 312 mg of compound C was dissolved in MeOH followed by hydrogenation by 10% Pd/C as a catalyst at RT overnight. The mixture was filtered and evaporated. The crude product was purified by cation exchange resin to give 100 mg of compound D (Example 68) as a yellow oil.

Example 69

4-[[1-Phenyl-2-L-amino]ethyl]oxazole

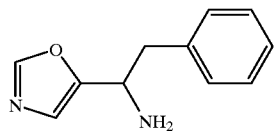

A solution of trimethylsilylmethyl isocyanide (500 mg, 4.4 mmol) was cooled to −78° C. in N₂. N-BuLi(1.6 M, 2.9 ml, 4.6 mmol) was added over 10 min, the mixture was stirred for 15 min at −78° C., and a solution of Boc-L-phenylalanine (490 mg, 1.80 mmol) in THF (2 mL) was introduced over 10 min. Stirring was continued at −78° C. for 10 min and the reaction was warmed to 0° C. for 15 min. After AcOH (0.26 ml, 4.6 mmol) was added, it was concentrated to give 4-[[1-Phenyl-2-L-amino]ethyl]oxazole (crude, 300 mg). This compound was dissolved in methylene chloride (5 ml), 4N HCl in 4 ml dioxane was added, and the mixture was stirred at RT for 3 h. Evaporation of the solvent, methylene chloride addition, and evaporation gave the above-titled compound (100 mg, HCl form).

Example 70

1-[2-Phenyl-1-L-amino]ethyl-2-methyl tetrazole and 1-[2-Phenyl-1-L-amino]ethyl-3-methyl tetrazole
(1:1)

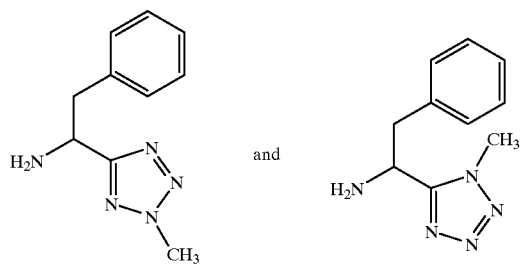

A. Boc-L-Phenylalanyl amide i-Butylchloroformate (0.66 ml, 5 mmol) was added to a solution of Boc-phenylalanine (1.38 g, 5 mmol) and NMM (0.55 ml, 5 mmol) in 25 ml of methylene chloride at −20° C. After stirring for 20 min. at −20° C., 25 ml of 2M ammonia/MeOH was added. After 5 min., the reaction mixture was partitioned between EtOAc (100 ml) and water (100 ml). The organic layer was washed with saturated KHSO₄ solution (100 ml), water (100 ml), saturated NaHCO₃ solution (100 ml) and brine (100 ml). Drying (over MgSO₄) and concentration afforded 1.33 g (99%) of product A as a white solid.

B. [[2-Phenyl-1-L-(tert-butyloxy)amino]ethyl]nitrile

A mixture of compound A (1.30 g, 4.9 mmol) and (methoxycarbonylsulfamoyl)-triethylammonium hydroxide, inner salt (1.7 g, 7.4 mmol) in 50 ml of THF was stirred 1 hr at RT. After removing the THF in vacuo, the residue was filtered through a 5×5 cm plug of silica gel and washed with EtOAc:Hex (1:1). The filtrate was concentrated to afford 1.19 g (99%) of compound B as a white solid.

C. 1-[[2-Phenyl-1-L-(tert-butyloxy)amino]ethyl]-tetrazole

To a cooled (−78° C.) solution of 1.8M diethylaluminum chloride in toluene (8.6 ml, 15 mmol) was added dropwise over 15 min. a solution of compound B (1.19 g, 4.8 mmol) and azidotrimethylsilane (2.4 ml, 17 mmol) in 20 ml of methylene chloride. After slowly warming to RT, the reaction mixture was stirred for 18 hr. 5% AcOH/MeOH (30 ml) was added in small portions with caution to quench the reaction mixture. After addition was complete, the resulting mixture was partitioned between EtOAc (150 ml) and water (150 ml). The organic layer was washed with water (150 ml) and brine (150 ml). Drying (over MgSO₄) and concentration afforded 884 mg (64%) of compound C as a white powder.

D. 3 and 2-Methyl-1-[[2-phenyl-1-L-(tert-butyloxy)amino]ethyl]-tetrazole

A mixture of compound C (400 mg, 1.4 mmol), K₂CO₃ (250 mg, 1.8 mmol) and iodomethane (256 mg, 1.8 mmol) in 2 ml of DMF was stirred for 3 h at RT. After partitioning the reaction mixture between EtOAc (100 ml) and water (100 ml), the organic layer was washed with water (2×100 ml) and brine (100 ml). Drying (MgSO₄) and concentration afforded 405 mg (96%) of D, a 1:1 mixture of the above-titled compounds as a light yellow solid.

E. 1-[2-phenyl-1-L-amino]ethyl-2 and 3-methyl tetrazole

A mixture of D (400 mg, 1.3 mmol) and 4N HCl/dioxane (3 ml; 12 mmol) in 10 ml of EtOAc was stirred for 18 hr at RT. Concentration and trituration with ethyl ether afforded 300 mg (96%) of a 1:1 mixture of the compounds of Example 70 as the hydrochloride salt.

Example 71

(3S)-2,3-Dihydro-5-methyl-3-(4-morpholinylmethyl)-N-pyrrolo [1,2,3-de]-1,4-benzoxazine-6-carboxylic acid chloride

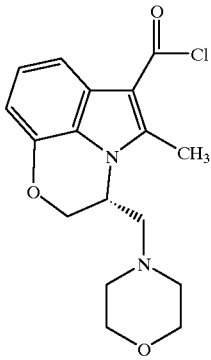

A. 2-Methyl-7-hydroxyindole

To 2-methyl-7-methoxyindole (5 g, 34 mmol) in CH$_2$Cl$_2$ (100 mL) cooled in an ice bath was slowly added neat BBr$_3$ (9.5 mL, 100 mmol). The reaction mixture was allowed to warm to RT and then stirred for an additional 12 h. After cooling to −10° C., the reaction was quenched by the addition of MeOH (32 mL) and the solvent removed in vacuo. The residue was triturated with Et$_2$O and filtered to give 6.86 g (95%) of compound A as light brown solid as the HBr salt. HPLC ret. t: 2.7 min (A).

B. 2-Methyl-7-((R)-2,3-oxo)propyloxy indole

To compound A (2.8 g, 20 mmol) in THF (40 mL) cooled to 0° C. was added freshly distilled (R)-(+)-glycidol (2.7 mL, 41 mmol) and PPh$_3$ (12 g, 45 mmol) followed by slow addition of DEAD (7.4 mL, 47.0 mmol). The reaction was allowed to warm to RT and stirred for an additional 12 h, then the solvent was removed in vacuo and the crude mixture purified by column chromatography to give 1.74 g (42.4%) of compound B as a thick oil. HPLC ret. t: 3.3 min. Compound B also was obtained by reaction of compound A in EtOH with (R)-(−)-epichlorohydrin using K$_2$CO$_3$ as base at 40° C. to give 73% of product B after purification.

C. 2-Methyl-7-(3-morpholino-2-(S)-hydroxy)propyloxyindole

To compound B (1.7 g, 8.6 mmol) in THF (5 mL) was added morpholine (8 mL) and the mixture heated to 60° C. for 1.5 h. After cooling to RT, water was added and extracted with EtOAc. The EtOAc was washed with saturated NaCl and dried over MgSO$_4$. The solvent was removed in vacuo to a small volume and the product was crystallized with addition of Et$_2$O. Filtration gave 1.65 g (67%) of compound C as a pale solid. HPLC ret. t: 2.31 min (A).

D. 2-Methyl-7-[3-morpholino-2(S)-(methylsulfonyl))propyloxyindole

To compound C (1.6 g, 5.48 mmol) in CH$_2$Cl$_2$ (30 mL) cooled to 0° C. was added TEA (1.5 mL, 11 mmol) followed by slow addition of methanesulfonyl chloride (0.6 mL, 6.0 mmol). The reaction was stirred at 0° C. for 0.5 h, then added to ice cold water and extracted with CH$_2$Cl$_2$. The organic layer was washed with saturated NaCl then dried over MgSO$_4$. The solvent was removed in vacuo, then anhydrous THF was added and removed in vacuo 2 times. The crude material was used immediately in the next step with no further purification. HPLC ret. t: 2.6 min (A).

E. (3S)-2,3-Dihydro-5-methyl-3-(4-morpholinylmethyl)-N-pyrrolo[1,2,3-de]-1,4-benzoxazine To NaH (400 mg, 17 mmol) in anhydrous THF (50 mL) cooled in an ice bath was added crude compound D in THF (50 mL) followed by the addition of DMF (20 mL). The reaction was allowed to slowly warm to RT then stirred for an additional 1 h. The reaction mixture was cooled in an ice bath, then quenched with HOAc and the solvent removed in vacuo. Water was added to the residue which was neutralized with NaOH then filtered to give 1.3 g (86.5%, 94.96% ee by chiral HPLC) of compound E as a crystalline solid. HPLC ret. t: 2.207 min (A).

F. (3S)-2,3-Dihydro-5-methyl-3-(4-morpholinylmethyl)-N-pyrrolo[1,2,3-de]-1,4-benzoxazine-6-trichloromethyl ketone To compound E (1.18 g, 4.33 mmol) in DCE (24 mL) was added trichloroacetyl chloride (1.45 mL, 13.0 mmol), and then the mixture was heated to reflux for 1.5 h. After the reaction was cooled in an ice bath, Et$_2$O was added and the precipitate collected by filtration to give 1.83 g (93%) of compound F as pale solid as the HCl salt. HPLC ret. t: 3.1 min (A).

G. (3S)-2,3-Dihydro-5-methyl-3-(4-morpholinylmethyl)-N-pyrrolo[1,2,3-de]-1,4-benzoxazine-6-carboxylic acid To compound F (1.8 g, 4.0 mmol) in THF (40 mL) was added NaOH (2.77 mL, 50% aq), and the mixture stirred at RT for 1 h. After the solvent was removed in vacuo, water was added and extracted with CH$_2$Cl$_2$. The aqueous layer was brought to pH 6 with HCl and the solid collected by filtration to give 0.97 g (76.5%) of compound G as a pale solid. HPLC ret. t: 1.96 min.

H. (3S)-2,3-Dihydro-5-methyl-3-(4-morpholinylmethyl)-N-pyrrolo[1,2,3-de]-1,4-benzoxazine-6-carboxylic acid chloride To compound G (0.35 g, 1.1 mmol) in CH$_2$Cl$_2$ (10 mL cooled in an ice bath) was slowly added oxalyl chloride (0.39 mL, 4.42 mmol) followed by 1 drop DMF. The reaction was allowed to warm to RT then stirred for an additional 0.5 h. Et$_2$O was added to precipitate the product as the HCl salt which was collected by filtration to give 410 mg (99.8%) of Example 71 as a light brown solid.

Examples 72–82

General Scheme for the Preparation of Tricyclic Amides

The compounds of Examples 72–82, wherein —NR$_1$R$_2$ have the values listed in Table 3, were prepared as follows. To Example 71 (40 mg, 0.11 mmol) in THF (0.7 mL) was added TEA (60 μL, 0.43 mmol) followed by the appropriate amine (25.6 mg, 0.118 mmol), and the mixture was stirred at RT for 1 h. The reaction was diluted with EtOAc and extracted with water. The EtOAc was dried over Na$_2$SO$_4$ and then the solvent removed in vacuo. The residue was dissolved in CH$_2$Cl$_2$ and 4N HCl in dioxane was added followed by Et$_2$O. The product was isolated by filtration as the HCl salt.

TABLE 3

| EXAMPLE NO. | —NR₁R2 | COMPOUND NAME | DATA MS (M + H⁺) |
|---|---|---|---|
| 72 | (2,2,6,6-tetramethylcyclohexyl)NH— | (3R)-2,3-Dihydro-5-methyl-3-(4-morpholinylmethyl)-N-(2,2,6,6-tetramethylcyclohexyl)pyrrolo[1,2,3-de]-1,4-benzoxazine-6-carboxamide | 454.39 |
| 73 | L-phenylalanine methyl ester NH— | N-[[(3R)-2,3-Dihydro-5-methyl-3-(4-morpholinylmethyl)pyrrolo[1,2,3-de]-1,4-benzoxazin-6-yl]carbonyl]-L-phenylalanine methyl ester | 478.33 |
| 74 | L-tyrosine methyl ester NH— | N-[[(3R)-2,3-Dihydro-5-methyl-3-(4-morpholinylmethyl)pyrrolo[1,2,3-de]-1,4-benzoxazin-6-yl]carbonyl]-L-tyrosine methyl ester | 494.31 |
| 75 | 2-(4-aminophenyl)ethyl-NH— | (3R)-N-[2-(4-Aminophenyl)ethyl]-2,3-dihydro-5-methyl-3-(4-morpholinylmethyl)pyrrolo[1,2,3-de-1,4-benzoxazine-6-carboxamide | 435.29 |
| 76 | (2,2-dimethylcyclopentyl)NH— | (3R)-N-(2,2-Dimethylcyclopentyl)-2,3-dihydro-5-methyl-3-(4-morpholinylmethyl)pyrrolo[1,2,3-de]-1,4-benzoxazine-6-carboxamide | 412.31 |
| 77 | [2-methyl-1-(1-methylethyl)propyl]NH— | (3R)-2,3-Dihydro-5-methyl-N-[2-methyl-1-(1-methylethyl)propyl]-3-(4-morpholinylmethyl)pyrrolo[1,2,3-de]-1,4-benzoxazine-6-carboxamide | 414.32 |

TABLE 3-continued

| EXAMPLE NO. | —NR₁R2 | COMPOUND NAME | DATA MS (M + H⁺) |
|---|---|---|---|
| 78 | [structure: H3C, CH3, H3C, O-CH3, NH, O] | N-[[(3R)-2,3-Dihydro-5-methyl-3-(4-morpholinylmethyl)pyrrolo[1,2,3-de]-1,4-benzoxazin-6-yl]carbonyl]-3-methyl-L-valine methyl ester | 444.32 |
| 79 | [structure: bicyclic with NHMe] | (3)-2,3-Dihydro-5-methyl-3-(4-morpholinylmethyl)-N-(1,3,3-trimethylbicyclo[2.2.1]heptan-2-yl)pyrrolo[1,2,3-de]-1,4-benzoxazine-6-carboxamide | 452.37 |

Examples 80–82

The following compounds were prepared following the procedure for Examples 72–79 except the (S)-(−)-glycidol 35 was utilized.

| EX. NO. | —NR₁R2 | COMPOUND NAME | DATA MS (M + H⁺) |
|---|---|---|---|
| 80 | [structure: phenylalanine methyl ester with NHMe] | N-[[(3S)-2,3-Dihydro-5-methyl-3-(4-morpholinylmethyl)pyrrolo[1,2,3-de]-1,4-benzoxazin-6-yl]carbonyl]-L-phenylalanine methyl ester | 478.34 |

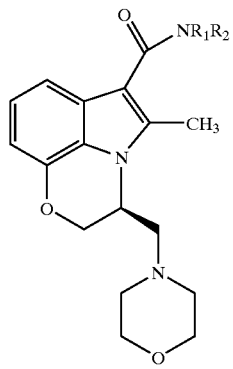

| EX. NO. | —NR₁R2 | COMPOUND NAME | DATA MS (M + H⁺) |
|---|---|---|---|
| 81 | H₃C, H₃C, CH₃, CH₃, NH | (3S)-2,3-Dihydro-5-methyl-3-(4-morpholinylmethyl)-N-(2,2,6,6-tetramethylcyclohexyl)pyrrolo[1,2,3-de]-1,4-benzoxazine-6-carboxamide | 454.39 |
| 82 | (bicyclic structure with NH) | (3S)-2,3-Dihydro-5-methyl-3-(4-morpholinylmethyl)-N-(1,3,3-trimethylbicyclo[2.2.1]heptan-2-yl)pyrrolo[1,2,3-de]-1,4-benzoxazine-6-carboxamide | 452.37 |

Example 83

2,3,4,5-Tetrahydro-6-methoxy-5-[2-(4-morpholinyl)ethyl]-2-[(1S,2S)-1,3,3-trimethylbicyclo[2.2.1]heptan-2-yl]-1H-pyrido[4,3-b]indol-1-one

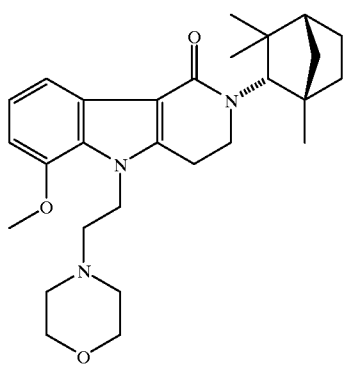

A. 3-[[(1S,2S)-1,3,3-Trimethylbicyclo[2.2.1]heptan-2-yl]amino]propanoic acid methyl ester

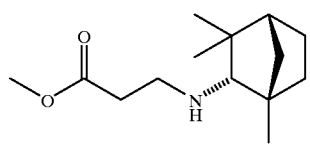

A solution of (S)-fenchyl amine.HCl (1.0 g, 5.32 mmol) in dry MeOH was cooled to 0° C. in a resealable tube. TEA (0.75 mL, 5.32 mmol) was added followed by methyl acrylate (0.527 mL, 5.9 mmol). The tube was sealed and the mixture stirred at RT for 5 days. The crude reaction mixture was concentrated in vacuo and used without further purification in the next step. 240.2 (M+H), ret. t: 1.35 min (B).

B. 3-Oxo-3-[(3-methoxy-3-oxopropyl)[(1S,2S)-1,3,3-trimethylbicyclo[2.2.1]heptan-2-yl]amino]propanoic acid ethyl ester

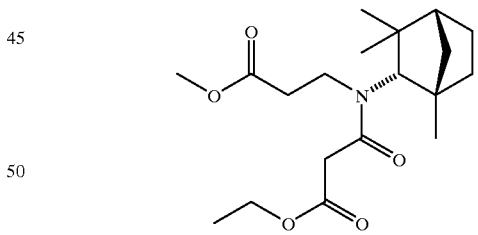

To a solution of the methyl ester from step A in $CH_2Cl_2$ (25 mL) at 0° C. was added TEA (1.11 mL, 8 mmol), followed slowly by ethyl 2-chloropropionate (0.84 mL, 5.85 mmol). The reaction vessel was allowed to warm to RT slowly. After 4 h, 15% $K_2CO_3$ (6 mL) was added and the reaction stirred rapidly for 15 min. The layers were separated and the organic layer washed with 1N HCl (15 mL). The organic layer was dried over $Na_2SO_4$, filtered, and concentrated in vacuo to an oil. The residue was purified by column chromatography (20% EtOAc/hex then 50% EtOAc/hex) to furnish the above compound B as a clear oil (1.15 g, 62% yield overall). 353.2 (M+H), ret. t.: 3.96 min (A).

C. 1-[(1S,2S)-1,3,3-Trimethylbicyclo[2.2.1]heptan-2-yl]-2,4-piperidinedione

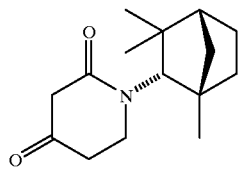

A suspension of NaH (130 mg, 60% in oil) in cyclohexane (7 mL) was heated at reflux. A solution of the ethyl ester from step B (500 mg, 1.41 mmol) in toluene (1 mL) was added dropwise via syringe over 1 h. The reaction mixture was heated at reflux an additional 5 h, and then allowed to cool and stir overnight. The solid was filtered off and washed with hex (2 mL). The solid was then added to 10% AcOH (11.3 mL) and heated at reflux for 4 h. The reaction mixture was allowed to cool and neutralized to pH 7 with dilute NaHCO$_3$. The aqueous solution was extracted with CH$_2$Cl$_2$ (3×35 mL), combined, dried (Na$_2$SO$_4$), and concentrated in vacuo. The residue was purified by column chromatography (25% EtOAc/hex then 40% EtOAc/hex) to furnish the above compound C (177 mg, 50% yield). 250.2 (M+H), ret. t: 3.49 min (A).

D. 5,6-Dihydro-4-[(2-iodo-6-methoxyphenyl)amino]-1-[(1S,2S)-1,3,3-trimethylbicyclo[2.2.1]heptan-2-yl]-2(1H)-pyridinone

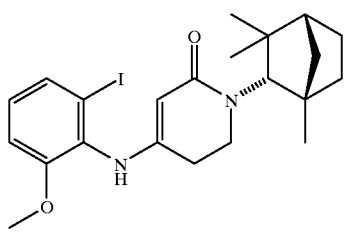

To a solution of 2-iodo-6-methoxy aniline and the ketone from step C in benzene (3 mL) was added TsOH.H$_2$O, and the mixture was heated at reflux with removal of water for 6 h. The reaction mixture was cooled, poured into EtOAc (40 mL), and washed with water (15 mL). The organic layer was dried (Na$_2$SO$_4$), filtered, and concentrated in vacuo. The residue was purified by column chromatography (25% EtOAc/hex then 50% EtOAc/hex) to furnish the above compound D (104 mg, 61% yield).

E. 2,3,4,5-Tetrahydro-6-methoxy-2-[(1S,2S)-1,3,3-trimethylbicyclo[2.2.1]heptan-2-yl]-1H-pyrido[4,3-b]indol-1-one

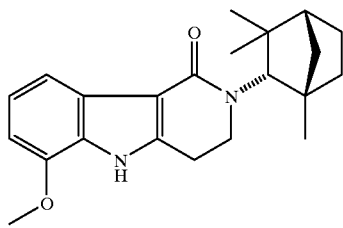

To the iodo-substituted pyridinone from step D (75 mg, 0.156 mmol) in a resealable tube was added 0.30 mL of a solution of Pd(OAc)$_2$ (20.1 mg, 0.089 mmol) and tri-ortho tolylphosphine (59 mg, 0.19 mmol) in DMF (0.89 mL). The mixture was degassed via three freeze pump thaw cycles, TEA was added (0.044 mL, 0.312 mmol), and the tube was sealed under N$_2$. The reaction tube was heated to 120° C. for 6 h. The reaction tube was cooled, EtOAc was added (2 mL), and the mixture was stirred in open air for 1 h. The reaction was directly purified by column chromatography (105% EtOAc/hex then 33% EtOAc/hex) to furnish the above compound E (54 mg, 99% yield). 353.3 (M+H), ret. t: 3.65 min (A).

F. 2,3,4,5-Tetrahydro-6-methoxy-5-[2-(4-morpholinyl)ethyl]-2-[(1S,2S)-1,3,3-trimethylbicyclo[2.2.1]heptan-2-yl]-1H-pyrido[4,3-b]indol-1-one To a solution of the indole from step E (15 mg, 0.042 mmol) in DMF (0.25 mL) was added 2-chloroethyl morpholine.HCl (9.5 mg, 0.051 mmol) and NaH (5.2 mg, 60% in oil), and the reaction was heated to 60° C. overnight. The reaction was cooled to RT, and water (2 mL) was added dropwise. The solids were collected to yield the above-titled compound (Example 83) (>98% purity, HPLC) (16.5 mg, 83% yield). 466.5 (M+H), ret. t: 3.46 min (A). (See also Example 2, step A).

Example 84

N-Ethyl-5-fluoro-7-methoxy-2-methyl-1-[2-(4-morpholinyl)ethyl]-1H-indole-3-carboxamide

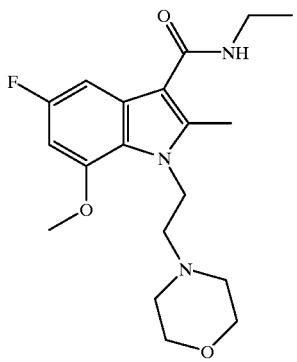

A. 5-Fluoro-7-methoxy-2-methyl-1H-indole-3-carboxylic acid methyl ester

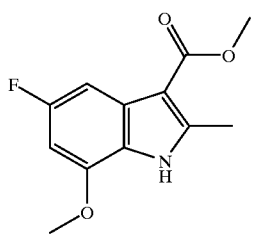

The above compound A was prepared from 2-bromo-4-fluoro-6-methoxy aniline and methyl acetoacetate according to the general procedure described above for Example 83, steps D and E. 238.0 (M+H), ret t: 3.64 min (A).

B. 5-Fluoro-7-methoxy-2-methyl-1-[2-(4-morpholinyl) ethyl]-1H-indole-3-carboxylic acid

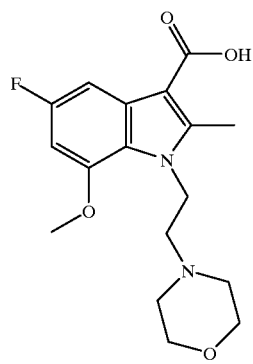

The above compound B was prepared according to the procedure in Example 2, steps A and B. 337.2 (M+H), rt 1.74 (A). The compound of Example 84 was then prepared from compound B according to the procedure described above for Examples 3–12. 364.3 (M+H), ret. t: 1.39 min (A).

Examples 85–108

Compounds of Examples 85–108 as shown in Table 5 were prepared following the same or similar procedure as described for Example 84.

TABLE 5

| EX. NO. | STRUCTURE | COMPOUND NAME | DATA (M + H)/HPLC ret. t. (min.) and conditions |
|---|---|---|---|
| 85 | 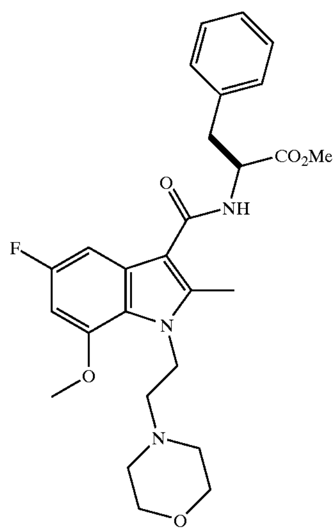 | N-[[5-Fluoro-7-methoxy-2-methyl-1-[2-(4-morpholinyl)ethyl]-1H-indol-3-yl]carbonyl]-L-phenylalanine methyl ester | 498.2/325 (A) |
| 86 | 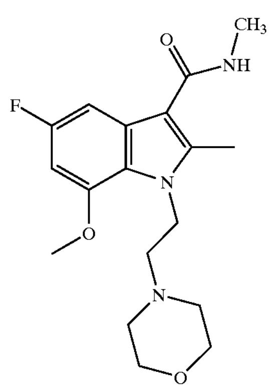 | 5-Fluoro-7-methoxy-N,2-dimethyl-1-[2-(4-morpholinyl)ethyl]-1H-indole-3-carboxamide | 350.3/0.89 (B) |

TABLE 5-continued

| EX. NO. | STRUCTURE | COMPOUND NAME | DATA (M + H)/HPLC ret. t. (min.) and conditions |
|---|---|---|---|
| 87 | 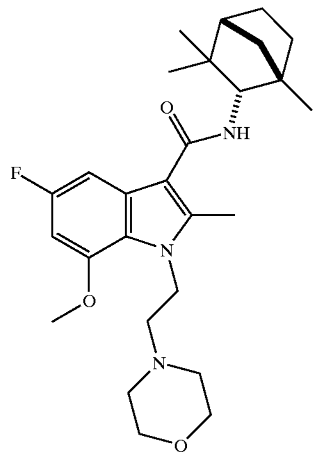 | 5-Fluoro-7-methoxy-2-methyl-1-[2-(4-morpholinyl)ethyl]-N-[(1S,2S)-1,3,3-trimethylbicyclo[2.2.1]heptan-2-yl]-1H-indole-2-carboxamide | 472.4/3.22 (A) |
| 88 | 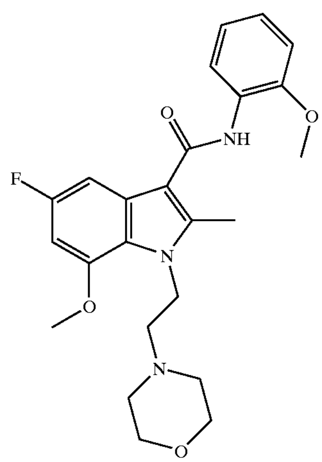 | 5-Fluoro-7-methoxy-N-(2-methoxyphenyl)-2-methyl-1-[2-(4-morpholinyl)ethyl]-1H-indole-3-carboxamide | 442.3/2.63 (A) |
| 89 | 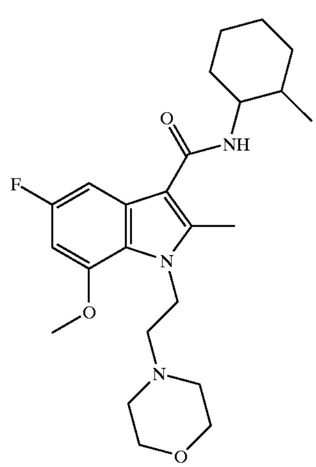 | 5-Fluoro-7-methoxy-2-methyl-N-(2-methylcyclohexanyl)-1-[2-(4-morpholinyl)ethyl]-1H-indole-3-carboxamide | 432.3/1.63 (B) |

TABLE 5-continued

| EX. NO. | STRUCTURE | COMPOUND NAME | DATA (M + H)/HPLC ret. t. (min.) and conditions |
|---------|-----------|---------------|-------------------------------------------------|
| 90 | 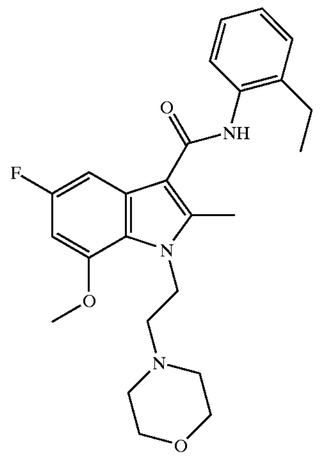 | N-(2-Ethylphenyl)-5-fluoro-7-methoxy-2-methyl-1-[2-(4-morpholinyl)ethyl]-1H-indole-3-carboxamide | 440.3/1.52 (B) |
| 99 | 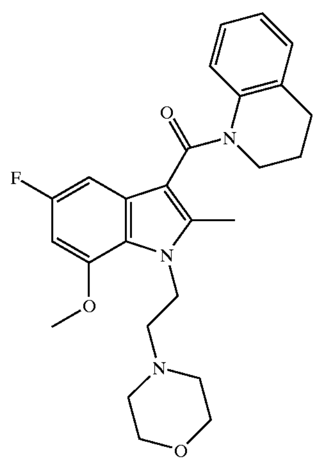 | 1-[[5-Fluoro-7-methoxy-2-methyl-1-[2-(4-morpholinyl)ethyl]-1H-indol-3-yl]carbonyl]-1,2,3,4-tetrahydroquinoline | 452.5/2.08 (A) |
| 100 | 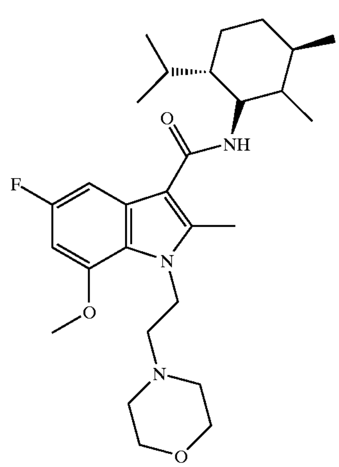 | 5-Fluoro-7-methoxy-2-methyl-N-[(1R,2S,5R)-5-methyl-2-(1-methylethyl)cyclohexanyl]-1-[2-(4-morpholinyl)ethyl]-1H-indole-3-carboxamide | 474.4/1.88 (B) |

TABLE 5-continued

| EX. NO. | STRUCTURE | COMPOUND NAME | DATA (M + H)/HPLC ret. t. (min.) and conditions |
|---|---|---|---|
| 101 | 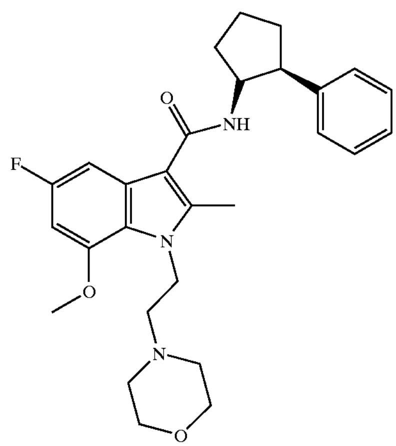 | 5-Fluoro-7-methoxy-2-methyl-1-[2-(4-morpholinyl)ethyl]-N-[(1S,2S)-2-phenylcyclopentyl]-1H-indole-3-carboxamide | 480.3 2.28 (A) |
| 102 | 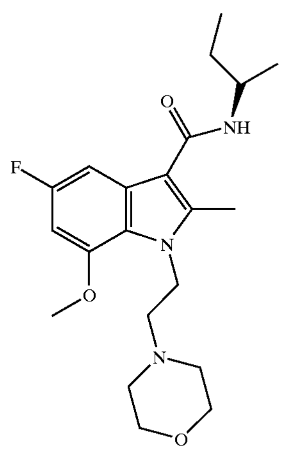 | 5-Fluoro-7-methoxy-2-methyl-N-[(1R)-1-methylpropyl]-1-[2-(4-morpholinyl)ethyl]-1H-indole-3-carboxamide | 392.3 1.24 (B) |
| 103 | 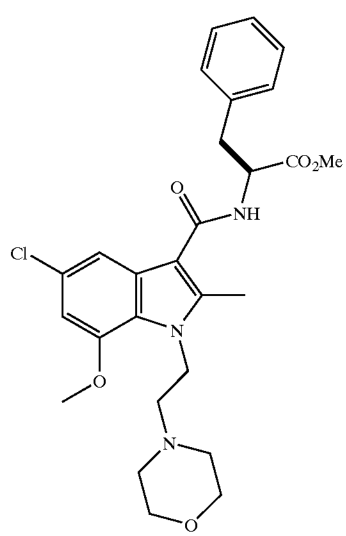 | N-[[5-Chloro-7-methoxy-2-methyl-1-[2-(4-morpholinyl)ethyl]-1H-indol-3-yl]carbonyl]-L-phenylalanine methyl ester | 514.3 3.35 (A) |

TABLE 5-continued

| EX. NO. | STRUCTURE | COMPOUND NAME | DATA (M + H)/HPLC ret. t. (min.) and conditions |
|---|---|---|---|
| 104 | 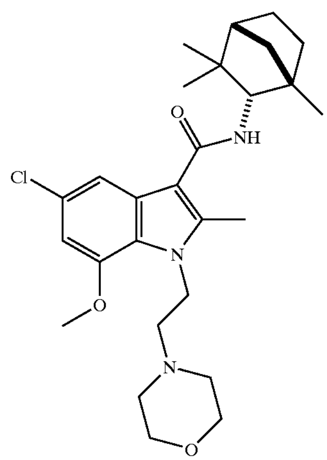 | 5-Chloro-7-methoxy-2-methyl-1-[2-(4-morpholinyl)ethyl]-N-[(1S,2S)-1,3,3-trimethylbicyclo[2.2.1]heptan-2-yl]-1H-indole-3-carboxamide | 488.4/4.00 (A) |
| 105 | 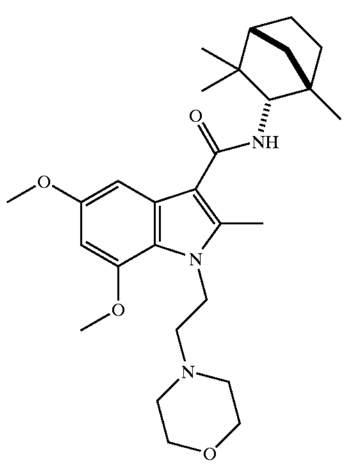 | 5,7-Dimethoxy-2-methyl-1-[2-(4-morpholinyl)ethyl]-N-[(1S,2S)-1,3,3-trimethylbicyclo[2.2.1]heptan-2-yl]-1H-indole-3-carboxamide | 484.4/2.46 (A) |
| 106 | 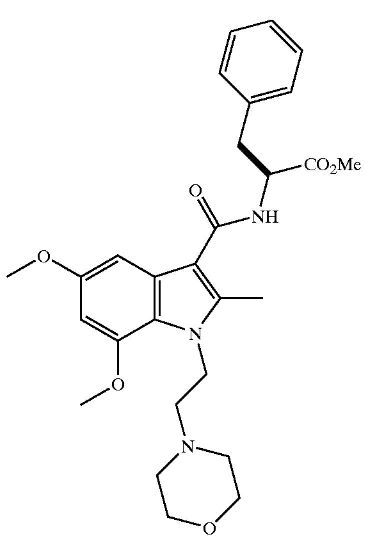 | N-[[5,7-Dimethoxy-2-methyl-1-[2-(4-morpholinyl)ethyl]-1H-indol-3-yl]carbonyl]-L-phenylalanine methyl ester | 510.3/3.79 (A) |

TABLE 5-continued

| EX. NO. | STRUCTURE | COMPOUND NAME | DATA (M + H)/HPLC ret. t. (min.) and conditions |
|---|---|---|---|
| 107 | 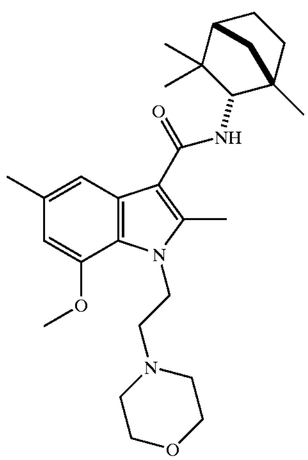 | 7-Methoxy-2,5-dimethyl-1-[2-(4-morpholinyl)ethyl]-N-[(1S,2S)-1,3,3-trimethylbicyclo[2.2.1]heptan-2-yl]-1H-indole-3-carboxamide | 468.4/3.52 (A) |
| 108 | 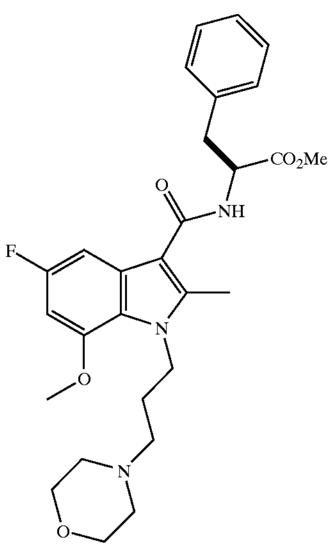 | 5-Fluoro-7-methoxy-2-methyl-1-[3-(4-morpholinyl)propyl]-N-[(1S,2S)-1,3,3-trimethylbicyclo[2.2.1]heptan-2-yl]-1H-indole-3-carboxamide | 486.4/3.34 (A) |

Example 109

6,7-Dihydro-7-(4-morpholinylmethyl)-N-[(1S,2S)-1,3,3-trimethylbicyclo[2.2.1]heptan-2-yl]-5H-pyrazolo[5,1-b][1,3]oxazine-2-carboxamide

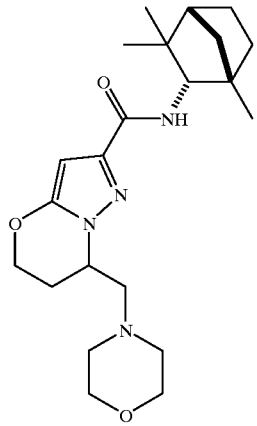

A. 5-(3-Butenyloxy)-1H-pyrazole-3-carboxylic acid ethyl ester

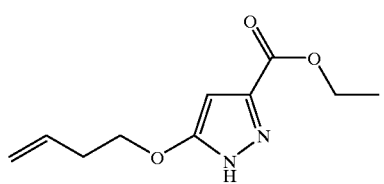

To a solution of ethyl 2-pyrazolin-5-one 3 carboxylate (537 mg, 3.43 mmol) and 4 bromo-1-butene (0.35 mL, 3.44 mmol) in MeCN (15 mL) was added $Cs_2CO_3$ (1.12 g, 3.44 mmol), and the reaction mixture was heated to 60° C. overnight. The reaction mixture was cooled and diluted with EtOAc (75 mL), and washed with water (2×35 mL) and brine (35 mL). The organic layer was dried ($Na_2SO_4$), filtered, and concentrated in vacuo to an oil. The residue was purified via column chromatography (10% EtOAc/hex then 25% EtOAc/hex) to furnish the alkylated product A (345 mg, 48% yield). 211.1 (M+H), ret. t: 3.49 min (A).

B. 6,7-Dihydro-7-(hydroxymethyl)-5H-pyrazolo[5,1-b][1,3]oxazine-2-carboxylic acid ethyl ester

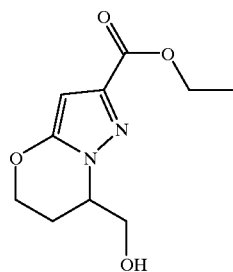

To a solution of the compound from step A (100 mg, 0.479 mmol) in $CH_2Cl_2$ (1 mL) at 0° C. was added m-CPBA (165 mg, 0.958 mmol), and the reaction mixture was allowed to warm to RT slowly. The reaction was stirred for 24 h and the diluted with $CH_2Cl_2$ (50 mL) and washed with dilute $NaHCO_3$ (1×20 mL). The aqueous layer was further extracted with $CH_2Cl_2$ (2×25 mL). The combined organic extracts were dried ($Na_2SO_4$), filtered, and concentrated in vacuo to an oil. The residue was purified via column chromatography (33% EtOAc/hex then 75% EtOAc/hex) to furnish the above compound B (56 mg, 52% yield). 227.1 (M+H), ret. t: 2.48 min (A).

C. 6,7-Dihydro-7-[[(methylsulfonyl)oxy]methyl]-5H-pyrazolo[5,1-b][1,3]oxazine-2-carboxylic acid ethyl ester

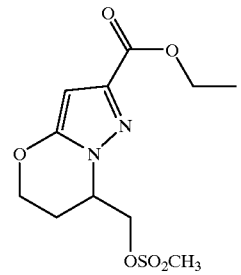

To a solution of the compound from step B (69 mg, 0.31 mmol) in $CH_2Cl_2$ (2 mL) was added methanesulfonyl chloride (0.036 mL, 0.46 mmol) and TEA (0.11 mL, 0.76 mmol), and the reaction mixture was stirred for 2 h. The reaction mixture was poured into $CH_2Cl_2$ (25 mL), washed with water (20 mL) and dried ($Na_2SO_4$). The organic extract was filtered and concentrated in vacuo to furnish the above crude ethyl ester C (92 mg, 99% yield). 305 (M+H), ret. t: 1.10 min (B).

D. 6,7-Dihydro-7-(4-morpholinylmethyl)-5H-pyrazolo[5,1-b][1,3]oxazine-2-carboxylic acid ethyl ester

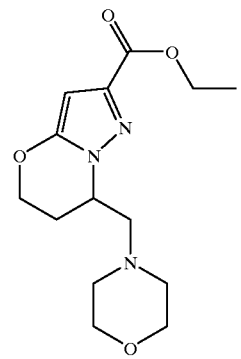

To the compound from step C (95 mg, 0.31 mmol) in dry THF (0.5 mL) was added morpholine (0.133 mL, 1.52 mmol) and the reaction was heated at reflux overnight. The reaction mixture was concentrated and purified directly by column chromatography (50% EtOAc/hex then 2% MeOH/$CH_2Cl_2$) to afford the above compound D (83 mg, 93% yield). 296.3 (M+H).

E. 6,7-Dihydro-7-(4-morpholinylmethyl)-5H-pyrazolo[5,1-b][1,3]oxazine-2-carboxylic acid

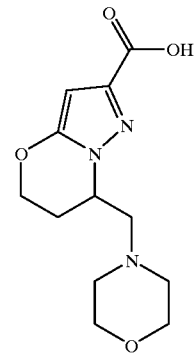

To a solution of the ester from step D (83 mg, 0.28 mmol) in McOH (0.6 mL) was added 3N NaOH (0.2 mL), and the reaction mixture was heated at reflux for 40 min. The reaction was cooled to RT and stirred overnight. The crude acid was purified via column chromatography (5% MeOH/CH$_2$Cl$_2$ then 20% MeOH/CHCl$_3$ saturated with NH$_3$). The product fractions were collected and concentrated with water three times to give the above-titled free acid E (94 mg, 99% yield), ret. t: 0.93 min (A).

F. 6,7-Dihydro-7-(4-morpholinylmethyl)-N-[(1S,2S)-1,3,3-trimethylbicyclo[2.2.1]heptan-2-yl]-5H-pyrazolo[5,1-b][1,3]oxazine-2-carboxamide The acid of step E was converted to the above-titled carboxamide using the general procedure described above for Examples 17–66. 403.3 (M+H), ret. t: 1.73 min (B).

Example 110

(2S)-1-[[6,7-Dihydro-7-(4-morpholinylmethyl)-5H-pyrazolo[5,1-b][1,3]oxazin-2-yl]carbonyl]-2-(methoxymethyl)pyrrolidine

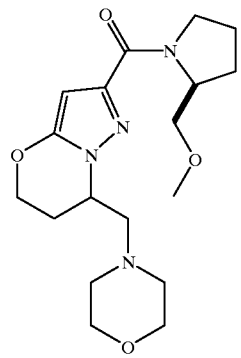

The above-titled compound was prepared using the procedure described for Example 109. 365.2 (M+H), ret. t: 1.48 min (B).

Example 111

N-[[7-Methoxy-2-methyl-1-[3-(4-morpholinyl)propyl]-1H-indol-3-yl]carbonyl]-L-phenylalanine methyl ester

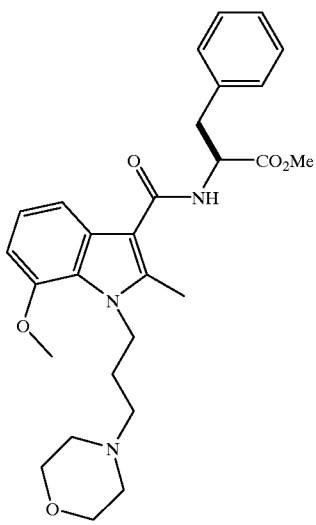

The above-titled compound was prepared following the procedure described for Example 13 using N-(3-chloropropyl)morpholine (Step F) followed by standard hydrolysis (Step H) and amide coupling (see procedure described for Examples 17–66). 494.3 (M+H), ret. t: 3.2 min (A).

Example 112

1-[2-(4-Morpholinyl)ethyl]-5-nitro-N-[(1S,2S)-1,3,3-trimethylbicyclo[2.2.1]heptan-2-yl]-1H-pyrazole-3-carboxamide (Isomer A), and 1-[2-(4-Morpholinyl)ethyl]-3-nitro-N-[(1S,2S)-1,3,3-trimethylbicyclo[2.2.1]heptan-2-yl]-1H-pyrazole-5-carboxamide (Isomer B)

(Isomer A)

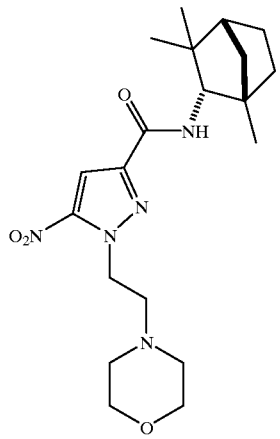

(Isomer B)

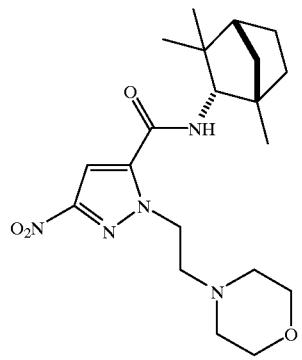

A. 5-Nitro-N-[(1S,2S)-1,3,3-trimethylbicyclo[2.2.1]heptan-2-yl]-1H-pyrazole-3-carboxamide

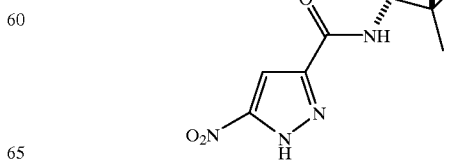

To 5-nitropyrazole-3-carboxylic acid (159 mg, 1.01 mmol) was added fenchylamine.HCl (226 mg, 1.2 mmol), EDC (249 mg, 1.3 mmol) and HOBT (176 mg, 1.3 mmol), in DMF (3 mL) and CH₂Cl₂ (3 mL) followed by DIPEA (0.53 mL, 3.0 mmol), and the reaction mixture was heated to 55° C. for 16 h. The reaction mixture was then cooled and water (25 mL) was added dropwise via addition funnel, and the mixture was stirred for 30 min. The solids were filtered off and purified by column chromatography (20% EtOAc/hex) to furnish compound A as a white solid (218 mg, 74% yield). 293.2 (M+H), ret. t: 3.2 min (A).

B. 1-[2-(4-Morpholinyl)ethyl]-5-nitro-N-[(1S,2S)-1,3,3-trimethylbicyclo[2.2.1]heptan-2-yl]-1H-pyrazole-3-carboxamide (Isomer A), and 1-[2-(4-Morpholinyl)ethyl]-3-nitro-N-[(1S,2S)-1,3,3-trimethylbicyclo[2.2.1]heptan-2-yl]-1H-pyrazole-5-carboxamide (Isomer B)

(Isomer A)

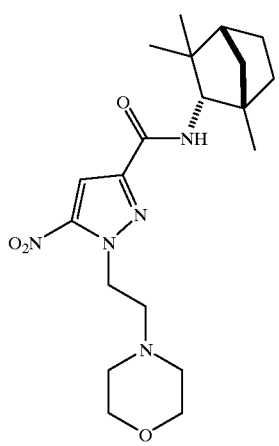

(Isomer B)

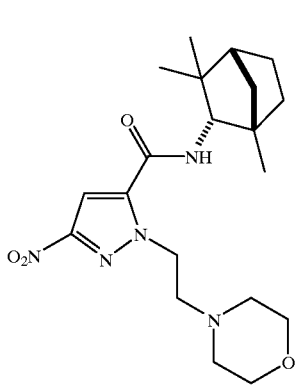

To a solution of the pyrazole-3-carboxamide from step A (111 mg, 0.38 mmol) in MeCN (5 mL) was added N-(2-chloroethyl)morpholine.HCl (92 mg, 0.49 mmol) and K₂CO₃ (157 mg, 1.13 mmol), and the reaction mixture was heated to 80° C. for 18 h. The reaction mixture was cooled and water was added (10 mL). After EtOAc (3×25 mL) extraction, the combined organic extracts were washed with water and brine, dried (Na₂SO₄), filtered and concentrated in vacuo. Purification by radial chromatography (2% MeOH/CH₂Cl₂) afforded the above two titled isomers. Isomer A, 406.3 (M+H), ret. t: 3.19 min (A); Isomer B, 406.3 (M+H), ret. t: 3.25 min (A).

Example 113

7-Methoxy-2-methyl-N-[(1S,2S)-1,3,3-trimethylbicyclo[2.2.1]heptan-2-yl]-1H-indole-3-carboxamide

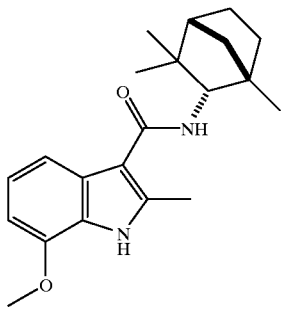

Methyl 2-methyl-7methoxy indole-3-carboxylate (0.5 g) was dissolved in THF (2 ml) and MeOH (10 ml). 4N NaOH (10 ml) was added, and the mixture was refluxed for 6 h. The reaction mixture was cooled and acidified with 1N HCl to pH 6.5. The solvent was removed under vacuum to give a yellow solid. CH₂Cl₂ (100 mL) was added and the mixture was stirred for 1 h, filtered, and washed with additional CH₂Cl₂ to give 0.32 g yellow acid after the solvent was removed. To the crude acid were added EDCI (338 mg, 1.77 mmol), HOBT (239 mg, 1.77 mmol), S-fenchylamine hydrochloride (336 mg, 1.77 mmol) and DMF (10 mL). DIPEA (675 mg, 5.3 mmol) was added, and the reaction mixture was heated to 60° C. overnight. EtOAc (100 mL) was added, and the mixture was washed with Na₂CO₃ (50 mL, sat) then brine (50 mL), and dried over Na₂SO₄. After removing the solvent, the residue was purified by column chromatography (25% EtOAc/hex) to give the above-titled compound as a yellow solid (0.54 g). 341.3 (M+H), ret. t: 4.52 min (A).

Example 114

7-Methoxy-2-methyl-1-pentyl-N-[(1S,2S)-1,3,3-trimethylbicyclo[2.2.1]heptan-2-yl]-1H-indole-3-carboxamide

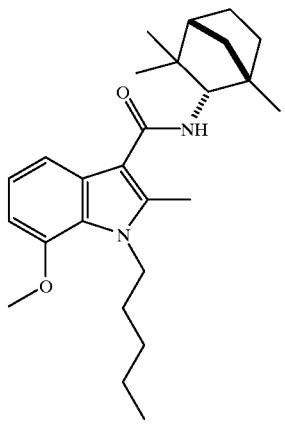

To the compound of Example 113 (14 mg, 0.04 mmol) in DMF (1 mL) was added NaH (12 mg, 0.3 mmol), and the reaction mixture was stirred for 10 min. n-Pentyl bromide (11 mg, 0.073 mmol) was added, and the mixture was heated at 60° C. overnight. The above-titled compound was purified directly by preparative HPLC (7.9 mg). 411.4 (M+H), ret. t: 2.32 min).

Examples 115–130

The compounds of Examples 115–130 as shown in Table 6 were prepared following the same or similar procedure as for Examples 113–114.

TABLE 6

| EX. NO. | STRUCTURE | COMPOUND NAME | DATA (M + H)/HPLC ret. t (min.) and conditions |
|---|---|---|---|
| 115 | 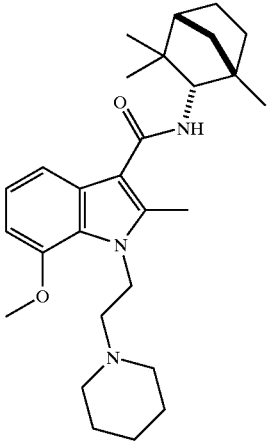 | 7-Methoxy-2-methyl-1-[2-(4-piperidyl)ethyl]-N-[(1S,2S)-1,3,3-trimethylbicyclo[2.2.1]heptan-2-yl]-1H-indole-3-carboxamide | 452.5/3.83 (A) |
| 116 | 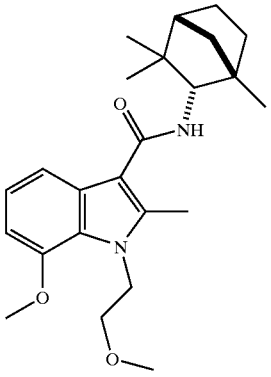 | 7-Methoxy-1-(2-methoxyethyl)-2-methyl-N-[(1S,2S)-1,3,3-trimethyl-bicyclo[2.2.1]heptan-2-yl]-1H-indole-3-carboxamide | 399.2/4.72 (A) |
| 117 | 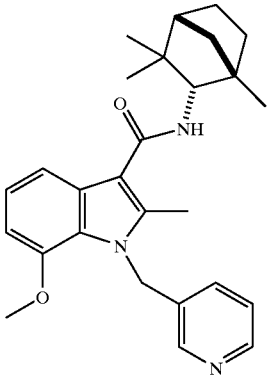 | 7-Methoxy-2-methyl-1-(3-pyridinyl-methyl)-N-[(1S,2S)-1,3,3-trimethyl-bicyclo[2.2.1]heptan-2-yl]-1H-indole-3-carboxmide | 432.3/4.08 (A) |

TABLE 6-continued

| EX. NO. | STRUCTURE | COMPOUND NAME | DATA (M + H)/HPLC ret. t (min.) and conditions |
|---|---|---|---|
| 118 | 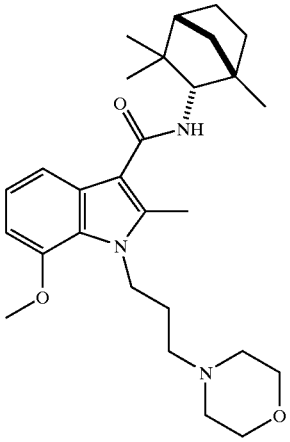 | 7-Methoxy-2-methyl-1-[3-(4-morpholinyl)propyl]-N-[(1S,2S)-1,3,3-trimethylbicylo[2.2.1]heptan-2-yl]-1H-indole-3-carboxamide | 468.3/3.87 (A) |
| 119 | 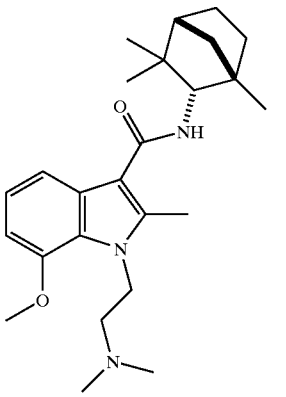 | 1-[2-(Dimethylamino)ethyl]-7-methoxy-2-methyl-N-[(1S,2S)-1,3,3-trimethylbicyclo[2.2.1]heptan-2-yl]-1H-indole-3-carboxamide | 412.4/3.79 (A) |
| 120 | 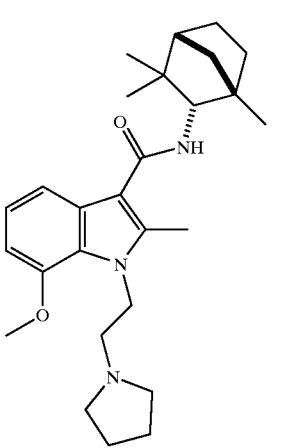 | 7-Methoxy-2-methyl-1-[2-(1-pyrrolidinyl)ethyl]-N-[(1S,2S)-1,3,3-trimethylbicyclo[2.2.1]heptan-2-yl]-1H-indole-3-carboxamide | 438.4/3.82 (A) |

TABLE 6-continued

| EX. NO. | STRUCTURE | COMPOUND NAME | DATA (M + H)/HPLC ret. t (min.) and conditions |
|---|---|---|---|
| 121 | 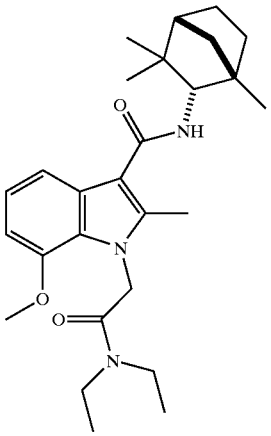 | N,N-Diethyl-7-methoxy-2-methyl-3-[[[(1S,2S)-1,3,3-trimethyl-bicyclo[2.2.1]heptan-2-yl]amino]carbonyl]-1H-indole-1-acetamide | 454.4/4.51 (A) |
| 122 | 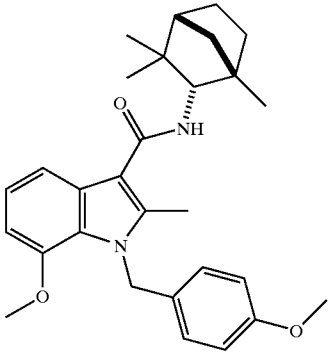 | 7-Methoxy-1-[(4-methoxyphenyl)methyl]-2-methyl-N-[(1S,2S)-1,3,3-trimethyl-bicyclo[2.2.1]heptan-2-yl]-1H-indole-3-carboxamide | 461.3/4.35 (A) |
| 123 | 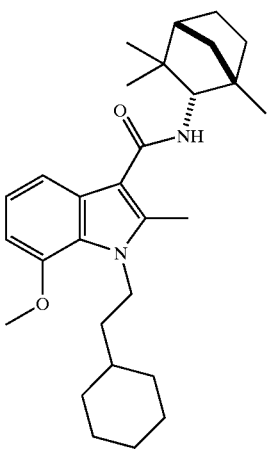 | 1-(2-Cyclohexylethyl)-7-methoxy-2-methyl-N-[(1S,2S)-1,3,3-trimethylbicyclo[2.2.1]heptan-2-yl]-1H-indole-3-carboxamide | 451.4/2.5 (B) |

TABLE 6-continued

| EX. NO. | STRUCTURE | COMPOUND NAME | DATA (M + H)/HPLC ret. t (min.) and conditions |
|---|---|---|---|
| 124 | 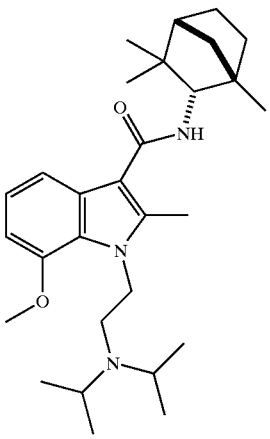 | 1-[2-[Bis-(1-methylethyl)amino]ethyl]-7-methoxy-2-methyl-N-[(1S,2S)-1,3,3-trimethylbicyclo[2.2.1]heptan-2-yl]-1H-indole-3-carboxamide | 468.5/3.86 (A) |
| 125 | 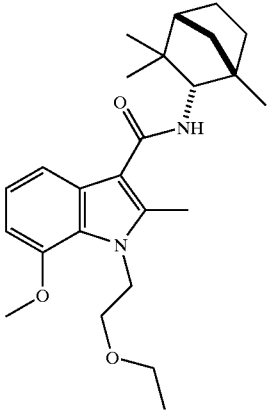 | 1-(2-Ethoxyethyl)-7-methoxy-2-methyl-N-[(1S,2S)-1,3,3-trimethylbicyclo[2.2.1]heptan-2-yl]-1H-indole-3-carboxamide | 413.3/4.82 (A) |
| 126 | 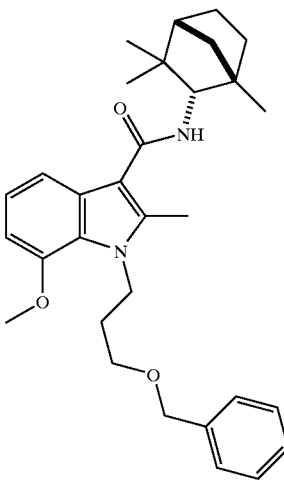 | 7-Methoxy-2-methyl-1-[3-(phenyl-methoxy)propyl]-N-[(1S,2S)-1,3,3-trimethylbicyclo[2.2.1]heptan-2-yl]-1H-indole-3-carboxamide | 489.4/5.22 (A) |

TABLE 6-continued

| EX. NO. | STRUCTURE | COMPOUND NAME | DATA (M + H)/HPLC ret. t (min.) and conditions |
|---|---|---|---|
| 127 | 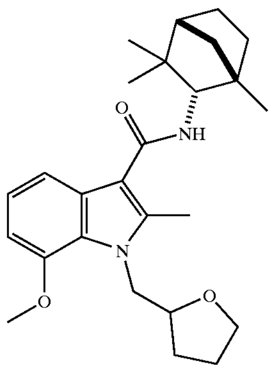 | 7-Methoxy-2-methyl-1-[(tetrahydro-2-furanyl)methyl]-N-[(1S,2S)-1,3,3-triethylbicyclo[2.2.1]heptan-2-yl]1H-indole-3-carboxamide | 425.3/4.74 (A) |
| 128 | 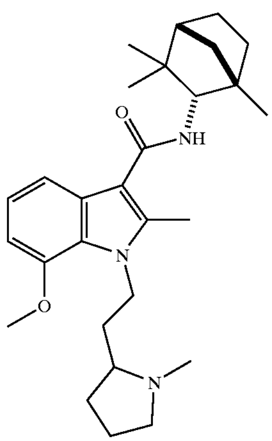 | 7-Methoxy-2-methyl-1-[2-(1-methyl-2-puyrrolidinyl)ethyl]-N-[(1S,2S)-1,3,3-trimethylbicyclo[2.2.1]heptan-3-yl]-1H-indole-3-carboxamide | 452.4/3.92 (A) |
| 129 | 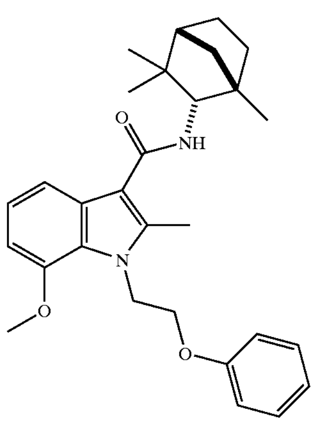 | 7-Methoxy-2-methyl-1-(2-phenoxyethyl)-N-[(1S,2S)-1,3,3-trimethylbicyclo[2.2.1]heptan-2-yl]-1H-indole-3-carboxamide | 461.4/5.04 (A) |

TABLE 6-continued

| EX. NO. | STRUCTURE | COMPOUND NAME | DATA (M + H)/HPLC ret. t (min.) and conditions |
|---|---|---|---|
| 130 | 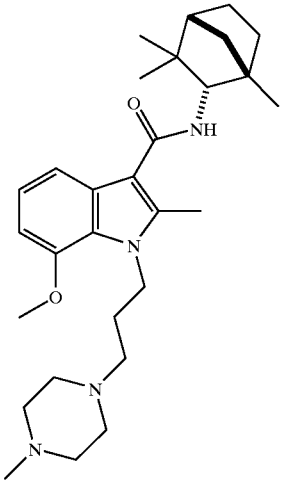 | 7-Methoxy-2-methyl-1-[3-(4-methyl-1-piperazinyl)propyl]-N-[(1S,2S)-1,3,3-trimethylbicyclo[2.2.1]heptan-2-yl]-1H-indole-3-carboxamide | 481.4/3.87 (A) |

Example 131
5-Methoxy-1-[2-(4-morpholinyl)ethyl]-N-[(1S,2S)-1,3,3-trimethylbicyclo[2.2.1]heptan-2-yl]-1H-pyrazole-3-carboxamide

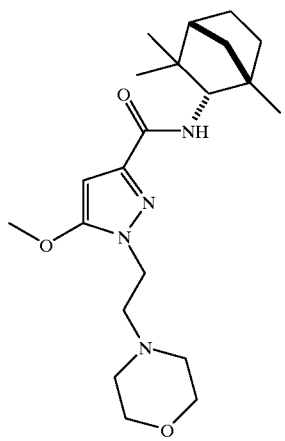

A. 5-Hydroxy-1-[2-(4-morpholinyl)ethyl]-1H-pyrazole-3-carboxylic acid ethyl ester

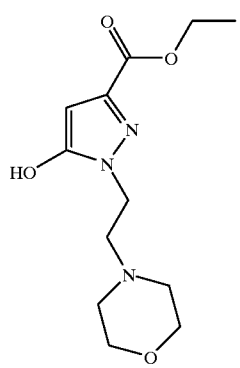

$H_2SO_4$ (conc., 0.98 g, 10 mmol) was added dropwise into a suspension of diethyloxalacetate sodium salt (10 mmol) in 100 mL anhydrous ethyl ether. $Na_2SO_4$ was filtered off after the addition. Excess acid was removed by 30 ml $KHCO_3$ (sat.) to give diethyl oxacetate. 2-(N-morpholinyl)ethylhydrazine (1.45 g, 10 mmol) in 2 ml EtOH was added, and the mixture was refluxed for 45 min. The solvent was removed under vacuum to yield 2.1 g of the crude pyrazole-based compound A.

B. 5-Methoxy-1-[2-(4-morpholinyl)ethyl]-1H-pyrazole-3-carboxylic acid ethyl ester

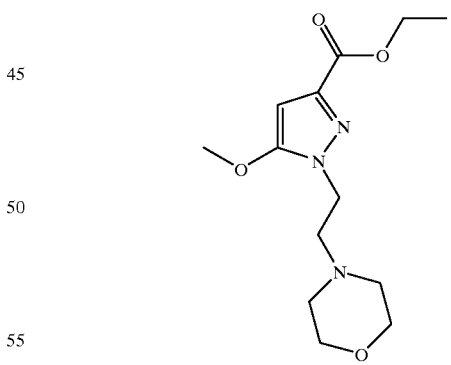

To a solution of the compound from step A (0.5 g, 1.85 mmol) in MeCN (20 mL) was added $K_2CO_3$. The reaction was stirred for 30 min and methyl iodide (2.2 mmol) was added, and then the mixture was stirred overnight. The solvent was removed, 50 ml brine was added, and the mixture was extracted with EtOAc (2×50 ml). The organic layers were combined, dried, and concentrated to give the above compound B as a yellow oil.

C–E. 5-Methoxy-1-[2-(4-morpholinyl)ethyl]-N-[(1S,2S)-1,3,3-trimethylbicyclo[2.2.1]heptan-2-yl]-1H-pyrazole-3-carboxamide The ethyl ester of step B was hydrolyzed to the acid (step C), converted to the acid chloride (step D), and then coupled with amine (step E), using the procedures as described for example 71G, 71H, and examples 72–82, to yield the above-titled compound of Example 131, 391.4 (M+H), ret. t: 3.19 min (A).

Examples 132–135

The compounds of Examples 132–135 as shown in Table 7 were prepared following the same or similar procedure as for Example 131.

TABLE 7

| EX. NO. | STRUCTURE | COMPOUND NAME | DATA (M + H)/HPLC ret. t (min.) and conditions |
|---|---|---|---|
| 132 | 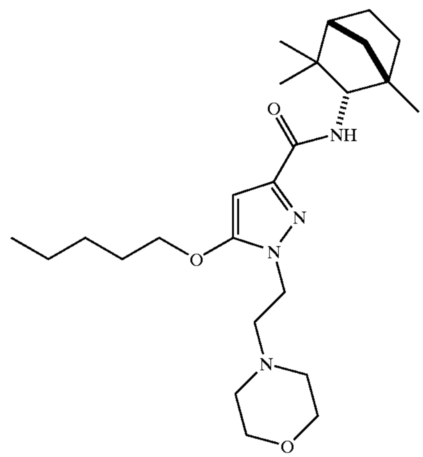 | 1-[2-(4-Morpholinyl)ethyl]-5-(pentyloxy)-N-[(1S,2S)-1,3,3-trimethylbicyclo[2.2.1]heptan-2-yl]-1H-pyrazole-3-carboxamide | 447.4/3.76 (A) |
| 133 | 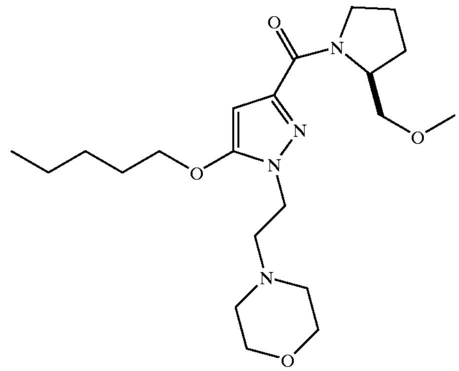 | (2S)-2-(Methoxymethyl)-1-[[1-[2-(4-morpholinyl)ethyl]-5-(pentyloxy)-1H-pyrazol-3-yl]carbonyl]pyrrolidine | 409.4/2.85 (A) |
| 134 | 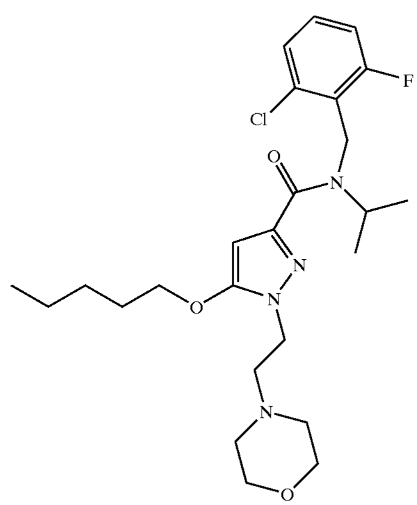 | N-[(2-Chloro-6-fluorophenyl)methyl]-N-(1-methylethyl)-1-[2-(4-morpholinyl)ethyl]-5-(pentyloxy)-1H-pyrazole-3-carboxamide | 495.4/3.67 (A) |

TABLE 7-continued

| EX. NO. | STRUCTURE | COMPOUND NAME | DATA (M + H)/HPLC ret. t (min.) and conditions |
|---|---|---|---|
| 135 | 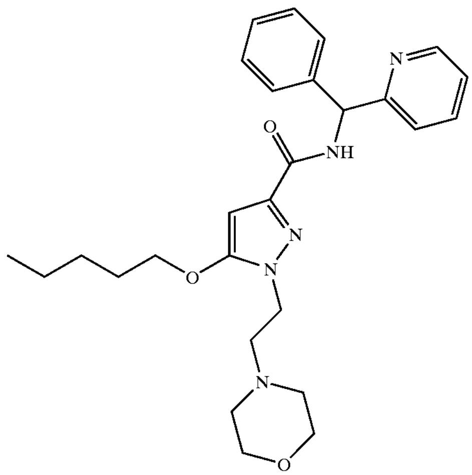 | 1-[2-(4-Morpholinyl)ethyl]-5-(pentyloxy)-N-[phenyl(2-pyridinyl)methyl]-1H-pyrazole-3-carboxamide | 478.4/3.67 (A) |

Examples 136–185

The compounds of Examples 136–185 as shown in Table 8 were prepared using the following procedure.

Indole amide and pyrrole amide starting materials were prepared using the procedure as described for Examples 17–66. to a −30° C. solution of the indole amide or pyrrole amide substrate (0.44 mmol) in 4 mL of anhydrous THF was added a 1.5 M stock solution of n-BuLi in hexanes. After allowing the resulting mixture to warm to 0° C. over 45 min, the solution was cooled to −30° C., and DMF (1.8 mmol) was added dropwise. The mixture was stirred at −30° C. for 15 min and then allowed to warm to RT. The resulting solution was transferred via cannula under an Ar atmosphere into well-stirred, degassed 10% aqueous HCl (4 mL) at RT and warmed to 55° C. for 17 h. After removing the THF on a rotary evaporator, the resulting aqueous portion was diluted with water (4 mL), and brought to pH of 10 by adding a 3 N aqueous solution of KOH. The mixture was extracted with DCM (3×20 mL), and the combined organic extracts were washed with water (20 mL) and brine (10 mL), then dried over anhydrous sodium sulfate, filtered, and concentrated in vacuo to afford the crude products. The crude products were generally purified by flash chromatography on silica gel using EtOAc/hex solvent mixtures as the eluant to provide the pure products in 54–87% overall yield.

TABLE 8

| EX. NO. | STRUCTURE | COMPOUND NAME | DATA: (M + H)/HPLC ret. time (min.) and conditions |
|---|---|---|---|
| 136 | 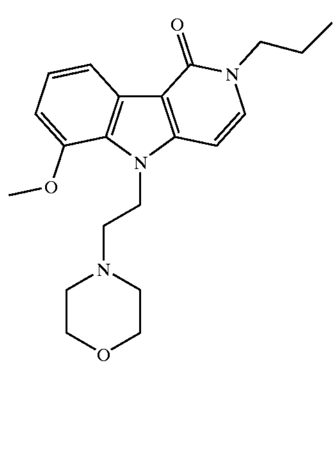 | 2,5-Dihydro-6-methoxy-5-[2-(4-morpholinyl)ethyl]-2-propyl-1H-pyrido[4,3-b]indol-1-one | 370.2/2.38 (A) |

TABLE 8-continued

| EX. NO. | STRUCTURE | COMPOUND NAME | DATA: (M + H)/HPLC ret. time (min.) and conditions |
|---|---|---|---|
| 137 | 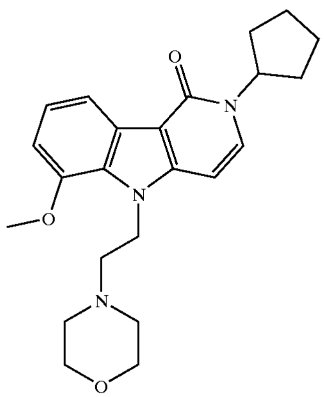 | 2-Cyclopentyl-2,5-dihydro-6-methoxy-5-[2-(4-morpholinyl)ethyl]-1H-pyrido[4,3-b]indol-1-one | 396.2/2.69 (A) |
| 138 | 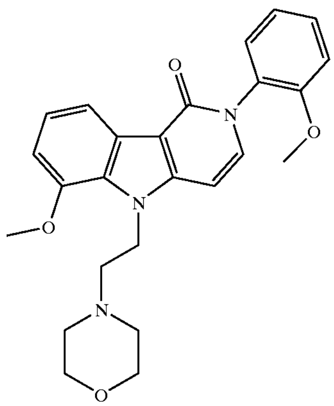 | 2,5-Dihydro-6-methoxy-2-(2-methoxyphenyl)-5-[2-(4-morpholinyl)ethyl]-1H-pyrido[4,3-b]indol-1-one | 434.1/2.42 (A) |
| 139 | 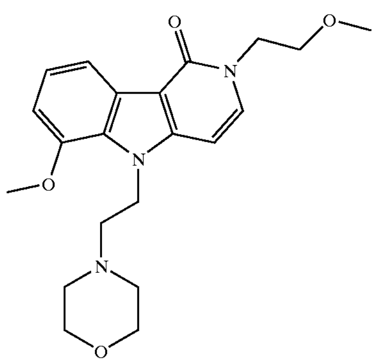 | 2,5-Dihydro-6-methoxy-2-(2-methoxyethyl)-5-[2-(4-morpholinyl)ethyl]-1H-pyrido[4,3-b]indol-1-one | 386.2/2.15 (A) |
| 140 | 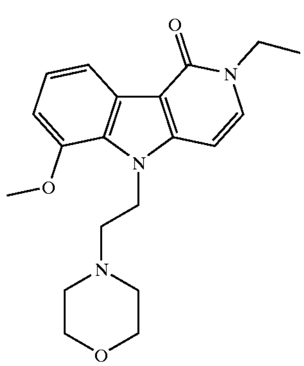 | 2-Ethyl-2,5-dihydro-6-methoxy-5-[2-(4-morpholinyl)ethyl]-1H-pyrido[4,3-b]indol-1-one | 356.2/2.14 (A) |

TABLE 8-continued

| EX. NO. | STRUCTURE | COMPOUND NAME | DATA: (M + H)/HPLC ret. time (min.) and conditions |
|---|---|---|---|
| 141 | 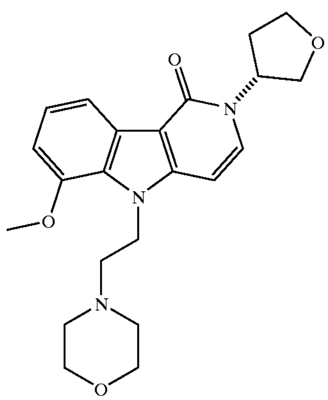 | 2,5-Dihydro-6-methoxy-5-[2-(4-morpholinyl)ethyl]-2-[(3R)-tetrahydro-3-furanyl]-1H-pyrido[4,3-b]indol-1-one | 398.2/2.21 (A) |
| 142 | 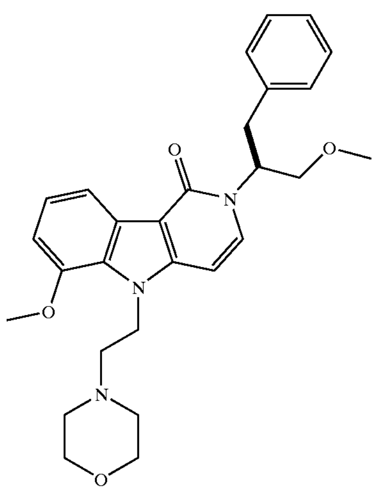 | 2,5-Dihydro-6-methoxy-2-[(1S)-2-methoxy-1-(phenylmethyl)ethyl]-5-[2-(4-morpholinyl)ethyl]-1H-pyrido[4,3-b]indol-1-one | 476.2/2.10 (A) |
| 143 | 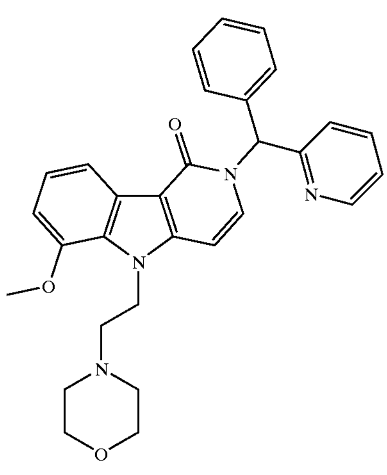 | 2,5-Dihydro-6-methoxy-5-[2-(4-morpholinyl)ethyl]-2-[phenyl(2-pyridinyl)methyl]-1H-pyrido[4,3-b]indol-1-one | 495.1/2.47 (A) |

TABLE 8-continued

| EX. NO. | STRUCTURE | COMPOUND NAME | DATA: (M + H)/HPLC ret. time (min.) and conditions |
|---|---|---|---|
| 144 | 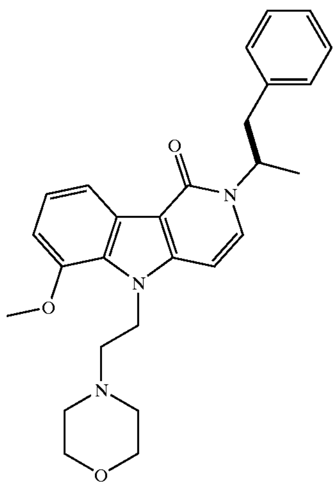 | 2,5-Dihydro-6-methoxy-5-[2-(4-morpholinyl)ethyl]-2-[(1R)-1-methyl-2-phenylethyl]-1H-pyrido[4,3-b]indol-1-one | 446.3/2.94(A) |
| 145 | 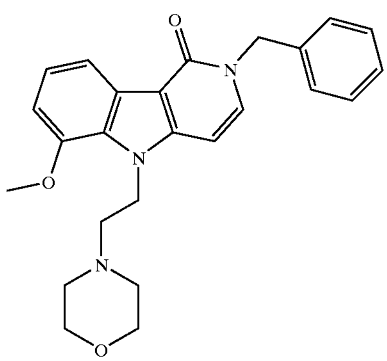 | 2,5-Dihydro-6-methoxy-5-[2-(4-morpholinyl)ethyl]-2-(phenylmethyl)-1H-pyrido[4,3-b]indol-1-one | 418.3/2.80 (A) |
| 146 | 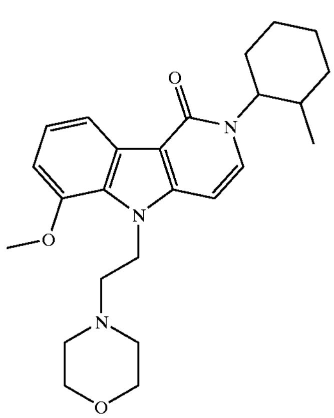 | 2,5-Dihydro-6-methoxy-2-(2-methylcyclohexanyl)-5-[2-(4-morpholinyl)ethyl]-1H-pyrido[4,3-b]indol-1-one | 424.2/2.96 (A) |

TABLE 8-continued
| EX. NO. | STRUCTURE | COMPOUND NAME | DATA: (M + H)/HPLC ret. time (min.) and conditions |
|---|---|---|---|
| 147 | 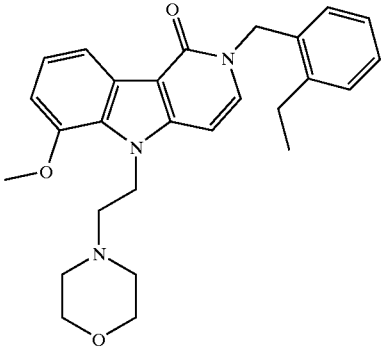 | 2-[(2-Ethylphenyl)methyl]-2,5-dihydro-6-methoxy-5-[2-(4-morpholinyl)ethyl]-1H-pyrido[4,3-b]indol-1-one | 432.2/2.78 (A) |
| 148 | 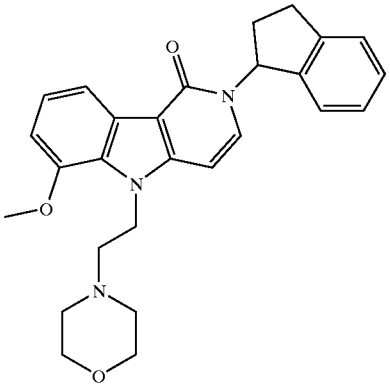 | 2-(2,3-Dihydro-1H-inden-1-yl)-2,5-dihydro-6-methoxy-5-[2-(4-morpholinyl)ethyl]-1H-pyrido[4,3-b]indol-1-one | 444.2/1.40 (B). |
| 149 | 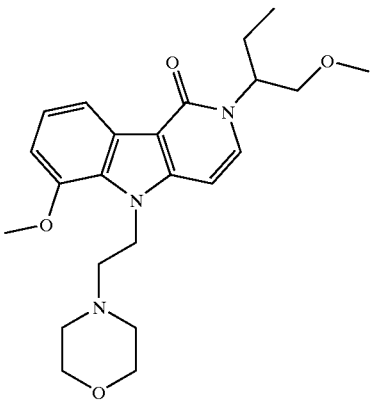 | 2,5-Dihydro-6-methoxy-2-[1-(methoxymethyl)propyl]-5-[2-(4-morpholinyl)ethyl]-1H-pyrido[4,3-b]indol-1-one | 414.2/1.23 (B). |

TABLE 8-continued

| EX. NO. | STRUCTURE | COMPOUND NAME | DATA: (M + H)/HPLC ret. time (min.) and conditions |
|---|---|---|---|
| 150 | 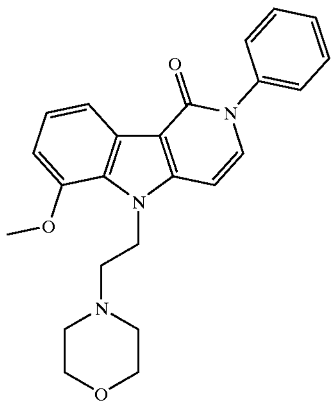 | 2,5-Dihydro-6-methoxy-5-[2-(4-morpholinyl)ethyl]-2-phenyl-1H-pyrido[4,3-b]indol-1-one | 404.2/2.52 (B) |
| 151 | 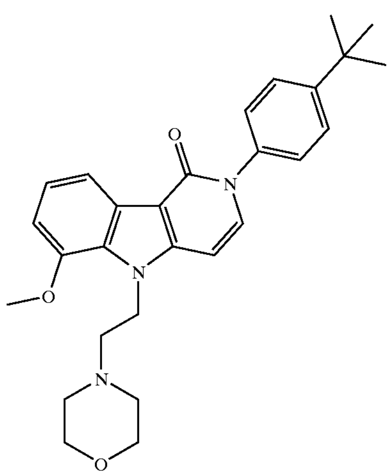 | 2-[4-(1,1-Dimethylethyl)phenyl]-2,5-dihydro-6-methoxy-5-[2-(4-morpholinyl)ethyl]-1H-pyrido[4,3-b]indol-1-one | 460.2/3.42 (A) |
| 152 | 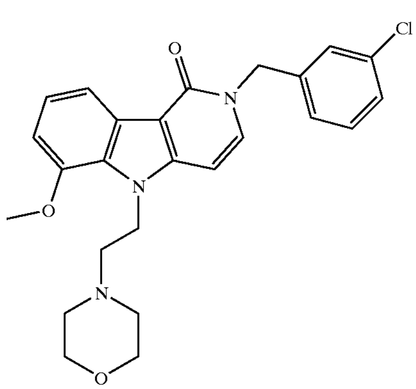 | 2-[(3-Chlorophenyl)methyl]-2,5-dihydro-6-methoxy-5-[2-(4-morpholinyl)ethyl]-1H-pyrido[4,3-b]indol-1-one | 452.2/3.06 (A) |

TABLE 8-continued
| EX. NO. | STRUCTURE | COMPOUND NAME | DATA: (M + H)/HPLC ret. time (min.) and conditions |
|---|---|---|---|
| 153 | 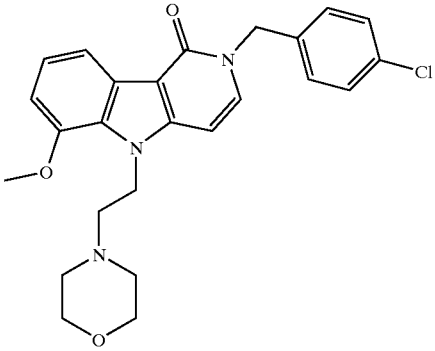 | 2-[(4-Chlorophenyl)methyl]-2,5-dihydro-6-methoxy-5-[2-(4-morpholinyl)ethyl]-1H-pyrido[4,3-b]indol-1-one | 452.1/3.11 (A) |
| 154 | 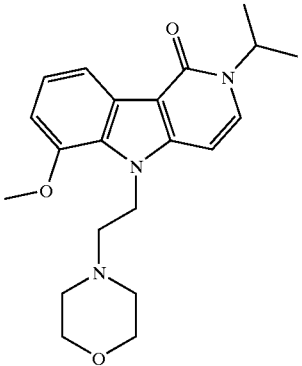 | 2,5-Dihydro-6-methoxy-2-(1-methylethyl)-5-[2-(4-morpholinyl)ethyl]-1H-pyrido[4,3-b]indol-1-one | 370.3/2.41 (A) |
| 155 | 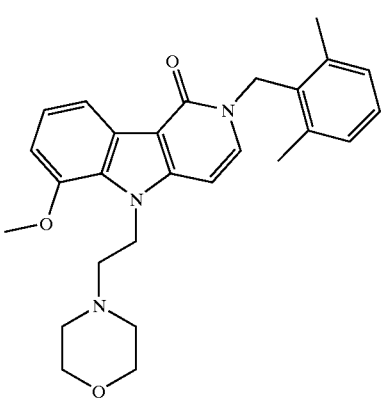 | 2-[(2,6-Dimethylphenyl)methyl]-2,5-dihydro-6-methoxy-5-[2-(4-morpholinyl)ethyl]-1H-pyrido[4,3-b]indol-1-one | 432.2/2.74 (A) |

TABLE 8-continued

| EX. NO. | STRUCTURE | COMPOUND NAME | DATA: (M + H)/HPLC ret. time (min.) and conditions |
|---|---|---|---|
| 156 | 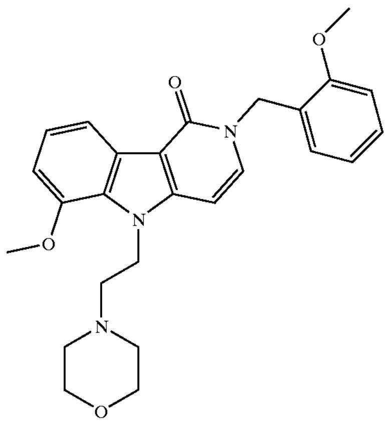 | 2,5-Dihydro-6-methoxy-2-[(2-methoxyphenyl)methyl]-5-[2-(4-morpholinyl)ethyl]-1H-pyridol[4,3-b]indol-1-one | 448.2/2.90 (A) |
| 157 | 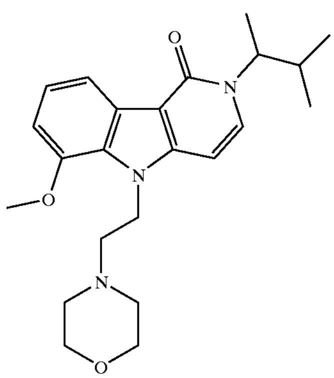 | 2-(1,2-Dimethylpropyl)-2,5-dihydro-6-methoxy-5-[2-(4-morpholinyl)ethyl]-1H-pyrido[4,3-b]indol-1-one | 398.3/2.70 (A) |
| 158 | 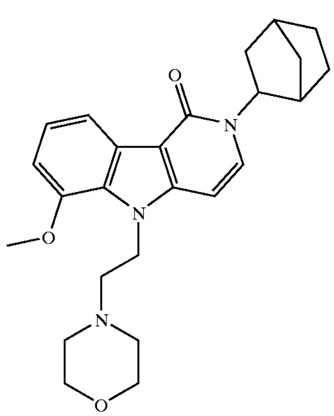 | 2-(Bicyclo[2.2.1]heptan-2-yl)-2,5-dihydro-6-methoxy-5-[2-(4-morpholinyl)ethyl]-1H-pyrido[4,3-b]indol-1-one | 422.3/2.93 (A) |

TABLE 8-continued
| EX. NO. | STRUCTURE | COMPOUND NAME | DATA: (M + H)/HPLC ret. time (min.) and conditions |
|---|---|---|---|
| 159 | 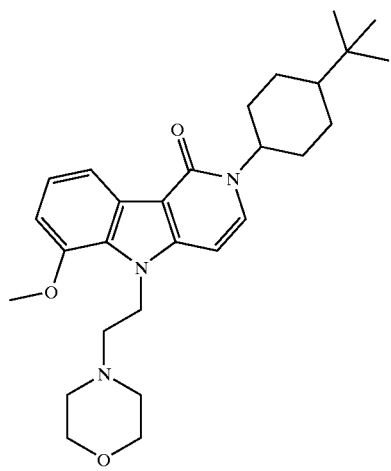 | 2-[4-(1,1-Dimethylethyl)cyclohexanyl]-2,5-dihydro-6-methoxy-5-[2-(4-morpholinyl)ethyl]-1H-pyrido[4,3-b]indol-1-one | 466.6/3.70 (A) |
| 160 | 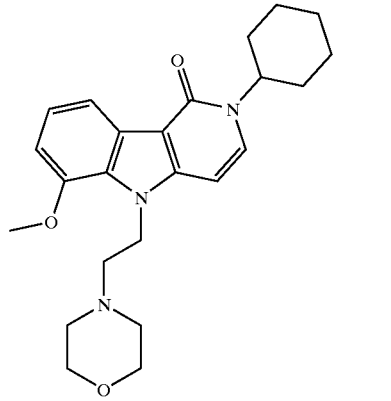 | 2-Cyclohexyl-2,5-dihydro-6-methoxy-5-[2-(4-morpholinyl)ethyl]-1H-pyrido[4,3-b]indol-1-one | 410.3/2.90 (A) |
| 161 | 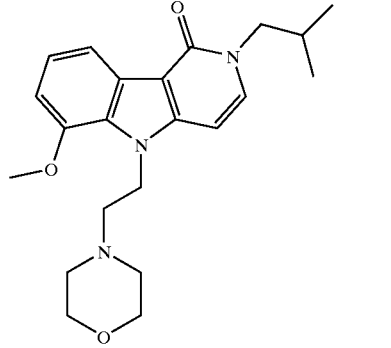 | 2,5-Dihydro-6-methoxy-2-(2-methylpropyl)-5-[2-(4-morpholinyl)ethyl]-1H-pyrido[4,3-b]indol-1-one | 384.3/2.71 (A) |

TABLE 8-continued

| EX. NO. | STRUCTURE | COMPOUND NAME | DATA: (M + H)/HPLC ret. time (min.) and conditions |
|---|---|---|---|
| 162 | 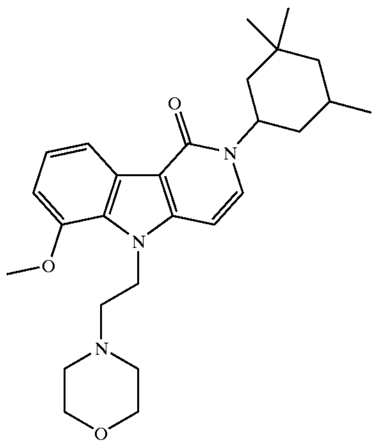 | 2,5-Dihydro-6-methoxy-5-[2-(4-morpholinyl)ethyl]-2-(3,3,5-trimethylcyclo-hexanyl)-1H-pyrido[4,3-b]indol-1-one | 452.4/3.52 (A) |
| 163 | 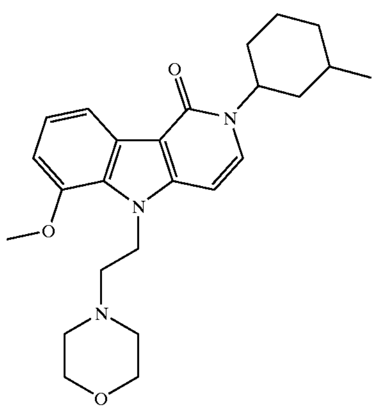 | 2,5-Dihydro-6-methoxy-5-[2-(4-morpholinyl)ethyl]-2-(3-methylcyclohexanyl)-1H-pyridol[4,3-b]indol-1-one | 424.3/3.14 (A) |
| 164 | 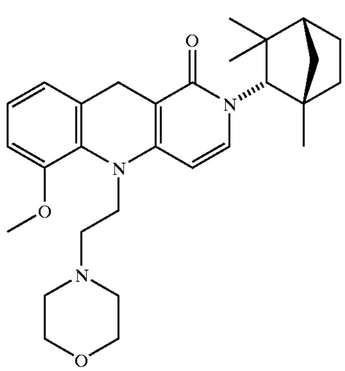 | 2,5-Dihydro-6-methoxy-3-methyl-5-[2-(4-morpholinyl)ethyl]-2-[(1S,2S)-1,3,3-trimethylbicyclo[2.2.1]heptan-2-yl]1H-pyrido[4,3-b]indol-1-one | 478.7/3.44 (A) |

TABLE 8-continued

| EX. NO. | STRUCTURE | COMPOUND NAME | DATA: (M + H)/HPLC ret. time (min.) and conditions |
|---|---|---|---|
| 165 | 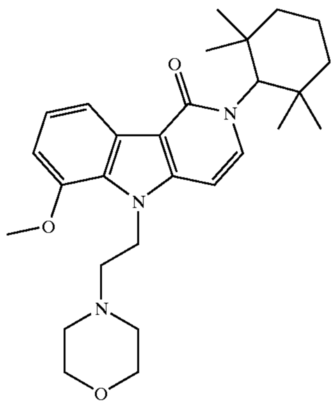 | 2,5-Dihydro-6-methoxy-5-[2-(4-morpholinyl)ethyl]-2-(2,2,6,6-tetramethylcyclo-hexanyl)-1H-pyridol[4,3-b]indol-1-one | 466.6/1.61 (B) |
| 166 | 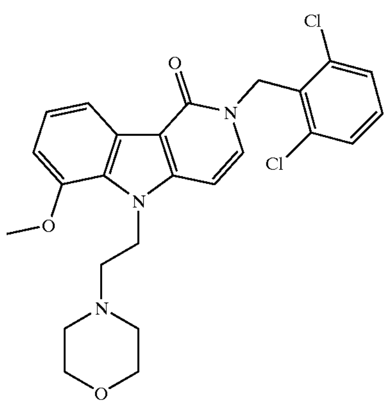 | 2-[(2,6-Dichlorophenyl)methyl]-2,5-dihydro-6-methoxy-5-[2-(4-morpholinyl)ethyl]-1H-pyrido[4,3-b]indol-1-one | 486.1 (M+)/ 3.13 (A) |
| 167 | 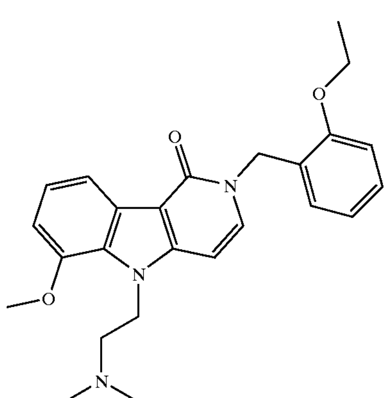 | 2-[(2-Ethoxyphenyl)methyl]-2,5-dihydro-6-methoxy-5-[2-(4-morpholinyl)ethyl]-1H-pyrido[4,3-b]indol-1-one | 462.2/3.11 (A) |

TABLE 8-continued

| EX. NO. | STRUCTURE | COMPOUND NAME | DATA: (M + H)/HPLC ret. time (min.) and conditions |
|---|---|---|---|
| 168 | 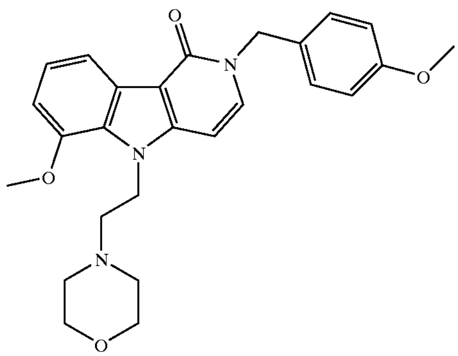 | 2,5-Dihydro-6-methoxy-2-[(4-methoxyphenyl)-methyl]-5-[2-(4-morpholinyl)ethyl]-1H-pyrido[4,3-b]indol-1-one | 448.3/2.75 (A) |
| 169 | 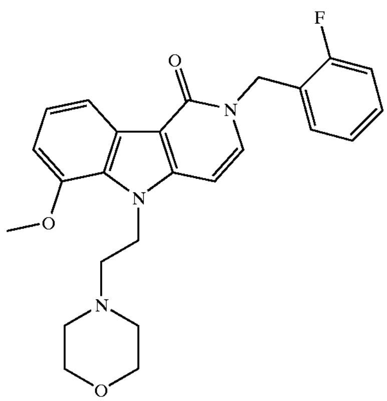 | 2-[(2-Fluorophenyl)methyl]-2,5-dihydro-6-methoxy-5-[2-(4-morpholinyl)ethyl]-1H-pyrido[4,3-b]indol-1-one | 436.2/2.80 (A) |
| 170 | 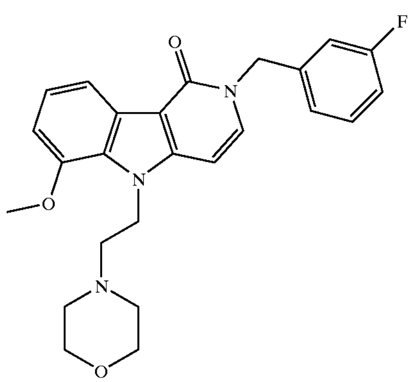 | 2-[(3-Fluorophenyl)methyl]-2,5-dihydro-6-methoxy-5-[2-(4-morpholinyl)ethyl]-1H-pyrido[4,3-b]indol-1-one | 436.3/2.84 (A) |
| 171 | 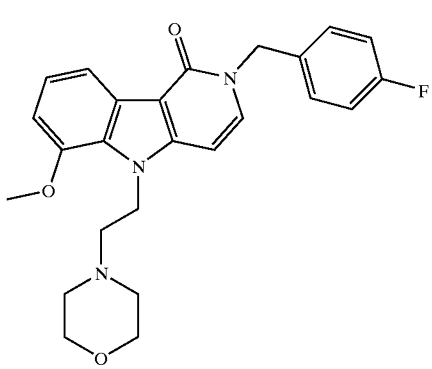 | 2-[(4-Fluorophenyl)methyl]-2,5-dihydro-6-methoxy-5-[2-(4-morpholinyl)ethyl]-1H-pyrido[4,3-b]indol-1-one | 436.3/2.82 (A) |

TABLE 8-continued

| EX. NO. | STRUCTURE | COMPOUND NAME | DATA: (M + H)/HPLC ret. time (min.) and conditions |
|---|---|---|---|
| 172 | 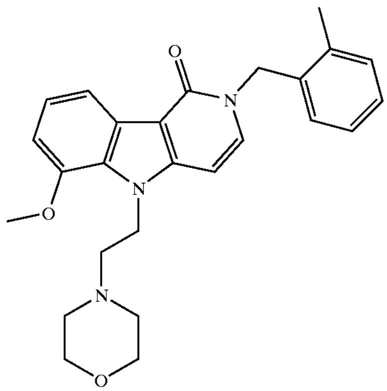 | 2,5-Dihydro-6-methoxy-2-[(2-methylphenyl)methyl]-morpholinyl)ethyl]-1H-pyrido[4,3-b]indol-1-one | 432.3/2.92 (A) |
| 173 | 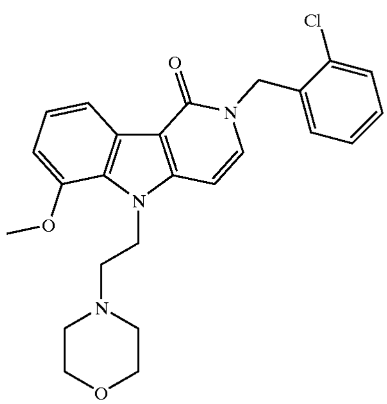 | 2-[(2-Chlorophenyl)methyl]-2,5-dihydro-6-methoxy-5-[2-(4-morpholinyl)ethyl]-1H-pyridol[4,3-b]indol-1-one | 452.2/3.00 (A) |
| 174 | 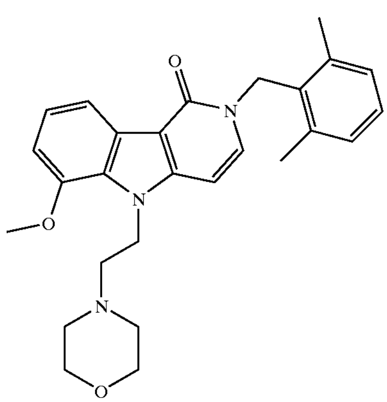 | 2-[(2,6-Dimethylphenyl)-methyl]-2,5-dihydro-6-methoxy-5-[2-(4-morpholinyl)ethyl]-1H-pyrido[4,3-b]indol-1-one | 446.3/3.14 (A) |

TABLE 8-continued

| EX. NO. | STRUCTURE | COMPOUND NAME | DATA: (M + H)/HPLC ret. time (min.) and conditions |
|---|---|---|---|
| 175 | 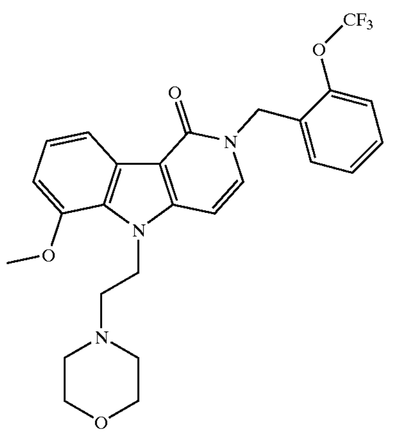 | 2,5-Dihydro-6-methoxy-5-[2-(4-morpholinyl)ethyl]-2-[[2-(trifluoromethoxy)phenyl]methyl]-1H-pyrido[4,3-b]indol-1-one | 502.2/3.22 (A) |
| 176 | 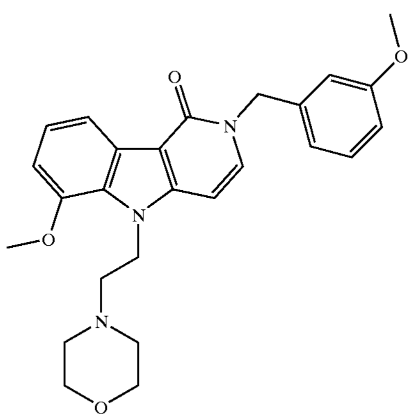 | 2,5-Dihydro-6-methoxy-2-[(3-methoxyphenyl)methyl]-5-[2-(4-morpholinyl)ethyl]-1H-pyrido[4,3-b]indol-1-one | 448.2/2.83 (A) |
| 177 | 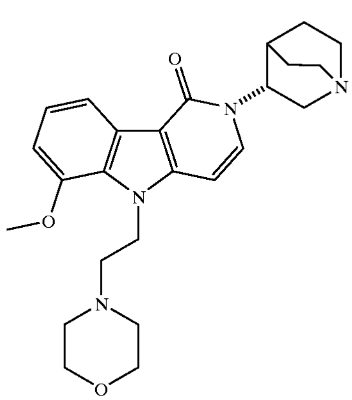 | 2-[(3R)-1-Azabicyclo[2.2.2]octan-3-yl]-2,5-dihydro-6-methoxy-5-[2-(4-morpholinyl)ethyl]-1H-pyrido[4,3-b]indol-1-one | 437.48/1.23 (A) |

TABLE 8-continued
| EX. NO. | STRUCTURE | COMPOUND NAME | DATA: (M + H)/HPLC ret. time (min.) and conditions |
|---|---|---|---|
| 178 | 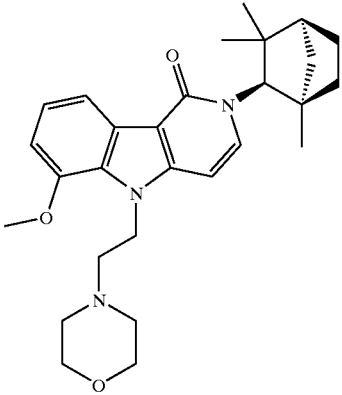 | 2,5-Dihydro-6-methoxy-5-[2-(4-morpholinyl)ethyl]-2-[(1R,2R)-1,3,3-trimethylbicyclo[2.2.1]-heptan-2-yl]-1H-pyrido[4,3-b]indol-1-one | 464.28/3.46 (A) |
| 179 | 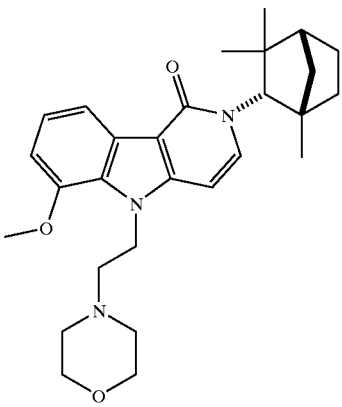 | 2,5-Dihydro-6-methoxy-5-[2-(4-morpholinyl)ethyl]-2-[(1S,2S)-1,3,3-trimethylbicyclo[2.2.1]heptan-2-yl]-1H-pyrido[4,3-b]indol-1-one | 464.58/3.46 (A) |
| 180 | 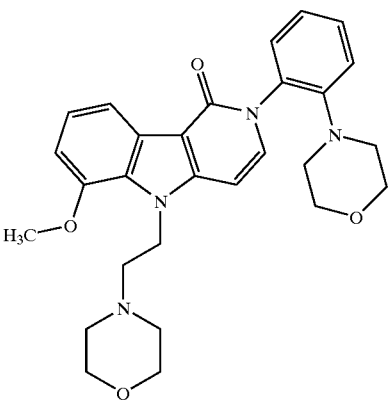 | 2,5-Dihydro-6-methoxy-5-[2-(4-morpholinyl)ethyl]-2-[2-(4-morpholinyl)phenyl]-1H-pyrido[4,3-b]indol-1-one | 489.38/1.19 (C) |

TABLE 8-continued
| EX. NO. | STRUCTURE | COMPOUND NAME | DATA: (M + H)/HPLC ret. time (min.) and conditions |
|---|---|---|---|
| 181 | 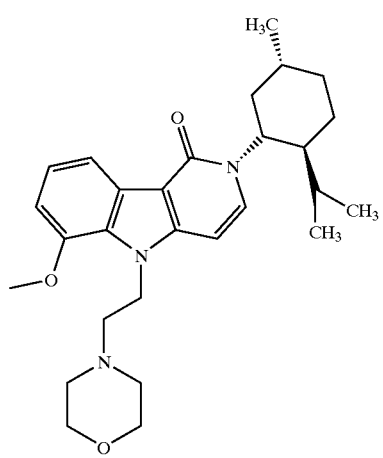 | 2,5-Dihydro-6-methoxy-5-[2-(4-morpholinyl)ethyl]-2-[(1R,2S,5R)-5-methyl-2-(1-methylethyl)cyclohexyl]-1H-pyrido[4,3-b]indol-1-one | 466.45/1.68 (C) |
| 182 | 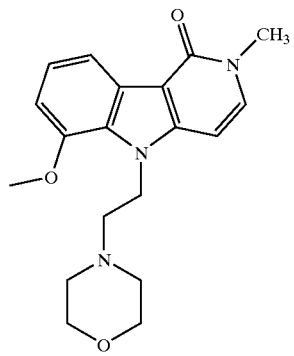 | 2,5-Dihydro-6-methoxy-2-methyl-5-[2-(4-morpholinyl)ethyl]-1H pyrido[4,3-b]indol-1-one | 342.22/0.94 (C) |
| 183 | 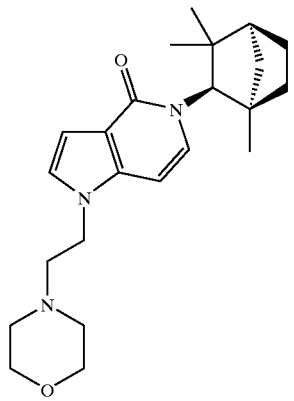 | 1,5-Dihydro-1-[2-(4-morpholinyl)ethyl]-5-[(1R,2R)-1,3,3-trimethylbicyclo[2.2.1]heptan-2-yl]-4H-pyrido[3,2-c]pyridin-4-one | 384.31/2.38 (A) |

TABLE 8-continued

| EX. NO. | STRUCTURE | COMPOUND NAME | DATA: (M + H)/HPLC ret. time (min.) and conditions |
|---|---|---|---|
| 184 | 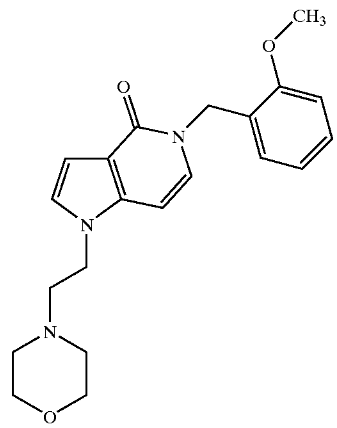 | 1,5-Dihydro-5-[(2-methoxyphenyl)methyl]-1-[2-(4-morpholinyl)ethyl]-4H-pyrido[3,2-c]pyridin-4-one | 368.27/0.94 (E) |
| 185 | 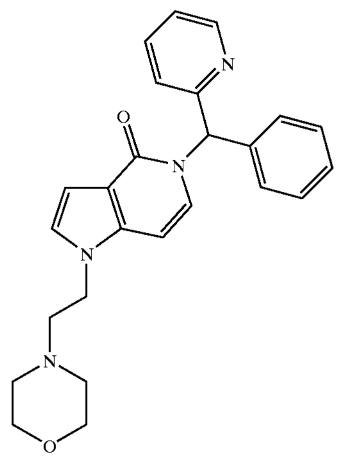 | 1,5-Dihydro-1-[2-(4-morpholinyl)ethyl]-5-[phenyl(2-pyridinyl)methyl]-4H-pyrido[3,2-c]pyridin-4-one | 460.64/2.81 (A) |

Example 186

2,5-Dihydro-6-methoxy-2-[(1S,2S)-1,3,3-trimethylbicyclo[2.2.1]heptan-2-yl]-1H-pyrido[4,3-b]indol-1-one

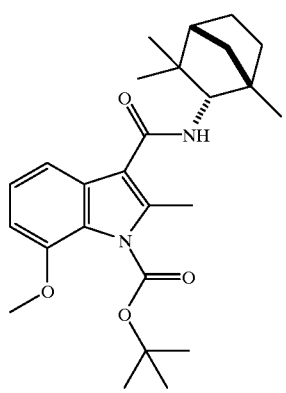

To 7-Methoxy-2-methyl-N-[(1S,2S)-1,3,3-trimethylbicyclo[2.2.1]heptan-2-yl]-H-indole-3-carboxamide (Example 113) (0.72 g, 2.11 mmol) in anhydrous THF (4 mL) at RT was added 60% sodium hydride dispersion in oil (254 mg, 6.34 mmol). The mixture was stirred for 0.5 h and DMAP (60 mg) was added followed by di-tert-butylcarbonate (2.3 mL, 1.0 M THF solution). After the addition was complete, the reaction mixture was stirred at RT for 10 min then quenched with water (20 mL) and extracted with EtOAc (200 mL). The organic layer was washed with water and brine and then dried over anhydrous $MgSO_4$ and concentrated in vacuo to afford the crude product. The crude product was further purified by flash column chromatography on silica gel to give Example 186 as a light yellow foam (1.02 g, 100%). LC/MS MH$^+$ 441.32, ret. t: 4.21 min (A).

Example 187

2,5-Dihydro-6-methoxy-2-[(1S,2S)-1,3,3-trimethylbicyclo[2.2.1]heptan-2-yl]-1H-pyrido[4,3-b]indol-1-one

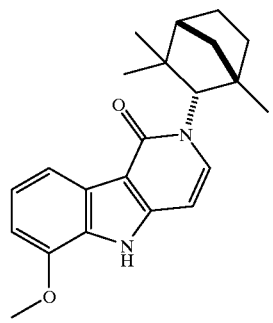

The above titled compound was prepared according to the general procedure described above for Examples 136–185. LC/MS MH⁺ 351.29, ret. t: 3.57 min (A).

Examples 188 to 190

The compounds of Examples 188 to 190, as shown in Table 9, were prepared via alkylation of Example 187, as follows. To a suspension of 2,5-Dihydro-6-methoxy-2-[(1S,2S)-1,3,3-trimethylbicyclo[2.2.1]heptan-2-yl]-1H-pyrido[4,3-b]indol-1-one (20 mg, 0.06 mmol) and $K_2CO_3$ (32 mg, 0.23 mmol) in 0.5 mL of DMF was added the appropriate alkyl bromide (0.11 mmol), and the mixture was stirred at RT under Ar overnight. The reaction mixture was quenched with water (10 mL), and the organic layer extracted with EtOAc (100 mL), washed with water and brine, then dried over $MgSO_4$, and concentrated in vacuo. The crude product was further purified by preparative HPLC to give the pure products in 72–92% overall yield.

TABLE 9

| EX. NO. | STRUCTURE | COMPOUND NAME | DATA: (M + H)/ HPLC ret. t (mm.) and conditions |
|---|---|---|---|
| 188 | 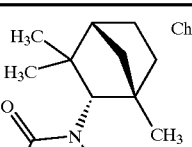 | 2,5-Dihydro-6-methoxy-5-(phenylmethyl)-2-[(1S,2S)-1,3,3-trimethylbicyclo[2.2.1]heptan-2-yl]1H-pyrido[4,3-b]indol-1-one | 441.32/ 4.16 (A) |
| 189 | 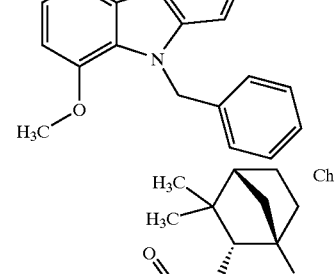 | 5-Butyl-2,5-dihydro-6-methoxy-2-[(1S,2S)-1,3,3-trimethylbicyclo[2.2.1]heptan-2-yl]-1H-pyrido[4,3-b]indol-1-one | 441.32/ 4.28 (A) |
| 190 | 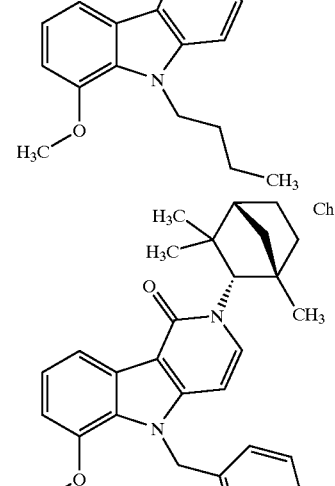 | 2,5-Dihydro-6-methoxy-5-(4-pyridinylmethyl)-2-[(1S,2S)-1,3,3-trimethylbicyclo[2.2.1]heptan-2-yl]-1H-pyrido[4,3-b]indol-1-one | 442.31/ 3.13 (A) |

Example 191

1,2-Dihydro-6-methoxy-1-oxo-2-[(1S,2S)-1,3,3-trimethylbicyclo[2.2.1]heptan-2-yl]-5H-pyrido[4,3-b]indole-5-propanoic acid

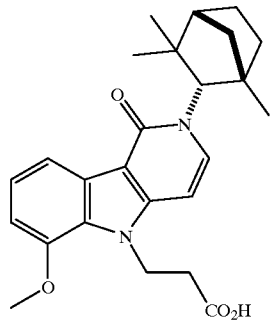

The methyl ester

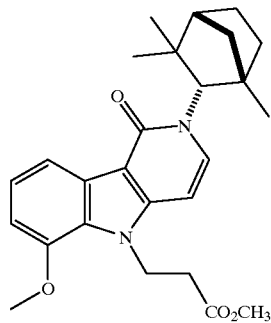

was prepared from the compound of Example 187 using the appropriate alkyl bromide as described above for Examples 188–190. To a solution of the methyl ester substrate (65 mg, 0.15 mmol) in MeOH (0.5 mL) at RT was added 3.0 M aqueous KOH (0.25 mL, 0.75 mmol), and the mixture was warmed to 45° C. overnight. The reaction mixture was diluted with water (10 mL) and acidified to pH of 1 using 1 N aqueous HCl. The resulting mixture was extracted with EtOAc (25 mL×4), and the combined organic extracts were washed with brine, dried over $MgSO_4$, and concentrated in vacuo. The crude product was further purified by preparative HPLC to give the above compound as a white solid (40 mg). LC/MS $MH^+$ 423.31, ret. t: 3.66 min.

Examples 192–197

4-Substituted-2,5-dihydro-6-methoxy-5-[2-(4-morpholinyl)ethyl]-2-[(1S,2S)-1,3,3-trimethylbicyclo[2.2.1]heptan-2-yl]-1H-pyrido[4,3-b]indol-1-ones (IIi)

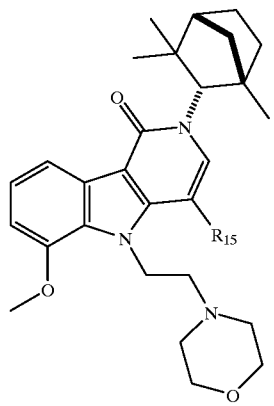

Compounds of formula (IIi), wherein $R_{15}$ has the values listed in Table 10, were prepared as follows:

Examples 192–194

To a RT solution of 2,5-Dihydro-6-methoxy-5-[2-(4-morpholinyl)ethyl]-2-[(1S,2S)-1,3,3-trimethylbicyclo[2.2.1]heptan-2-yl]-1H-pyrido[4,3-b]indol-1-one (Example 179) (30 mg, 54 μmol) in chloroform (0.5 mL) was added NBS (11 mg, 64 μmol) for Example 192, NCS for Example 193, and SELECTFLUOR™ for Example 194. The resulting mixture was stirred for 17 h, concentrated in vacuo, and the crude product purified by preparative HPLC.

Examples 195–197

To a -78° C. solution of Example 192 (50 mg, 86 μmol) in anhydrous THF (0.9 mL) was added a 1.7 M solution of t-BuLi in pentane (112 μL, 190 μmol), and the resulting solution was stirred at -78° C. for 10 min. To this mixture was added ethyl iodide (8 μL, 95 μmol) for Example 195, p-toluenesulfonyl cyanide for Example 196, and methyl iodide for Example 197. The mixture was allowed to warm to RT after stirring at -78° C. for 10 min. The reaction mixture was quenched by adding 0.1 mL of MeOH, and the mixture was concentrated on a rotary evaporator to afford the crude product which was purified by preparative HPLC.

TABLE 10

| EX. NO. | $R_{15}$ | COMPOUND NAME | DATA: (LC/MS MH+)/ HPLC ret. t (min.) and Conditions |
|---|---|---|---|
| 192 | Br | 4-Bromo-2,5-dihydro-6-methoxy-5-[2-(4-morpholinyl)ethyl]-2-[(1S,2S)-1,3,3-trimethylbicyclo]2.2.1]heptan-2-yl]-1H-pyrido[4,3-b]indol-1-one | 543.28/1.72 (E) (pale yellow solid, 19 mg, 72% yield). |
| 193 | Cl | 4-Chloro-2,5-dihydro-6-methoxy-5-[2-(4-morpholinyl)ethyl]-2-[(1S,2S)-1,3,3-trimethylbicyclo[2.2.1]heptan-2-yl]-1H-pyrido[4,3-b[indol-1-one | 498.22/ 3.10 (A) (pale yellow solid). |
| 194 | F | 4-Fluoro-2,5-dihydro-6-methoxy-5-[2-(4-morpholinyl)ethyl]-2-[(1S,2S)-1,3,3-trimethylbicyclo[2.2.1]heptan-2-yl]-1H-pyrido[4,3-b]indol-1-one | 482.33/ ret. t: 2.93 (A) (off white solid). |
| 195 | —$CH_2CH_3$ | 4-Ethyl-2,5-dihydro-6-methoxy-5-[2-(4-morpholinyl)ethyl]-2-[(1S,2S)-1,3,3-trimethylbicyclo[2.2.1]heptan-2-yl]-1H-pyrido[4,3-b]indol-1-one | 492.57/1.71 (E) (white solid: 25 mg, 48% yield) |
| 196 | —CN | 4-Cyano-2,5-dihydro-6-methoxy-5-[2-(4-morpholinyl)ethyl]-2-[(1S,2S)-1,3,3-trimethylbicyclol[2.2.1]heptan-2-yl]-1H-pyridol[4,3-b]indol-1-one | 489.43/1.70 (E) |
| 197 | —$CH_3$ | 4-Methyl-2,5-dihydro-6-methoxy-5-[2-(4-morpholinyl)ethyl]-2-[(1S,2S)-1,3,3-trimethylbicyclo[2.2.1]heptan-2-yl]-1H-pyrido[4,3-b]indol-1-one | 478.51/2.89 (A) |

Example 198

2-Methyl-1-[2-(4-morpholinyl)ethyl]-5-phenyl-N-[(1S,2S)-1,3,3-trimethylbicyclo[2.2.1]heptan-2-yl]-1H-pyrrole-3-carboxamide

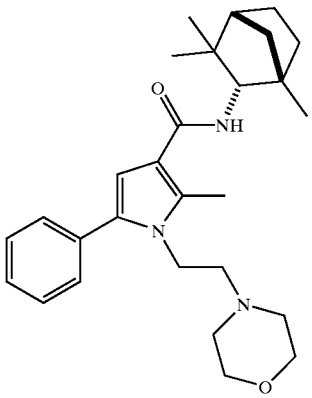

A.

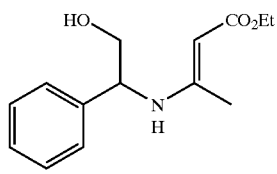

A neat mixture of 2-phenylglycinol (5.0 g, 36 mmol) and ethyl-3-aminocrotonate (4.2 mL, 33 mmol) was heated at 80° C. for 16 h, and the resulting oil was cooled to RT, dissolved into DCM (10 mL), and filtered through a pad of silica gel washing with a 1:1 mixture of EtOAc and hexanes. The resulting filtrate was concentrated in vacuo to afford compound A as a pure product (7.45 g, 90%). LC/MS MH$^+$ 250.10, ret. t: 2.51 min (A).

B.

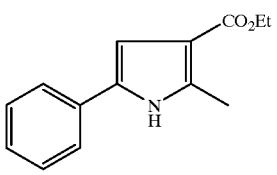

A degassed solution of the compound from step A (0.5 g, 2.0 mmol) and 2-bromomesitylene (0.3 mL, 2.0 mmol) in 10 mL of anhydrous DMF was added via cannula to a reaction flask containing $K_2CO_3$ (0.6 g, 4.0 mmol) and Pd(PPh$_3$)$_4$ (58 mg, 5.0 μmol), and the resulting mixture was heated to 150° C. for 5 h. After cooling to RT, the mixture was diluted with water (50 mL) and extracted with EtOAc (3×40 mL). The combined organic extracts were washed with water (3×20 mL) and brine (20 mL), then dried over sodium sulfate, filtered, and concentrated in vacuo. The crude product was purified by flash chromatography on silica gel using 25% EtOAc in hexanes as the eluant to afford after concentration in vacuo compound B as a tan solid (0.43 g, 94% yield). LC/MS MH$^+$ 230.10, ret. t: 3.23 min (A).

C.

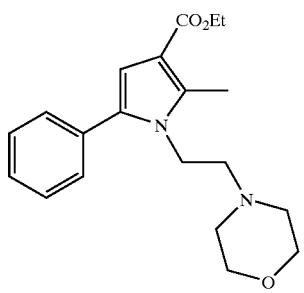

Compound C was prepared from the compound of step B in 81% yield following the procedure for Example 2, step A. LC/MS MH$^+$ 343.40, ret. t: 2.35 min (A).

D.

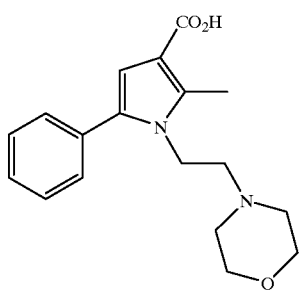

To a solution of the compound from step C (2.5 g, 7.3 mmol) in MeOH (6.5 mL) was added 3N aqueous KOH (6.5 mL), and the resulting mixture was heated in a 90° C. oil bath for 20 h then cooled to RT. The MeOH was removed on a rotary evaporator and the remaining aqueous portion was diluted with water (total volume ~50 mL) and brought to a pH=6 or 7 by slow addition of 20% aqueous HCl. The resulting mixture was extracted with DCM (3×30 mL), and the combined organic extracts were washed with brine (20 mL), dried over sodium sulfate, filtered, and concentrated in vacuo to afford 2.1 g (92%) of compound D as a white solid. LC/MS MH$^+$ 315.30, ret. t: 1.67 min. (A).

E. 2-Methyl-1-[2-(4-morpholinyl)ethyl]-5-phenyl-N-[(1S,2S)-1,3,3-trimethylbicyclo[2.2.1]heptan-2-yl]-1H-pyrrole-3-carboxamide (Example 198)

A mixture of compound D (0.25 g, 0.80 mmol), EDCI (0.20 g, 1.0 mmol), 1-hydroxybenzotriazole (0.13 g, 0.95 mmol), DIPEA (0.55 mL, 3.2 mmol), and (S)-fenchylamine (0.20 g, 0.87 mmol) in 2 mL of DMF was heated to 60° C. for 18 h then cooled to RT. The mixture was diluted with water (30 mL) and extracted with EtOAc (3×30 mL). The combined organic extracts were washed with saturated aqueous NaHCO$_3$ (3×15 mL), water (3×15 mL), and brine (30 mL), then dried over sodium sulfate, filtered, and concentrated in vacuo to afford the crude product. Purification by flash chromatography on silica gel using 80–100% EtOAc-hexanes mixture as the eluant afforded Example 198 as an off-white solid (0.30 g, 83% yield). LC/MS MH$^+$ 450.74, ret. t: 3.32 min. (A).

Example 199

2-Methyl-1-[2-(4-morpholinyl)ethyl]-4,5-diphenyl-N-[(1S,2S)-1,3,3-trimethylbicyclo[2.2.1]heptan-2-yl]-1H-pyrrole-3-carboxamide

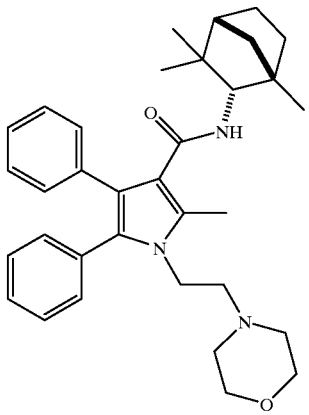

The compound of Example 199 was prepared following the procedure described above for Example 198. LC/MS MH+ 526.74, ret. t: 3.60 min (A).

Examples 200 and 201

1,5-Dihydro-1-[2-(4-morpholinyl)ethyl]-2-phenyl-5-[(1S,2S)-1,3,3-trimethylbicyclo[2.2.1]heptan-2-yl]-4H-pyrido[3,2-c]pyridin-4-one (Ex. 200), and 1,5-Dihydro-1-[2-(4-morpholinyl)ethyl]-2,3-diphenyl-5-[(1S,2S)-1,3,3-trimethylbicyclo[2.2.1]heptan-2-yl]-4H-pyrido[3,2-c]pyridin-4-one (Ex. 201)

(Ex. 200)

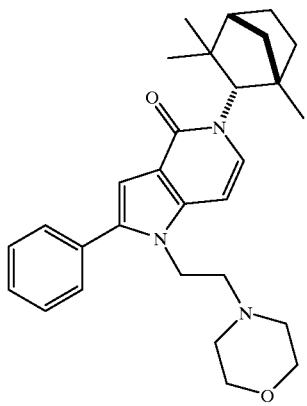

(Ex. 201)

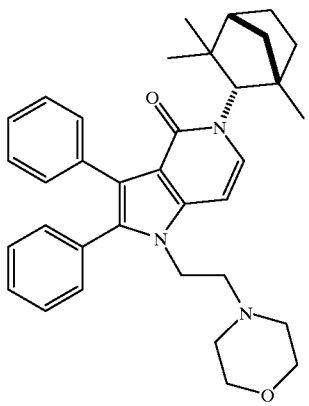

The compounds of Examples 200 and 201 were prepared from Examples 198 and 199, respectively, following the general cyclization procedure described above for Example 83. For Example 200, LC/MS MH+ 415.42, ret. t: 0.90 min (E), and for Example 201, LC/MS MH+ 536.60, ret. t: 3.18 min (A).

Examples 202–500

The compounds of Examples 202–500, as shown in Table 11, were prepared using the general procedure below.

7-methoxy-1-(morpholinylethyl)indazole-3-acid chloride hydrochloride salt was prepared as follows. To 7-methoxy-1-morpholinoethyl indazole-3-carboxylic acid sodium salt (3.0 g, 9 mmol) in anhydrous DCM (86 mL) at RT were added DMF (0.04 mL, 0.05 mmol) and oxalyl chloride (4.3 mL, 49 mmol). After stirring at RT for 2 h, the solvent was removed in vacuo and the resulting pale yellow solid was triturated with three 75 mL portions of hexanes. The resulting solid was dried in vacuo to afford 3.1 g (91%) of the crude acid chloride hydrochloride salt containing 1 eq. NaCl. This crude material was used directly in the procedure below without any further purification. LCMS (M+H)= 324.70, ret. t: 2.16 min (A).

General Procedure

To a slurry of an indazole acid chloride HCl salt (25 mg, 0.06 mmol) in 0.5 mL of DCE at RT were added TEA (28 μL, 0.20 mmol) and the amine or aniline substrate (0.05 mmol). The resulting mixture was stirred at RT for 16 h for the aliphatic amine cases or 70° C. for 16 h for the aniline cases. The reaction mixture was diluted with chloroform (1 mL) and shaken with 1 N aqueous NaOH (0.5 mL). The organic layer was removed and concentrated in vacuo to afford the desired amide products having sufficient purity. In some cases, purification by flash chromatography using silica gel and EtOAc/hex solvent mixtures as the eluant was necessary to obtain the pure products.

TABLE 11
| EX. NO. | STRUCTURE | COMPOUND NAME | DATA: MS (M + H)/ HPLC ret. time (min.) and conditions |
|---|---|---|---|
| 202 | 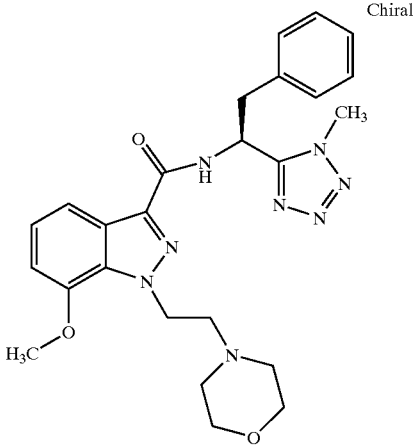 Chiral | 7-Methoxy-N-[(1S)-1-(1-methyl-1H-tetrazol-5-yl)-2-phenylethyl]-1-[2-(4-morpholinyl)ethyl]-1H-indazole-3-carboxamide | 491.31/ 2.87 (A) |
| 203 | 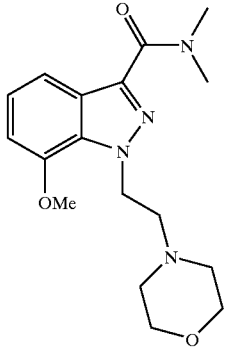 | 7-Methoxy-N,N-dimethyl-1-[2-(4-morpholinyl)ethyl]-1H-indazole-3-carboxamide | 333.40/ 1.98 (A) |
| 204 | 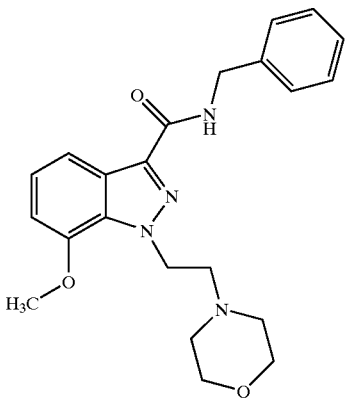 | 7-Methoxy-1-[2-(4-morpholinyl)ethyl]-N-(phenylmethyl)-1H-indazole-3-carboxamide | 394.52/ 2.80 (A) |

TABLE 11-continued

| EX. NO. | STRUCTURE | COMPOUND NAME | DATA: MS (M + H)/ HPLC ret. time (min.) and conditions |
|---|---|---|---|
| 205 | 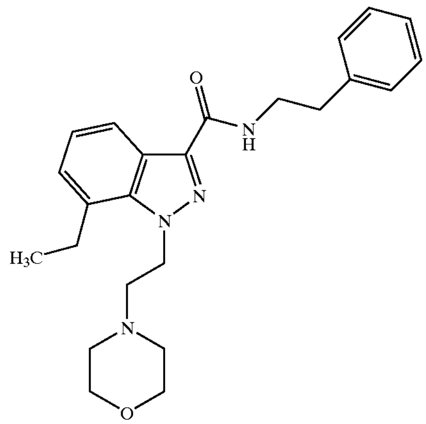 | 7-Methoxy-1-[2-(4-morpholinyl)ethyl]-N-(2-phenylethyl)-1H-indazole-3-carboxamide | 409.51/ 2.98 (A) |
| 206 | Chiral | 7-Methoxy-N-[(1S)-2-(methylamino)-2-oxo-1-(phenylmethyl)ethyl]-1-[2-(4-morpholinyl)ethyl]-1H-indazole-3-carboxamide | 466.60/ 2.81 (A) |
| 207 | Chiral | 7-Methoxy-1-[2-(4-morpholinyl)ethyl]-N-[(1S)-1-hydroxy-2-(phenylmethyl)ethyl]-1H-indazole-3-carboxamide | 439.53/ 2.87 (A) |

TABLE 11-continued
| EX. NO. | STRUCTURE | COMPOUND NAME | DATA: MS (M + H)/ HPLC ret. time (min.) and conditions |
|---|---|---|---|
| 208 | 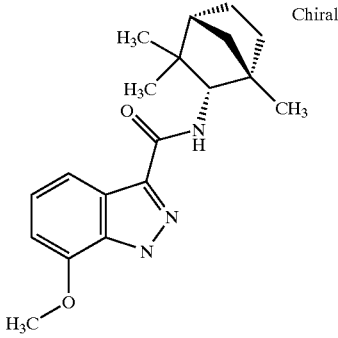 Chiral | 7-Methoxy-N-[(1S,2S)-1,3,3-trimethylbicyclo[2.2.1]heptan-2-yl]-1H-indazole-3-carboxamide | 328.42/ 4.35 (A) |
| 209 | 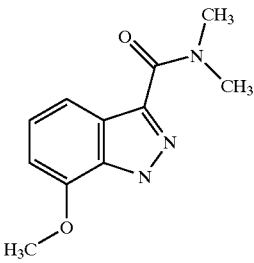 | 7-Methoxy-N,N-dimethyl-1H-indazole-3-carboxamide | 220.26/ 2.72 (A) |
| 210 | 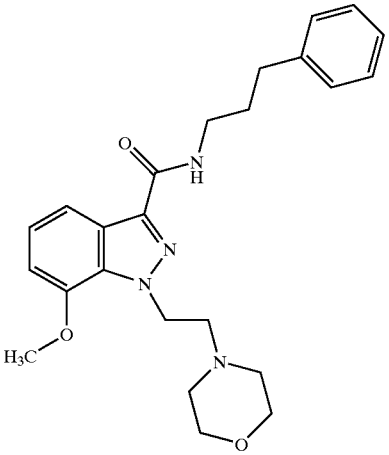 | 7-Methoxy-1-[2-(4-morpholinyl)ethyl]-N-(3-phenylpropyl)-1H-indazole-3-carboxamide | 423.20/ 1.49 (B) |

TABLE 11-continued

| EX. NO. | STRUCTURE | COMPOUND NAME | DATA: MS (M + H)/ HPLC ret. time (min.) and conditions |
|---|---|---|---|
| 211 | 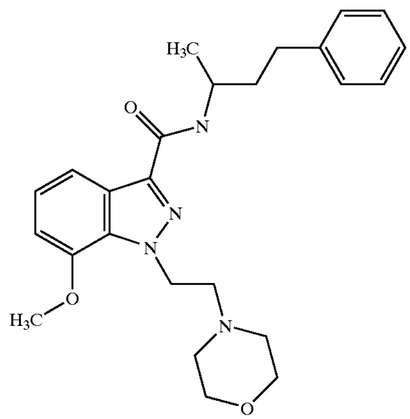 | 7-Methoxy-N-(1-methyl-3-phenylpropyl)-1-[2-(4-morpholinyl)ethyl]-1H-indazole-3-carboxamide | 437.39/ 1.43 (C) |
| 212 | 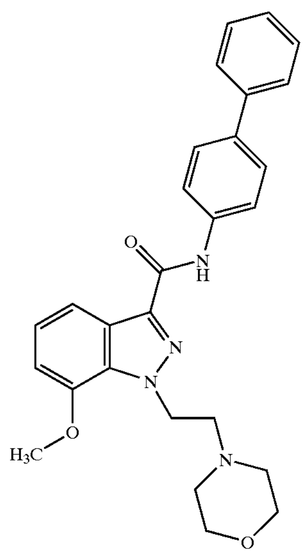 | N-([1,1'-Biphenyl]-4-yl)-7-methoxy-1-[2-(4-morpholinyl)ethyl]-1H-indazole-3-carboxamide | 457.41/ 3.11 (A) |
| 213 | Chiral | 7-Methoxy-N-[(1S)-1-(1-methyl-1H-imidazol-2-yl)-2-phenylethyl]-1-[2-(4-morpholinyl)ethyl]-1H-indazole-3-carboxamide | 603.26/ 1.17 (B) |

TABLE 11-continued

| EX. NO. | STRUCTURE | COMPOUND NAME | DATA: MS (M + H)/ HPLC ret. time (min.) and conditions |
|---|---|---|---|
| 214 | 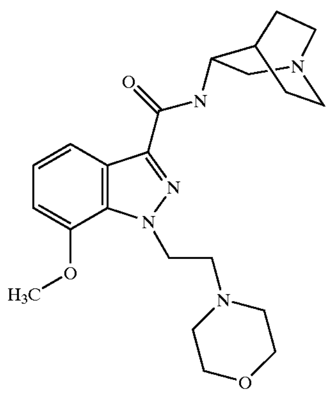 | N-[(3R)-1-Azabicyclo[2.2.2]octan-3-yl]-7-methoxy-1-[2-(4-morpholinyl)ethyl]-1H-indazole-3-carboxamide | 414.34/ 0.74 (C) |
| 215 | Chiral | N-[(1R,2S)-2,3-Dihydro-1H-inden-3-yl]-7-methoxy-1-[2-(4-morpholinyl)ethyl]-1H-indazole-3-carboxamide | 437.31/ 1.24 (C) |
| 216 | Chiral | N-[(1S,2R)-2,3-Dihydro-1H-inden-3-yl]-7-methoxy-1-[2-(4-morpholinyl)ethyl]-1H-indazole-3-carboxamide | 437.31/ 1.22 (C) |

TABLE 11-continued

| EX. NO. | STRUCTURE | COMPOUND NAME | DATA: MS (M + H)/ HPLC ret. time (min.) and conditions |
|---|---|---|---|
| 217 | 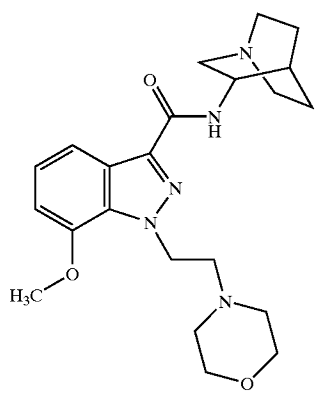 | N-[(3S)-1-Azabicyclo[2.2.2]octan-3-yl]-7-methoxy-1-[2-(4-morpholinyl)ethyl]-1H-indazole-3-carboxamide | 414.42/ 1.17 (A) |
| 218 | 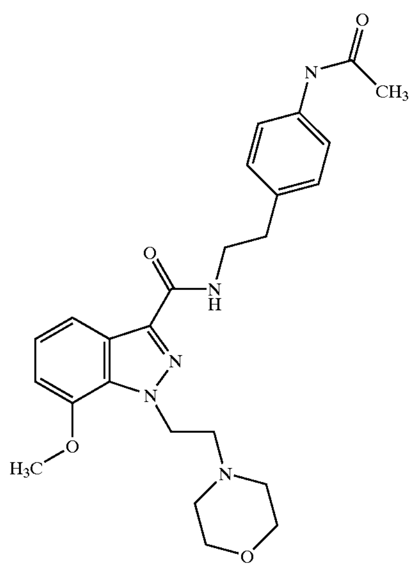 | N-[2-[4-(Acetylamino)phenyl]ethyl]-7-methoxy-1-[2-(4-morpholinyl)ethyl]-1H-indazole-3-carboxamide | 466.38/ 1.11 (C) |
| 219 | 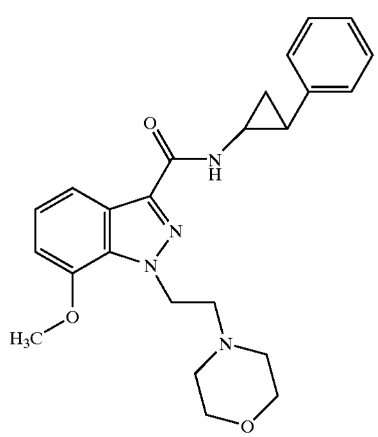 | 7-Methoxy-1-[2-(4-morpholinyl)ethyl]-N-(2-phenylcyclopropyl)-1H-indazole-3-carboxamide | 421.29/ 1.35 (C) |

TABLE 11-continued
| EX. NO. | STRUCTURE | COMPOUND NAME | DATA: MS (M + H)/ HPLC ret. time (min.) and conditions |
|---|---|---|---|
| 220 | 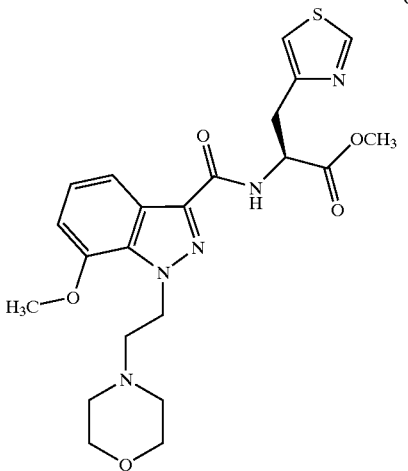 Chiral | N-[[7-Methoxy-1-[2-(4-morpholinyl)ethyl]-1H-indazol-3-yl]carbonyl]-3-(4-thiazolyl)-L-alanine methyl ester | 474.55/ 2.50 (A) |
| 221 | 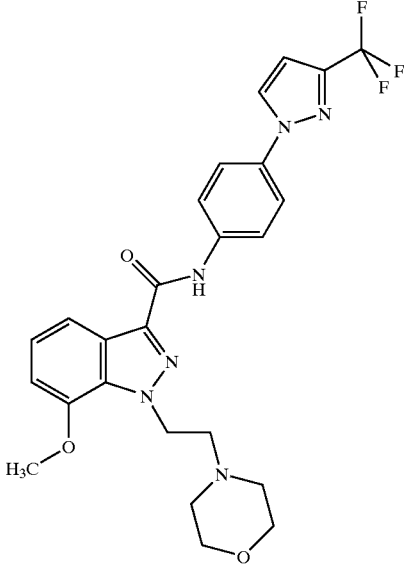 | 7-Methoxy-1-[2-(4-morpholinyl)ethyl]-N-[4-[3-(trifluoromethyl)-1H-pyrazol-1-yl]phenyl]-1H-indazole-3-carboxamide | 515.50/ 3.55 (A) |
| 222 | 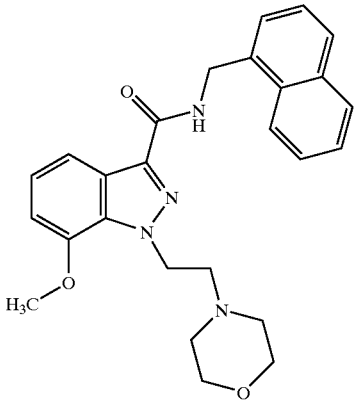 | 7-Methoxy-1-[2-(4-morpholinyl)ethyl]-N-(1-naphthalenylmethyl)-1H-indazole-3-carboxamide | 445.53/ 3.29 (A) |

TABLE 11-continued

| EX. NO. | STRUCTURE | COMPOUND NAME | DATA: MS (M + H)/ HPLC ret. time (min.) and conditions |
|---|---|---|---|
| 223 | 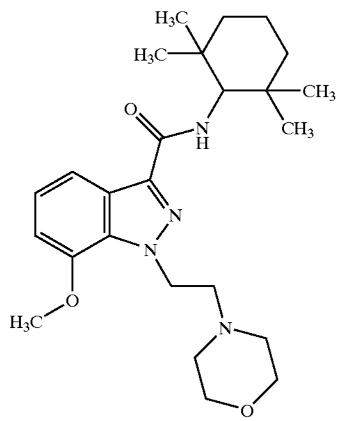 | 7-Methoxy-1-[2-(4-morpholinyl)ethyl]-N-(2,2,6,6-tetramethylcyclohexyl)-1H-indazole-3-carboxamide | 443.62/ 3.26 (A) |
| 224 | 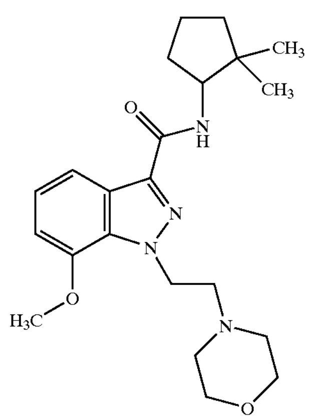 | N-(2,2-Dimethylcyclopentyl)-7-methoxy-1-[2-(4-morpholinyl)ethyl]-1H-indazole-3-carboxamide | 401.54/ 3.10 (A) |
| 225 | 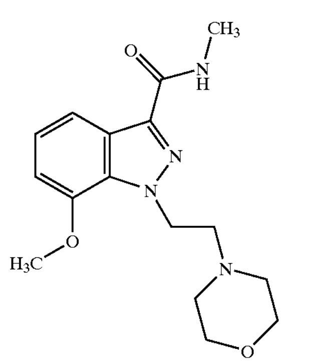 | 7-Methoxy-N-methyl-1-[2-(4-morpholinyl)ethyl]-1H-indazole-3-carboxamide | 319.29/ 1.45 (A) |

TABLE 11-continued

| EX. NO. | STRUCTURE | COMPOUND NAME | DATA: MS (M + H)/ HPLC ret. time (min.) and conditions |
|---|---|---|---|
| 226 | Chiral | N-[[7-Methoxy-1-[2-(4-morpholinyl)ethyl]-1H-indazol-3-yl]carbonyl]-L-phenylalanine 1,1-dimethylethyl ester | 509.62/ 3.00 (A) |
| 227 | Chiral | 7-Methoxy-N-[(1S,2S)-2-hydroxy-1-(methoxymethyl)-2-phenylethyl]-1-[2-(4-morpholinyl)ethyl]-1H-indazole-3-carboxamide | 469.56/ 2.37 (A) |
| 228 | Chiral | 7-Methoxy-N-[(1R,2S,3R,4S)-3-(hydroxymethyl)bicyclo[2.2.1]-heptan-2-yl]-1-[2-(4-morpholinyl)ethyl]-1H-indazole-3-carboxamide | 429.54/ 3.24 (A) |

TABLE 11-continued
| EX. NO. | STRUCTURE | COMPOUND NAME | DATA: MS (M + H)/ HPLC ret. time (min.) and conditions |
|---|---|---|---|
| 229 | 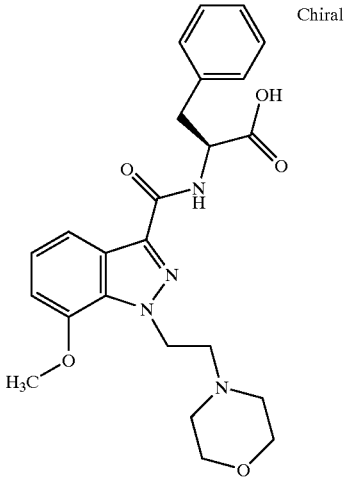 Chiral | N-[[7-Methoxy-1-[2-(4-morpholinyl)ethyl]-1H-indazol-3-yl]carbonyl]-L-phenylalanine | 453.59/ 2.15 (A) |
| 230 | 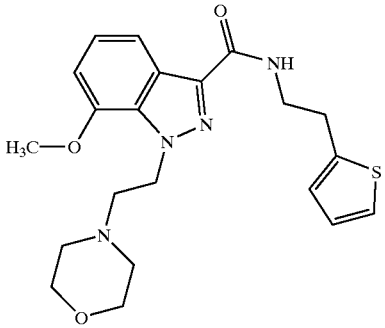 | 7-Methoxy-1-[2-(4-morpholinyl)ethyl]-N-[2-(2-thienyl)ethyl]-1H-indazole-3-carboxamide | 415.16/ 2.51 (D) |
| 231 | 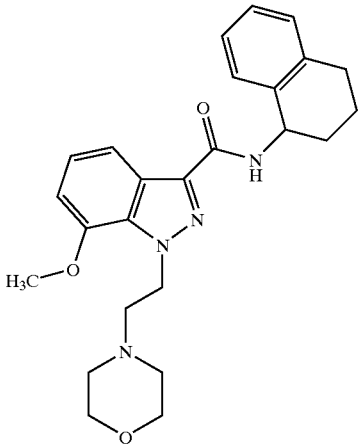 | 7-Methoxy-1-[2-(4-morpholinyl)ethyl]-N-(1,2,3,4-tetrahydro-1-naphthalenyl)-1H-indazole-3-carboxamide | 435.22/ 2.85 (D) |

TABLE 11-continued

| EX. NO. | STRUCTURE | COMPOUND NAME | DATA: MS (M + H)/ HPLC ret. time (min.) and conditions |
|---|---|---|---|
| 232 | 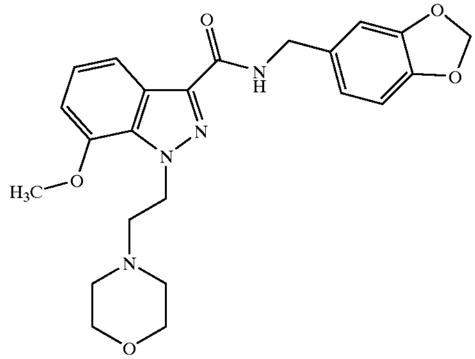 | N-(1,3-Benzodioxol-5-ylmethyl)-7-methoxy-1-[2-(4-morpholinyl)ethyl]-1H-indazole-3-carboxamide | 439.16/ 1.35 (D) |
| 233 | 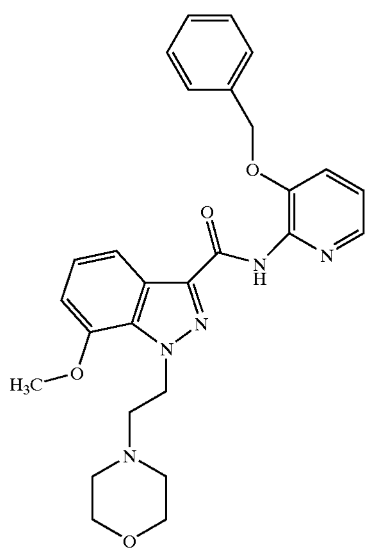 | 7-Methoxy-1-[2-(4-morpholinyl)ethyl]-N-[3-(phenylmethoxy)-2-pyridinyl]-1H-indazole-3-carboxamide | 488.26/ 1.30 (D) |
| 234 | 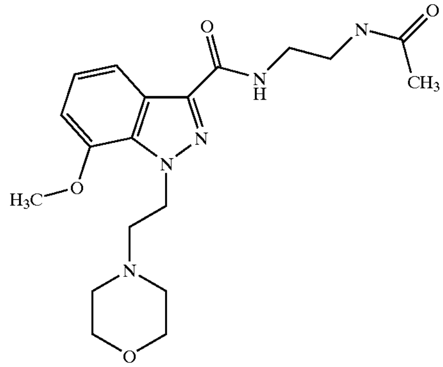 | N-[2-(Acetylamino)ethyl]-7-methoxy-1-[2-(4-morpholinyl)ethyl]-1H-indazole-3-carboxamide | 390.22/ 1.66 (D) |

TABLE 11-continued

| EX. NO. | STRUCTURE | COMPOUND NAME | DATA: MS (M + H)/ HPLC ret. time (min.) and conditions |
|---|---|---|---|
| 235 | 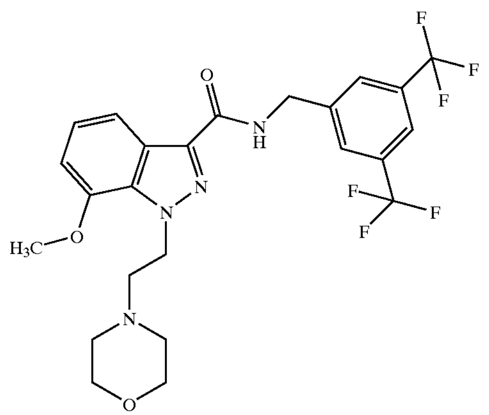 | N-[[3,5-Bis(trifluoromethyl)phenyl]methyl]-7-methoxy-1-[2-(4-morpholinyl)ethyl]-1H-indazole-3-carboxamide | 531.18/ 3.24 (D) |
| 236 | 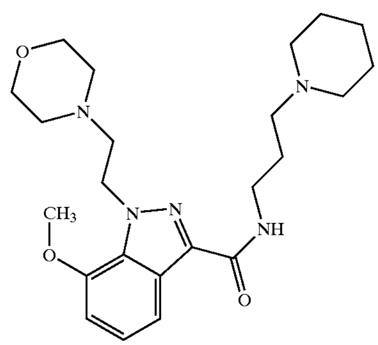 | 7-Methoxy-1-1[2-(4-morpholinyl)ethyl]-N-[3-(1-piperidinyl)propyl]-1H-indazole-3-carboxamide | 430.26/ 1.64 (D) |
| 237 | 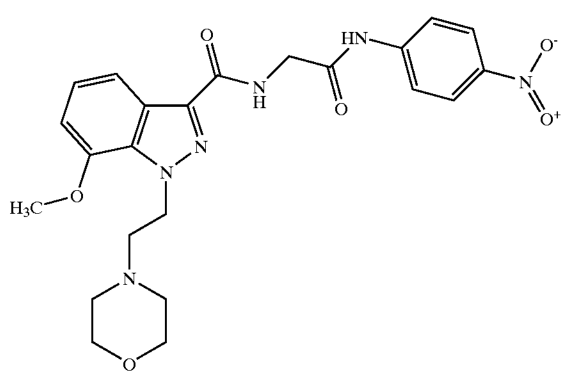 | 7-Methoxy-N-[2-[4-nitrophenyl)amino]-2-oxoethyl]-1-[2-(4-morpholinyl)ethyl]-1H-indazole-3-carboxamide | 483.16/ 2.50 (D) |
| 238 | 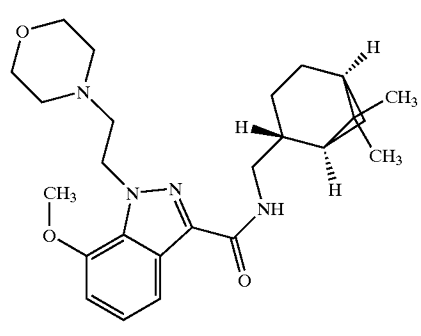 | N-[[(1R)-3,3-Dimethylcyclohexyl]methyl]-7-methoxy-1-[2-(4-morpholinyl)ethyl]-1H-indazole-3-carboxamide | 441.27/ 3.26 (D) |

TABLE 11-continued

| EX. NO. | STRUCTURE | COMPOUND NAME | DATA: MS (M + H)/ HPLC ret. time (min.) and conditions |
|---|---|---|---|
| 239 | 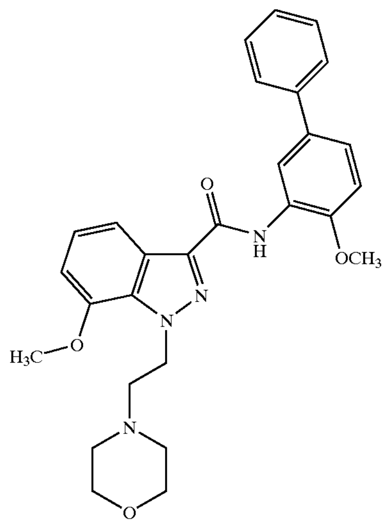 | 7-Methoxy-N-(4-methoxy[1,1'-biphenyl]-3-yl)-1-[2-(4-morpholinyl)ethyl]-1H-indazole-3-carboxamide | 487.22/ 3.29 (D) |
| 240 | 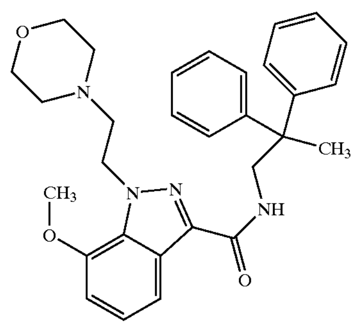 | N-(2,2-Diphenylpropyl)-7-methoxy-1-[2-(4-morpholinyl)ethyl]-1H-indazole-3-carboxamide | 499.27/ 3.21 (D) |
| 241 | 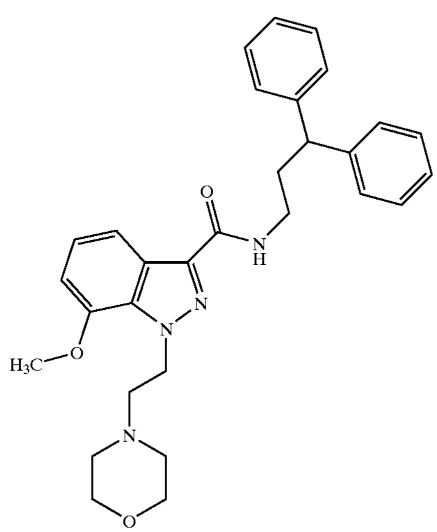 | N-(3,3-Diphenylpropyl)-7-methoxy-1-[2-(4-morpholinyl)ethyl]-1H-indazole-3-carboxamide | 499.27/ 3.20 (D) |

TABLE 11-continued

| EX. NO. | STRUCTURE | COMPOUND NAME | DATA: MS (M + H)/ HPLC ret. time (min.) and conditions |
|---|---|---|---|
| 242 | 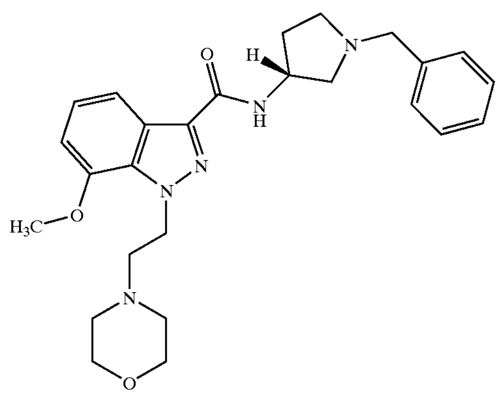 | 7-Methoxy-1-[2-(4-morpholinyl)ethyl]-N-[(3R)-1-(phenylmethyl)-3-pyrrolidinyl]-1H-indazole-3-carboxamide | 464.28/ 2.03 (D) |
| 243 | 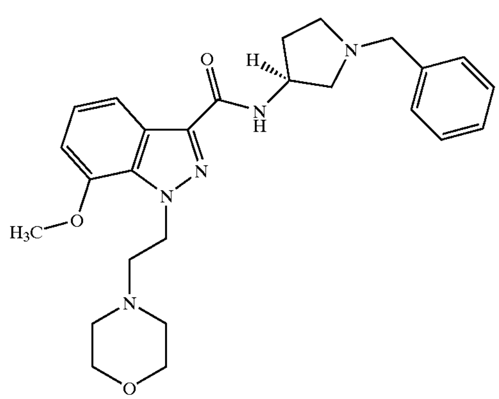 | 7-Methoxy-1-[2-(4-morpholinyl)ethyl]-N-[(3S)-1-(phenylmethyl)-3-pyrrolidinyl]-1H-indazole-3-carboxamide | 464.29/ 2.01 (D) |
| 244 | 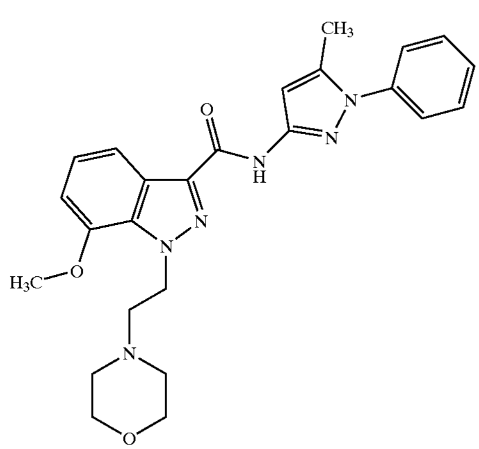 | 7-Methoxy-N-(5-methyl-1-phenyl-1H-pyrazol-3-yl)-1-[2-(4-morpholinyl)ethyl]-1H-indazole-3-carboxamide | 461.23/ 1.32 (D) |

TABLE 11-continued

| EX. NO. | STRUCTURE | COMPOUND NAME | DATA: MS (M + H)/ HPLC ret. time (min.) and conditions |
|---|---|---|---|
| 245 | 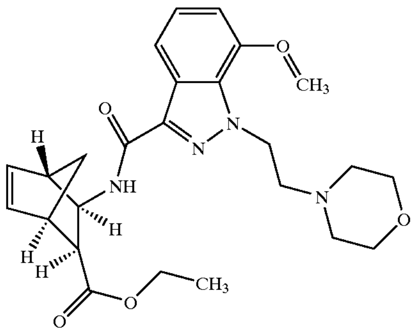 | (2-endo,3-endo)-3-[[[7-methoxy-1-[2-(4-morpholinyl)ethyl]-1H-indazol-3-yl]carbonyl]amino]bicyclo-[2.2.1]hept-5-ene-2-carboxylic acid ethyl ester | 469.26/ 2.66 (D) |
| 246 | 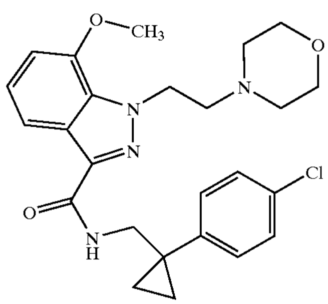 | N-[[1-(4-Chlorophenyl)-cyclopropyl]methyl]-7-methoxy-1-[2-(4-morpholinyl)ethyl]-1H-indazole-3-carboxamide | 469.23/ 3.05 (D) |
| 247 | 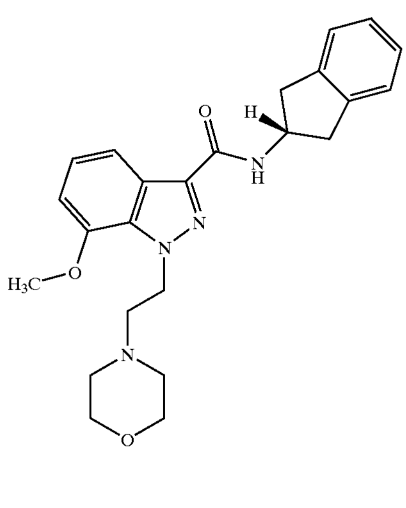 | N-[(1R)-2,3-Dihydro-1H-inden-1-yl]-7-methoxy-1-[2-(4-morpholinyl)ethyl]-1H-indazole-3-carboxamide | 421.22/ 2.69 (D) |

TABLE 11-continued

| EX. NO. | STRUCTURE | COMPOUND NAME | DATA: MS (M + H)/ HPLC ret. time (min.) and conditions |
|---|---|---|---|
| 248 | 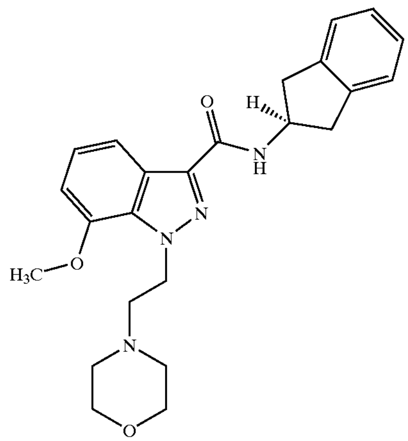 | N-[(1S)-2,3-Dihydro-1H-inden-1-yl]-7-methoxy-1-[2-(4-morpholinyl)ethyl]-1H-indazole-3-carboxamide | 421.19/ 2.69 (D) |
| 249 | 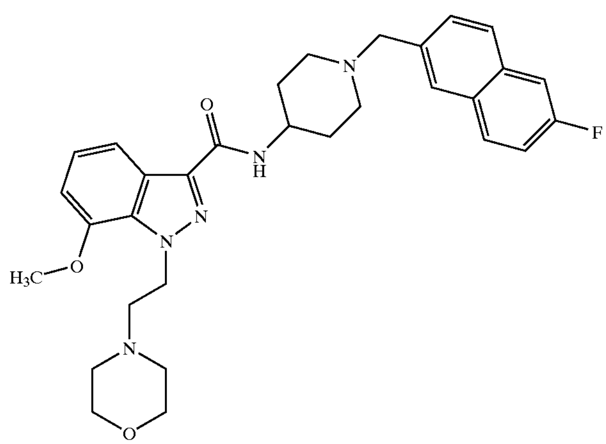 | N-[1-[(6-Fluoro-2-naphthalenyl)methyl]-4-piperidinyl]-7-methoxy-1-[2-(4-morpholinyl)ethyl]-1H-indazole 3-carboxamide | 546.29/ 1.68 (D) |
| 250 | 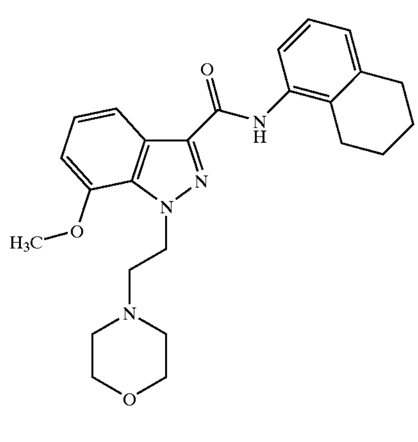 | 7-Methoxy-1-[2-(4-morpholinyl)ethyl]-N-(5,6,7,8-tetrahydro-1-naphthalenyl)-1H-indazole-3-carboxamide | 435.22/ 2.81 (D) |

TABLE 11-continued

| EX. NO. | STRUCTURE | COMPOUND NAME | DATA: MS (M + H)/ HPLC ret. time (min.) and conditions |
|---|---|---|---|
| 251 | 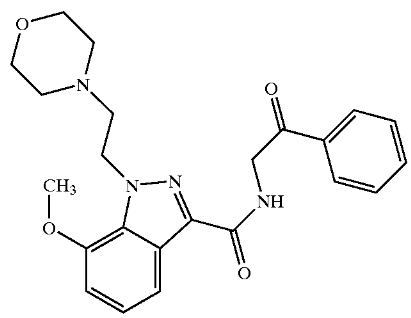 | 7-Methoxy-1-[2-(4-morpholinyl)-ethyl]-N-(2-oxo-2-phenylethyl)-1H-indazole-3-carboxamide | 423.19/ 2.47 (D) |
| 252 | 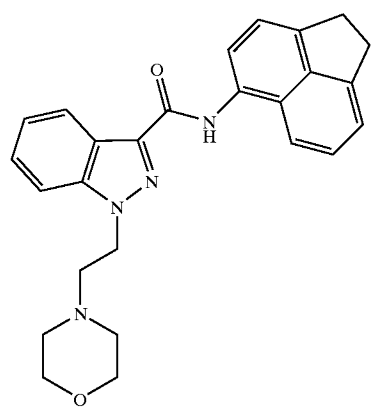 | N-(1,2-Dihydro-5-acenaphthylenyl)-7-methoxy-1-[2-(4-morpholinyl)ethyl]-1H-indazole-3-carboxamide | 457.19/ 2.89 (D) |
| 253 | 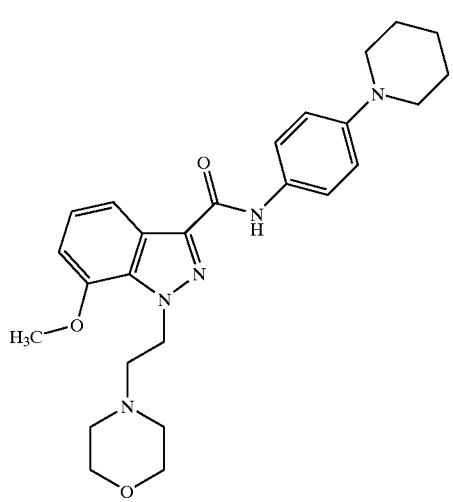 | 7-Methoxy-1-[2-(4-morpholinyl)ethyl]-N-[4-(1-piperidinyl)phenyl]-1H-indazole-3-carboxamide | 464.27/ 2.06 (D) |

TABLE 11-continued

| EX. NO. | STRUCTURE | COMPOUND NAME | DATA: MS (M + H)/ HPLC ret. time (min.) and conditions |
|---|---|---|---|
| 254 | 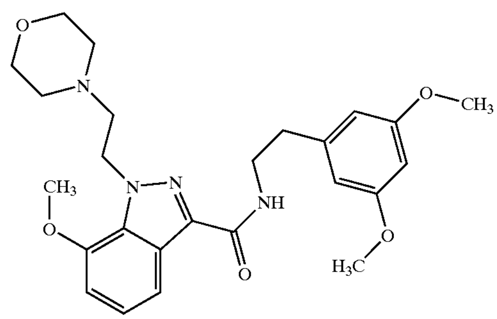 | N-[2-(3,5-Dimethoxyphenyl)ethyl]-7-methoxy-1-[2-(4-morpholinyl)ethyl]-1H-indazole-3-carboxamide | 469.26/ 2.63 (D) |
| 255 | 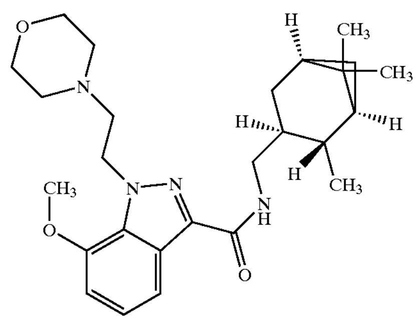 | 7-Methoxy-1-[2-(4-morpholinyl)-ethyl]-N-[[(1S,2S)-2,4,4-trimethylcyclohexyl]methyl]-1H-indazole-3-carboxamide | 455.31/ 3.40 (D) |
| 256 | 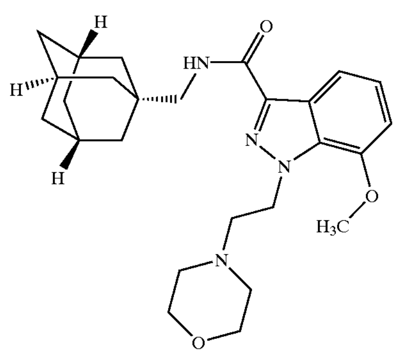 | N-(1-Adamantylmethyl)-7-methoxy-1-[2-(4-morpholinyl)-ethyl]-1H-indazole-3-carboxamide | 453.31/ 3.25 (D) |
| 257 | 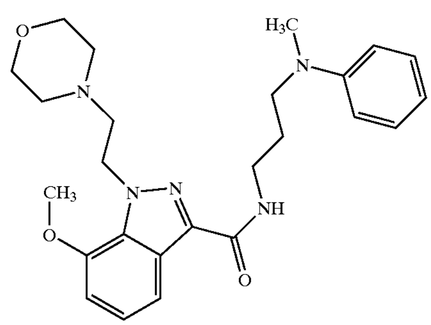 | 7-Methoxy-N-[3-(methylphenylamino)propyl]-1-[2-(4-morpholinyl)ethyl]-1H-indazole-3-carboxamide | 452.28/ 1.90 (D) |

TABLE 11-continued

| EX. NO. | STRUCTURE | COMPOUND NAME | DATA: MS (M + H)/ HPLC ret. time (min.) and conditions |
|---|---|---|---|
| 258 | 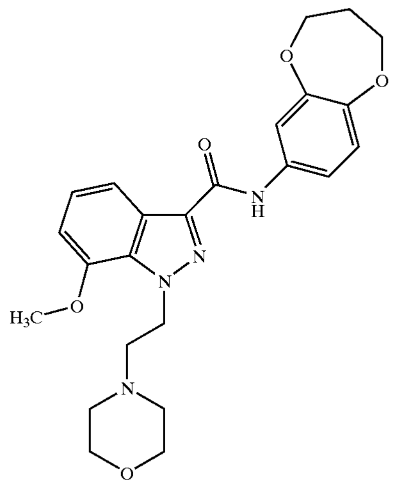 | N-(3,4-Dihydro-2H-1,5-benzodioxepin-7-yl)-7-methoxy-1-[2-(4-morpholinyl)ethyl]-1H-indazole-3-carboxamide | 453.23/ 2.61 (D) |
| 259 | 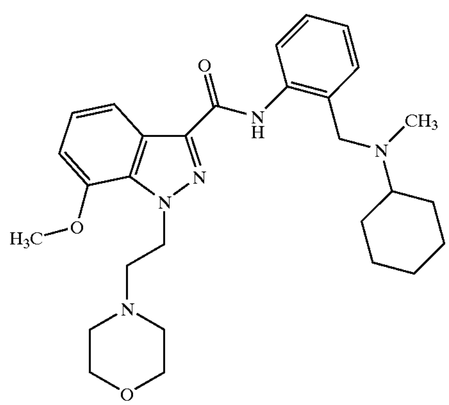 | N-[2-[(Cyclohexylmethylamino)methyl]-phenyl]-7-methoxy-1-[2-(4-morpholinyl)ethyl]-1H-indazole-3-carboxamide | 506.31/ 2.32 (D) |
| 260 | 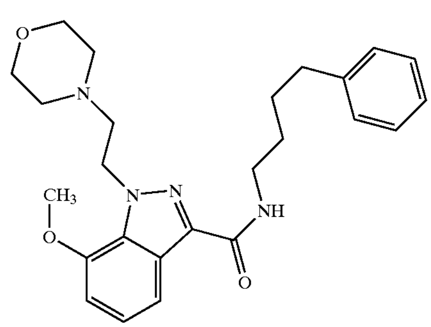 | 7-Methoxy-1-[2-(4-morpholinyl)ethyl]-N-(4-phenylbutyl)-1H-indazole-3-carboxamide | 437.24/ 2.95 (D) |

TABLE 11-continued

| EX. NO. | STRUCTURE | COMPOUND NAME | DATA: MS (M + H)/ HPLC ret. time (min.) and conditions |
|---|---|---|---|
| 261 | 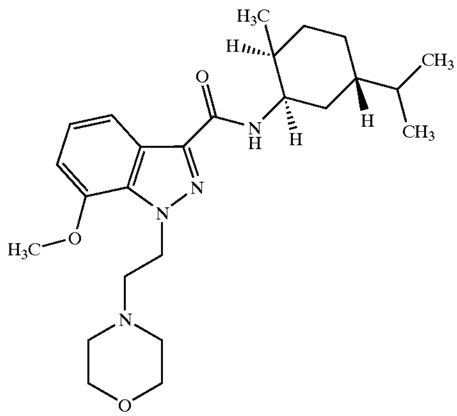 | 7-Methoxy-N-[(1R,2S,5R)-5-methyl-2-(1-methylethyl)cyclohexyl]-1-[2-(4-morpholinyl)ethyl]-1H-indazole-3-carboxamide | 443.30/ 3.27 (D) |
| 262 | 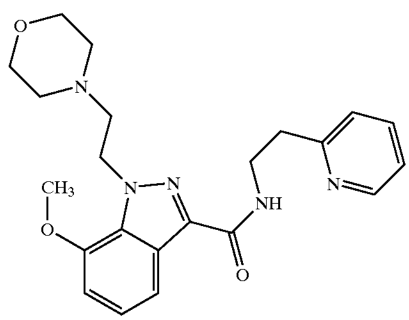 | 7-Methoxy-1-[2-(4-morpholinyl)ethyl]-N-[2-(2-pyridinyl)ethyl]-1H-indazole-3-carboxamide | 410.21/ 1.55 (D) |
| 263 | 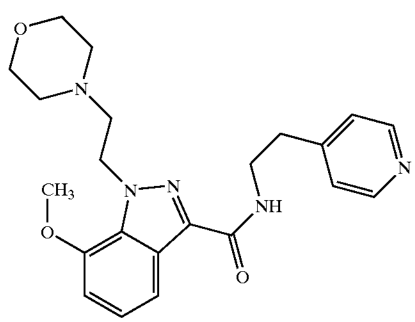 | 7-Methoxy-1-[2-(4-morpholinyl)ethyl]-N-[2-(4-pyridinyl)ethyl]-1H-indazole-3-carboxamide | 410.19/ 1.56 (D) |
| 264 | 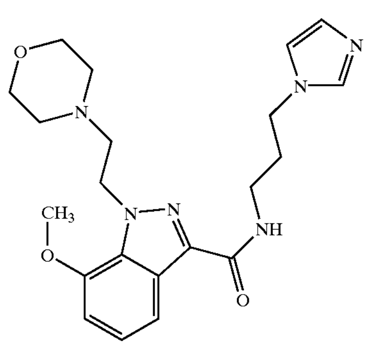 | N-[3-(1H-Imidazol-1-yl)propyl]-7-methoxy-1-[2-(4-morpholinyl)ethyl]-1H-indazole-3-carboxamide | 413.22/ 1.52 (D) |

TABLE 11-continued

| EX. NO. | STRUCTURE | COMPOUND NAME | DATA: MS (M + H)/ HPLC ret. time (min.) and conditions |
|---|---|---|---|
| 265 | 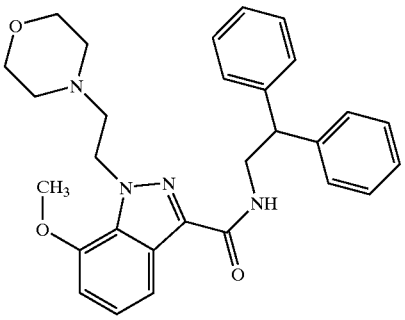 | N-(2,2-Diphenylethyl)-7-methoxy-1-[2-(4-morpholinyl)ethyl]-1H-indazole-3-carboxamide | 485.26/ 3.03 (D) |
| 266 | 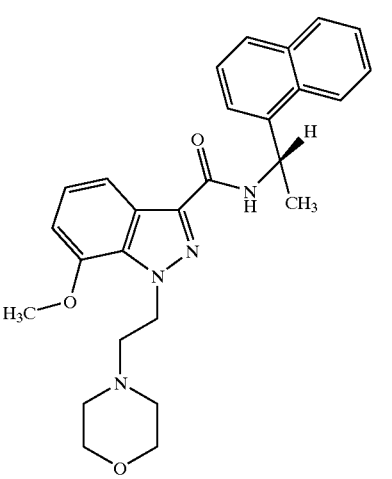 | 7-Methoxy-1-[2-(4-morpholinyl)ethyl]-N-[(1S)-1-(1-naphthalenyl)ethyl]-1H-indazole-3-carboxamide | 459.23/ 2.76 (D) |
| 267 | 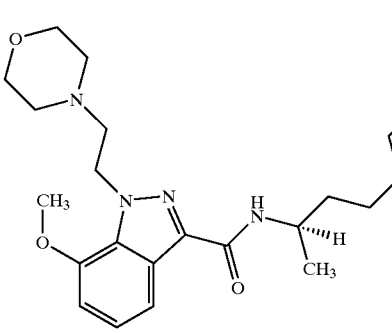 | 7-Methoxy-N-[(1R)-1-methyl-3-phenylpropyl]-1-[2-(4-morpholinyl)ethyl]-1H-indazole-3-carboxamide | 437.24/ 2.88 (D) |
| 268 | 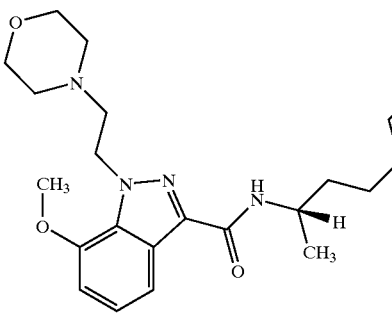 | 7-Methoxy-N-[(1S)-1-methyl-3-phenylpropyl]-1-[2-(4-morpholinyl)ethyl]-1H-indazole-3-carboxamide | 437.24/ 2.87 (D) |

TABLE 11-continued

| EX. NO. | STRUCTURE | COMPOUND NAME | DATA: MS (M + H)/ HPLC ret. time (min.) and conditions |
|---|---|---|---|
| 269 | 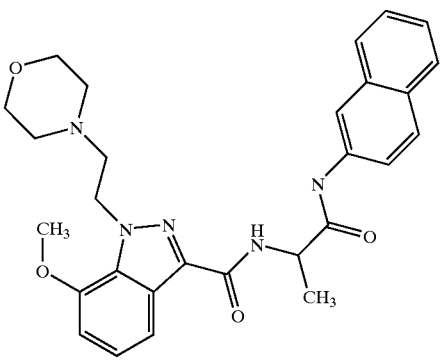 | 7-Methoxy-N-[1-methyl-2-(2-naphthalenylamino)-2-oxoethyl]-1-[2-(4-morpholinyl)ethyl]-1H-indazole-3-carboxamide | 502.24/ 2.95 (D) |
| 270 | 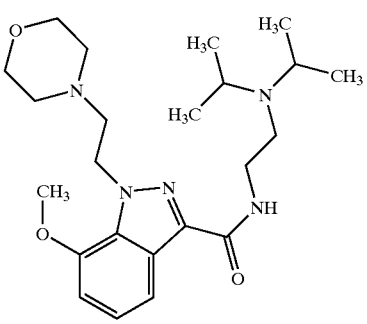 | N-[2-[Bis(1-methylethyl)amino]ethyl]-7-methoxy-1-[2-(4-morpholinyl)ethyl]-1H-indazole-3-carboxamide | 432.29/ 1.32 (D) |
| 271 | 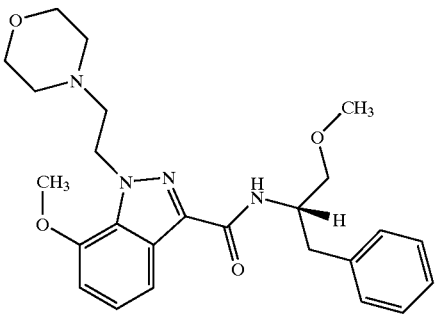 | 7-Methoxy-N-[(1S)-2-methoxy-1-(2-phenylmethyl)ethyl]-1-[2-(4-morpholinyl)ethyl]-1H-indazole-3-carboxamide | 453.27/ 2.67 (D) |
| 272 | 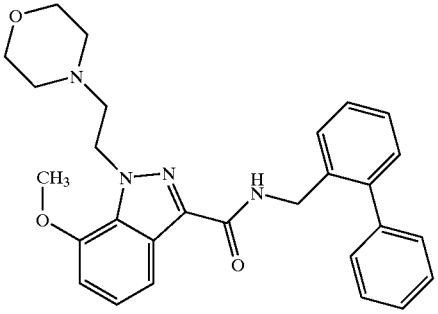 | N-([1,1'-Biphenyl]-2-ylmethyl)-7-methoxy-1-[2-(4-morpholinyl)ethyl]-1H-indazole-3-carboxamide | 471.26/ 3.05 (D) |

TABLE 11-continued

| EX. NO. | STRUCTURE | COMPOUND NAME | DATA: MS (M + H)/ HPLC ret. time (min.) and conditions |
|---|---|---|---|
| 273 | 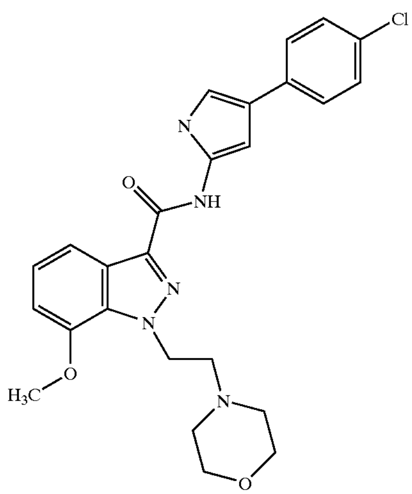 | N-[4-(4-Chlorophenyl)-1H-pyrrol-2-yl]-7-methoxy-1-[2-(4-morpholinyl)ethyl]-1H-indazole-3-carboxamide | 480.90/ 3.13 (A) |
| 274 | 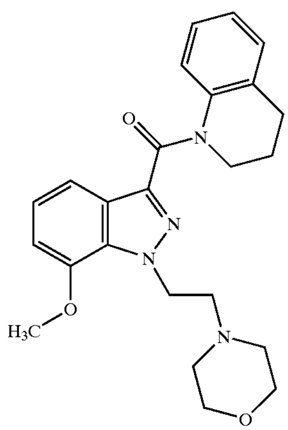 | 1,2,3,4-Tetrahydro-1-[[7-methoxy-1-[2-(4-morpholinyl)ethyl]-1H-indazol-3-yl]carbonyl]quinoline | 421.23/ 2.20 (A) |
| 275 | 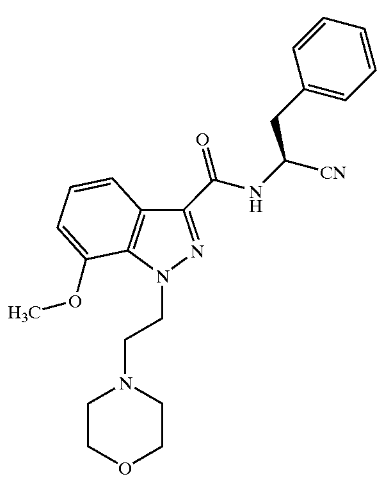 | N-[(1S)-1-Cyano-2-phenylethyl]-7-methoxy-1-[2-(4-morpholinyl)ethyl]-1H-indazole-3-carboxamide | 434.25/ 1.23 (C) |

TABLE 11-continued

| EX. NO. | STRUCTURE | COMPOUND NAME | DATA: MS (M + H)/ HPLC ret. time (min.) and conditions |
|---|---|---|---|
| 276 | 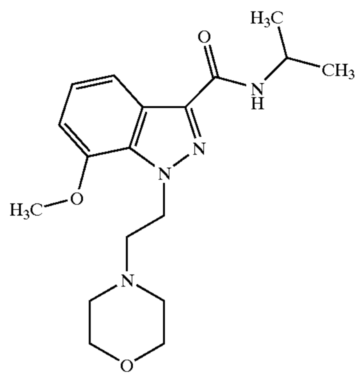 | 7-Methoxy-N-(1-methylethyl)-1-[2-(4-morpholinyl)ethyl]-1H-indazole-3-carboxamide | 347.28/ 1.76 (A) |
| 277 | 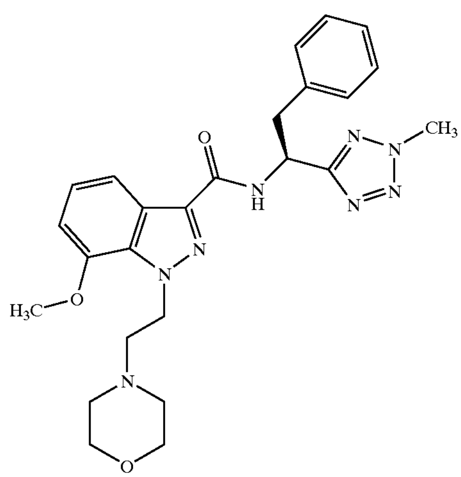 | 7-Methoxy-N-[(1S)-1-(2-methyl-2H-tetrazol-5-yl)-2-phenylethyl]-1-[2-(4-morpholinyl)ethyl]-1H-indazole-3-carboxamide | 491.31/ 1.23 (B) |
| 278 | 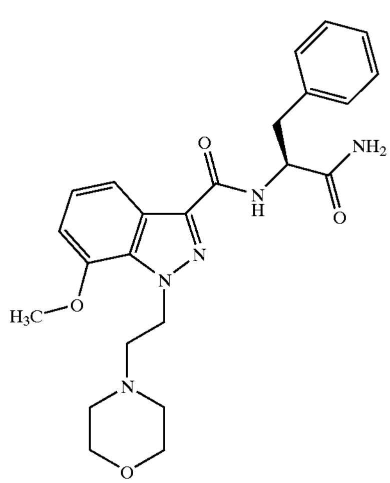 | N-[(1S)-1-(Aminocarbonyl)-2-phenylethyl]-7-methoxy-1-[2-(4-morpholinyl)ethyl]-1H-indazole-3-carboxamide | 452.25/ 1.21 (B) |

TABLE 11-continued

| EX. NO. | STRUCTURE | COMPOUND NAME | DATA: MS (M + H)/ HPLC ret. time (min.) and conditions |
|---|---|---|---|
| 279 | 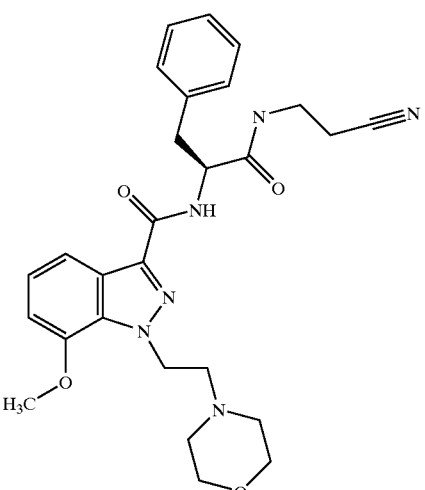 Chiral | N-[(1S)-1-[[(2-Cyanoethyl)amino]carbonyl]-2-phenylethyl]-7-methoxy-1-[2-(4-morpholinyl)ethyl]-1H-indazole-3-carboxamide | 505.29/ 1.14 (C) |
| 280 | 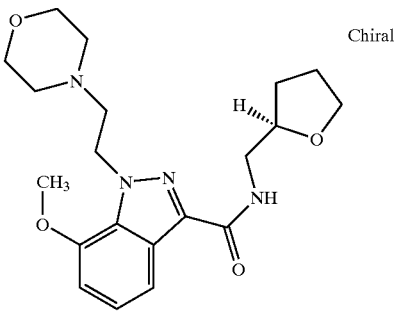 Chiral | 7-Methoxy-1-[2-(4-morpholinyl)ethyl]-N-[[(2R)-tetrahydro-2-furanyl]methyl]-1H-indazole-3-carboxamide | 389.26/ 1.10 (B) |
| 281 | 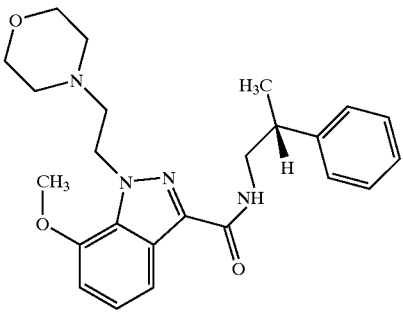 Chiral | N-[2-(2,6-Dimethylphenoxy)-1-methylethyl]-7-methoxy-1-[2-(4-morpholinyl)ethyl]-1H-indazole-3-carboxamide | 467.30/ 1.48 (B) |
| 282 | 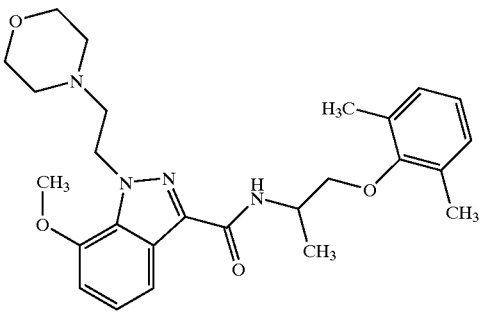 | 7-Methoxy-1-[2-(4-morpholinyl)ethyl]-N-[(2R)-2-phenylpropyl]-1H-indazole-3-carboxamide | 423.24/ 1.33 (B) |

TABLE 11-continued
| EX. NO. | STRUCTURE | COMPOUND NAME | DATA: MS (M + H)/ HPLC ret. time (min.) and conditions |
|---|---|---|---|
| 283 | 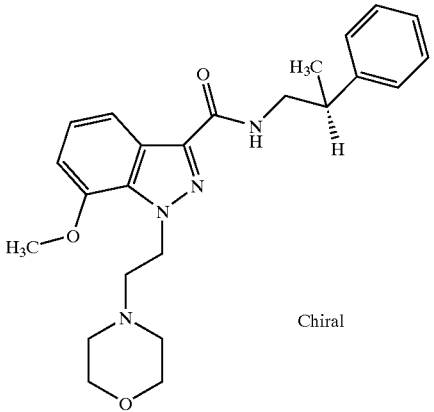 Chiral | 7-Methoxy-1-[2-(4-morpholinyl)ethyl]-N-[2S)-2-phenylpropyl]-1H-indazole-3-carboxamide | 423.24/ 1.32 (B) |
| 284 | 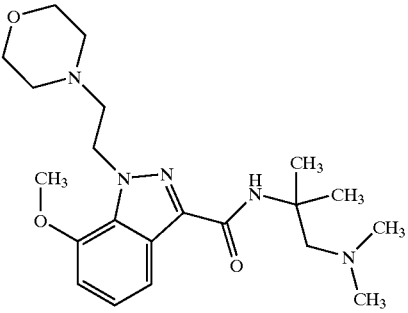 | N-[2-(Dimethylamino)-1,1dimethylethyl]-7-methoxy-1-[2-(4-morpholinyl)ethyl]-1H-indazole-3-carboxamide | 404.30/ 0.87 (B) |
| 285 | 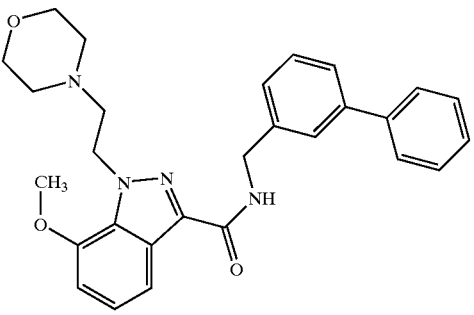 | N-([1,1'-Biphenyl]-3-ylmethyl)-7-methoxy-1-[2-(4-morpholinyl)ethyl]-1H-indazole-3-carboxamide | 471.26/ 1.58 (B) |

TABLE 11-continued

| EX. NO. | STRUCTURE | COMPOUND NAME | DATA: MS (M + H)/ HPLC ret. time (min.) and conditions |
|---|---|---|---|
| 286 | 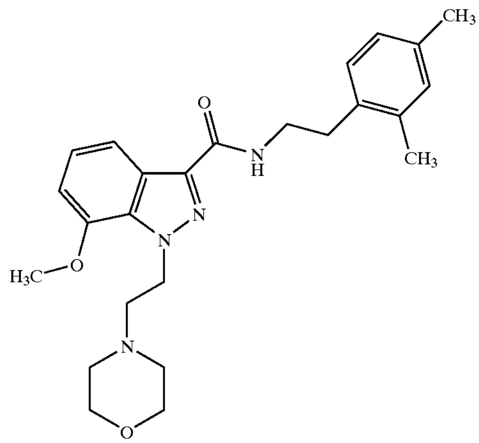 | N-[2-(2,4-Dimethylphenyl)ethyl]-7-methoxy-1-[2-(4-morpholinyl)ethyl]-1H-indazole-3-carboxamide | 437.27/ 1.56 (B) |
| 287 | Chiral | 7-Methoxy-1-[2-(4-morpholinyl)ethyl]-N-[(1S)-1-phenylpropyl]-1H-indazole-3-carboxamide | 467.26/ 1.40 (B) |
| 288 | Chiral | 7-Methoxy-1-[2-(4-morpholinyl)ethyl]-N-[(1R)-1-phenylpropyl]-1H-indazole-3-carboxamide | 423.25/ 1.40 (B) |
| 289 | 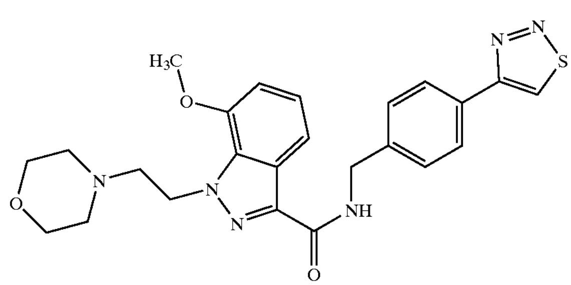 | 7-Methoxy-1-[2-(4-morpholinyl)ethyl]-N-[[4-(1,2,3-thiadiazol-4-yl)phenyl]methyl]-1H-indazole-3-carboxamide | 423.25/ 1.31 (B) |

TABLE 11-continued

| EX. NO. | STRUCTURE | COMPOUND NAME | DATA: MS (M + H)/ HPLC ret. time (min.) and conditions |
|---|---|---|---|
| 290 | 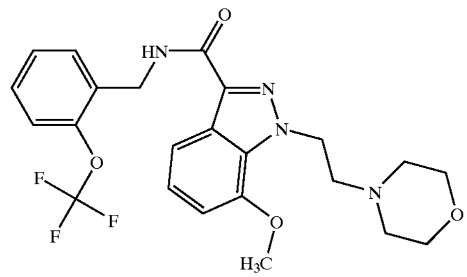 | 7-Methoxy-1-[2-(4-morpholinyl)ethyl]-N-[[2-(trifluoromethoxy)phenyl]methyl]-1H-indazole-3-carboxamide | 479.2/ 1.48 (B) |
| 291 | 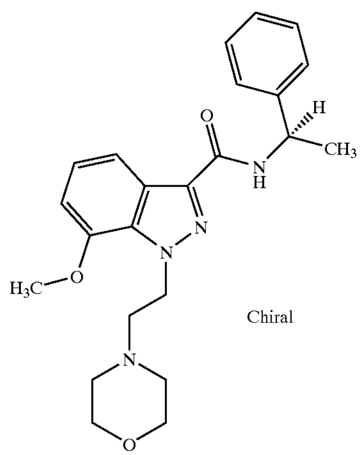 | 7-Methoxy-1-[2-(4-morpholinyl)ethyl]-N-[[(2S)-tetrahydro-2-furanyl]methyl]-1H-indazole-3-carboxamide | 479.21/ 1.10 (B) |
| 292 | 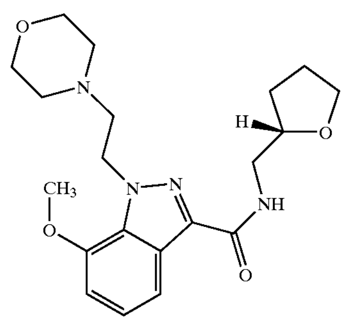 | 7-Methoxy-1-[2-(4-morpholinyl)ethyl]-N-[phenyl(2-pyridinyl)methyl]-1H-indazole-3-carboxamide | 389.25/ 1.18 (B) |
| 293 | 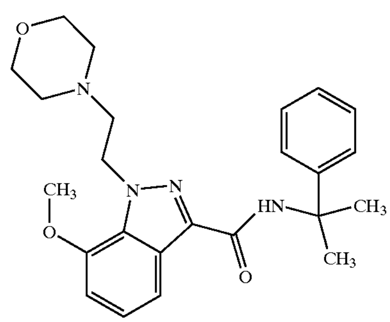 | 7-Methoxy-N-(1-methyl-1-phenylethyl)-1-[2-(4-morpholinyl)ethyl]-1H-indazole-3-carboxamide | 423.24/ 1.37 (B) |

TABLE 11-continued

| EX. NO. | STRUCTURE | COMPOUND NAME | DATA: MS (M + H)/ HPLC ret. time (min.) and conditions |
|---|---|---|---|
| 294 | Chiral | N-[(1R,2S)-2-(Aminocarbonyl)cyclohexyl]-7-methoxy-1-[2-(4-morpholinyl)ethyl]-1H-indazole-3-carboxamide | 430.25/ 1.19 (B) |
| 295 | 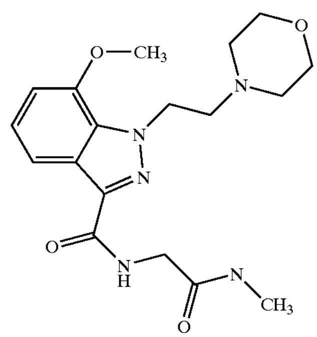 | 7-Methoxy-N-[2-(methylamino)-2-oxoethyl]-1-[2-(4-morpholinyl)ethyl]-1H-indazole-3-carboxamide | 376.23/ 0.84 (B) |
| 296 | 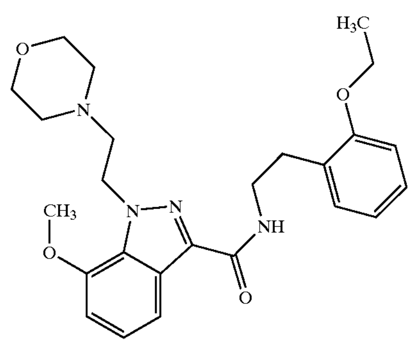 | N-[2-(2-Ethoxyphenyl)ethyl]-7-methoxy-1-[2-(4-morpholinyl)ethyl]-1H-indazole-3-carboxamide | 453.26/ 1.59 (B) |
| 297 | Chiral | 4-[[[7-Methoxy-1-[2-(4-morpholinyl)ethyl]-1H-indazol-3-yl]carbonyl]amino]-1-piperidinecarboxylic acid ethyl ester | 460.27/ 1.29 (B) |

TABLE 11-continued

| EX. NO. | STRUCTURE | COMPOUND NAME | DATA: MS (M + H)/ HPLC ret. time (min.) and conditions |
|---|---|---|---|
| 298 | 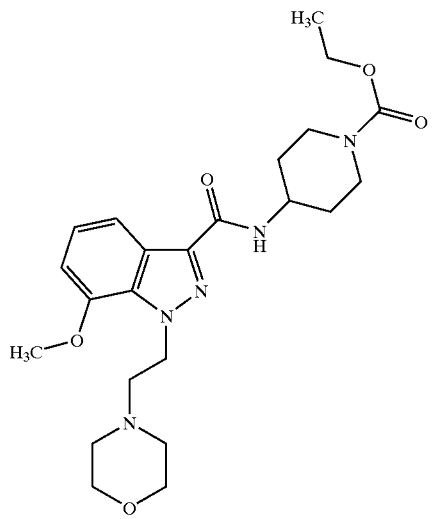 | 7-Methoxy-1-[2-(4-morpholinyl)ethyl]-N-[(1R)-1-phenylethyl]-1H-indazole-3-carboxamide | 409.25/ 1.33 (B) |
| 299 | 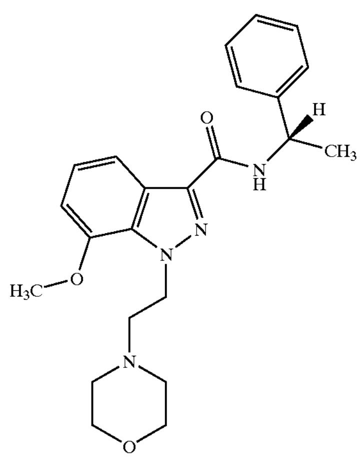 | 7-Methoxy-1-[2-(4-morpholinyl)ethyl]-N-[(1S)-1-phenylethyl]-1H-indazole-3-carboxamide | 409.24/ 1.32 (B) |
| 300 | Chiral | 7-Methoxy-1-[2-(4-morpholinyl)ethyl]-N-[(1R,2S)-2-hydroxy-1-methyl-2-phenylethyl]-1H-indazole-3-carboxamide | 439.24/ 1.29 (B) |

TABLE 11-continued

| EX. NO. | STRUCTURE | COMPOUND NAME | DATA: MS (M + H)/ HPLC ret. time (min.) and conditions |
|---|---|---|---|
| 301 | 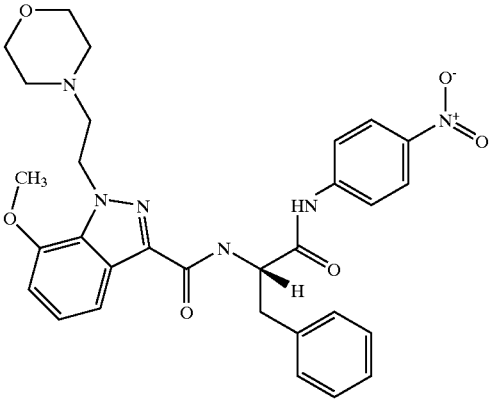 Chiral | N-(Hexahydro-2-oxo-1H-azepin-3-yl)-7-methoxy-1-[2-(4-morpholinyl)ethyl]-1H-indazole-3-carboxamide | 416.23/ 1.15 (B) |
| 302 | 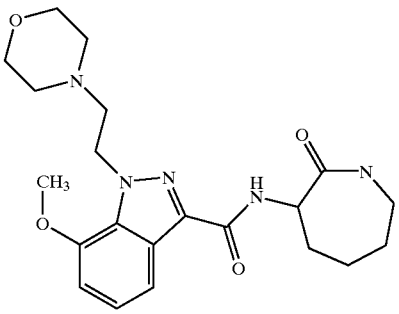 | 7-Methoxy-1-[2-(4-morpholinyl)ethyl]-N-[(1S)-1-[[(4-nitrophenyl)amino]-carbonyl]-2-phenylethyl]-1H-indazole-3-carboxamide | 573.21/ 1.57 (B) |
| 303 | 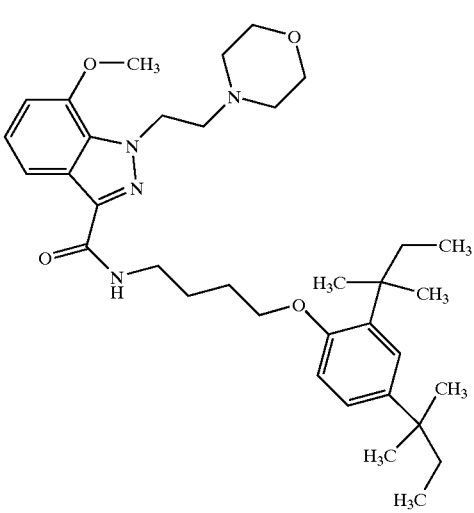 | N-[4-[2,4-Bis(1,1-dimethylpropyl)phenoxy]butyl]-7-methoxy-1-[2-(4-morpholinyl)ethyl]-1H-indazole-3-carboxamide | 593.33/ 2.12 (B) |

TABLE 11-continued

| EX. NO. | STRUCTURE | COMPOUND NAME | DATA: MS (M + H)/ HPLC ret. time (min.) and conditions |
|---|---|---|---|
| 304 | 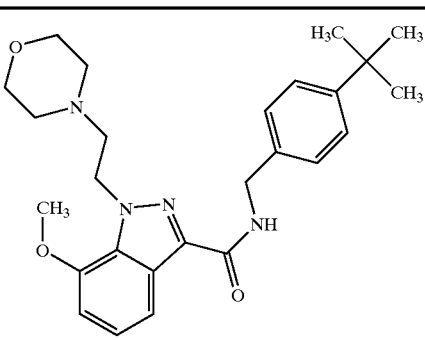 | N-[[4-(1,1-Dimethylethyl)phenyl]methyl]-7-methoxy-1-[2-(4-morpholinyl)ethyl]-1H-indazole-3-carboxamide | 451.28/ 1.62 (B) |
| 305 | 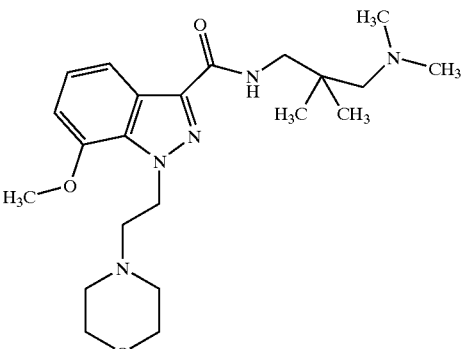 | N-[3-(Dimethylamino)-2,2-dimethylpropyl]-7-methoxy-1-[2-(4-morpholinyl)ethyl]-1H-indazole-3-carboxamide | 418.28/ 0.83 (B) |
| 306 | 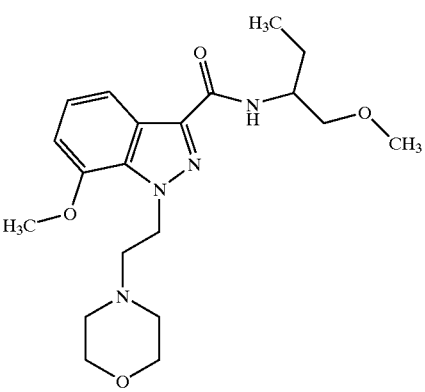 | 7-Methoxy-N-[1-(methoxymethyl)propyl]-1-[2-(4-morpholinyl)ethyl]-1H-indazole-3-carboxamide | 391.25/ 1.15 (B) |
| 307 | 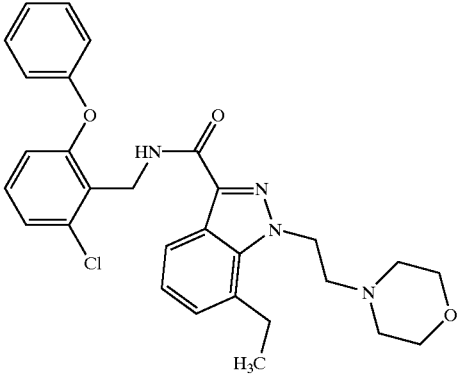 | N-[(2-Chloro-6-phenoxyphenyl)methyl]-7-methoxy-1-[2-(4-morpholinyl)ethyl]-1H-indazole-3-carboxamide | 521.17/ 1.64 (B) |

TABLE 11-continued

| EX. NO. | STRUCTURE | COMPOUND NAME | DATA: MS (M + H)/ HPLC ret. time (min.) and conditions |
|---|---|---|---|
| 308 | 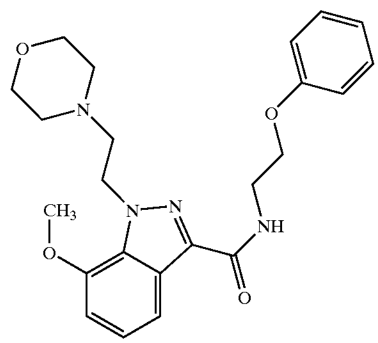 | 7-Methoxy-1-[2-(4-morpholinyl)ethyl]-N-(2-phenoxyethyl)-1H-indazole-3-carboxamide | 425.21/ 1.35 (B) |
| 309 | 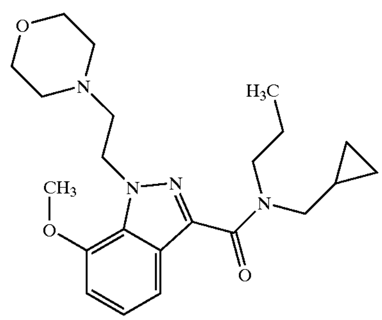 | N-(Cyclopropylmethyl)-7-methoxy-1-[2-(4-morpholinyl)ethyl]-N-propyl-1H-indazole-3-carboxamide | 401.28/ 1.38 (B) |
| 310 | 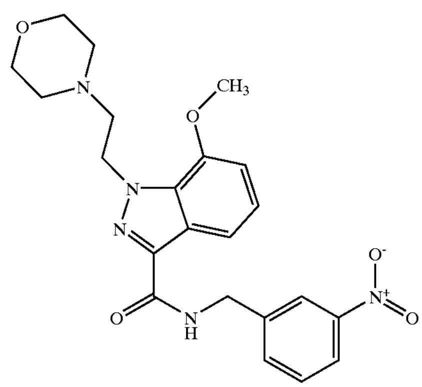 | 7-Methoxy-1-[2-(4-morpholinyl)ethyl]-N-[(3-nitrophenyl)methyl]-1H-indazole-3-carboxamide | 440.19/ 1.30 (B) |
| 311 | 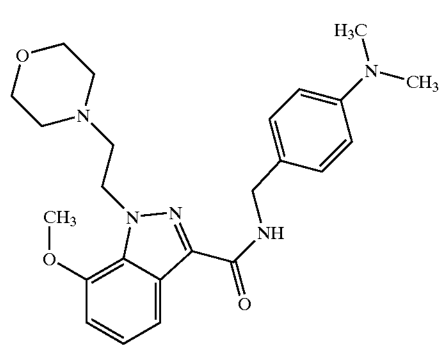 | N-[[4-(Dimethylamino)-phenyl]methyl]-7-methoxy-1-[2-(4-morpholinyl)ethyl]-1H-indazole-3-carboxamide | 438.25/ 0.91 (B) |

TABLE 11-continued

| EX. NO. | STRUCTURE | COMPOUND NAME | DATA: MS (M + H)/ HPLC ret. time (min.) and conditions |
|---|---|---|---|
| 312 | 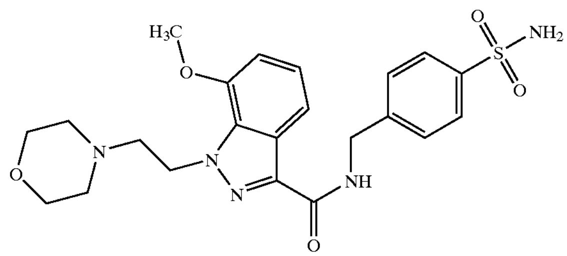 | N-[[4-(Aminosulfonyl)-phenyl]methyl]-7-methoxy-1-[2-(4-morpholinyl)ethyl]-1H-indazole-3-carboxamide | 474.19/ 1.25 (B) |
| 313 | 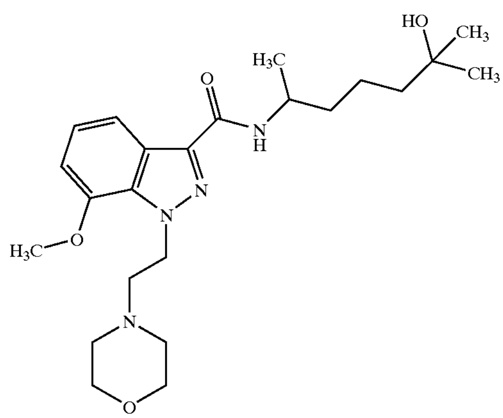 | N-(5-Hydroxy-1,5-dimethylhexyl)-7-methoxy-1-[2-(4-morpholinyl)ethyl]-1H-indazole-3-carboxamide | 433.28/ 1.26 (B) |
| 314 | 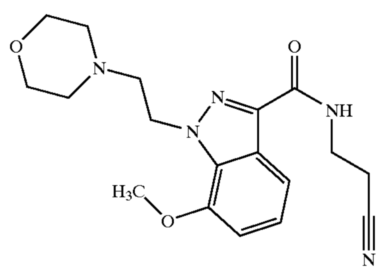 | N-(2-Cyanoethyl)-7-methoxy-1-[2-(4-morpholinyl)ethyl]-1H-indazole-3-carboxamide | 358.21/ 0.92 (B) |
| 315 | 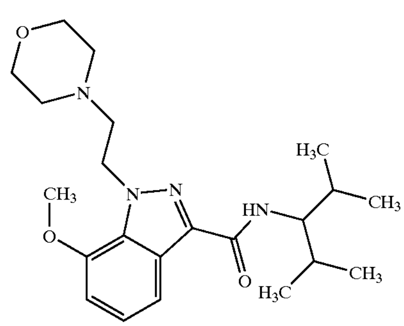 | 7-Methoxy-N-[2-methyl-1-(1-methylethyl)propyl]-1-[2-(4-morpholinyl)ethyl]-1H-indazole-3-carboxamide | 403.29/ 1.43 (B) |

TABLE 11-continued

| EX. NO. | STRUCTURE | COMPOUND NAME | DATA: MS (M + H)/ HPLC ret. time (min.) and conditions |
|---|---|---|---|
| 316 | 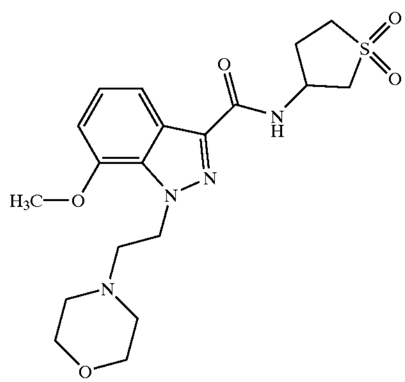 | 7-Methoxy-1-[2-(4-morpholinyl)ethyl]-N-(tetrahydro-1,1-dioxido-3-thienyl)-1H-indazole-3-carboxamide | 423.17/ 0.95 (B) |
| 317 | 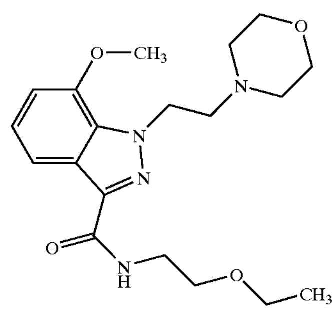 | N-(2-Ethoxyethyl)-7-methoxy-1-[2-(4-morpholinyl)ethyl]-1H-indazole-3-carboxamide | 377.25/ 1.09 (B) |
| 318 | 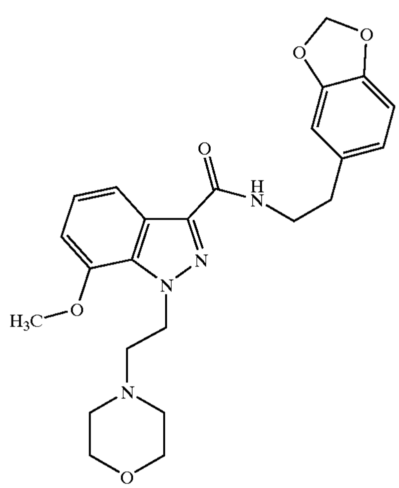 | N-[2-(1,3-Benzodioxol-5-yl)ethyl]-7-methoxy-1-[2-(4-morpholinyl)ethyl]-1H-indazole-3-carboxamide | 453.22/ 1.36 (B) |
| 319 | 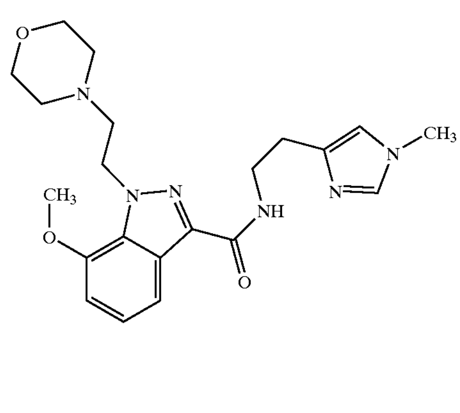 | 7-Methoxy-N-[2-(1-methyl-1H-imidazol-4-yl)ethyl]-1-[2-(4-morpholinyl)ethyl]-1H-indazole-3-carboxamide | 413.24/ 0.80 (B) |

TABLE 11-continued

| EX. NO. | STRUCTURE | COMPOUND NAME | DATA: MS (M + H)/ HPLC ret. time (min.) and conditions |
|---|---|---|---|
| 320 | 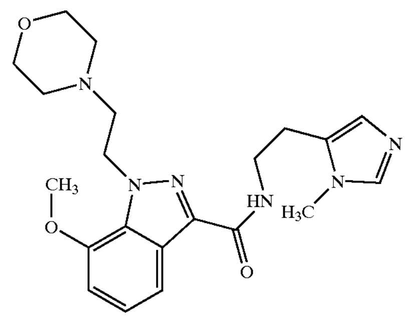 | 7-Methoxy-N-[2-(1-methyl-1H-imidazol-5-yl)ethyl]-1-[2-(4-morpholinyl)ethyl]-1H-indazole-3-carboxamide | 413.24/ 0.81 (B) |
| 321 | 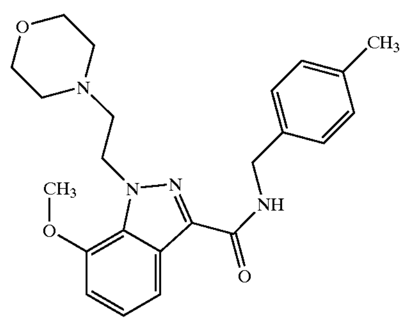 | 7-Methoxy-N-[(4-methylphenyl)methyl]-1-[2-(4-morpholinyl)ethyl]-1H-indazole-3-carboxamide | 409.23/ 1.38 (B) |
| 322 | 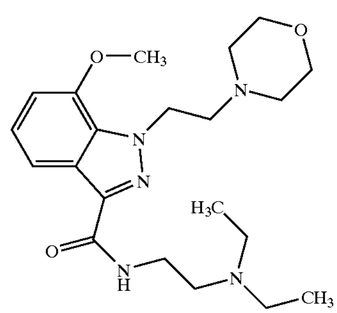 | N-[2-(Diethylamino)ethyl]-7-methoxy-1-[2-(4-morpholinyl)ethyl]-1H-indazole-3-carboxamide | 404.28/ 0.48 (B) |
| 323 | 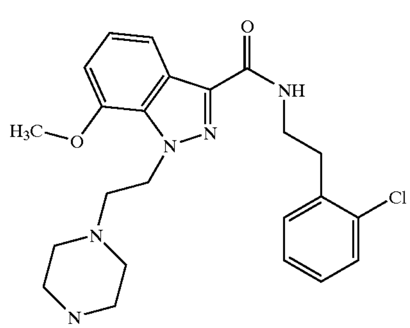 | N-[2-(2-Chlorophenyl)ethyl]-7-methoxy-1-[2-(4-morpholinyl)ethyl]-1H-indazole-3-carboxamide | 443.18/ 1.46 (B) |

TABLE 11-continued

| EX. NO. | STRUCTURE | COMPOUND NAME | DATA: MS (M + H)/ HPLC ret. time (min.) and conditions |
|---|---|---|---|
| 324 | 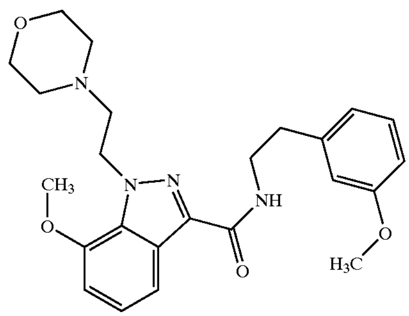 | 7-Methoxy-N-[2-(3-methoxyphenyl)ethyl]-1-[2-(4-morpholinyl)ethyl]-1H-indazole-3-carboxamide | 439.23/ 1.37 (B) |
| 325 | 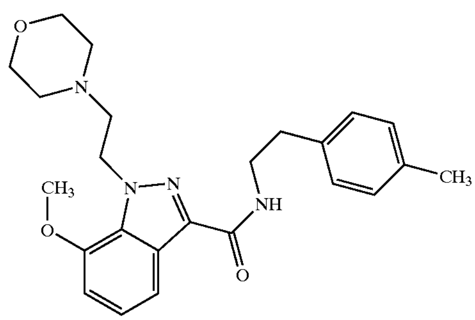 | 7-Methoxy-N-[2-(4-methylphenyl)ethyl]-1-[2-(4-morpholinyl)ethyl]-1H-indazole-3-carboxamide | 423.24/ 1.47 (B) |
| 326 | 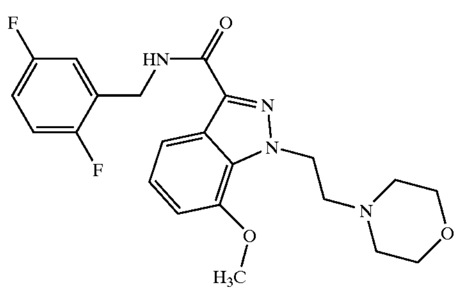 | N-[3-(Diethylamino)propyl]-7-methoxy-1-[2-(4-morpholinyl)ethyl]-1H-indazole-3-carboxamide | 418.27/ 0.84 (B) |
| 327 | 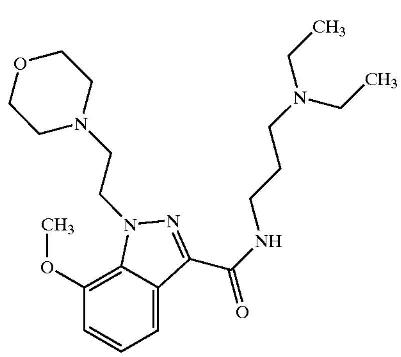 | N-[(2,5-Difluorophenyl)methyl]-7-methoxy-1-[2-(4-morpholinyl)ethyl]-1H-indazole-3-carboxamide | 431.18/ 1.35 (B) |

TABLE 11-continued

| EX. NO. | STRUCTURE | COMPOUND NAME | DATA: MS (M + H)/ HPLC ret. time (min.) and conditions |
|---|---|---|---|
| 328 | 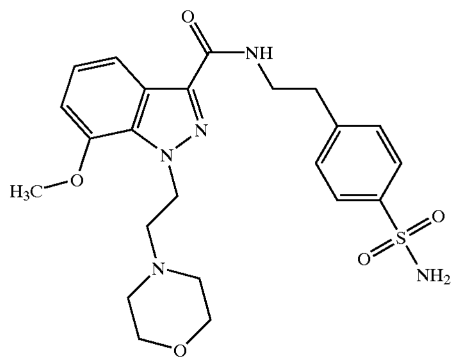 | N-[2-[4-(Aminosulfonyl)-phenyl]ethyl]-7-methoxy-1-[2-(4-morpholinyl)ethyl]-1H-indazole-3-carboxamide | 488.17/ 1.26 (B) |
| 329 | 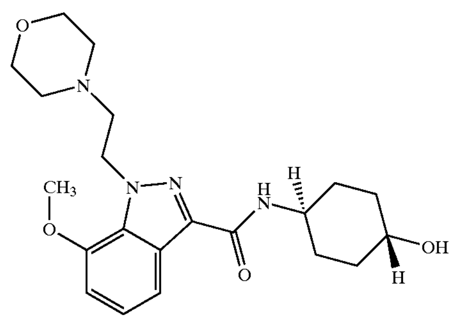 | N-(trans-4-Hydroxycyclohexyl)-7-methoxy-1-[2-(4-morpholinyl)ethyl]-1H-indazole-3-carboxamide | 403.24/ 1.02 (B) |
| 330 | 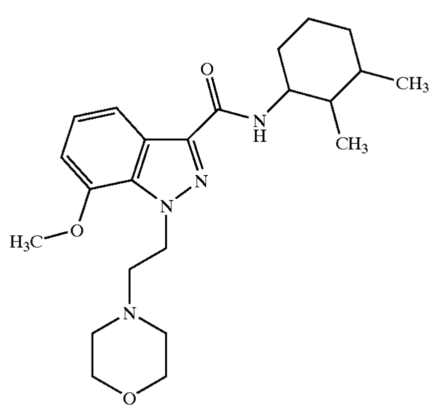 | N-(1H-Benzimidazol-2-ylmethyl)-7-methoxy-1-[2-(4-morpholinyl)ethyl]-1H-indazole-3-carboxamide | 435.21/ 1.07 (B) |
| 331 | 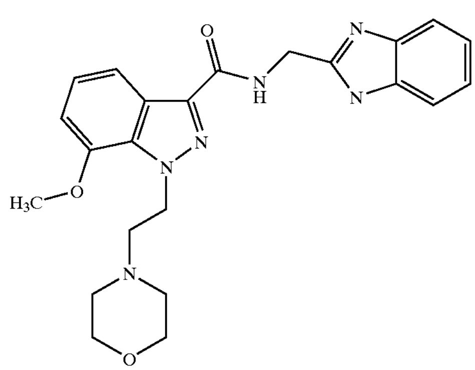 | N-(2,3-Dimethylcyclohexyl)-7-methoxy-1-[2-(4-morpholinyl)ethyl]-1H-indazole-3-carboxamide | 415.27/ 1.52 (B) |

TABLE 11-continued

| EX. NO. | STRUCTURE | COMPOUND NAME | DATA: MS (M + H)/ HPLC ret. time (min.) and conditions |
|---|---|---|---|
| 332 | 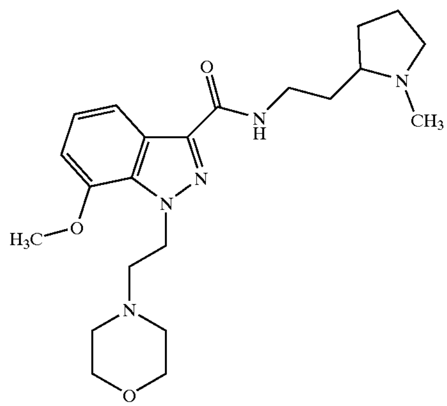 | 7-Methoxy-N-[2-(1-methyl-2-pyrrolidinyl)ethyl]-1-[2-(4-morpholinyl)ethyl]-1H-indazole-3-carboxamide | 416.26/ 0.84 (B) |
| 333 | 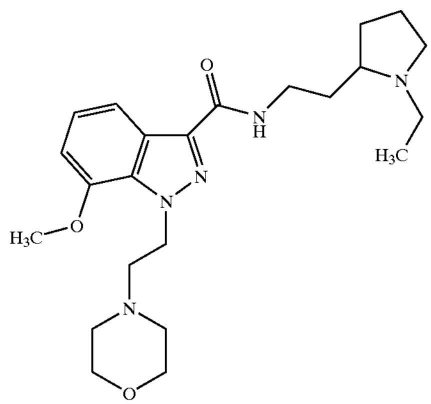 | N-[(1-Ethyl-2-pyrrolidinyl)methyl]-7-methoxy-1-[2-(4-morpholinyl)ethyl]-1H-indazole-3-carboxamide | 416.26/ 0.86 (B) |
| 334 | 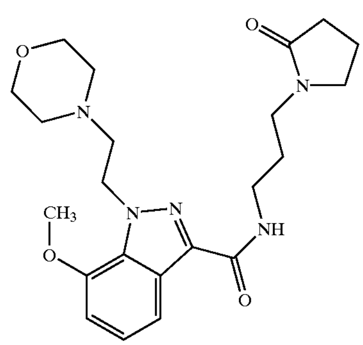 | 7-Methoxy-N-[3-(2-oxo-1-pyrrolidinyl)propyl]-1-[2-(4-morpholinyl)ethyl]-1H-indazole-3-carboxamide | 430.24/ 1.06 (B) |
| 335 | 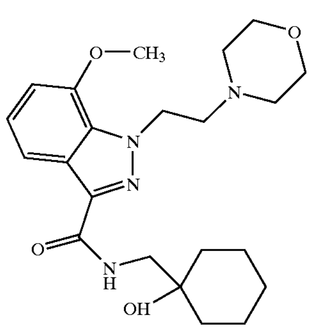 | N-[(1-Hydroxycyclohexyl)-methyl]-7-methoxy-1-[2-(4-morpholinyl)ethyl]-1H-indazole-3-carboxamide | 417.24/ 1.29 (B) |

TABLE 11-continued

| EX. NO. | STRUCTURE | COMPOUND NAME | DATA: MS (M + H)/ HPLC ret. time (min.) and conditions |
|---|---|---|---|
| 336 | Chiral | N-[2-(4-Chlorophenyl)-1-(hydroxymethyl)ethyl]-7-methoxy-1-[2-(4-morpholinyl)ethyl]-1H-indazole-3-carboxamide | 473.20/ 1.44 (B) |
| 337 | 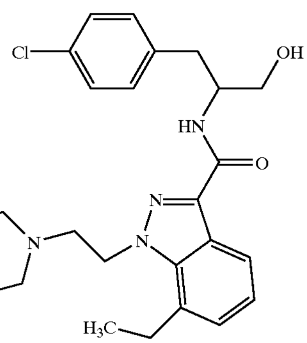 | N-[(1R)-1-(Hydroxymethyl)-3-methylbutyl]-7-methoxy-1-[2-(4-morpholinyl)ethyl]-1H-indazole-3-carboxamide | 405.26/ 1.28 (B) |
| 338 | 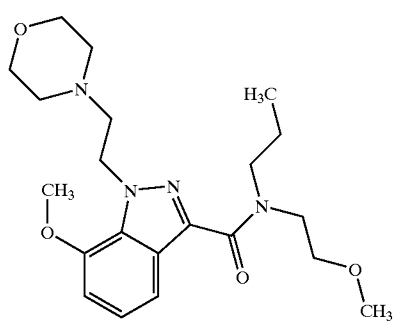 | 7-Methoxy-N-(2-methoxyethyl)-1-[2-(4-morpholinyl)ethyl]-N-propyl-1H-indazole-3-carboxamide | 405.26/ 1.22 (B) |
| 339 | 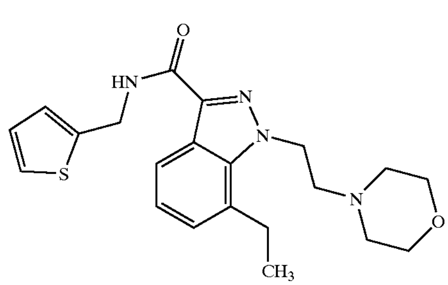 | 7-Methoxy-1-[2-(4-morpholinyl)ethyl]-N-(2-thienylmethyl)-1H-indazole-3-carboxamide | 401.18/ 1.23 (B) |

TABLE 11-continued

| EX. NO. | STRUCTURE | COMPOUND NAME | DATA: MS (M + H)/ HPLC ret. time (min.) and conditions |
|---|---|---|---|
| 340 | 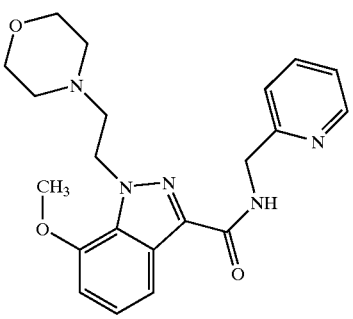 | 7-Methoxy-1-[2-(4-morpholinyl)ethyl]-N-(2-pyridinylmethyl)-1H-indazole-3-carboxamide | 396.22/ 0.80 (B) |
| 341 | 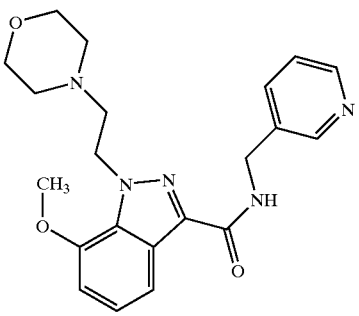 | 7-Methoxy-1-[2-(4 morpholinyl)ethyl]-N-(3-pyridinylmethyl)-1H-indazole-3-carboxamide | 396.23/ 0.79 (B) |
| 342 | 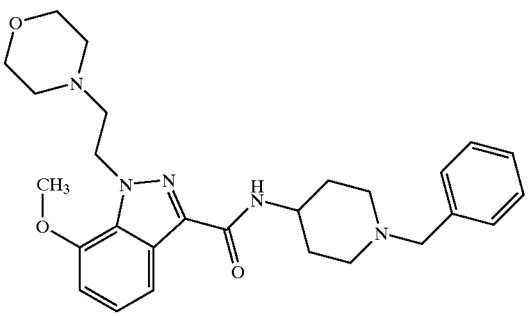 | 7-Methoxy-1-[2-(4-morpholinyl)ethyl]-N-[1-(phenylmethyl)-4-piperidinyl]-1H-indazole-3-carboxamide | 478.28/ 1.05 (B) |
| 343 | 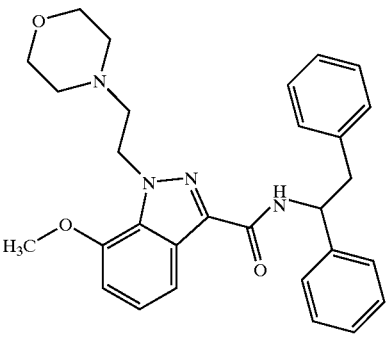 | N-(1,2-Diphenylethyl)-7-methoxy-1-[2-(4-morpholinyl)ethyl]-1H-indazole-3-carboxamide | 485.25/ 1.56 (B) |

TABLE 11-continued

| EX. NO. | STRUCTURE | COMPOUND NAME | DATA: MS (M + H)/ HPLC ret. time (min.) and conditions |
|---|---|---|---|
| 344 | 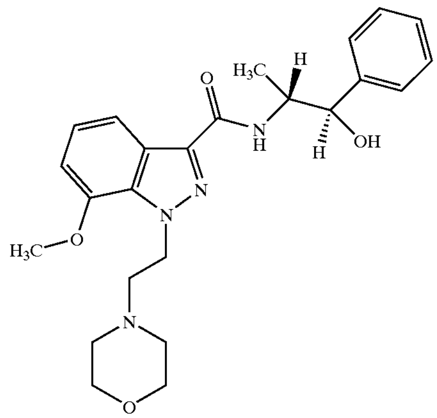 | N-[(1S,2S)-2-Hydroxy-1-methyl-2-phenylethyl]-7-methoxy-1-[2-(4-morpholinyl)ethyl]-1H-indazole-3-carboxamide | 439.22/ 1.30 (B) |
| 345 | 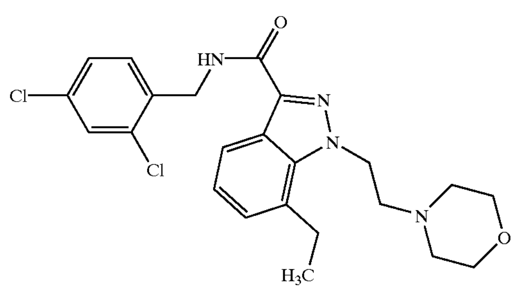 | N-[(2,4-Dichlorophenyl)methyl]-7-methoxy-1-[2-(4-morpholinyl)ethyl]-1H-indazole-3-carboxamide | 463.14/ 1.56 (B) |
| 346 | 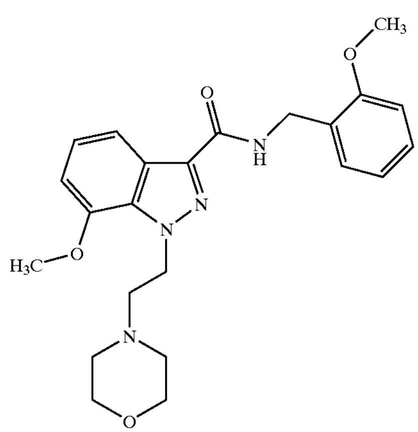 | 7-Methoxy-N-[(2-methoxyphenyl)methyl]-1-[2-(4-morpholinyl)ethyl]-1H-indazole-3-carboxamide | 425.20/ 1.33 (B) |
| 347 | 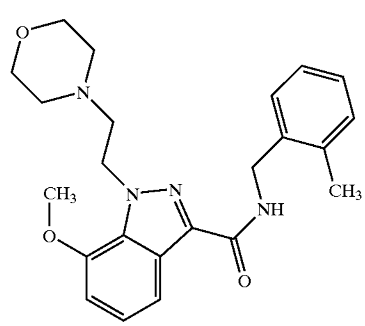 | 7-Methoxy-N-[(2-methylphenyl)methyl]-1-[2-(4-morpholinyl)ethyl]-1H-indazole-3-carboxamide | 409.22/ 1.35 (B) |

TABLE 11-continued

| EX. NO. | STRUCTURE | COMPOUND NAME | DATA: MS (M + H)/ HPLC ret. time (min.) and conditions |
|---|---|---|---|
| 348 | 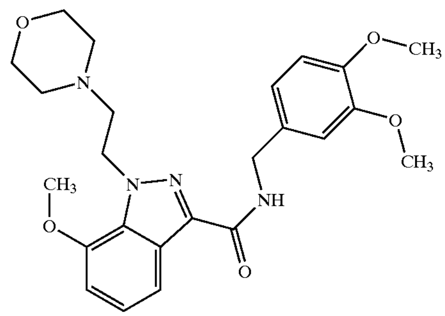 | N-[(3,4-Dimethoxyphenyl)-methyl]-7-methoxy-1-[2-(4-morpholinyl)ethyl]-1H-indazole-3-carboxamide | 455.19/ 1.21 (B) |
| 349 | 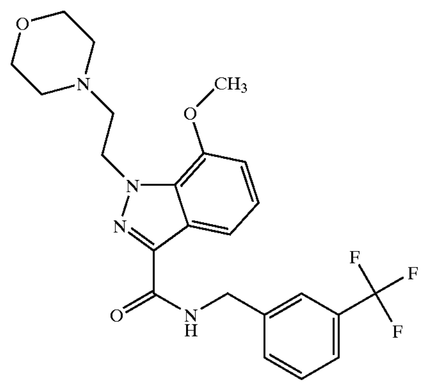 | 7-Methoxy-1-[2-(4-morpholinyl)ethyl]-N-[[3-(trifluoromethyl)phenyl]methyl]-1H-indazole-3-carboxamide | 463.20/ 1.49 (B) |
| 350 | Chiral | 7-Methoxy-1-[2-(4-morpholinyl)ethyl]-N-[(1S)-1-(2-naphthalenyl)ethyl]-1H-indazole-3-carboxamide | 459.24/ 1.54 (B) |
| 351 | Chiral | N-[[(1R,2R)-2-Hydroxycyclohexyl]methyl]-7-methoxy-1-[2-(4-morpholinyl)ethyl]-1H-indazole-3-carboxamide | 417.24/ 1.27 (B) |

TABLE 11-continued

| EX. NO. | STRUCTURE | COMPOUND NAME | DATA: MS (M + H)/ HPLC ret. time (min.) and conditions |
|---|---|---|---|
| 352 | Chiral | N-[(1S)-1-(Hydroxymethyl)-2,2-dimethylpropyl]-7-methoxy-1-[2-(4-morpholinyl)ethyl]-1H-indazole-3-carboxamide | 405.26/ 1.24 (B) |
| 353 | Chiral | 7-Methoxy-N-[(1S)-2-methyl-1-[[(4-nitrophenyl)amino]-carbonyl]propyl]-1-[2-(4-morpholinyl)ethyl]-1H-indazole-3-carboxamide | 525.21/ 1.48 (B) |
| 354 | 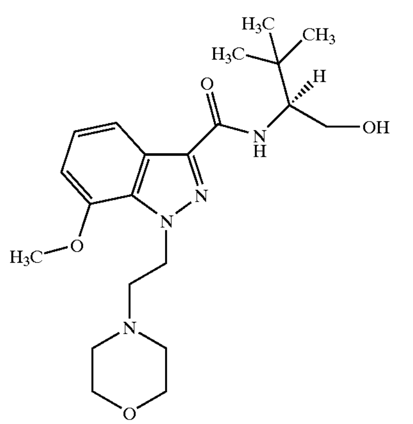 | 7-Methoxy-N-[(1S)-3-methyl-1-[[(4-nitrophenyl)amino]-carbonyl]butyl]-1-[2-(4-morpholinyl)ethyl]-1H-indazole-3-carboxamide | 539.23/ 1.56 (B) |
| 355 | Chiral | 7-Methoxy-N-[(1S)-1-methylpropyl]-1-[2-(4-morpholinyl)ethyl]-1H-indazole-3-carboxamide | 361.24/ 1.18 (B) |

TABLE 11-continued

| EX. NO. | STRUCTURE | COMPOUND NAME | DATA: MS (M + H)/ HPLC ret. time (min.) and conditions |
|---|---|---|---|
| 356 | 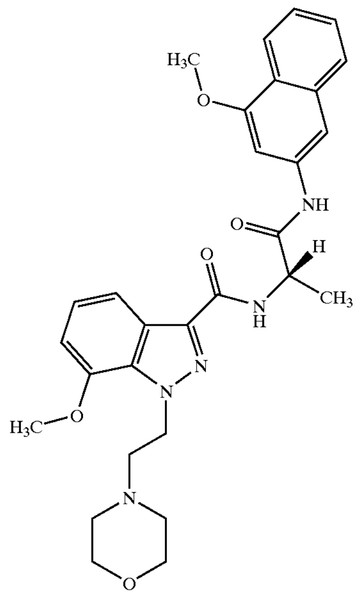 | N-[2-(4-Chlorophenyl)-1-methylethyl]-7-methoxy-1-[2-(4-morpholinyl)ethyl]-1H-indazole-3-carboxamide | 457.20/ 1.55 (B) |
| 357 | 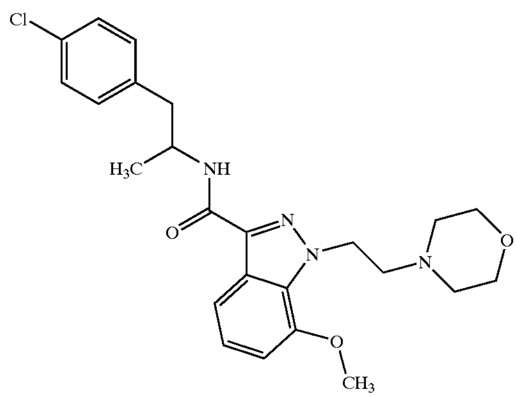 | 7-Methoxy-N-[(1S)-2-[(4-methoxy-2-naphthalenyl)amino]-1-methyl-2-oxoethyl]-1-[2-(4-morpholinyl)ethyl]-1H-indazole-3-carboxamide | 532.21/ 1.59 (B) |
| 358 | Chiral | 1-[[7-Methoxy-1-[2-(4-morpholinyl)ethyl]-1H-indazol-3-yl]carbonyl]-L-prolinamide | 402.23/ 0.90 (B) |

TABLE 11-continued

| EX. NO. | STRUCTURE | COMPOUND NAME | DATA: MS (M + H)/ HPLC ret. time (min.) and conditions |
|---|---|---|---|
| 359 | 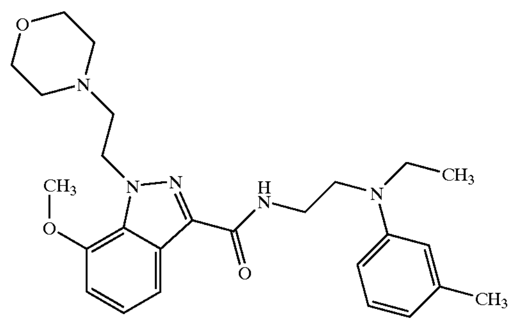 | N-[2-[Ethyl(3-methylphenyl)-amino]ethyl]-7-methoxy-1-[2-(4-morpholinyl)ethyl]-1H-indazole-3-carboxamide | 466.30/ 1.16 (B) |
| 360 | 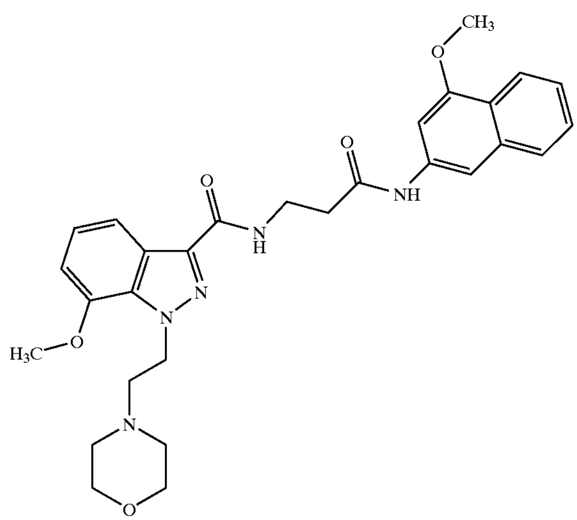 | 7-Methoxy-N-[3-[(4-methoxy-2-naphthalenyl)amino]-3-oxopropyl]-1-[2-(4-morpholinyl)ethyl]-1H-indazole-3-carboxamide | 532.22/ 1.52 (B) |
| 361 | 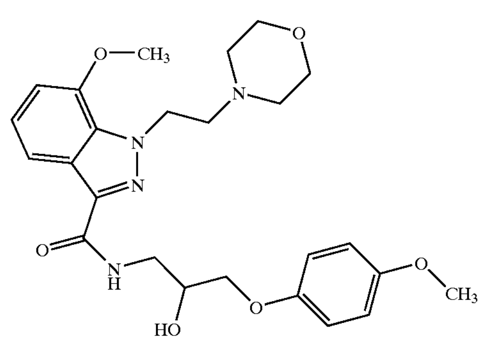 | N-[2-Hydroxy-3-(4-methoxyphenoxy)propyl]-7-methoxy-1-[2-(4-morpholinyl)ethyl]-1H-indazole-3-carboxamide | 485.24/ 1.30 (B) |

TABLE 11-continued

| EX. NO. | STRUCTURE | COMPOUND NAME | DATA: MS (M + H)/ HPLC ret. time (min.) and conditions |
|---|---|---|---|
| 362 | 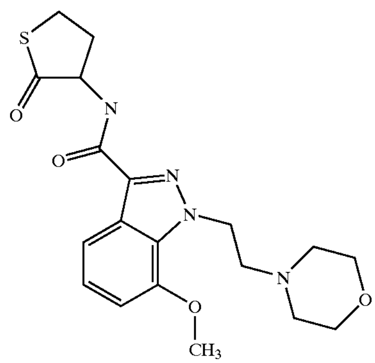 | 7-Methoxy-1-[2-(4-morpholinyl)ethyl]-N-(tetrahydro-2-oxo-3-thienyl)-1H-indazole-3-carboxanciide | 405.18/ 1.03 (B) |
| 363 | 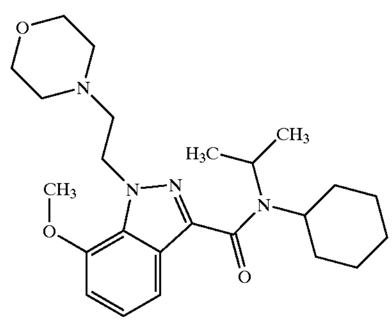 | N-Cyclohexyl-7-methoxy-N-(1-methylethyl)-1-[2-(4-morpholinyl)ethyl]-1H-indazole-3-carboxamide | 429.30/ 1.57 (B) |
| 364 | 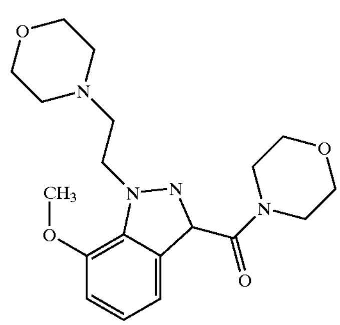 | 4-[[7-Methoxy-1-[2-(4-morpholinyl)ethyl]-1H-indazol-3-yl]carbonyl]morpholine | 375.24/ 0.95 (B) |
| 365 | 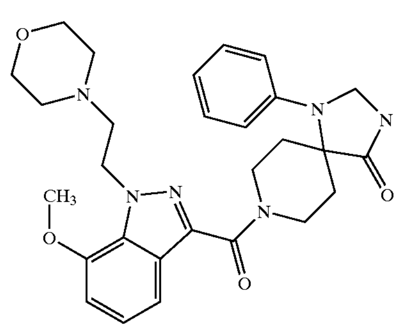 | 7-[[7-Methoxy-1-[2-(4-morpholinyl)ethyl]-1H-indazol-3-yl]carbonyl]-1-phenyl-1,3,8-triazaspiro[4.5]decan-4-one | 519.25/ 1.30 (B) |

TABLE 11-continued

| EX. NO. | STRUCTURE | COMPOUND NAME | DATA: MS (M + H)/ HPLC ret. time (min.) and conditions |
|---|---|---|---|
| 366 | 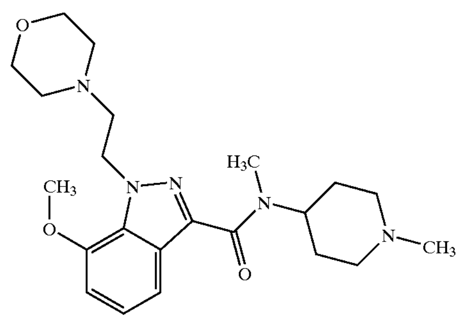 | 7-Methoxy-N-(1-methyl-4-piperidinyl)-N-methyl-1-[2-(4-morpholinyl)ethyl]-1H-indazole-3-carboxamide | 416.27/ 0.72 (B) |
| 367 | 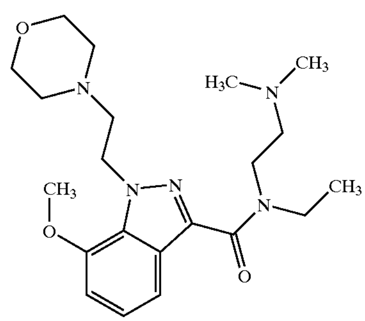 | N-[2-(Dimethylamino)ethyl]-N-ethyl-7-methoxy-1-[2-(4-morpholinyl)ethyl]-1H-indazole-3-carboxamide | 404.29/ 0.78 (B) |
| 368 | 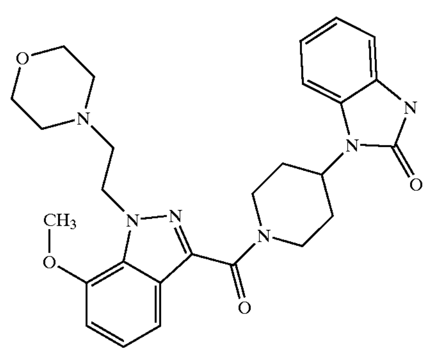 | 4-(2,3-Dihydro-2-oxo-1H-benzimidazol-1-yl)-1-[[7-methoxy-1-[2-(4-morpholinyl)-ethyl]-1H-indazol-3-yl]carbonyl]-piperidine | 505.24/ 1.26 (B) |
| 369 | 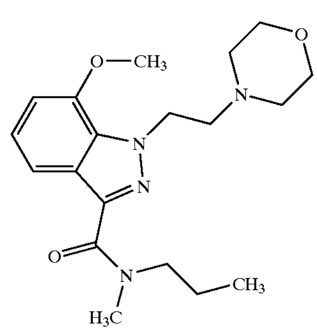 | 7-Methoxy-N-methyl-1-[2-(4-morpholinyl)ethyl]-N-propyl-1H-indazole-3-carboxamide | 361.27/ 1.14 (B) |

TABLE 11-continued

| EX. NO. | STRUCTURE | COMPOUND NAME | DATA: MS (M + H)/ HPLC ret. time (min.) and conditions |
|---|---|---|---|
| 370 | 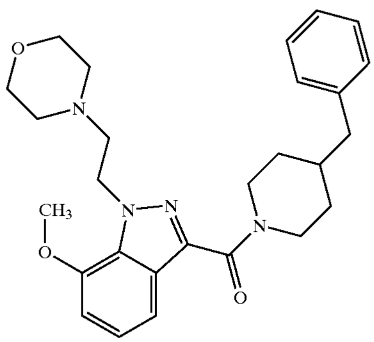 | 1-[[7-Methoxy-1-[2-(4-morpholinyl)ethyl]-1H-indazol-3-yl]carbonyl]-4-(phenylmethyl)-piperidine | 463.29/ 1.57 (B) |
| 371 | 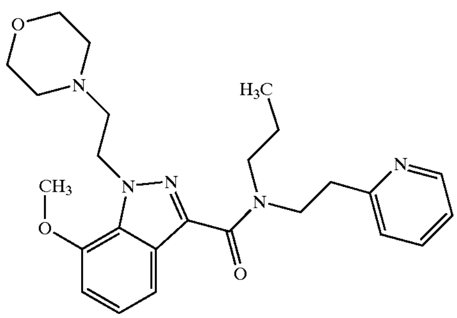 | 7-Methoxy-1-[2-(4-morpholinyl)ethyl]-N-propyl-N-[2-(2-pyridinyl)ethyl]-1H-indazole-3-carboxamide | 452.29/ 0.92 (B) |
| 372 | 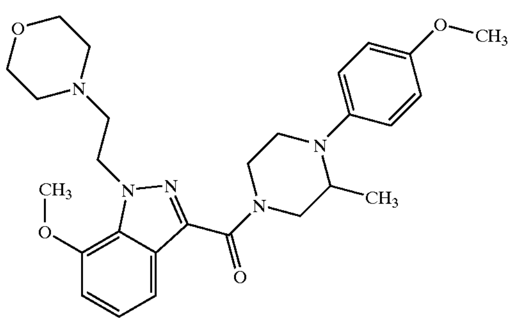 | 4-[[7-Methoxy-1-[2-(4-morpholinyl)ethyl]-1H-indazol-3-yl]carbonyl]-1-(4-methoxyphenyl)-2-methylpiperazine | 494.28/ 1.06 (B) |
| 373 | 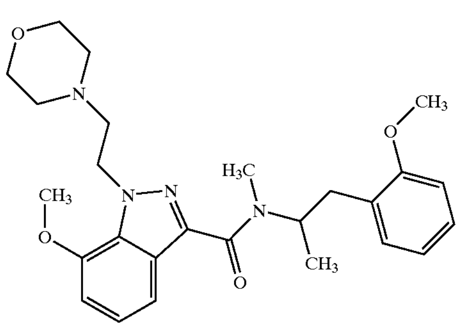 | 7-Methoxy-N-[2-(1-methoxyphenyl)-1-methylethyl]-N-methyl-1-[2-(4-morpholinyl)ethyl]-1H-indazole-3-carboxamide | 467.29/ 1.42 (B) |

TABLE 11-continued

| EX. NO. | STRUCTURE | COMPOUND NAME | DATA: MS (M + H)/ HPLC ret. time (min.) and conditions |
|---|---|---|---|
| 374 | 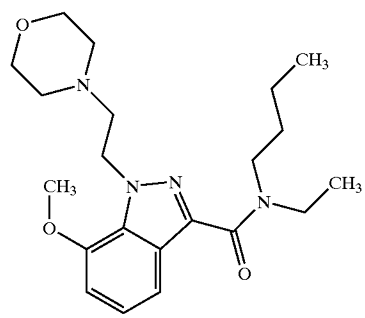 | N-Butyl-N-ethyl-7-methoxy-1-[2-(4-morpholinyl)ethyl]-1H-indazole-3-carboxamide | 389.28/ 1.37 (B) |
| 375 | 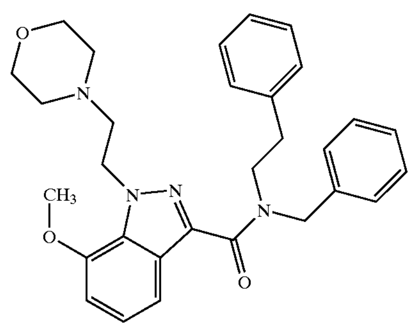 | 7-Methoxy-1-[2-(4-morpholinyl)ethyl]-N-(phenylmethyl)-N-(2-phenylethyl)-1H-indazole-3-carboxamide | 499.26/ 1.64 (B) |
| 376 | 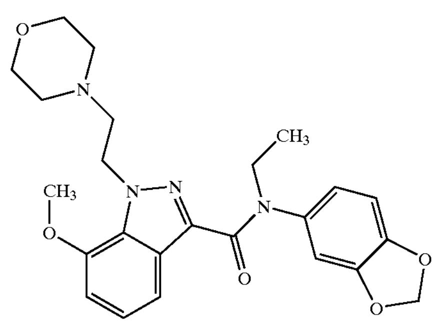 | N-(1,3-Benzodioxol-5-yl)-N-ethyl-7-methoxy-1-[2-(4-morpholinyl)ethyl]-1H-indazole-3-carboxamide | 453.23/ 1.32 (B) |
| 377 | 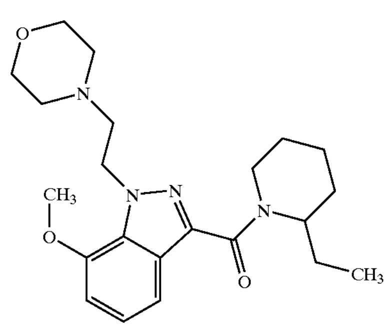 | 2-Ethyl-1-[[7-methoxy-1-[2-(4-morpholinyl)ethyl]-1H-indazol-3-yl]carbonyl]piperidine | 401.28/ 1.35 (B) |

TABLE 11-continued

| EX. NO. | STRUCTURE | COMPOUND NAME | DATA: MS (M + H)/ HPLC ret. time (min.) and conditions |
|---|---|---|---|
| 378 | 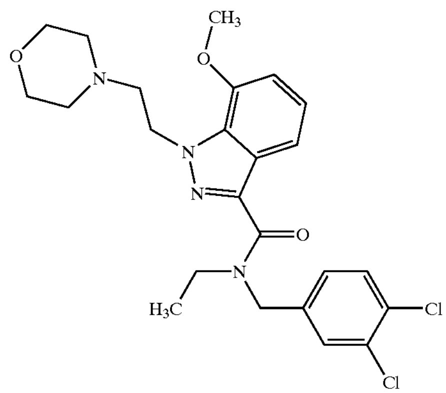 | N-[(4-Chlorophenyl)methyl]-N-ethyl-7-methoxy-1-[2-(4-morpholinyl)ethyl]-1H-indazole-3-carboxamide | 491.15/ 1.60 (B) |
| 379 | 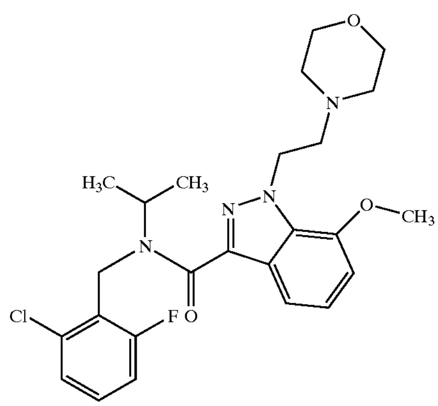 | N-[(2-Chloro-6-fluorophenyl)methyl]-7-methoxy-N-(1-methylethyl)-1-[2-(4-morpholinyl)ethyl]-1H-indazole-3-carboxamide | 489.20/ 1.53 (B) |
| 380 | 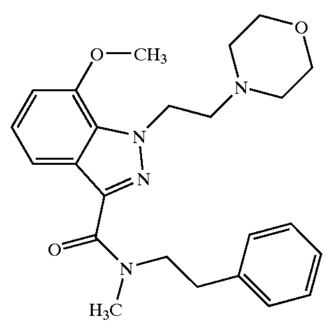 | 7-Methoxy-N-methyl-1-[2-(4-morpholinyl)ethyl]-N-(2-phenylethyl)-1H-indazole-3-carboxamide | 423.24/ 1.35 (B) |
| 381 | 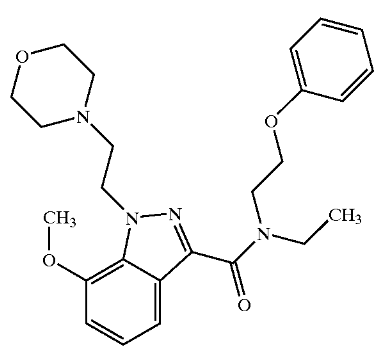 | N-Ethyl-7-methoxy-1-[2-(4-morpholinyl)ethyl]-N-(2-phenoxyethyl)-1H-indazole-3-carboxamide | 453.33/ 1.35 (B) |

TABLE 11-continued

| EX. NO. | STRUCTURE | COMPOUND NAME | DATA: MS (M + H)/ HPLC ret. time (min.) and conditions |
|---|---|---|---|
| 382 | Chiral | (2S)-2-(Methoxymethyl)-1-[[7-methoxy-1-[2-(4-morpholinyl)ethyl]-1H-indazol-3-yl]carbonyl]pyrrolidine | 403.25/ 1.14 (B) |
| 383 | 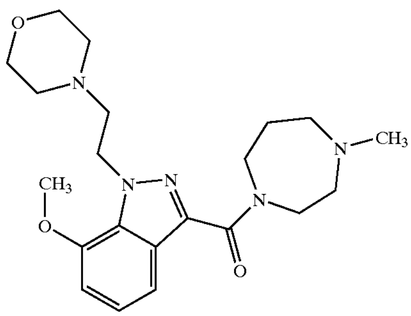 | Hexahydro-1-[[7-methoxy-1-[2-(4-morpholinyl)ethyl]-1H-indazol-3-yl]carbonyl]-4-methyl-1H-1,4-diazepine | 402.27/ 0.71 (B) |
| 384 | 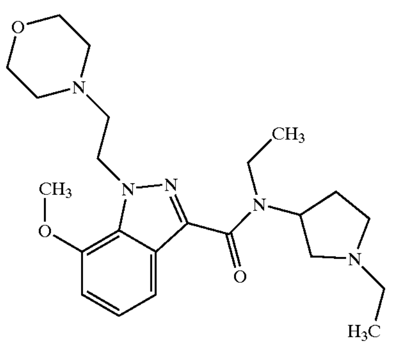 | N-Ethyl-N-(1-ethyl-3-pynolidinyl)-7-methoxy-1-[2-(4-morpholinyl)ethyl]-1H-indazole-3-carboxamide | 430.32/ 0.75 (B) |
| 385 | 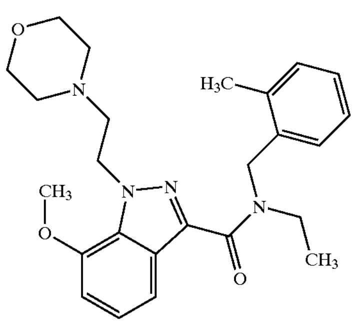 | N-Ethyl-7-methoxy-N-[(2-methylphenyl)methyl]-1-[2-(4-morpholinyl)ethyl]-1H-indazole-3-carboxamide | 437.25/ 1.47 (B) |

TABLE 11-continued

| EX. NO. | STRUCTURE | COMPOUND NAME | DATA: MS (M + H)/ HPLC ret. time (min.) and conditions |
|---|---|---|---|
| 386 | 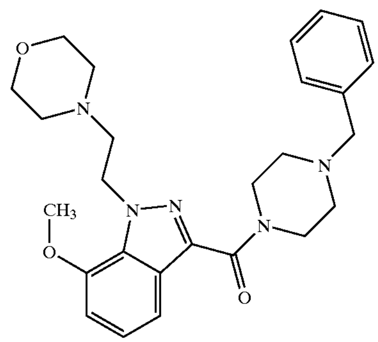 | 1-[[7-Methoxy-1-[2-(4-morpholinyl)ethyl]-1H-indazol-3-yl]carbonyl]-4-(phenylmethyl)piperazine | 464.29/ 0.92 (B) |
| 387 | 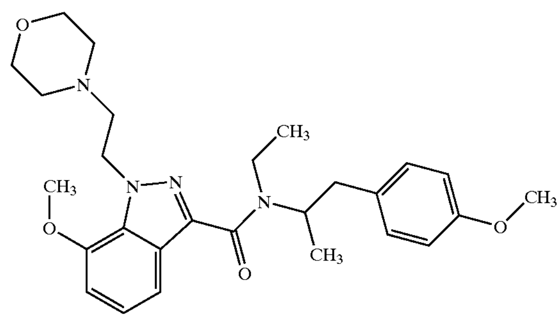 | N-Ethyl-7-methoxy-N-[2-(4-methoxyphenyl)-1-methylethyl]-1-[2-(4-morpholinyl)ethyl]-1H-indazole-3-carboxamide | 481.28/ 1.46 (B) |
| 388 | 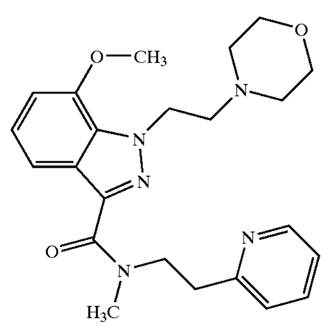 | 7-Methoxy-N-methyl-1-[2-(4-morpholinyl)ethyl]-N-[2-(2-pyridinyl)ethyl]-1H-indazole-3-carboxamide | 424.23/ 0.72 (B) |
| 389 | 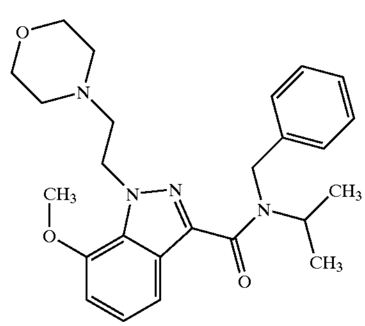 | 7-Methoxy-N-(1-methylethyl)-1-[2-(4-morpholinyl)ethyl]-N-(phenylmethyl)-1H-indazole-3-carboxamide | 437.25/ 1.44 (B) |

TABLE 11-continued

| EX. NO. | STRUCTURE | COMPOUND NAME | DATA: MS (M + H)/ HPLC ret. time (min.) and conditions |
|---|---|---|---|
| 390 | 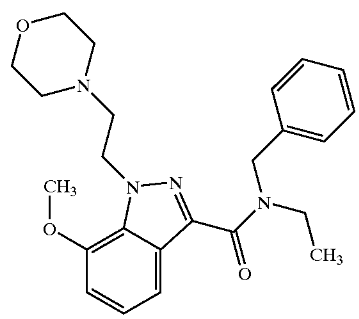 | N-Ethyl-7-methoxy-1-[2-(4-morpholinyl)ethyl]-N-(phenylmethyl)-1H-indazole-3-carboxamide | 423.23/ 1.38 (B) |
| 391 | 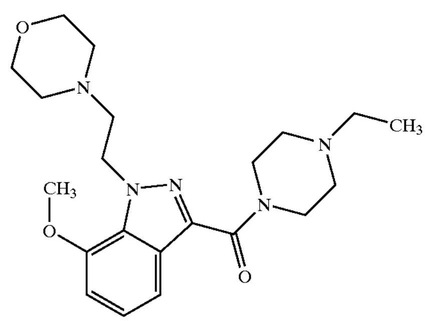 | 1-Ethyl-4-[[7-methoxy-1-[2-(4-morpholinyl)ethyl]-1H-indazol-3-yl]carbonyl]piperazine | 402.27/ 0.68 (B) |
| 392 | 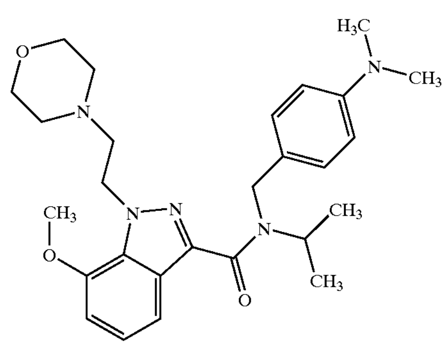 | N-[[4-(Dimethylamino)phenyl]methyl]-7-methoxy-N-(1-methylethyl)-1-[2-(4-morpholinyl)-ethyl]-1H-indazole-3-carboxamide | 480.30/ 1.03 (B) |
| 393 | 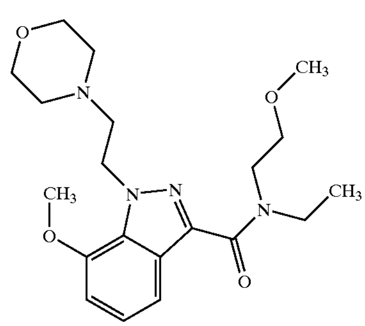 | N-Ethyl-7-methoxy-N-(2-methoxyethyl)-1-[2-(4-morpholinyl)ethyl]-1H-indazole-3-carboxamide | 391.26/ 1.08 (B) |

TABLE 11-continued

| EX. NO. | STRUCTURE | COMPOUND NAME | DATA: MS (M + H)/ HPLC ret. time (min.) and conditions |
|---|---|---|---|
| 394 | 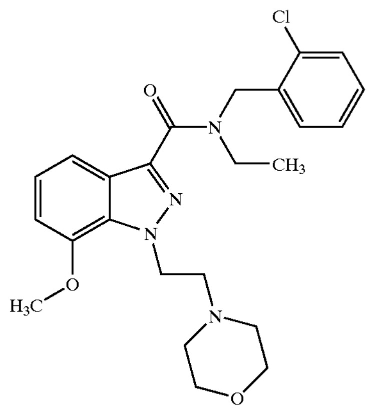 | N-[(2-Chlorophenyl)methyl]-N-ethyl-7-methoxy-1-[2-(4-morpholinyl)ethyl]-1H-indazole-3-carboxamide | 457.49/ 1.56 (C) |
| 395 | 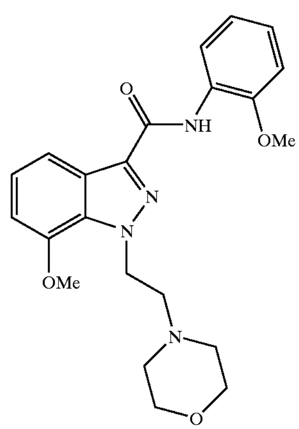 | 7-Methoxy-N-(2-methoxyphenyl)-1-[2-(4-morpholinyl)ethyl]-1H-indazole-3-carboxamide | 411.21/ 1.46 (B) |
| 396 | 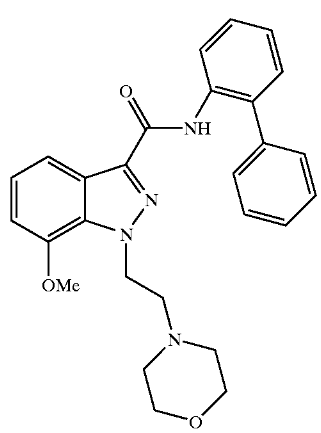 | N-(1,1'-Biphenyl]-2-yl)-7-methoxy-1-[2-(4-morpholinyl)ethyl]-1H-indazole-3-carboxamide | 457.25/ 1.62 (B) |

TABLE 11-continued

| EX. NO. | STRUCTURE | COMPOUND NAME | DATA: MS (M + H)/ HPLC ret. time (min.) and conditions |
|---|---|---|---|
| 397 | 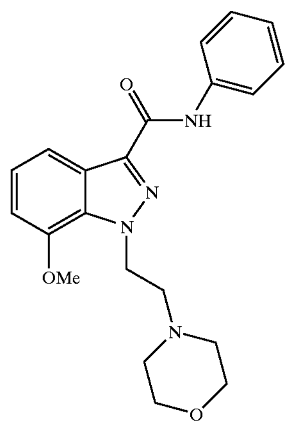 | 7-Methoxy-1-[2-(4-morpholinyl)ethyl]-N-phenyl-1H-indazole-3-carboxamide | 381.24/ 1.36 (B) |
| 398 | 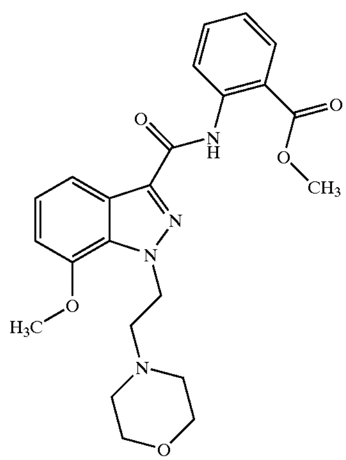 | 2-[[7-Methoxy-1-[2-(4-morpholinyl)ethyl]-1H-indazol-3-yl]carbonyl]amino]benzoic acid methyl ester | 439.25/ 1.60 (B) |
| 399 | 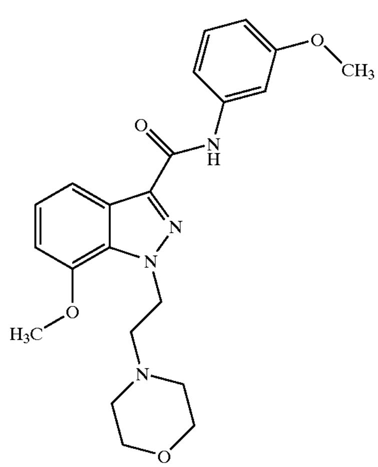 | 7-Methoxy-N-(3-methoxyphenyl)-1-[2-(4-morpholinyl)ethyl]-1H-indazole-3-carboxamide | 411.20/ 1.39 (B) |

TABLE 11-continued

| EX. NO. | STRUCTURE | COMPOUND NAME | DATA: MS (M + H)/ HPLC ret. time (min.) and conditions |
|---|---|---|---|
| 400 | 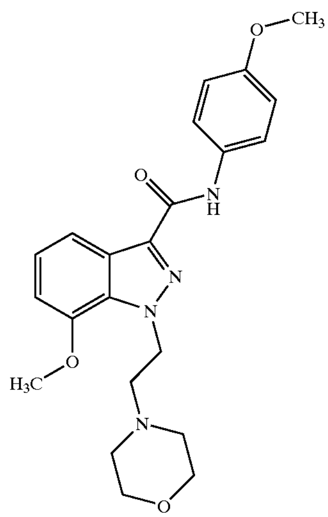 | 7-Methoxy-N-(4-methoxyphenyl)-1-[2-(4-morpholinyl)ethyl]-1H-indazole-3-carboxamide | 411.21/ 1.34 (B) |
| 401 | 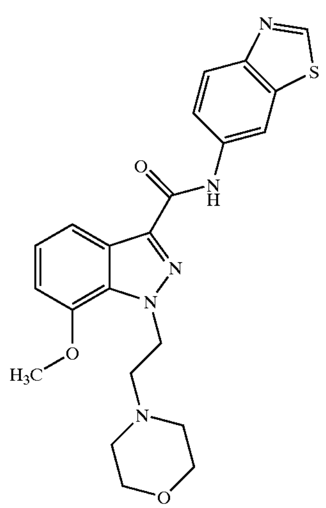 | N-(6-Benzothiazolyl)-7-methoxy-1-[2-(4-morpholinyl)ethyl]-1H-indazole-3-carboxamide | 438.19/ 1.37 (B) |
| 402 | 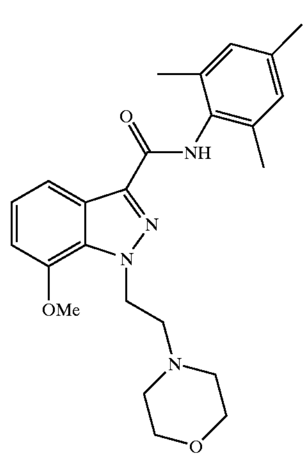 | 7-Methoxy-1-[2-(4-morpholinyl)ethyl]-N-(2,4,6-trimethylphenyl)-1H-indazole-3-carboxamide | 423.25/ 1.41 (B) |

TABLE 11-continued

| EX. NO. | STRUCTURE | COMPOUND NAME | DATA: MS (M + H)/ HPLC ret. time (min.) and conditions |
|---|---|---|---|
| 403 | 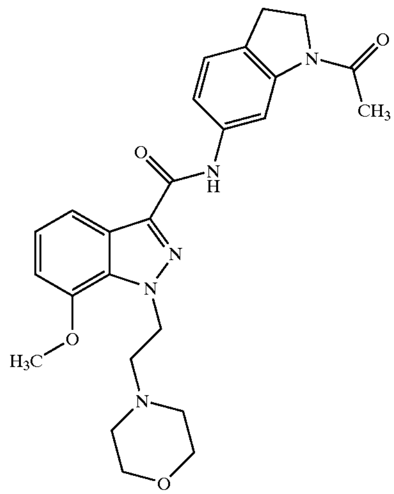 | N-(1-Acetyl-2,3-dihydro-1H-indol-6-yl)-7-methoxy-1-[2-(4-morpholinyl)ethyl]-1H-indazole-3-carboxamide | 464.27/ 1.32 (B) |
| 404 | 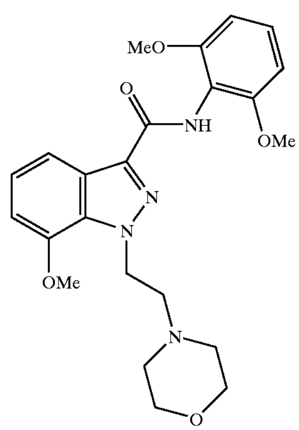 | N-(2,6-Dimethoxyphenyl)-7-methoxy-1-[2-(4-morpholinyl)ethyl]-1H-indazole-3-carboxamide | 441.24/ 1.15 (B) |
| 405 | 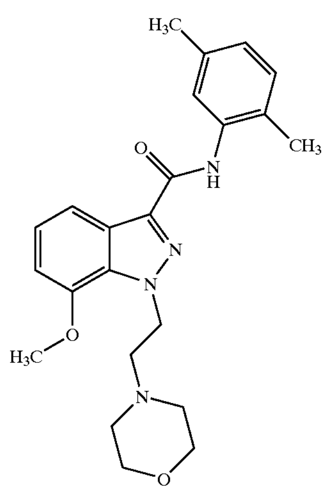 | N-(2,5-Dimethylphenyl)-7-methoxy-1-[2-(4-morpholinyl)-ethyl]-1H-indazole-3-carboxamide | 409.27/ 1.44 (E) |

TABLE 11-continued

| EX. NO. | STRUCTURE | COMPOUND NAME | DATA: MS (M + H)/ HPLC ret. time (min.) and conditions |
|---|---|---|---|
| 406 | 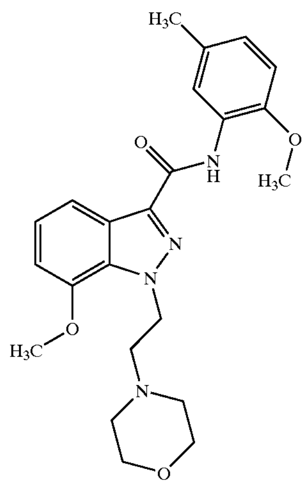 | 7-Methoxy-N-(2-methoxy-5-methylphenyl)-1-[2-(4-morpholinyl)ethyl]-1H-indazole-3-carboxamide | 425.26/ 1.59 (E) |
| 407 | 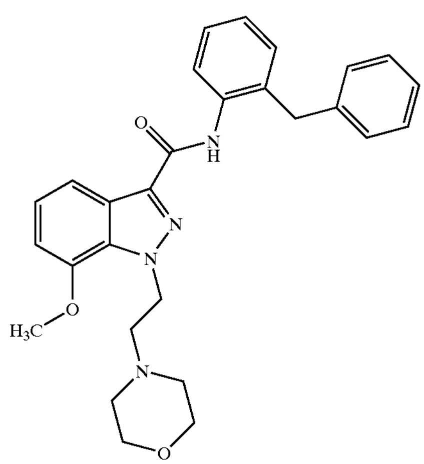 | 7-Methoxy-1-[2-(4-morpholinyl)ethyl]-N-[2-(phenylmethyl)phenyl]-1H-indazole-3-carboxamide | 471.30/ 1.60 (B) |
| 408 | 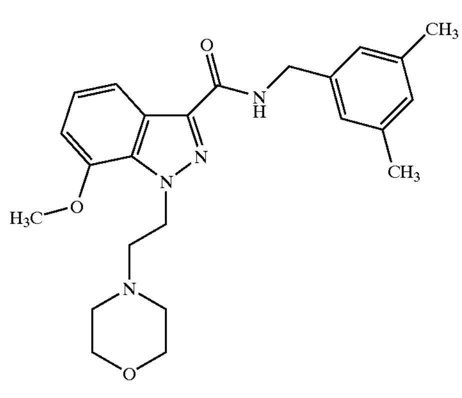 | N-(3,5-Dimethylphenyl)-7-methoxy-1-[2-(4-morpholinyl)ethyl]-1H-indazole-3-carboxamide | 409.23/ 1.55 (B) |

TABLE 11-continued

| EX. NO. | STRUCTURE | COMPOUND NAME | DATA: MS (M + H)/ HPLC ret. time (min.) and conditions |
|---|---|---|---|
| 409 | 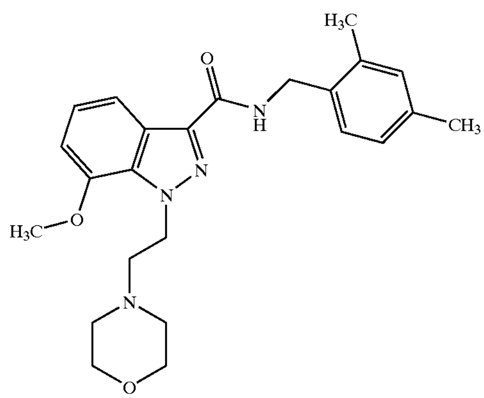 | N-(2,4-Dimethylphenyl)-7-methoxy-1-[2-(4-morpholinyl)ethyl]-1H-indazole-3-carboxamide | 409.27/ 1.43 (E) |
| 410 | 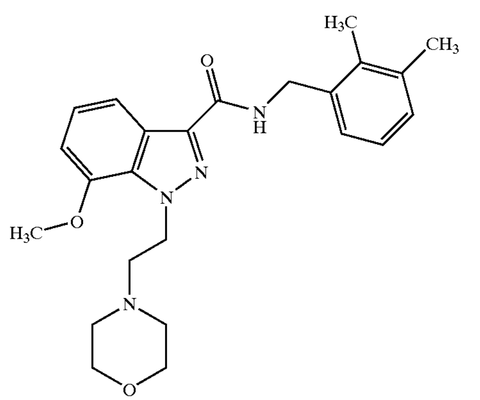 | N-(2,3-Dimethylphenyl)-7-methoxy-1-[2-(4-morpholinyl)ethyl]-1H-indazole-3-carboxamide | 409.25/ 1.39 (B) |
| 411 | 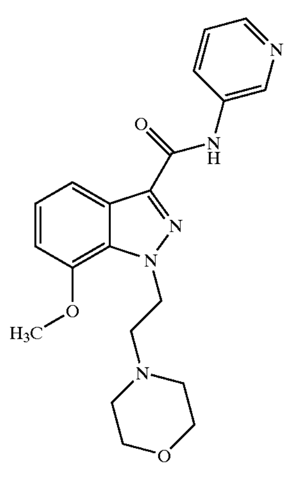 | 7-Methoxy-1-[2-(4-morpholinyl)ethyl]-N-(3-pyridinyl)-1H-indazole-3-carboxamide | 382.27/ 0.94 (E) |

TABLE 11-continued

| EX. NO. | STRUCTURE | COMPOUND NAME | DATA: MS (M + H)/ HPLC ret. time (min.) and conditions |
|---|---|---|---|
| 412 | 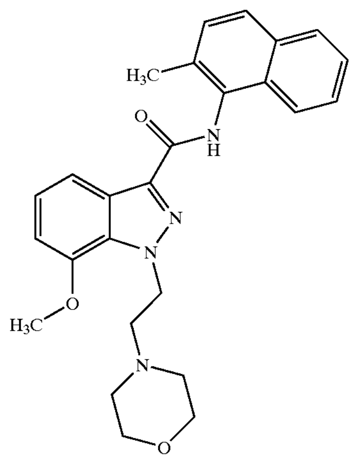 | 7-Methoxy-N-(2-methyl-1-naphthalenyl)-1-[2-(4-morpholinyl)ethyl]-1H-indazole-3-carboxamide | 445.25/ 1.39 (B) |
| 413 | 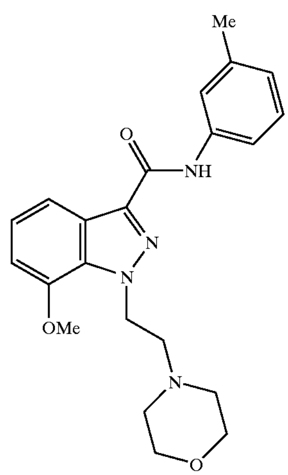 | 7-Methoxy-N-(4-methyl-2-pyridinyl)-1-[2-(4-morpholinyl)ethyl]-1H-indazole-3-carboxamide | 396.26/ 0.97 (C) |
| 414 | 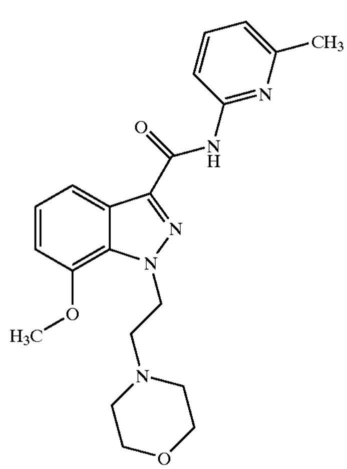 | 7-Methoxy-N-(6-methyl-2-pyridinyl)-1-[2-(4-morpholinyl)ethyl]-1H-indazole-3-carboxamide | 396.26/ 1.29 (B) |

TABLE 11-continued

| EX. NO. | STRUCTURE | COMPOUND NAME | DATA: MS (M + H)/ HPLC ret. time (min.) and conditions |
|---|---|---|---|
| 415 | 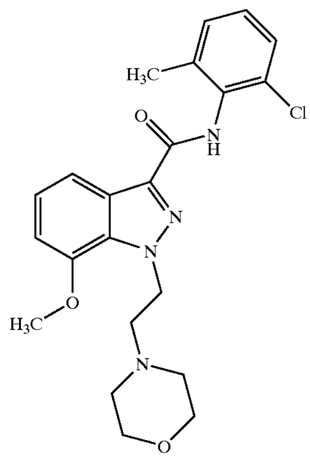 | N-(2-Chloro-6-methylphenyl)-7-methoxy-1-[2-(4-morpholinyl)ethyl]-1H-indazole-3-carboxamide | 429.18/ 1.41 (B) |
| 416 | 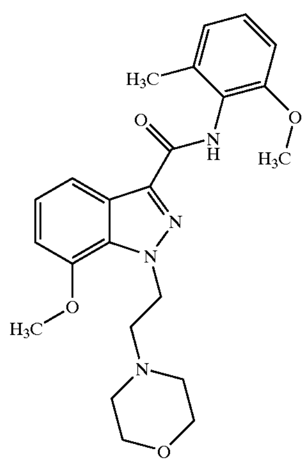 | 7-Methoxy-N-(2-methoxy-6-methylphenyl)-1-[2-(4-morpholinyl)ethyl]-1H-indazole-3-carboxamide | 425.27/ 1.36 (B) |
| 417 | 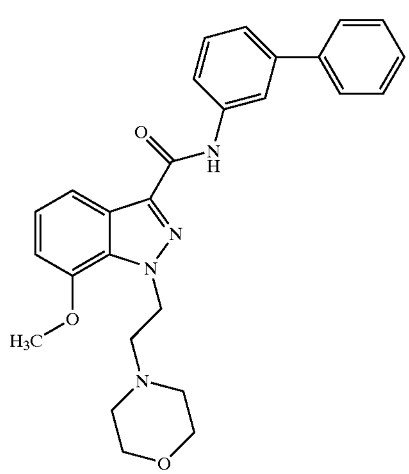 | N-([1,1'-Biphenyl]-3-yl)-7-methoxy-1-[2-(4-morpholinyl)ethyl]-1H-indazole-3-carboxamide | 457.31/ 1.70 (E) |

TABLE 11-continued

| EX. NO. | STRUCTURE | COMPOUND NAME | DATA: MS (M + H)/ HPLC ret. time (min.) and conditions |
|---|---|---|---|
| 418 | 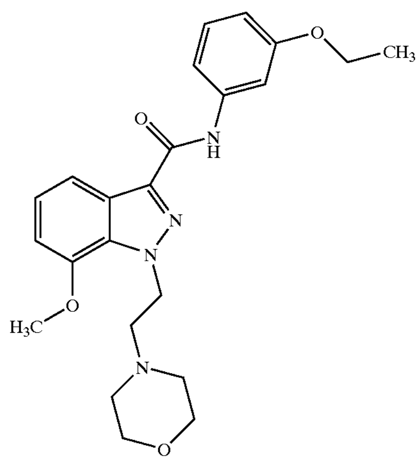 | N-(3-Ethoxyphenyl)-7-methoxy-1-[2-(4-morpholinyl)ethyl]-1H-indazole-3-carboxamide | 425.19/ 1.49 (B) |
| 419 | 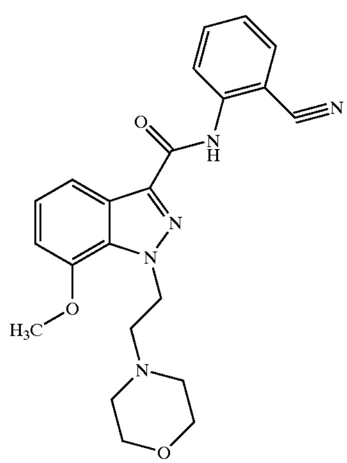 | N-(2-Cyanophenyl)-7-methoxy-1-[2-(4-morpholinyl)ethyl]-1H-indazole-3-carboxamide | 406.20/ 1.37 (B) |
| 420 | 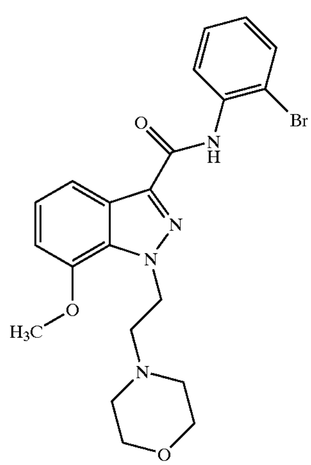 | N-(2-Bromophenyl)-7-methoxy-1-[2-(4-morpholinyl)ethyl]-1H-indazole-3-carboxamide | 459.10/ 1.52 (B) |

TABLE 11-continued

| EX. NO. | STRUCTURE | COMPOUND NAME | DATA: MS (M + H)/ HPLC ret. time (min.) and conditions |
|---|---|---|---|
| 421 | 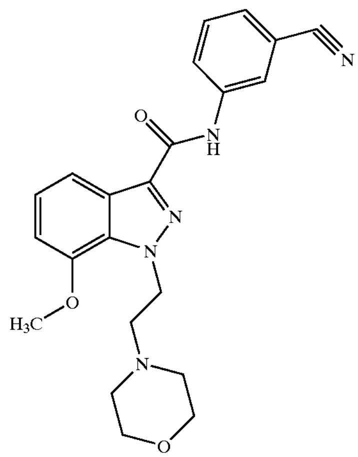 | N-(3-Cyanophenyl)-7-methoxy-1-[2-(4-morpholinyl)ethyl]-1H-indazole-3-carboxamide | 406.21/ 1.40 (B) |
| 422 | 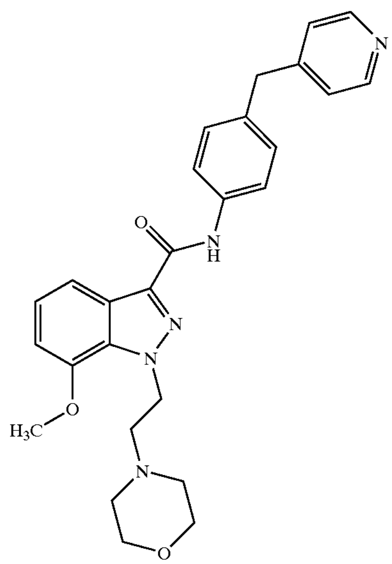 | 7-Methoxy-1-[2-(4-morpholinyl)ethyl]-N-[4-(4-pyridinylmethyl)phenyl]-1H-indazole-3-carboxamide | 472.26/ 1.10 (B) |
| 423 | 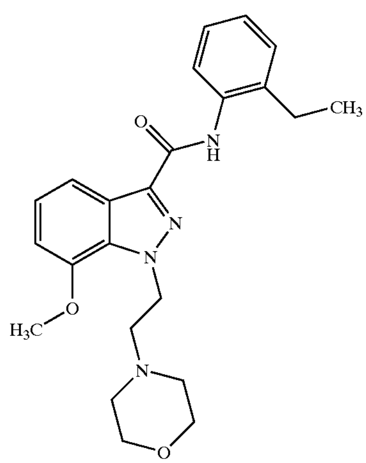 | N-(2-Ethylphenyl)-7-methoxy-1-[2-(4-morpholinyl)ethyl]-1H-indazole-3-carboxamide | 409.24/ 1.42 (B) |

TABLE 11-continued

| EX. NO. | STRUCTURE | COMPOUND NAME | DATA: MS (M + H)/ HPLC ret. time (min.) and conditions |
|---|---|---|---|
| 424 | 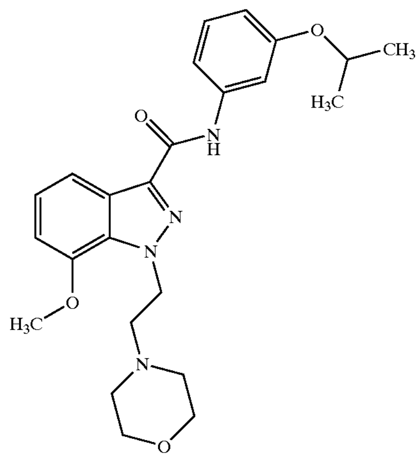 | 7-Methoxy-N-[3-(1-methylethoxy)phenyl]-1-[2-(4-morpholinyl)ethyl]-1H-indazole-3-carboxamide | 439.29/ 1.56 (E) |
| 425 | 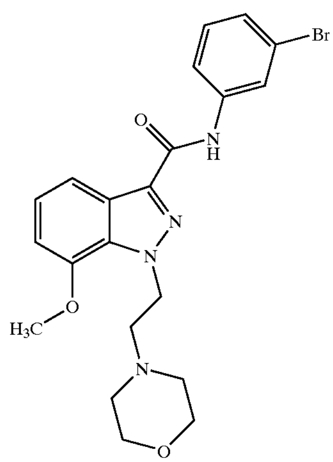 | N-(3-Bromophenyl)-7-methoxy-1-[2-(4-morpholinyl)ethyl]-1H-indazole-3-carboxamide | 459.10/ 1.59 (B) |
| 426 | 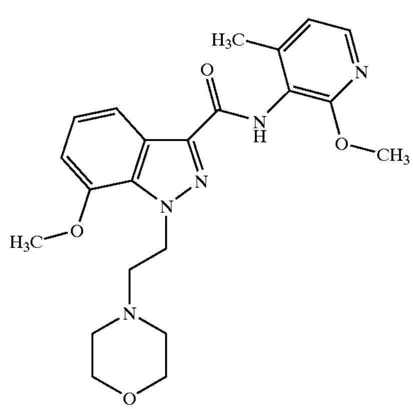 | 7-Methoxy-N-(2-methoxy-4-methyl-3-pyridinyl)-1-[2-(4-morpholinyl)ethyl]-1H-indazole-3-carboxamide | 426.22/ 1.16 (B) |

TABLE 11-continued

| EX. NO. | STRUCTURE | COMPOUND NAME | DATA: MS (M + H)/ HPLC ret. time (min.) and conditions |
|---|---|---|---|
| 427 | 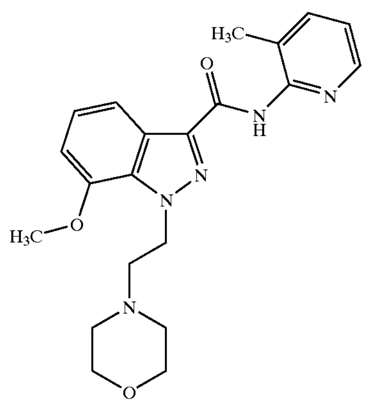 | 7-Methoxy-N-(3-methyl-2-pyridinyl)-1-[2-(4-morpholinyl)ethyl]-1H-indazole-3-carboxamide | 396.23/ 0.93 (B) |
| 428 | 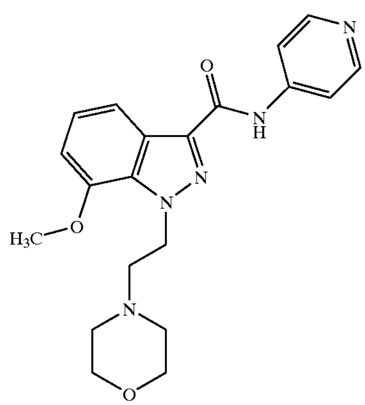 | 7-Methoxy-1-[2-(4-morpholinyl)ethyl]-N-(4-pyridinyl)-1H-indazole-3-carboxamide | 382.22/ 0.97 (B) |
| 429 | 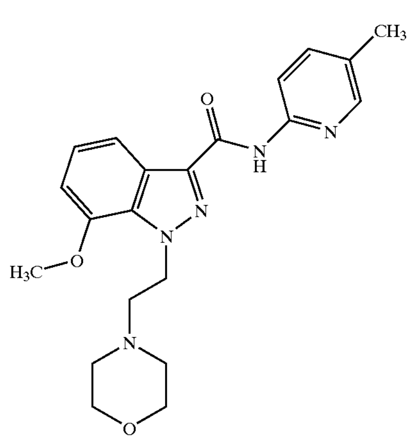 | 7-Methoxy-N-[4-(5-methyl-2-pyridinyl)-1-[2-(4-morpholinyl)ethyl]-1H-indazole-3-carboxamide | 392.22/ 1.14 (B) |

TABLE 11-continued

| EX. NO. | STRUCTURE | COMPOUND NAME | DATA: MS (M + H)/ HPLC ret. time (min.) and conditions |
|---|---|---|---|
| 430 | 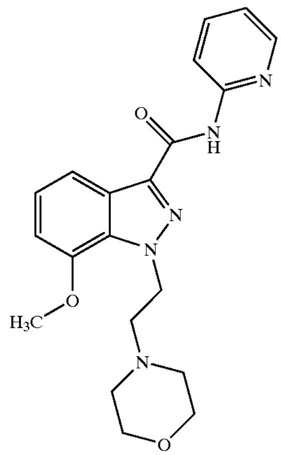 | 7-Methoxy-1-[2-(4-morpholinyl)ethyl]-N-(2-pyridinyl)-1H-indazole-3-carboxamide | 382.21/ 1.08 (B) |
| 431 | 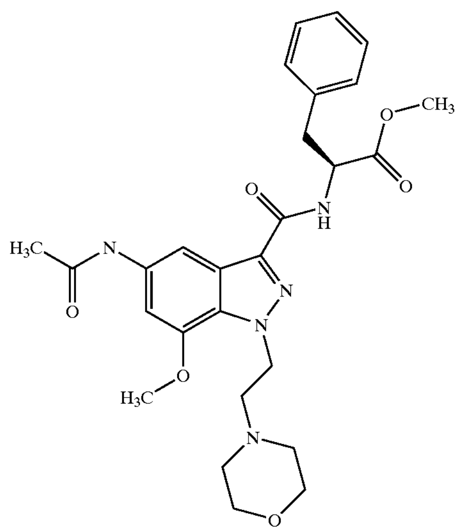 | N-[[5-(Acetylamino)-7-methoxy-1-[2-(4-morpholinyl)ethyl]-1H-indazol-3-yl]carbonyl]-L-phenylalanine methyl ester | 524.29/ 1.17 (C) |
| 432 | 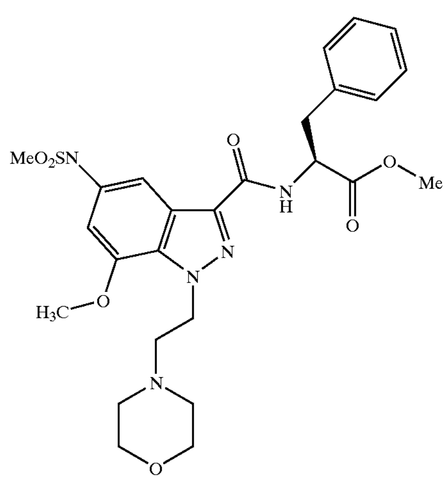 | N-[[7-Methoxy-5-[(methylsulfonyl)amino]-1-[2-(4-morpholinyl)ethyl]-1H-indazol-3-yl]carbonyl]-L-phenylalanine methyl ester | 560.31/ 1.14 (C) |

TABLE 11-continued

| EX. NO. | STRUCTURE | COMPOUND NAME | DATA: MS (M + H)/ HPLC ret. time (min.) and conditions |
|---|---|---|---|
| 433 | 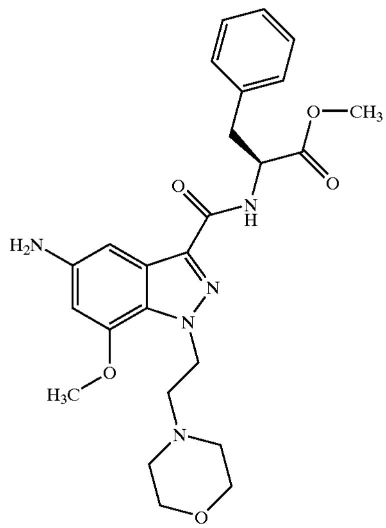 | N-[[5-Amino-7-methoxy-1-[2-(4-morpholinyl)ethyl]-1H-indazol-3-yl]carbonyl]-L-phenylalanine methyl ester | 482.32/ 0.93 (C) |
| 434 | 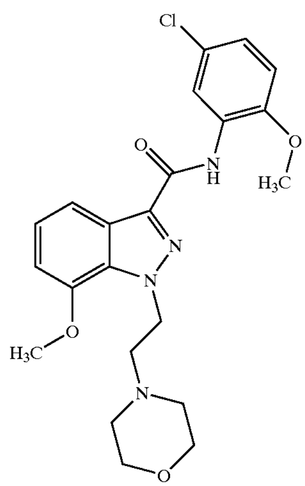 | N-(5-Chloro-2-methoxyphenyl)-7-methoxy-1-[2-(4-morpholinyl)ethyl]-1H-indazole-3-carboxamide | 445.30/ 1.51 (C) |
| 435 | 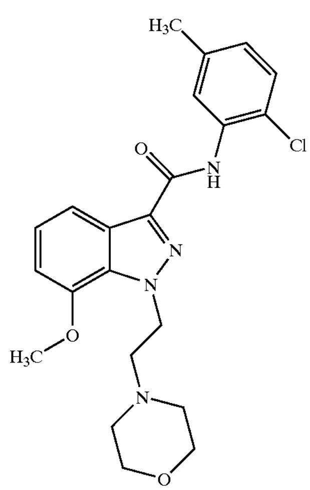 | N-(2-Chloro-5-methylphenyl)-7-methoxy-1-[2-(4-morpholinyl)ethyl]-1H-indazole-3-carboxamide | 429.26/ 1.49 (C) |

TABLE 11-continued

| EX. NO. | STRUCTURE | COMPOUND NAME | DATA: MS (M + H)/ HPLC ret. time (min.) and conditions |
|---|---|---|---|
| 436 | 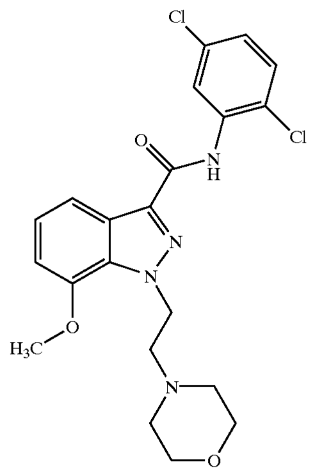 | N-(2,5-Dichlorophenyl)-7-methoxy-1-[2-(4-morpholinyl)ethyl]-1H-indazole-3-carboxamide | 449.25/ 1.57 (C) |
| 437 | 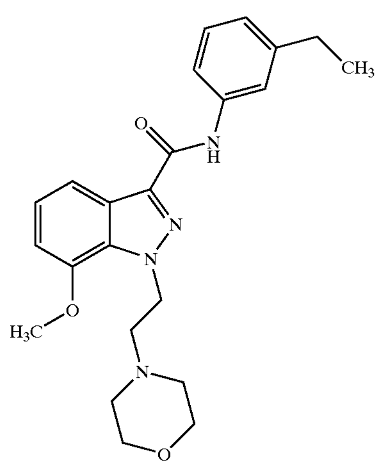 | N-(3-Ethylphenyl)-7-methoxy-1-[2-(4-morpholinyl)ethyl]-1H-indazole-3-carboxamide | 409.32/ 1.42 (C) |
| 438 | 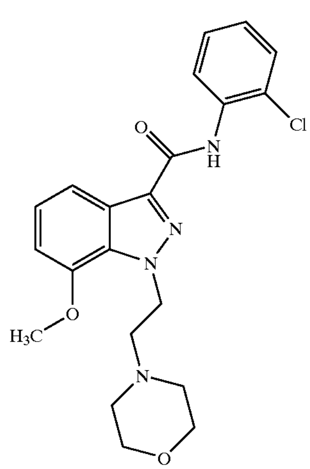 | N-(2-Chlorophenyl)-7-methoxy-1-[2-(4-morpholinyl)ethyl]-1H-indazole-3-carboxamide | 415.24/ 1.37 (C) |

TABLE 11-continued
| EX. NO. | STRUCTURE | COMPOUND NAME | DATA: MS (M + H)/ HPLC ret. time (min.) and conditions |
|---|---|---|---|
| 439 | 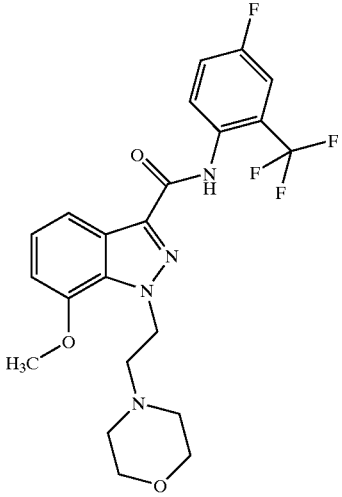 | N-[4-Fluoro-2-(trifluoromethyl)phenyl]-7-methoxy-1-[2-(4-morpholinyl)ethyl]-1H-indazole-3-carboxamide | 467.35/ 1.34 (C) |
| 440 | 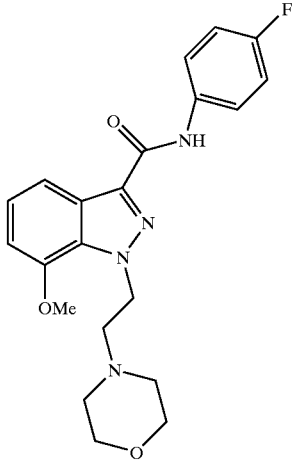 | N-(4-Fluorophenyl)-7-methoxy-1-[2-(4-morpholinyl)ethyl]-1H-indazole-3-carboxamide | 399.30/ 1.27 (C) |
| 441 | 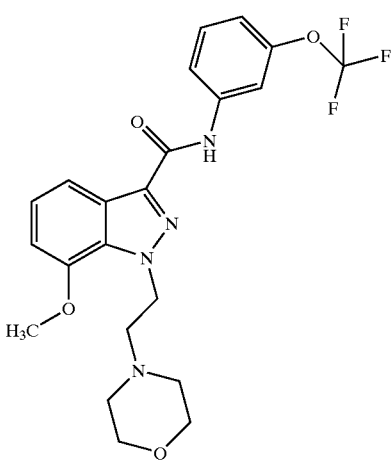 | 7-Methoxy-1-[2-(4-morpholinyl)ethyl]-N-[3-(trifluoromethoxy)phenyl]-1H-indazole-3-carboxamide | 465.35/ 1.50 (C) |

TABLE 11-continued

| EX. NO. | STRUCTURE | COMPOUND NAME | DATA: MS (M + H)/ HPLC ret. time (min.) and conditions |
|---|---|---|---|
| 442 | 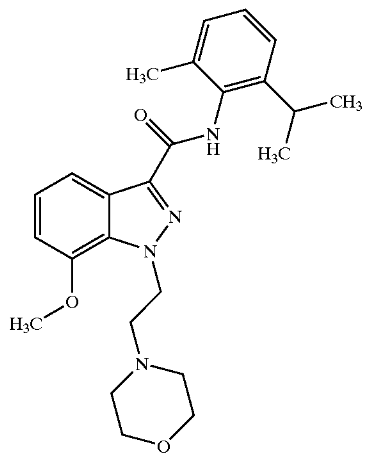 | 7-Methoxy-N-[2-methyl-6-(1-methylethyl)phenyl]-1-[2-(4-morpholinyl)ethyl]-1H-indazole-3-carboxamide | 437.38/ 1.33 (C) |
| 443 | 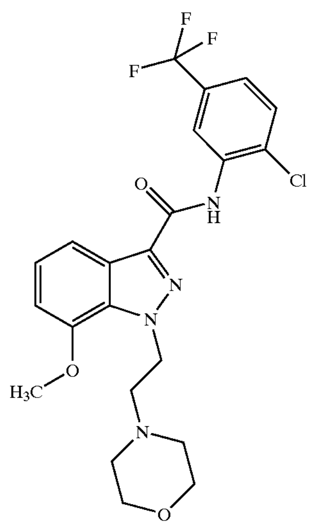 | N-[2-Chloro-5-(trifluoromethyl)phenyl]-7-methoxy-1-[2-(4-morpholinyl)ethyl]-1H-indazole-3-carboxamide | 483.31/ 1.59 (C) |
| 444 | 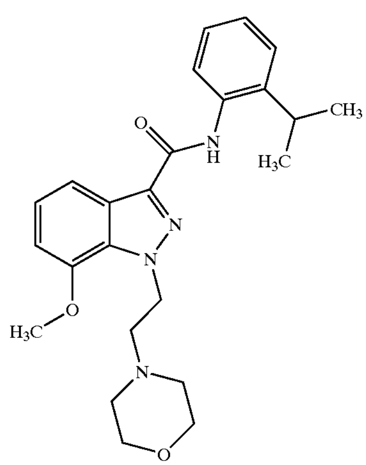 | 7-Methoxy-N-[2-(1-methylethyl)phenyl]-1-[2-(4-morpholinyl)ethyl]-1H-indazole-3-carboxamide | 423.34/ 1.34 (C) |

TABLE 11-continued

| EX. NO. | STRUCTURE | COMPOUND NAME | DATA: MS (M + H)/ HPLC ret. time (min.) and conditions |
|---|---|---|---|
| 445 | 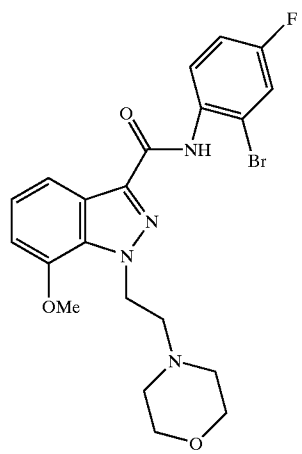 | N-(2-Bromo-4-fluorophenyl)-7-methoxy-1-[2-(4-morpholinyl)ethyl]-1H-indazole-3-carboxamide | 477.27/ 1.39 (C) |
| 446 | 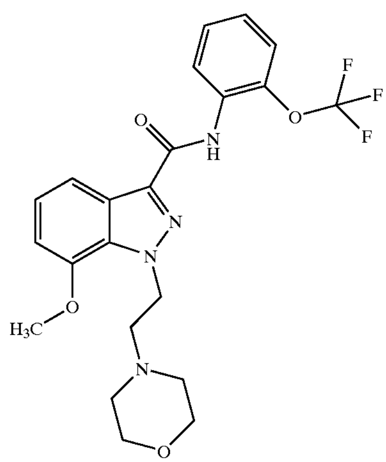 | 7-Methoxy-1-[2-(4-morpholinyl)ethyl]-N-[2-(trifluoromethoxy)phenyl]-1H-indazole-3-carboxamide | 465.32/ 1.43 (C) |
| 447 | 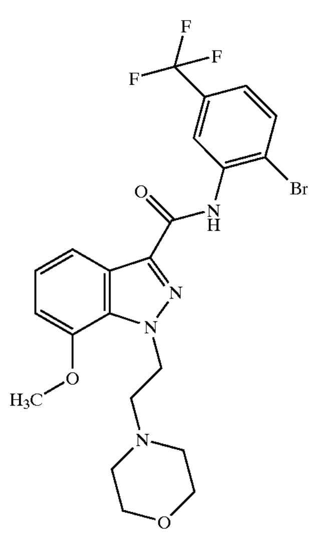 | N-[2-Bromo-5-(trifluoromethyl)phenyl]-7-methoxy-1-[2-(4-morpholinyl)ethyl]-1H-indazole-3-carboxamide | 529.17/ 1.63 (C) |

TABLE 11-continued

| EX. NO. | STRUCTURE | COMPOUND NAME | DATA: MS (M + H)/ HPLC ret. time (min.) and conditions |
|---|---|---|---|
| 448 | 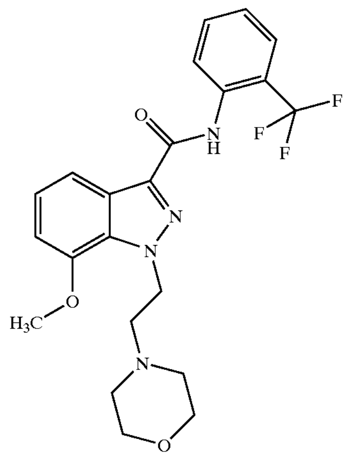 | 7-Methoxy-1-[2-(4-morpholinyl)ethyl]-N-[2-(trifluoromethyl)phenyl]-1H-indazole-3-carboxamide | 449.28/ 1.35 (C) |
| 449 | 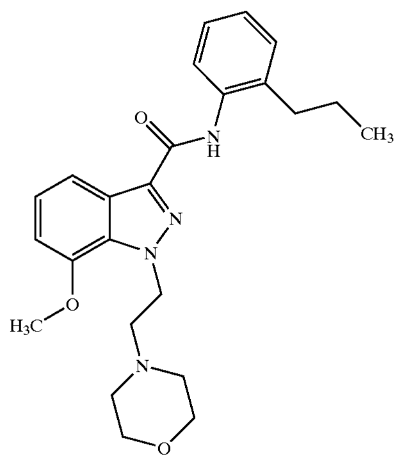 | 7-Methoxy-1-[2-(4-morpholinyl)ethyl]-N-(2-propylphenyl)-1H-indazole-3-carboxamide | 423.30/ 1.39 (C) |
| 450 | 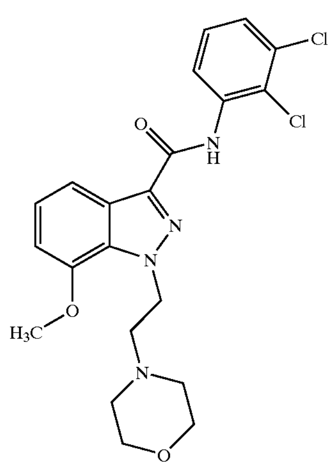 | N-(2,3-Dichlorophenyl)-7-methoxy-1-[2-(4-morpholinyl)ethyl]-1H-indazole-3-carboxamide | 449.19/ 1.53 (C) |

TABLE 11-continued

| EX. NO. | STRUCTURE | COMPOUND NAME | DATA: MS (M + H)/ HPLC ret. time (min.) and conditions |
|---|---|---|---|
| 451 | 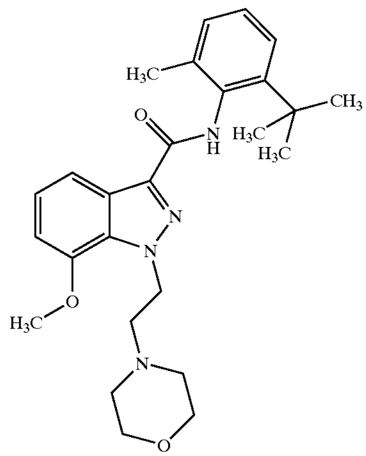 | N-[2-(1,1-Dimethylethyl)-6-methylphenyl]-7-methoxy-1-[2-(4-morpholinyl)ethyl]-1H-indazole-3-carboxamide | 451.36/ 1.38 min,C |
| 452 | 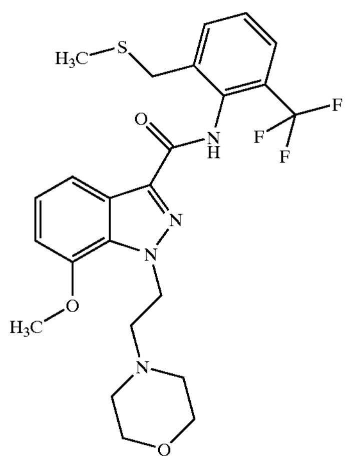 | 7-Methoxy-N-[2-[(methylthio)methyl]-6-(trifluoromethyl)phenyl]-1-[2-(4-morpholinyl)ethyl]-1H-indazole-3-carboxamide | 509.24/ 1.28 (C) |
| 453 | 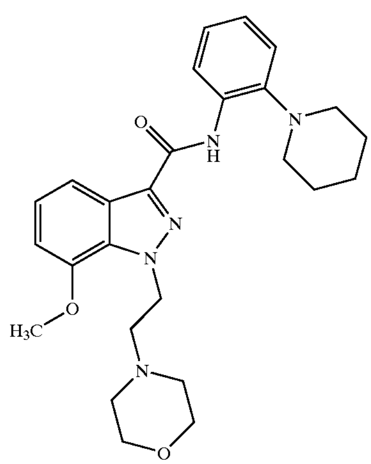 | 7-Methoxy-1-[2-(4-morpholinyl)ethyl]-N-[2-(1-piperidinyl)phenyl]-1H-indazole-3-carboxamide | 464.36/ 1.31 (C) |

TABLE 11-continued

| EX. NO. | STRUCTURE | COMPOUND NAME | DATA: MS (M + H)/ HPLC ret. time (min.) and conditions |
|---|---|---|---|
| 454 | 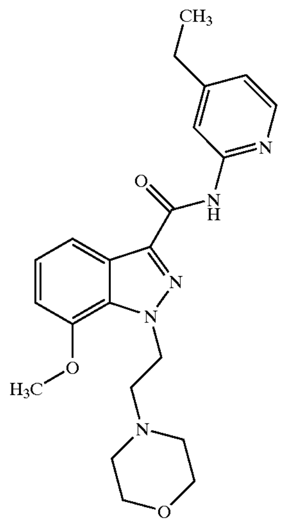 | N-(4-Ethyl-2-pyridinyl)-7-methoxy-1-[2-(4-morpholinyl)ethyl]-1H-indazole-3-carboxamide | 410.26/ 1.09 (C) |
| 455 | 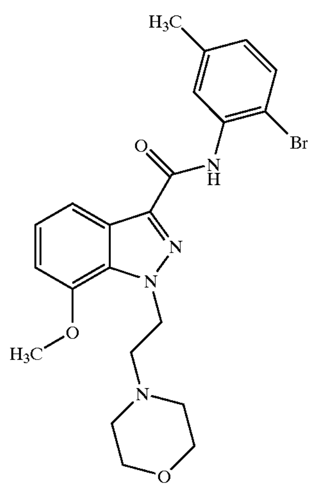 | N-(2-Bromo-5-methylphenyl)-7-methoxy-1-[2-(4-morpholinyl)ethyl]-1H-indazole-3-carboxamide | 475.21/ 1.52 (C) |
| 456 | 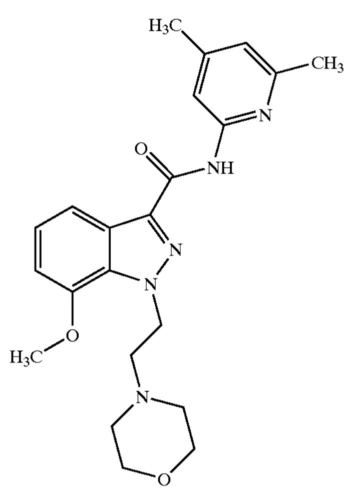 | N-(4,6-Dimethyl-2-pyridinyl)-7-methoxy-1-[2-(4-morpholinyl)ethyl]-1H-indazole-3-carboxamide | 410.26/ 1.07 (C) |

TABLE 11-continued

| EX. NO. | STRUCTURE | COMPOUND NAME | DATA: MS (M + H)/ HPLC ret. time (min.) and conditions |
|---|---|---|---|
| 457 | 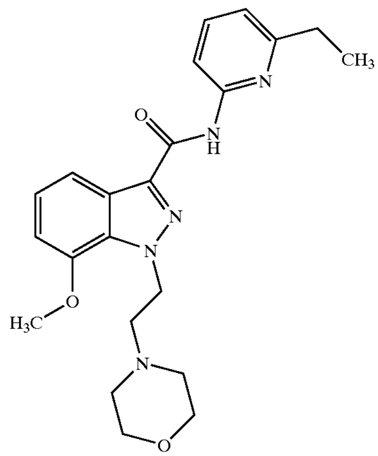 | N-(6-Ethyl-2-pyridinyl)-7-methoxy-1-[2-(4-morpholinyl)ethyl]-1H-indazole-3-carboxamide | 410.23/ 1.31 (B) |
| 458 | 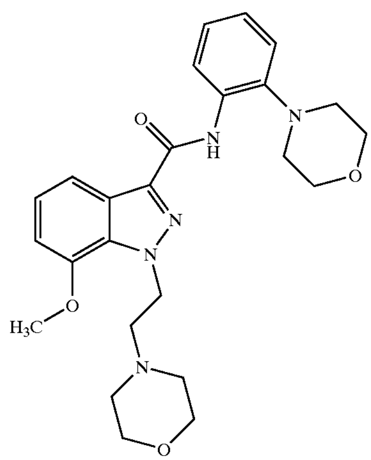 | 7-Methoxy-1-[2-(4-morpholinyl)ethyl]-N-[2-(4-morpholinyl)phenyl]-1H-indazole-3-carboxamide | 466.27/ 1.52 (B) |
| 459 | 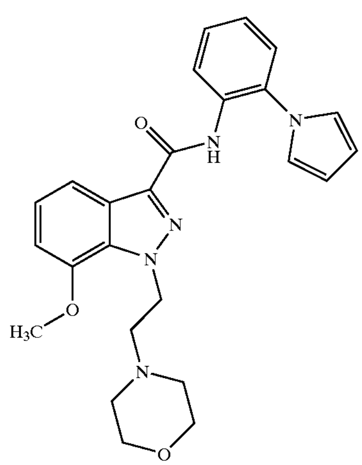 | 7-Methoxy-1-[2-(4-morpholinyl)ethyl]-N-[2-(1H-pyrrol-1-yl)phenyl]-1H-indazole-3-carboxamide | 446.23/ 1.55 (B) |

TABLE 11-continued

| EX. NO. | STRUCTURE | COMPOUND NAME | DATA: MS (M + H)/ HPLC ret. time (min.) and conditions |
|---|---|---|---|
| 460 | 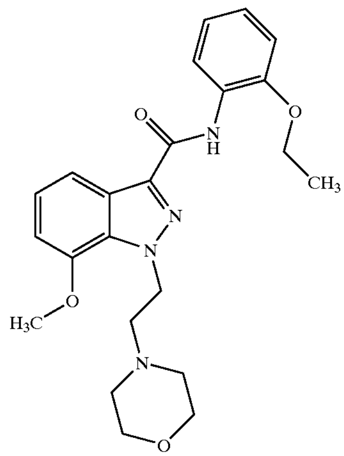 | N-(2-Ethoxyphenyl)-7-methoxy-1-[2-(4-morpholinyl)ethyl]-1H-indazole-3-carboxamide | 425.23/ 1.54 (B) |
| 461 | 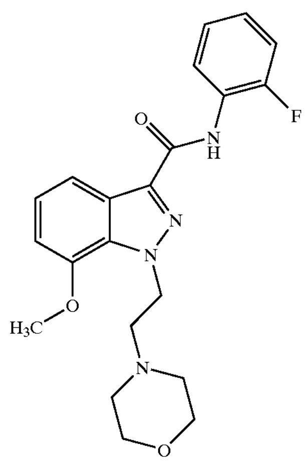 | N-(2-Fluorophenyl)-7-methoxy-1-[2-(4-morpholinyl)ethyl]-1H-indazole-3-carboxamide | 399.21/ 1.37 (B) |
| 462 | 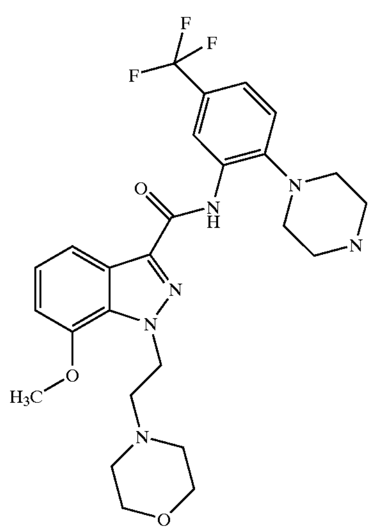 | 7-Methoxy-1-[2-(4-morpholinyl)ethyl]-N-[2-(4-morpholinyl)-5-(trifluoromethyl)phenyl]-1H-indazole-3-carboxamide | 534.22/ 1.72 (B) |

TABLE 11-continued
| EX. NO. | STRUCTURE | COMPOUND NAME | DATA: MS (M + H)/ HPLC ret. time (min.) and conditions |
|---|---|---|---|
| 463 | 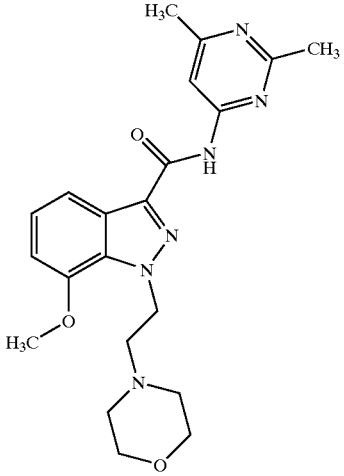 | N-(2,6-Dimethyl-4-pyrimidinyl)-7-methoxy-1-[2-(4-morpholinyl)ethyl]-1H-indazole-3-carboxamide | 411.23/ 1.08 (B) |
| 464 | 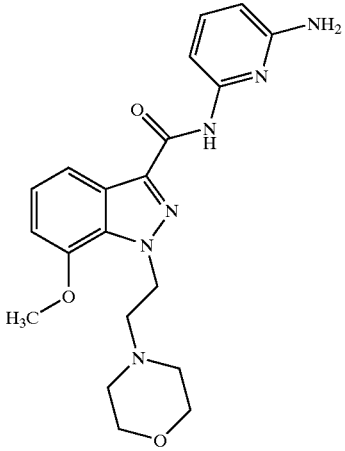 | N-(6-Amino-2-pyridinyl)-7-methoxy-1-[2-(4-morpholinyl)-ethyl]-1H-indazole-3-carboxamide | 397.28/ 1.06 (B) |
| 465 | 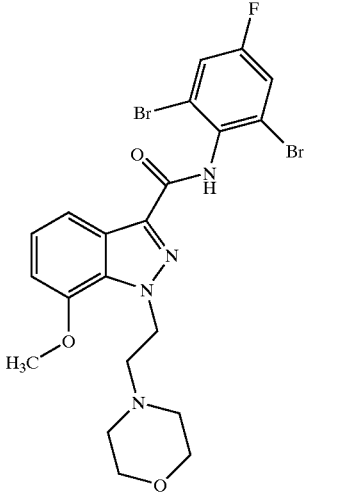 | N-(2,6-Dibromo-4-fluorophenyl)-7-methoxy-1-[2-(4-morpholinyl)-ethyl]-1H-indazole-3-carboxamide | 557.22/ 1.24 (C) |

TABLE 11-continued

| EX. NO. | STRUCTURE | COMPOUND NAME | DATA: MS (M + H)/ HPLC ret. time (min.) and conditions |
|---|---|---|---|
| 466 | 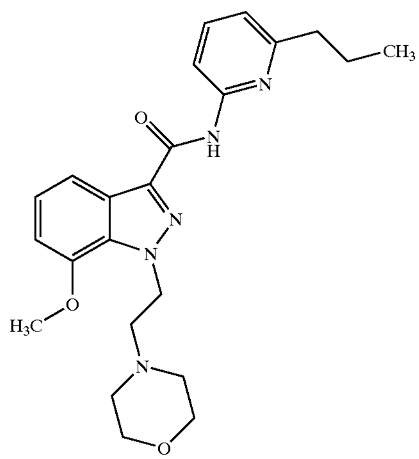 | 7-Methoxy-1-[2-(4-morpholinyl)-ethyl]-N-(6-propyl-2-pyridinyl)-1H-indazole-3-carboxamide | 424.29/ 1.30 (C) |
| 467 | 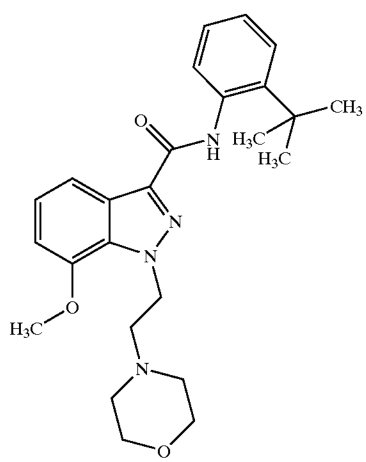 | N-[2-(1,1-Dimethylethyl)-phenyl]-7-methoxy-1-[2-(4-morpholinyl)ethyl]-1H-indazole-3-carboxamide | 437.32/ 1.40 (C) |
| 468 | 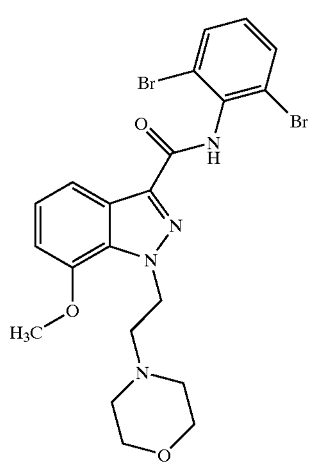 | N-(2,6-Dibromophenyl)-7-methoxy-1-[2-(4-morpholinyl)ethyl]-1H-indazole-3-carboxamide | 539.08/ 1.17 (C) |

TABLE 11-continued

| EX. NO. | STRUCTURE | COMPOUND NAME | DATA: MS (M + H)/ HPLC ret. time (min.) and conditions |
|---|---|---|---|
| 469 | 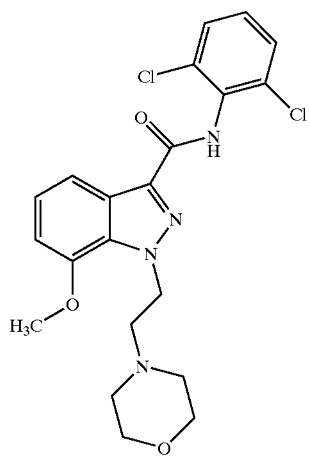 | N-(2,6-Dichlorophenyl)-7-methoxy-1-[2-(4-morpholinyl)-ethyl]-1H-indazole-3-carboxamide | 449.18/ 1.15 (C) |
| 470 | 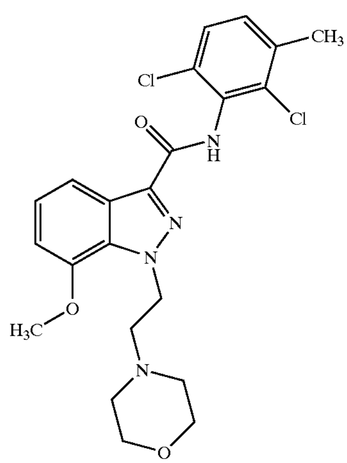 | N-(2,6-Dichloro-3-methylphenyl)-7-methoxy-1-[2-(4-morpholinyl)ethyl]-1H-indazole-3-carboxamide | 463.21/ 1.26 (C) |
| 471 | 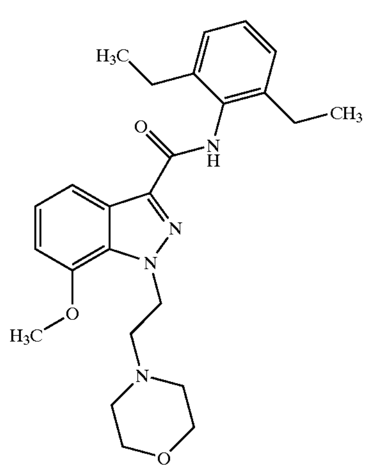 | N-(2,6-Diethylphenyl)-7-methoxy-1-[2-(4-morpholinyl)-ethyl]-1H-indazole-3-carboxamide | 437.30/ 1.31 (C) |

TABLE 11-continued

| EX. NO. | STRUCTURE | COMPOUND NAME | DATA: MS (M + H)/ HPLC ret. time (min.) and conditions |
|---|---|---|---|
| 472 | 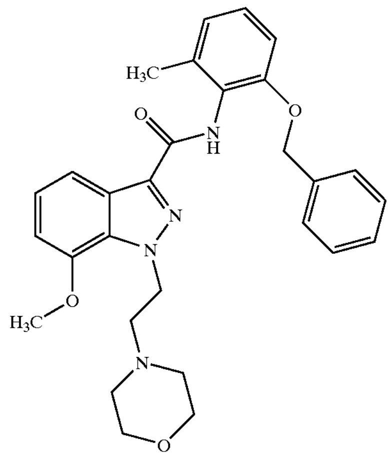 | 7-Methoxy-N-[2-methyl-6-(phenylmethoxy)phenyl]-1-[2-(4-morpholinyl)ethyl]-1H-indazole-3-carboxamide | 501.30/ 1.40 (C) |
| 473 | 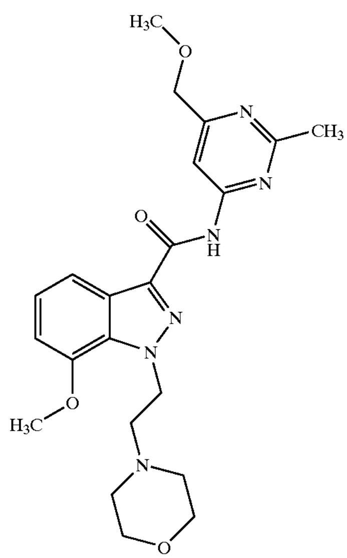 | 7-Methoxy-N-[6-(methoxymethyl)-2-methyl-4-pyrimidinyl]-1-[2-(4-morpholinyl)ethyl]-1H-indazole-3-carboxamide | 441.28/ 1.16 (C) |
| 474 | 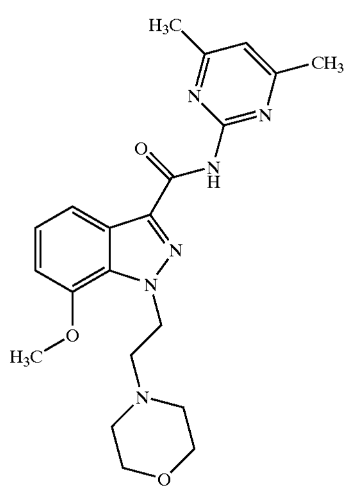 | N-(4,6-Dimethyl-2-pyrimidinyl)-7-methoxy-1-[2-(4-morpholinyl)-ethyl]-1H-indazole-3-carboxamide | 411.26/ 1.04 (C) |

TABLE 11-continued

| EX. NO. | STRUCTURE | COMPOUND NAME | DATA: MS (M + H)/ HPLC ret. time (min.) and conditions |
|---|---|---|---|
| 475 | 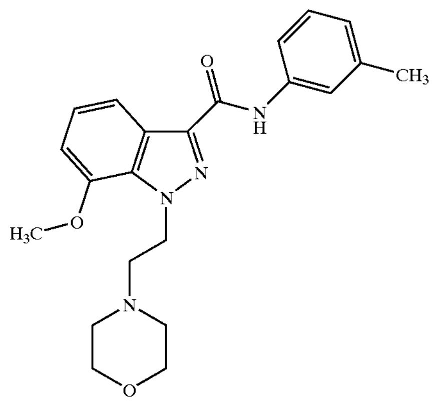 | 7-Methoxy-N-(3-methylphenyl)-1-[2-(4-morpholinyl)ethyl]-1H-indazole-3-carboxamide | 395.28/ 1.33 (C) |
| 476 | 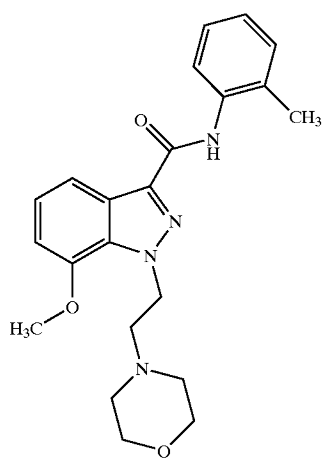 | 7-Methoxy-N-(2-methylphenyl)-1-[2-(4-morpholinyl)ethyl]-1H-indazole-3-carboxamide | 395.27/ 1.20 (C) |
| 477 | 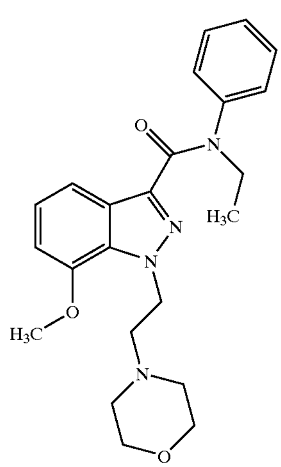 | N-Ethyl-7-methoxy-1-[2-(4-morpholinyl)ethyl]-N-phenyl-1H-indazole-3-carboxamide | 409.27/ 1.20 (C) |

TABLE 11-continued

| EX. NO. | STRUCTURE | COMPOUND NAME | DATA: MS (M + H)/ HPLC ret. time (min.) and conditions |
|---|---|---|---|
| 478 | 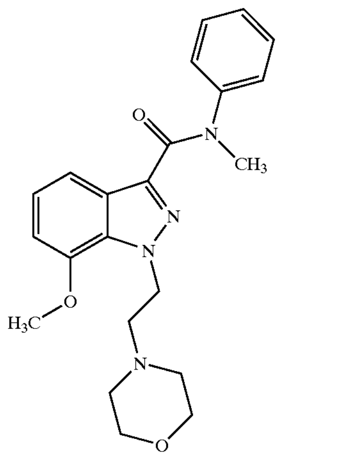 | 7-Methoxy-N-methyl-1-[2-(4-morpholinyl)ethyl]-N-phenyl-1H-indazole-3-carboxamide | 395.33/ 1.11 (C) |
| 479 | 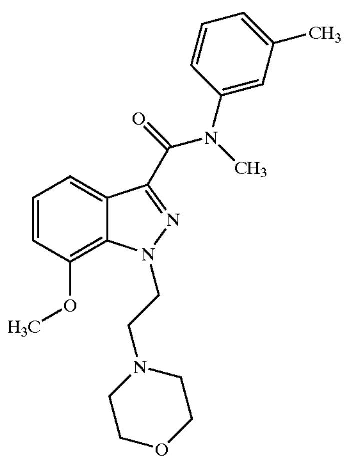 | 7-Methoxy-N-methyl-N-(3-methylphenyl)-1-[2-(4-morpholinyl)ethyl]-1H-indazole-3-carboxamide | 409.33/ 1.22 (C) |
| 480 | 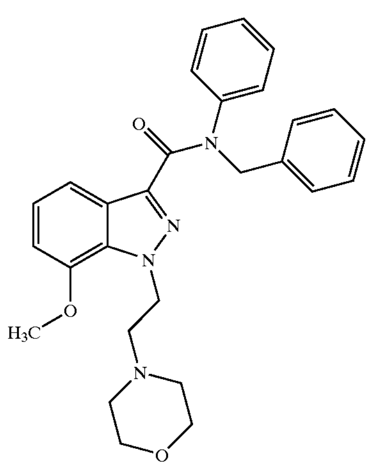 | 7-Methoxy-1-[2-(4-morpholinyl)ethyl]-N-phenyl-N-(phenylmethyl)-1H-indazole-3-carboxamide | 471.41/ 1.42 (C) |

TABLE 11-continued

| EX. NO. | STRUCTURE | COMPOUND NAME | DATA: MS (M + H)/ HPLC ret. time (min.) and conditions |
|---|---|---|---|
| 481 | 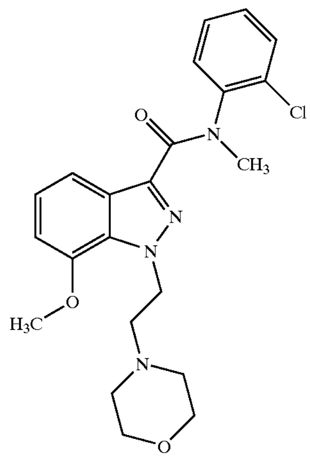 | N-(2-Chlorophenyl)-7-methoxy-N-methyl-1-[2-(4-morpholinyl)-ethyl]-1H-indazole-3-carboxamide | 429.28/ 1.22 (C) |
| 482 | 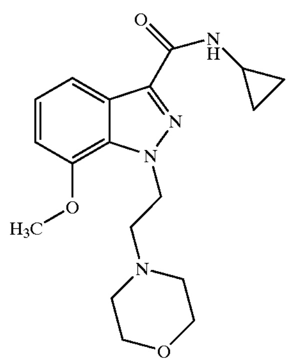 | N-Cyclopropyl-7-methoxy-1-[2-(4-morpholinyl)ethyl]-1H-indazole-3-carboxamide | 359.23/ 1.58 (A) |
| 483 | 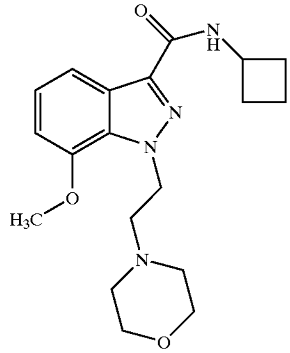 | N-Cyclobutyl-7-methoxy-1-[2-(4-morpholinyl)ethyl]-1H-indazole-3-carboxamide | 361.25/ 1.89 (A) |

TABLE 11-continued
| EX. NO. | STRUCTURE | COMPOUND NAME | DATA: MS (M + H)/ HPLC ret. time (min.) and conditions |
|---|---|---|---|
| 484 | 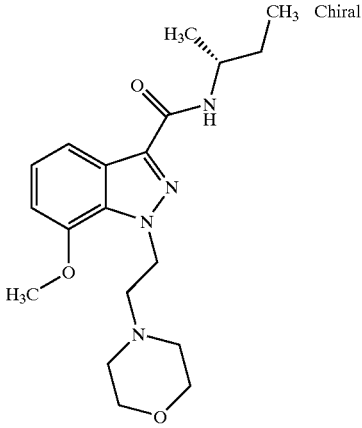 | 7-Methoxy-N-[(1R)-1-methylpropyl]-1-[2-(4-morpholinyl)ethyl]-1H-indazole-3-carboxamide | 375.29/ 1.94 (A) |
| 485 | 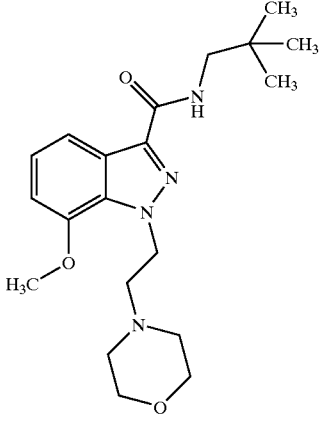 | N-(2,2-Dimethylpropyl)-7-methoxy-1-[2-(4-morpholinyl)-ethyl]-1H-indazole-3-carboxamide | 375.29/ 2.23 (A) |
| 486 | 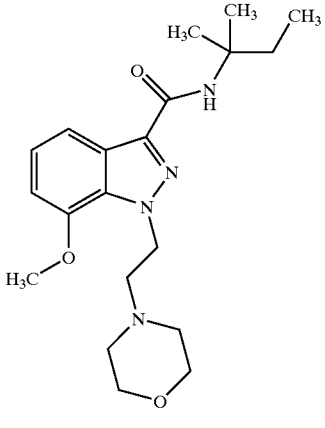 | N-(1,1-Dimethylpropyl)-7-methoxy-1-[2-(4-morpholinyl)-ethyl]-1H-indazole-3-carboxamide | 375.30/ 2.24 (A) |

TABLE 11-continued

| EX. NO. | STRUCTURE | COMPOUND NAME | DATA: MS (M + H)/ HPLC ret. time (min.) and conditions |
|---|---|---|---|
| 487 | 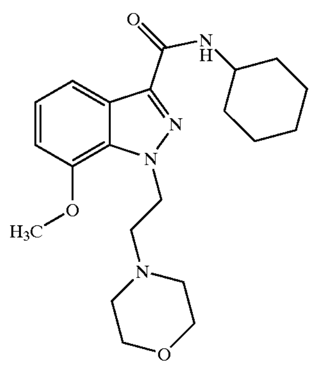 | N-Cyclohexyl-7-methoxy-1-[2-(4-morpholinyl)ethyl]-1H-indazole-3-carboxamide | 389.28/ 2.33 (A) |
| 488 | 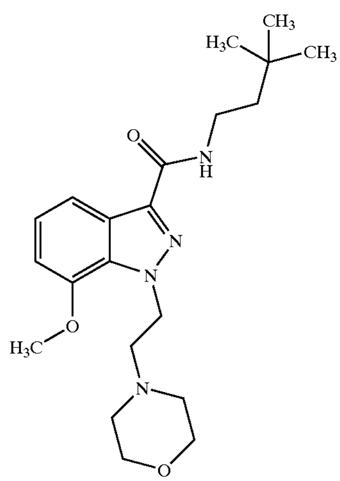 | N-(3,3-Dimethylbutyl)-7-methoxy-1-[2-(4-morpholinyl)-ethyl]-1H-indazole-3-carboxamide | 389.28/ 2.24 (A) |
| 489 | 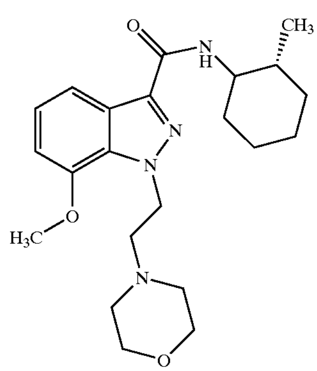 | 7-Methoxy-N-(2-methylcyclohexyl)-1-[2-(4-morpholinyl)ethyl]-1H-indazole-3-carboxamide | 401.28/ 2.46 (A) |

TABLE 11-continued

| EX. NO. | STRUCTURE | COMPOUND NAME | DATA: MS (M + H)/ HPLC ret. time (min.) and conditions |
|---|---|---|---|
| 490 | 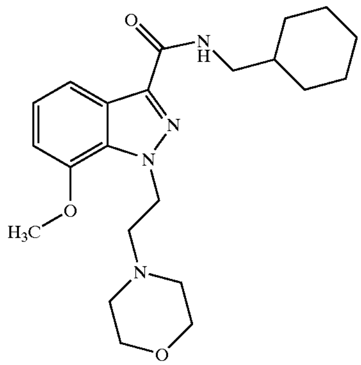 | N-(Cyclohexylmethyl)-7-methoxy-1-[2-(4-morpholinyl)-ethyl]-1H-indazole-3-carboxamide | 425.27/ 2.59 (A) |
| 491 | 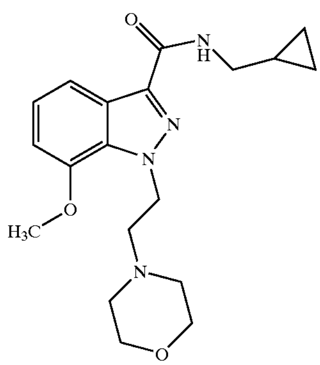 | N-(Cyclopropylmethyl)-7-methoxy-1-[2-(4-morpholinyl)-ethyl]-1H-indazole-3-carboxamide | 375.28/ 1.87 (A) |
| 492 | 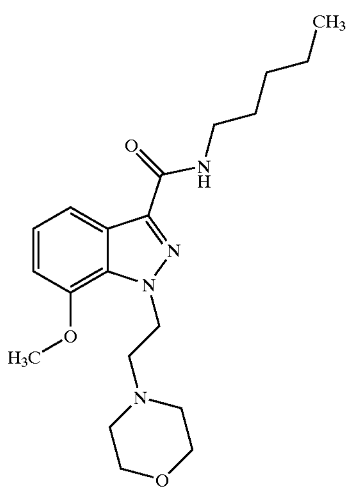 | 7-Methoxy-1-[2-(4-morpholinyl)-ethyl]-N-pentyl-1H-indazole-3-carboxamide | 361.26/ 2.38 (A) |

TABLE 11-continued

| EX. NO. | STRUCTURE | COMPOUND NAME | DATA: MS (M + H)/ HPLC ret. time (min.) and conditions |
|---|---|---|---|
| 493 | 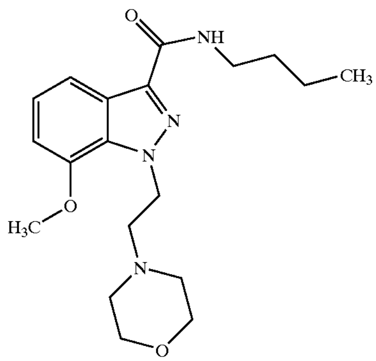 | N-Butyl-7-methoxy-1-[2-(4-morpholinyl)ethyl]-1H-indazole-3-carboxamide | 347.23/ 2.08 (A) |
| 494 | 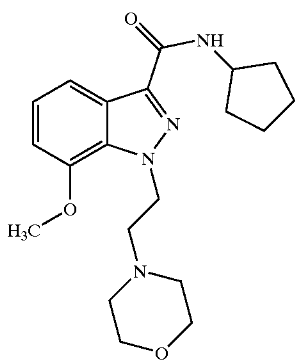 | N-(Cyclopentyl)-7-methoxy-1-[2-(4-morpholinyl)ethyl]-1H-indazole-3-carboxamide | 373.00/ 2.07 (A) |
| 495 | 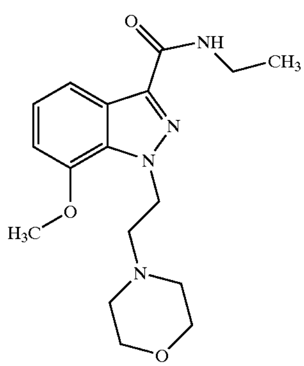 | N-Ethyl-7-methoxy-1-[2-(4-morpholinyl)ethyl]-1H-indazole-3-carboxamide | 333.20/ 1.52 (A) |
| 496 | 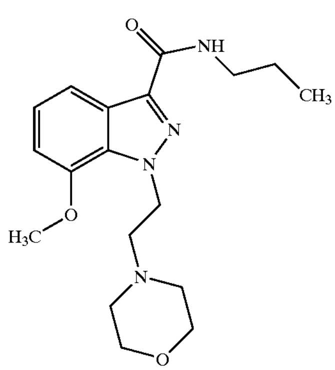 | 7-Methoxy-1-[2-(4-morpholinyl)ethyl]-N-propyl-1H-indazole-3-carboxamide | 347.23/ 1.77 (A) |

TABLE 11-continued

| EX. NO. | STRUCTURE | COMPOUND NAME | DATA: MS (M + H)/ HPLC ret. time (min.) and conditions |
|---|---|---|---|
| 497 | 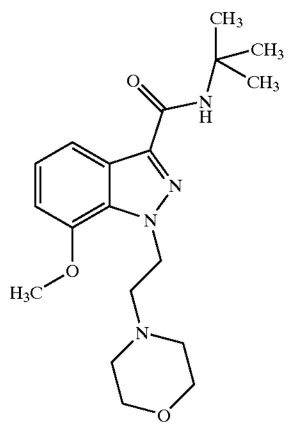 | N-(1,1-Dimethylethyl)-7-methoxy-1-[2-(4-morpholinyl)-ethyl]-1H-indazole-3-carboxamide | 361.27/ 2.03 (A) |
| 498 | 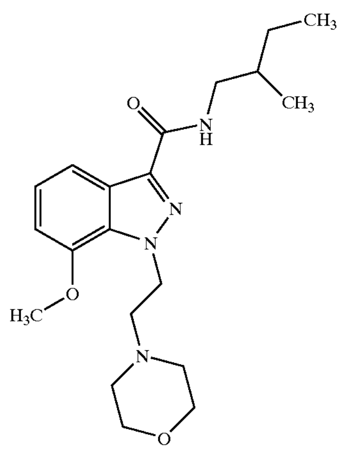 | 7-Methoxy-N-(2-methylbutyl)-1-[2-(4-morpholinyl)ethyl]-1H-indazole-3-carboxamide | 357.29/ 2.27 (A) |
| 499 | 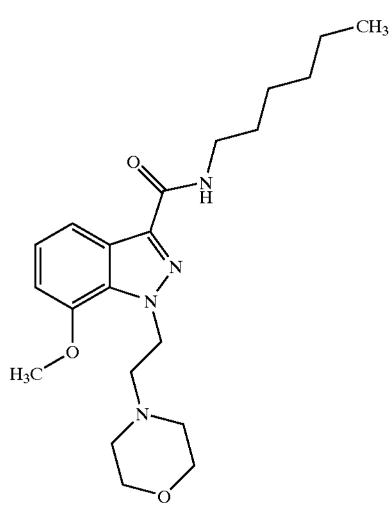 | N-Hexyl-7-methoxy-1-[2-(4-morpholinyl)ethyl]-1H-indazole-3-carboxamide | 389.28/ 2.66 (A) |

TABLE 11-continued

| EX. NO. | STRUCTURE | COMPOUND NAME | DATA: MS (M + H)/ HPLC ret. time (min.) and conditions |
|---|---|---|---|
| 500 | 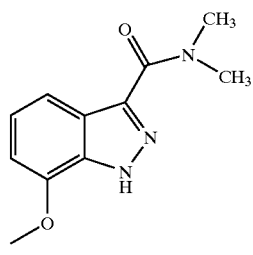 Chiral | N-[(1S)-1-Cyclohexylethyl]-7-methoxy-1-[2-(4-morpholinyl)-ethyl]-1H-indazole-3-carboxamide | 415.31/ 2.70 (A) |

Example 501

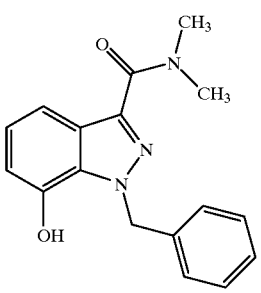

The above compound was prepared following the procedures previously described.

Example 502

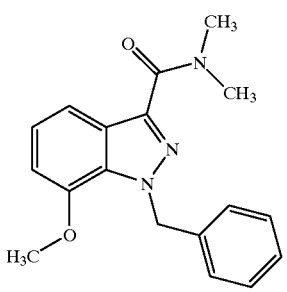

To a suspension of Example 501 (0.5 g, 2.28 mmol) in CH₃CN (5 mL) was added K₂CO₃ (0.945 g, 6.85 mmol) and benzyl bromide (285 µL, 2.39 mmol) and the mixture was heated to reflux for 2 h. After cooling to RT, CH₂Cl₂ (30 mL) was added and the mixture filtered. The solvent was removed in vacuo and the residue crystallized from Et₂O/Hexane to give the compound of Example 502 as a pure product (610 mg, 86.6%). HPLC ret. t: 3.247 min (A).

Example 503

To the compound of Example 502 (1.42 g, 4.59 mmol) dissolved in CH₂Cl₂ (30 mL) was added slowly BBr₃ (20 mL, 1M solution in CH₂Cl₂) at RT. The reaction was stirred for 3 h then slowly added to a stirred mixture of ice water and CH₂Cl₂. The pH of the mixture was adjusted to 3 with 1N NaOH, and the layers were separated. The aqueous layer was extracted twice more with CH₂Cl₂ and then dried over MgSO₄. After removal of the solvent, the residue was purified by column chromatography on silica gel with CH₂Cl₂ followed by 20% EtOAc/CH₂Cl₂ to give 592 mg (43.7%) of the above compound. HPLC ret. t: 2.883 min (A).

Example 504

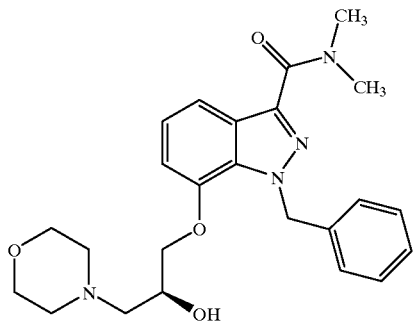

To the compound of Example 503 (787 mg, 2.67 mmol) dissolved in EtOH (30 mL) was added K₂CO₃ (9.2 g, 66.6 mmol) followed by a portion wise addition of (R)-(−)-epichlorohydrin (4.2 mL, 53.4 mmol) at RT over a 3 h period. To the reaction was added CH₂Cl₂ and the mixture filtered. The solvent was removed in vacuo and the residue dissolved in THF (4 mL) followed by the addition of morpholine (4 mL). The reaction mixture was then heated to 60° C. When done, the reaction was poured into saturated brine and extracted twice with EtOAc. The EtOAc was dried over MgSO₄ and then the solvent removed in vacuo. The residue was purified by column cromatography with EtOAc and 2% MeOH/EtOAc to give the above compound (990 mg, 84.6%) as a thick oil. HPLC ret. t: 1.9 min (A).

Example 505

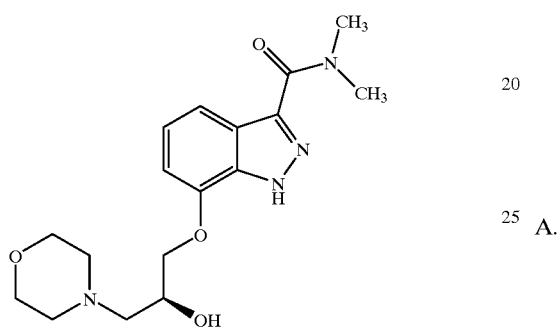

The compound of Example 504 (990 mg, 2.26 mmol) was hydrogenated in MeOH (20 mL) and concentrated HCl (2 mL) with moist Pd(OH)₂/C under 50 psi H₂ for 12 h. The mixture was filtered and the solvent removed in vacuo. To the residue was added saturated NaHCO₃ and extracted 4 times with CH₂Cl₂, dried over MgSO₄ and rotvaped to give the above compound (678 mg, 86%). HPLC ret. t: 1.37 min (A).

Example 506

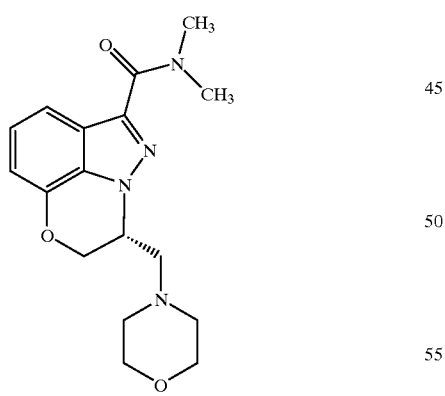

To Example 505 (600 mg, 1.72 mmol) dissolved in THF (15 mL) cooled in an ice bath was added PPh₃ (994 mg, 3.79 mmol) followed by DEAD (623 μL, 3.96 mmol). The ice bath was removed and the reaction stirred for 15 min. The reaction was diluted with EtOAc and extracted twice with 1N HCl. The HCl layer was washed with EtOAc then neutralized with 1N NaOH, saturated with NaCl and extracted 3 times with EtOAc. After drying with MgSO₄, the solvent was removed and the residue dissolved in CH₂Cl₂ followed by the addition of 4N HCl in dioxane. The HCl salt was filtered with CH₂Cl₂ rinse to give the above compound (43 6 mg, 69% as HCl salt). HPLC ret. t: 1.376 min (A).

Example 507

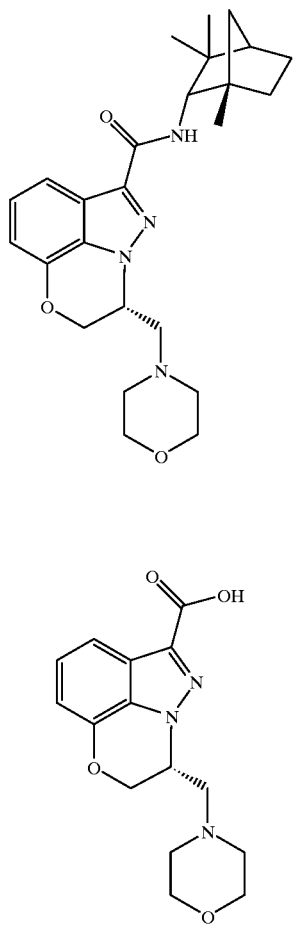

A.

To Example 506 (405 mg, 1.1 mmol) in IPA (2 mL) was added water (130 μL) and KOH (180 mg, 3.2 mmol). The mixture was heated to 90° C. for 12 h then cooled in ice neutralized with 4N HCl/dioxane and filtered. The IPA was removed in vacuo and the residue dissolved in CH₂Cl₂, filtered, and the product precipitated with hexane to give 277.5 mg (83%) of compound A, above. HPLC ret. t: 1.48 min (A).

B.

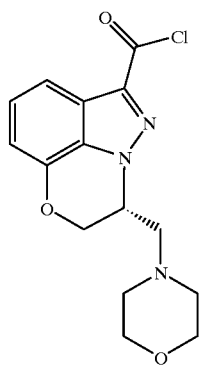

To a suspension of compound from step A (250 mg, 0.825 mmol) in $CH_2Cl_2$ (10 ml) was added oxalyl chloride (288 µL, 3.3 mmol) followed by 1 drop of DMF. The reaction was stirred for 15 min then $Et_2O$ (40 mL) was added and the product filtered to give 276 mg (93.5%) of the above compound B as the HCl salt.

C. Example 507

To compound B (80 mg, 0.22 mmol) in THF (1 mL) was added TEA (124 µL, 0.89 mmol) followed by fenchel amine HCl (41.7 mg, 0.22 mmol). When done the solvent was removed in vacuo, 1N NaOH was added and extracted three times with $CH_2Cl_2$. After drying over $MgSO_4$, the solvent was removed and the residue purified by column chromatography on silica gel with 25% EtOAc/Hexane to give Example 507 (58.2 mg, 60%). MS (M+H$^+$) 439, ret. t: 3.229 min (A).

Example 508

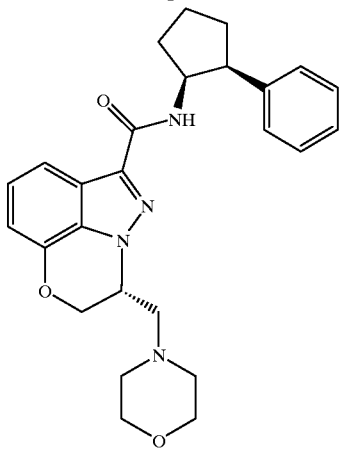

To Example 507 (50 mg, 0.14 mmol) in THF (1 mL) was added TEA (78 µL, 0.56 mmol) followed by cis-2-phenylcyclopentalamine (22.5 mg, 0.22 mmol). When done, the solvent was removed in vacuo, and 1N NaOH was added and extracted 3 times with $CH_2Cl_2$. After drying over $MgSO_4$, the solvent was removed and the residue purified by column chromatography on silica gel with 25% EtOAc/Hexane to give Example 508 (23 mg, 37%). MS (M+H$^+$) 447, ret. t: 2.912 min (A).

Examples 509–513

(Iq)

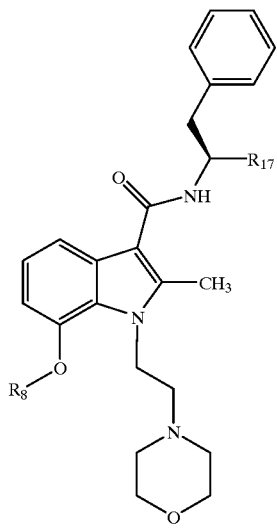

Compounds of Examples 509–513 having the formula (Iq) wherein $R_8$ and $R_{17}$ have the values listed in Table 12, were prepared following the procedures previously described above for Examples 202–500.

TABLE 12

| EXAMPLE NO. | $R_8$ | $R_{17}$ | DATA MS (M + H)/ HPLC ret. t. (min) and conditions |
|---|---|---|---|
| 509 | —(CH$_2$)$_4$CH$_3$ | —CO$_2$Me | 536.5/3.83 (A) |
| 510 | —(CH$_2$)$_2$CH$_3$ | —CO$_2$Me | 508.35/3.45 (A) |
| 511 | H | —CO$_2$Me | 466.4/2.94 (A) |
| 512 | —CH$_2$CH$_3$ | —CO$_2$Me | 494.4/3.21 (A) |
| 513 | —CH$_3$ | —CN | 447.3/2.84 (A) |

Examples 514–515

Compounds of Examples 514–515 were prepared following the procedures previously described above for Examples 202–500.

TABLE 13

| EXAMPLE NO. | STRUCTURE | DATA MS (M + H)/ HPLC ret. t. (min.) and conditions |
|---|---|---|
| 514 | ![structure] | 480.2/3.20 (A) |

TABLE 13-continued

| EXAMPLE NO. | STRUCTURE | DATA MS (M + H)/ HPLC ret. t. (min.) and conditions |
|---|---|---|
| 515 | 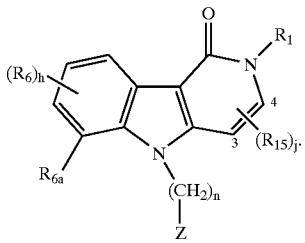 | 466.3/2.89(A) |

We claim:

1. A compound having the formula,

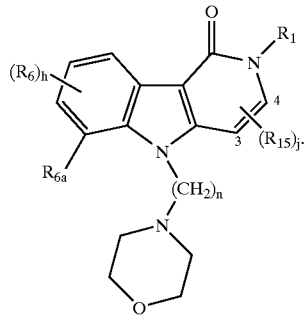

or a pharmaceutically-acceptable salt or hydrate thereof, in which:

$R_1$ is (i) $CHR_{17}R_{18}$; or (ii) aryl, heterocyclo, or cycloalkyl optionally substituted with one to four groups selected from $C_{1-6}$alkyl, $C_{1-6}$alkoxy, hydroxy, halogen, cyano, nitro, trifluoromethyl, trifluoromethoxy, amino, $C_{1-4}$alkylamino, aryl, cycloalkyl, and heterocyclo;

$R_6$ at each occurrence independent of each other $R_6$ is selected from hydrogen, alkyl, substituted alkyl, heterocycloalkyl, alkenyl, substituted alkenyl, alkynyl, substituted alkynyl, aryl, cycloalkyl, heterocyclo, hydroxy, alkoxy, amino, aminoalkyl, cyano, halogen, alkylamide, nitro, $NR_8C(=O)R_9$, $S(O)_uR_{10}$, $—C(=O)R_8$, $—CO_2R_8$, $—S(O)_2NR_8R_9$, $—C(=O)N(R_8)O(R_9)$, $—C(=O)NR_8R_9$, and $—OC(=O)R_{10}$;

$R_{6a}$ is selected from hydrogen, alkyl, substituted alkyl, heterocycloalkyl, alkenyl, substituted alkenyl, alkynyl, substituted alkynyl, aryl, cycloalkyl, heterocyclo, hydroxy, alkoxy, cyano, halogen, alkylamide, nitro, $NR_8C(=O)R_9$, $S(O)_uR_{10}$, $—C(=O)R_8$, $—CO_2R_8$, $—S(O)_2NR_8R_9$, $—C(=O)N(R_8)O(R_9)$, $—C(=O)NR_8R_9$, and $—OC(=O)R_{10}$;

$R_8$ and $R_9$ at each occurrence are independently selected from hydrogen, alkyl, substituted alkyl, heterocycloalkyl, alkenyl, substituted alkenyl, alkynyl, substituted alkynyl, cycloalkyl, aryl, and heterocyclo; or $R_8$ and $R_9$ together form a three-to-eight membered heterocyclo;

$R_{10}$ at each occurrence independent of each other $R_{10}$ is selected from alkyl, substituted alkyl, heterocycloalkyl, alkenyl, substituted alkenyl, alkynyl, and substituted alkynyl;

$R_{15}$ is at each occurrence selected from hydrogen, $C_{1-4}$alkyl, hydroxy, halogen, cyano, $C_{1-4}$alkoxy, trifluoromethyl, trifluoromethoxy, amino, $NH(CH_3)$, $NH(Et)$, $N(CH_3)_2$, and $C_{1-2}$alkyl substituted with amino, hydroxy, cyano, halogen, trifluoromethyl, and/or trifluoromethoxy;

$R_{17}$ and $R_{18}$ are $(CR_{21}R_{22})_s$—W;

W at each occurrence is selected from hydrogen, alkyl, alkylamide, aminoalkyl, alkylthio, alkoxy, hydroxy, cyano, $—CO_2R_{19}$, $—C(=O)R_{19}$, $—C(=O)N(R_{19})O(R_{20})$, $—NR_{19}(C=O)R_{20}$, aryl, cycloalkyl, and heterocyclo;

$R_{19}$ and $R_{20}$ are selected from hydrogen, alkyl, substituted alkyl, heterocycloalkyl, alkenyl, substituted alkenyl, cycloalkyl, aryl, and heterocyclo;

$R_{21}$ and $R_{22}$ are independently hydrogen, alkyl, hydroxy, or hydroxyalkyl;

Z is optionally-substituted heterocyclo;

h is 2 or 3;

j is 2 when the bond linking C3 and C4 is a double bond and j is 4 when said bond is a single bond;

n is 1, 2, 3, or 4;

s is 0, 1, 2, 3 or 4; and u is 0, 1, 2 or 3.

2. A compound according to claim 1, or a pharmaceutically-acceptable salt or hydrate thereof, in which:

$R_{15}$ at at least one occurrence is methyl, ethyl, halogen, or cyano, and at each other occurrence is selected from hydrogen, methyl, ethyl, halogen, and cyano.

3. A compound according to claim 1, in which:

Z is selected from morpholinyl and pyridinyl in turn optionally substituted with one to two of $C_{1-4}$alkyl, hydroxy, halogen, cyano, $C_{1-4}$alkoxy, trifluoromethyl, trifluoromethoxy, amino, $C_{1-4}$alkylamino, acetylamino and $C_{1-4}$alkyl substituted with amino, hydroxy, cyano, halogen, $C_{1-4}$alkoxy, trifluoromethyl, and/or trifluoromethoxy.

4. A compound according to claim 1, having the formula,

5. A compound according to claim 1, in which $R_1$ is the group

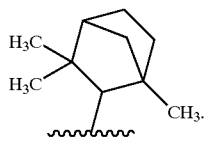

6. A compound which is selected from (i):
2,3,4,5-Tetrahydro-6-methoxy-5-[2-(4-morpholinyl)ethyl]-2-[(1S,2S)-1,3,3-trimethylbicyclo[2.2.1]heptan-2-yl]-1H-pyrido[4,3-b]indol-1-one;
2,5-Dihydro-6-methoxy-5-[2-(4-morpholinyl)ethyl]-2-propyl-1H-pyrido[4,3-b]indol-1-one;
2-Cyclopentyl-2,5-dihydro-6-methoxy-5-[2-(4-morpholinyl)ethyl]-1H-pyrido[4,3-b]indol-1-one;
2,5-Dihydro-6-methoxy-2-(2-methoxyphenyl)-5-[2-(4-morpholinyl)ethyl]-1H-pyrido[4,3-b]indol-1-one;
2,5-Dihydro-6-methoxy-2-(2-methoxyethyl)-5-[2-(4-morpholinyl)ethyl]-1H-pyrido[4,3-b]indol-1-one;
2,5-Dihydro-6-methoxy-5-[2-(4-morpholinyl)ethyl]-2-[(3R)-tetrahydro-3-furanyl]-1H-pyrido[4,3-b]indol-1-one;
2,5-Dihydro-6-methoxy-5-[2-(4-morpholinyl)ethyl]-2-[(1R)-1-methyl-2-phenylethyl]-1H-pyrido[4,3-b]indol-1-one;
2-(2,3-Dihydro-1H-inden-1-yl)-2,5-dihydro-6-methoxy-5-[2-(4-morpholinyl)ethyl]-1H-pyrido[4,3-b]indol-1-one;
2-(Bicyclo[2.2.1]heptan-2-yl)-2,5-dihydro-6-methoxy-5-[2-(4-morpholinyl)ethyl]-1H-pyrido[4,3-b]indol-1-one;
2,5-Dihydro-6-methoxy-5-[2-(4-morpholinyl)ethyl]-2-(3,3,5-trimethylcyclo-hexanyl)-1H-pyrido[4,3-b]indol-1-one;
2,5-Dihydro-6-methoxy-3-methyl-5-[2-(4-morpholinyl)ethyl]-2-[(1S,2S)-1,3,3-trimethylbicyclo[2.2.1]heptan-2-yl]-1H-pyrido[4,3-b]indol-1-one;
2-[(2-Fluorophenyl)methyl]-2,5-dihydro-6-methoxy-5-[2-(4-morpholinyl)ethyl]-1H-pyrido[4,3b]indol-1-one;
2-[(2,6-Dimethylphenyl)-methyl]-2,5-dihydro-6-methoxy-5-[2-(4-morpholinyl)ethyl]-1H-pyrido[4,3-b]indol-1-one;
2,5-Dihydro-6-methoxy-5-[2-(4-morpholinyl)ethyl]-2-[(1R,2R)-1,3,3-trimethylbicyclo[2.2.1]heptan-2-yl]-1H-pyrido[4,3-b]indol-1-one;
2,5-Dihydro-6-methoxy-5-[2-(4-morpholinyl)ethyl]-2-[(1S,2S)-1,3,3-trimethylbicyclo[2.2.1]heptan-2-yl]-1H-pyrido[4,3-b]indol-1-one;
2,5-Dihydro-6-methoxy-5-(phenylmethyl)-2-[(1S,2S)-1,3,3-trimethylbicyclo[2.2.1]heptan-2-yl]-1H-pyrido[4,3-b]indol-1-one;
5-Butyl-2,5-dihydro-6-methoxy-2-[(1S,2S)-1,3,3-trimethylbicyclo[2.2.1]heptan-2-yl]-1H-pyrido[4,3-b]indol-1-one;
4-Methyl-2,5-dihydro-6-methoxy-5-[2-(4-morpholinyl)ethyl]-2-[(1S,2S)-1,3,3-trimethylbicyclo[2.2.1]heptan-2-yl]-1H-pyrido[4,3-b]indol-1-one;
4-Fluoro-2,5-dihydro-6-methoxy-5-[2-(4-morpholinyl)ethyl]-2-[(1S,2S)-1,3,3-trimethylbicyclo[2.2.1]heptan-2-yl]-1H-pyrido[4,3-b]indol-1-one; and (ii) a pharmaceutically-acceptable salt or hydrate thereof.

7. A pharmaceutical composition comprising a therapeutically-effective amount of at least one compound according to claim 1 and a pharmaceutically-acceptable carrier or diluent.

8. A pharmaceutical composition comprising (i) one or more of the compounds of claim 1, (ii) one or more second compounds effective for treating a leukocyte-activation associated disease in a mammal; and (iii) a pharmaceutically-acceptable carrier or diluent.

* * * * *